US012478079B2

(12) United States Patent
Pandya et al.

(10) Patent No.: US 12,478,079 B2
(45) **Date of Patent: *Nov. 25, 2025**

(54) COMPOSITIONS COMPRISING A CASEIN AND METHODS OF PRODUCING THE SAME

(71) Applicant: Perfect Day, Inc., Berkeley, CA (US)

(72) Inventors: Ryan Pandya, Berkeley, CA (US); Perumal Gandhi, Santa Clara, CA (US); Shaowen Ji, Berkeley, CA (US); Derek Beauchamp, Dexter, MI (US); Louis Hom, San Carlos, CA (US)

(73) Assignee: PERFECT DAY, INC., Berkeley, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 18/362,555

(22) Filed: Jul. 31, 2023

(65) Prior Publication Data

US 2023/0371547 A1 Nov. 23, 2023

Related U.S. Application Data

(63) Continuation of application No. 17/081,167, filed on Oct. 27, 2020, which is a continuation of application No. 15/505,557, filed as application No. PCT/US2015/046428 on Aug. 21, 2015, now Pat. No. 11,076,615.

(60) Provisional application No. 62/040,393, filed on Aug. 21, 2014.

(51) Int. Cl.

| | |
|---|---|
| *A23G 9/40* | (2006.01) |
| *A23C 9/123* | (2006.01) |
| *A23C 9/13* | (2006.01) |
| *A23C 9/15* | (2006.01) |
| *A23C 9/152* | (2006.01) |
| *A23C 11/04* | (2025.01) |
| *A23C 11/08* | (2006.01) |
| *A23C 15/12* | (2006.01) |
| *A23C 19/05* | (2006.01) |
| *A23C 19/055* | (2006.01) |
| *A23J 3/10* | (2006.01) |
| *A23L 9/20* | (2016.01) |
| *C07K 14/00* | (2006.01) |
| *C07K 14/47* | (2006.01) |
| *C07K 14/76* | (2006.01) |

(52) U.S. Cl.

CPC ................ *A23G 9/40* (2013.01); *A23C 9/123* (2013.01); *A23C 9/1307* (2013.01); *A23C 9/1315* (2013.01); *A23C 9/1512* (2013.01); *A23C 11/04* (2013.01); *A23C 11/08* (2013.01); *A23C 15/12* (2013.01); *A23C 19/053* (2013.01); *A23C 19/055* (2013.01); *A23J 3/10* (2013.01); *A23L 9/22* (2016.08); *C07K 14/00* (2013.01); *C07K 14/4717* (2013.01); *C07K 14/4732* (2013.01); *C07K 14/76* (2013.01); *A23V 2002/00* (2013.01)

(58) Field of Classification Search

CPC ..... A23C 19/053; A23C 11/06; A23C 19/056; C07K 14/4717; C07K 14/4732

See application file for complete search history.

(56) References Cited

U.S. PATENT DOCUMENTS

| | | | |
|---|---|---|---|
| 4,614,653 | A | 9/1986 | Kakade |
| 4,834,994 | A | 5/1989 | Kueata |
| 5,061,504 | A | 10/1991 | Kong-Chan et al. |
| 5,882,704 | A | 3/1999 | Yamaguchi et al. |
| 5,882,705 | A | 3/1999 | Sato et al. |
| 5,942,274 | A | 8/1999 | Slattery et al. |
| 6,181,421 | B1 | 1/2001 | Aspnes et al. |
| 6,232,094 | B1 | 5/2001 | Hansson |
| 6,270,827 | B1 | 8/2001 | Gaull et al. |
| 6,290,974 | B1 | 9/2001 | Swaisgood et al. |
| 8,809,259 | B2 | 8/2014 | Berry et al. |
| 9,591,872 | B2 | 3/2017 | Rosado Loria et al. |
| 2003/0078392 | A1 | 4/2003 | Leaver |
| 2005/0170062 | A1 | 8/2005 | Burling |
| 2007/0116830 | A1 | 5/2007 | Prakash |
| 2010/0119691 | A1 | 5/2010 | Huang et al. |
| 2010/0223682 | A1 | 9/2010 | Katz |
| 2013/0189398 | A1 | 7/2013 | Rosado Loria et al. |
| 2014/0013294 | A1 | 1/2014 | Berkovitz et al. |
| 2014/0065264 | A1 | 3/2014 | Do et al. |
| 2014/0099444 | A1 | 4/2014 | Catchmark et al. |
| 2014/0134294 | A1 | 5/2014 | Merill et al. |
| 2017/0273328 | A1 | 9/2017 | Pandya et al. |
| 2018/0271111 | A1 | 9/2018 | Pandya et al. |
| 2021/0037848 | A1 | 2/2021 | Pandaya et al. |
| 2021/0037849 | A1 | 2/2021 | Pandaya et al. |

FOREIGN PATENT DOCUMENTS

| | | |
|---|---|---|
| EP | 2649884 | 10/2013 |
| JP | 3475221 | 12/2009 |
| WO | WO 1991/08675 | 6/1991 |
| WO | WO 1995/02692 | 1/1995 |

(Continued)

OTHER PUBLICATIONS

[No Author Listed], "96$^{th}$ Annual Collegiate Dairy Products Evaluation Contest" Apr. 17, 2019, 10 pages.

(Continued)

*Primary Examiner* — Jeffrey P Mornhinweg

(74) *Attorney, Agent, or Firm* — David R. Conklin; Kirton McConkie

(57) ABSTRACT

Disclosed herein are methods and compositions including casein, and methods for making these compositions.

20 Claims, 9 Drawing Sheets

Specification includes a Sequence Listing.

(56) References Cited

FOREIGN PATENT DOCUMENTS

| | | |
|---|---|---|
| WO | WO 2004/091306 | 10/2004 |
| WO | WO 2013/09182 | 1/2013 |
| WO | WO 2013/148221 | 10/2013 |
| WO | WO 2013/148328 | 10/2013 |
| WO | WO 2013/148330 | 10/2013 |
| WO | WO 2013/148331 | 10/2013 |
| WO | WO 2013/148332 | 10/2013 |
| WO | WO 2016/029193 | 2/2016 |

OTHER PUBLICATIONS

Adapa et al., "Rheological Properties of Ice Cream Mixes and Frozen Ice Creams Containing Fat and Fat Replacers", Journal of Dairy Science, May 2000, 83:2224-2229.

Arora et al., "Variations in the fat unsaponifiable matter and cholesterol contents of goat milk," Ind. J. Dairy Sci., Sep. 1976, 29:191.

AU Opposition, "Amended Statement of Grounds and Particulars," in Australian Appln. No. 2015305271, Dec. 24, 2020, 2 pages.

AU Opposition, "Opposition Statement of Grounds and Particulars," in Australian Appln. No. 2015305271, Jan. 5, 2021, 15 pages.

AU Opposition, "Applicant-Initiated Interview Summary," Exhibit G in Australian Appln. No. 2015305271, dated Sep. 22, 2020, 4 pages.

AU Opposition, "Correspondence," in Australian Appl. No. 2015305271, dated Feb. 2021, 2 pages.

AU Opposition, "Declaration by Dr. Jeremy Paul Hill," Exhibit JH-1 in Australian Appln. No. 2015305271, dated Dec. 18, 2020, 14 pages.

AU Opposition, "Declaration of Dr. Colin Robert South: "Declaration of Dr. Colin Robert South," In the Matter of Australian Patent Application 2015305271 in the name of Perfect Day, Inc. and in the Matter of an Opposition Thereto by Fonterra Co-operative Group Limited," Exhibit CS-2, Federal Court of Australia, Jun. 22, 2013, 3 pages.

AU Opposition, "Declaration of Dr. Stephen Richard Davis," In the Matter of Australian patent application 2015305271 in the name of Perfect Day, Inc. and in the Matter of an opposition thereto by Fonterra Co-operative Group Limited, dated Jun. 23, 2020, 16 pages.

AU Opposition, Declaration of Dr. Steven Richard Davis: "Expert witness in proceedings in the Federal Court of Australia," Exhibit SRD-2, Federal Court of Australia, Jun. 2013, 3 pages.

AU Opposition, "Declaration of Tiffany Reiter, PH.D.,J.D.," Exhibit A in Australian Appln. No. 2015305271, dated, Sep. 20, 2020, 4 pages.

AU Opposition, "Declaration of Tiffany Reiter, PH.D.,J.D.," in Australian Appln. No. 2015305271, dated, Sep. 20, 2020, 4 pages.

AU Opposition, "First Declaration of Donald McMahon, PH.D.," Exhibit A in Australian Appln. No. 2015305271, dated Oct. 12, 2020, 29 pages.

AU Opposition, "First Declaration of Donald McMahon, PH.D.," Exhibit B in Australian Appln. No. 2015305271, dated Oct. 12, 2020, 14 pages.

AU Opposition, "First Declaration of Donald McMahon, PH.D.," Exhibit C in Australian Appln. No. 2015305271, dated Oct. 12, 2020, 4 pages.

AU Opposition, "First Declaration of Donald McMahon, PH.D.," Exhibit D in Australian Appln. No. 2015305271, dated Oct. 12, 2020, 4 pages.

AU Opposition, "First Declaration of Donald McMahon, PH.D.," in Australian Appln. No. 2015305271, dated Oct. 12, 2020, 30 pages.

AU Opposition, "First Declaration of Tonya Schoenfuss, PH.D, Huppertz et al., "Effect of NaC1 on some physico-chemical properties of concentrated bovine milk," International Diary J., 2005, 16(2006):1142-1148" Exhibit I in Australian Appl No. 2015305271, dated Sep. 2020, 8 pages.

AU Opposition, "First Declaration of Tonya Schoenfuss, PH.D," Loch et al., "Two modes of fatty acid binding to bovine β-lactoglobulin-crystallographic and spectroscopic studies," J. of Molecular Recognition, 2011, 24:341-349, Exhibit D in Australian Appln. No. 2015305271, dated Sep. 22, 2020, 10 pages.

AU Opposition, "First Declaration of Tonya Schoenfuss, PH.D.," "Expert Evidence of practice note(GPN-EXPT)" Federal Court of Australia, Exhibit B in Australian Appln. No. 201530271, dated Sep. 22, 2020, 14 pages.

AU Opposition, "First Declaration of Tonya Schoenfuss, PH.D.," Chrysina et al., "Crystal structures of apo- and holo-bovine x-lacralbumin at 2.2—a resolution reveal an effect of calcium on inter-lobe interactions," J. of Biology Chemistry, 2000, 37021-37029, Exhibit E in Australian Appl. No. 2015305271, dated Sep. 22, 2020, 10 pages.

AU Opposition, "First Declaration of Tonya Schoenfuss, PH.D.," Curriculum Vitae, Exhibit A in Australian Appl. No. 2015305271, dated Sep. 22, 2020, 6 pages.

AU Opposition, "First Declaration of Tonya Schoenfuss, PH.D.," dated Sep. 22, 2020, 32 pages.

AU Opposition, "First Declaration of Tonya Schoenfuss, PH.D.," Exhibit F in Australian Appln. No. 2015305271, dated Sep. 22, 2020, 12 pages.

AU Opposition, "First Declaration of Tonya Schoenfuss, PH.D.," Exhibit H in Australian Appln. No. 2015305271, dated Sep. 22, 2020, 4 pages.

AU Opposition, "First Declaration of Tonya Schoenfuss, PH.D.," Exhibit J in Australian Appln. No. 2015305271, dated Sep. 22, 2020, 36 pages.

AU Opposition, First Declaration of Tonya Schoenfuss, PH.D., Farrell et al., "Nomenclature of the proteins of cows' milk-sixth revision," J. Diary Sci., , 2004, 1641-1674, Exhibit C in Australian Appl. No. 2015305271, dated Sep. 22, 2020, 35 pages.

AU Opposition, "Letter to The Commisioner of Patents-Applicants Response" in Australian Appl No. 2015305271, dated Jun. 17, 2021, 4 pages.

AU Opposition, "Reply declaration by Dr. Jeremy Paul Hill," in Australian Appln. No. 2015305271, dated Dec. 18, 2020, 10 pages.

AU Opposition, Reply Declaration by Dr. Stephen Richard Davis, dated Dec. 21, 2020, 8 pages.

AU Opposition, "Reply declaration of Dr. Colin Robert South," Exhibit CS-11 in Australian Appln. No. 2015305271, dated Dec. 21, 2020, 7 pages.

AU Opposition, "Reply declaration of Dr. Stephen Richard Davis," Exhibit SRD-10 in Australian Appln. No. 2015305271, dated Dec. 21, 2020, 7 pages.

AU Opposition, "Reply Declaration of Professor Matt Duncan Golding, " in Australian Appln. No. 2015305271, dated Dec. 23, 2020, 14 pages.

AU Opposition, "Reply declaration of Professor Matt Duncan Golding, "Exhibit MDG-1 in Australian Appln. No. 2015305271, 20 pages.

AU Opposition, "Reply Declaration" by Dr. Colin South, dated, Dec. 21, 2020, 12 pages.

Au Opposition, "Response to Directors Letter", in Australian Appl. No. 2015305271, dated Feb. 1, 2021, 6 pages.

AU Opposition, "Second Declaration of Donald McMahon, PH.D.," in Australian Appln. No. 2015305271, dated Sep. 22, 2020, 3 pages.

AU Opposition, "Second Declaration of Dr. Colin Robert South," In the Matter of Australian patent application 2015305271 in the name of Perfect Day, Inc. and in the Matter of an opposition thereto by Fonterra Co-operative Group Limited, dated Jun. 22, 2020, 10 pages.

AU Opposition, "Second Declaration of Dr. Colin Robert South: Comment on opposed patent, with patent specification as reviewed attached," Exhibit CS-6, Australian Appln No. 2015305271, dated Aug. 21, 2015, 225 pages.

AU Opposition, "Second Declaration of Tonya Schoenfuss, PH.D.," in Australian Appln. No. 2015305271, dated Sep. 21, 2020, 5 pages.

AU Opposition, "Statement of Grounds and Particulars," in Australian Application No. 2015305271, dated Mar. 23, 2020, 14 pages.

(56) References Cited

OTHER PUBLICATIONS

AU Opposition, "Declaration of Dr. Stephen Richard Davis: AU 2015305271 Table comparing claim features with disclosure of U.S. Pat. No. 8,809,259(D1)," Exhibit SRD-9, 8 pages.
AU Patent Application No. 2015305271 Opposition, "Declaration of Dr. Colin Robert South," In the Matter of Australian Patent Application 2015305271 in the name of Perfect Day, Inc. and in the Matter of an Opposition Thereto by Fonterra Co-operative Group Limited, dated Jun. 22, 2020, 15 pages.
Beare-Rogers et al., "Lexicon of lipid nutration (IUPAC Technical Report)," Pure and Applied Chemistry 73(4):685-744, 2001.
Bill et al., "Play catch-up with *Escherichia coli*: using yeast to increase success rates in recombinant protein production experiments", Frontiers in Microbio., vol. 5, article 85, 5 pages, 2014.
BR Office Action in Brazilian Appln. No. BR112017003414-0, dated Oct. 31, 2019, 5 pages (with English translation).
Brignon et al., "Preparation and amino acid sequences of human kappa-casein," FEBS Lett. 188(1):48-54, 1985.
CA Office Action in Canadian Appln. No. 2958858, dated Aug. 5, 2020, 4 pages.
CA Office Action in Canadian Appln. No. 2958858, dated Jul. 29, 2019, 3 pages.
Chapter 5, "Post-translational Modification of Caseins," in Milk Proteins from Expression to Food, Second Edition, Singh et al. (Eds), Elsevier, Boston, MA, pp. 141-162, 2014.
Chatel et al., "Expression, Purification and Immunochemical Characterization of Recombinant Bovine Beta-Lactoglobulin, A Major Cow Milk Allergen," Molecular Immunology, Aug. 1996, 33(14):1113-1118.
Choi and Jimenez-Flores, "Expression and purification of glycosylated bovine beta-casein (L70S/P71S) in Pichia pastoris," J. Agric. Food Chem. 49(4):1761-1766, 2001.
Choi et al., "Studies on Physical and Sensory Properties of Premium Vanilla Ice Cream Distributed in Korean Market", Korean J. Food Sci. An., Dec. 2014, 34(6): 757-762.
CN Office Action in Chinese Application No. 201580057456, dated Mar. 18, 2020, 5 pages.
CN Office Action in Chinese Appln. No. 201580057456.4, dated Jan. 15, 2020, 22 pages (with English translation).
CN Office Action in Chinese Appln. No. 201580057456.4, dated Oct. 30, 2020, 23 pages (with English Translation).
Conesa et al., "Recombinant human lactoferrin: A valuable protein for pharmaceutical products and functional foods," Biotechnology Advances, 2010, 28:831-838.
Declaration by Ravi Jhala, in Australian Patent Application No. 2015305271, dated Jun. 14, 2021, 12 pages.
Desai et al., "Sensory properties and drivers of liking for Greek yogurts", Journal of Diary Science, Oct. 28, 2013, 96(12): 7454-7466.
Deshpande et al., "Protein Glycosylation Pathways in Filamentus Fungi," Glycobiology 18(8):626-637, 2008.
European Office Action in Application No. 15/763,136.7, dated Jun. 5, 2019, 9 pages.
European Office Action in Application No. 15/763,136.7, dated Nov. 9, 2020, 10 pages.
Examination Report in Australian Patent Application No. 2015305271, dated Nov. 12, 2018.
Farrell Jr., et al., "Casein Micelle Structure: What Can Be Learned from Milk Synthesis and Structural Biology?" Curr. Opin. Colloid Interface Sci. 11:135-147, 2006.
Firebaugh et al., "Emulsifying and Foaming Properties of a Derivatized Whey Protein Ingredient", International Journal of Food Properties, 2005, 8:243-253.
Goda et al., "Production of Synthetic Methionine-Free and Synthetic Methionine-Limited Alpha Casein: Protein Foodstuff for Patients with Homocystinuria due to Cystathionine Beta-Synthase Deficiency", Protein J., 29: 44-49, 2010.
Greenberg et al., "Human beta-casein. Amino acid sequence and identification of phosphorylation sites," J. Biol. Chem., 1984, 259(8):5132-5138.
Hansson et al., "Expression of human milk beta-casein in *Escherichia coli*: comparison of recombinant protein with native isoforms," Protein Expr. Purif. 4(5):373-381, 1993.
Idiris et al., "Engineering of protein secretion in yeast: strategies and impact on protein production," Appl. Microbiol. Biotechnol. 86(2):403-417, 2010.
Imafidon et al., "Isolation, purification, and alteration of some functional groups of major milk proteins: a review," Crit. Rev. Food. Sci. Nutr. 37(7):663-689, 1997.
Indian Office Action in Application No. 201737009683, dated Nov. 24, 2020, 7 pages.
International Preliminary Report on Patentability in International Application No. PCT/US2015/046428, dated Feb. 21, 2017.
International Search Report for PCT/US2015/046428, mailed Feb. 5, 2016, 8 pages.
Jenness, "Composition and Characteristics of Goat Milk: Review 1968-1979," J. Dairy Sci., 1980, 63(10):1605-1630.
Jensen, "Bovine milk lipids," in Handbook of Milk Composition, Academic Press, 1995, 543-575.
Jimenez-Flores et al., "Expression of bovine B-casein in *Saccharomyces cerevisiae* and characterization of the protein produced in vivio", J. Agric. Food Chem., 36, 1134-1141, 1990.
JP Notice of Opposition No. in Japanese Appln. No. 2017-529979, dated Aug. 30, 2022, 2 pages, (with English translation).
JP Office Action in Japanese Appln No. 2017-529979, dated, Oct. 13, 2020, 14 pages (with Machine translation).
JP Opposition, Notice of Reasons for Revocation in Japanese Appln. No. 2017- 529979, mailed Jan. 17, 2023, 32 pages (with English translation).
JP Opposition, Written Opposition, in Japanese Appl. No. 2017-529979, dated Oct. 27, 2022, 106 pages (with English Translation).
Juarez et al., "Physico-Chemical Characteristics of Goat's Milk as Distinct From Those of Cow's Milk," Int. Dairy Fed. Bulletin, 1986, 202: 54-67.
Kang et al., "Molecular cloning and expression of bovine k-casein in *Escherichia coli*", J. Dairy Sci., 71: 29-40, 1988.
Kawai et al., "Transformation of *Saccharomyces cerevisiae* and other fungi," Bioengineered Bugs, 2010, 1: 395-403.
Khan et al., "Humanizing glycosylation pathways in eukaryotic expression systems", World J. Microbiol. Biotechnol. 2017, 33:4.
Kim et al., "Production of human caseinomacropeptide in recombinant *Saccharomyces cerevisiae* and Pichia pastoris", Journal of Industrial Microbiology & Biotechnology ; Official Journal of the Society for Industrial Microbiology, Springer, Berlin, DE, vol. 32, No. 9, pp. 402-408, 2005.
Kim et al., "High-Level Expression of Bovine β-Lactoglobulin in Pichia pastoris and Characterization of Its Physicial Properties," Protein Engineering 10(11):1339-1345, 1997.
Kneifel et al., "Water-holding capacity of proteins with special regard to milk proteins and methodological aspects", Journal of Diary Science, 1991, 74:2027-2041.
Koc et al., "Physical properties of yoghurt powder produced by spray drying", Journal Food Science Technology, Jul. 2014, 51(7): 1377-1383.
Lee et al., "Impact of Gelation Conditions and Structural Breakdown on the Physical and Sensory Properties of Stirred Yogurts", Journal of Diary Science, Jul. 2006, 89:2374-2385.
Li et al., "Cell culture processes for monoclonal antibody production," Landes Bioscience, 2010, 2: 466-477.
Lonnerdal, "Recombinant Human Milk Proteins—An Opportunity and a Challenge," Am. J. Clin. Nutr. 63(4):622S-626S, 1996; Abstract only.
Lonnerdal, "Recombinant Human Milk Proteins," Nestle Nutr. Workshop Ser. Pediatr. Program 58:207-217, 2006.
Lorenzen et al., "A Comparative study of the gelation properties of whey protein concentrate and whey protein isolate" Le Lait 86(4):259-271, 2006.
MacGibbon et al., "Compositions and structure of bovine milk lipids," in Advanced Dairy Chemistry, vol. 2 Lipids, Springer, US, pp. 1-42, 2006.
Mansson, "Fatty acids in bovine milk fat," Food & Nutrition Research, 2008, 52:1.

(56) References Cited

OTHER PUBLICATIONS

Milk Proteins: From Expression to Food, 2009, Chapter 4, pp. 107-132.
MY Office Action in Malaysian Appln. No. PI2017000254, dated May 21, 2019, 4 pages.
O'Connell et al., "The two-stage coagulation of milk proteins in the minimum of the heat coagulation time-pH profile pf milk: Effect of casein micelle size", J Diary Sci. 2000, 83:378-386.
Office Action in Australian Appln. No. 2015305271, dated Nov. 12, 2018, 5 pages.
Office Action in Brazilian Appln. No. BR112017003414-0, dated Aug. 21, 2015, 6 pages(with English translation).
Office Action in Brazilian Appln. No. BR122020004762-3, dated Aug. 21, 2015, 24 pages(with English translation).
Office Action in Brazilian Appln. No. BR122020004774-7, dated Jun. 4, 2022, 10 pages (with machine translation).
Office Action in Brazilian Appln. No. BR122020004774-7, dated Nov. 11, 2021, 8 pages(with English translation).
Office Action in Canadian Appl. No. 2,958,858, dated Aug. 17, 2023, 3 pages.
Office Action in Canadian Appl. No. 2,958,858, dated Aug. 5, 2020, 3 pages.
Office Action in Canadian Appl. No. 2,958,858, dated Jul. 29, 2019, 3 pages.
Office Action in Canadian Appl. No. 2958858, dated Jul. 28, 2021, 4 pages.
Office Action in Chinese Application No. 202111188178.X, dated Jul. 6, 2023, 23 pages (with English Translation).
Office Action in Chinese Appln. No. 201580057456.4, dated Jan. 15, 2020, 21 pages.
Office Action in Chinese Appln. No. 201580057456.4, dated May 17, 2021, 22 pages, ( with English translation).
Office Action in Chinese Appln. No. 201580057456.4, dated Oct. 30, 2020, 23 pages.
Office Action in Indian Appln. No. 201737009683, dated Nov. 11, 2020, 8 pages.
Office Action in Japanese Application No. 2021-155495, mailed Jul. 18, 2023, 7 pages (with English Translation).
Office Action in Japanese Application No. 2021-155495, mailed Nov. 22, 2022, 9 pages (with English translation).
Office Action in Japanese Appln. No. 2017-529979, dated May 25, 2021, 14 pages, (with English translation).
Office Action in Japanese Appln. No. 2017-529979, dated Nov. 11, 2020, 12 pages, (with English translation).
Office Action in Japanese Appln. No. 2017-529979, dated Nov. 12, 2019, 16 pages (with English translation).
Office Action in Malaysian Appln. No. PI 2017000254, dated May 21, 2019, 4 pages.
Office Action in U.S. Appl. No. 15/438,273, dated Aug. 23, 2017, 10 pages.
Office Action in U.S. Appl. No. 15/505,557, dated Sep. 26, 2019, 25 pages.
Office Action in U.S. Appl. No. 16/002,818, dated Aug. 31, 2018, 14 pages.
Office Action in U.S. Appl. No. 16/002,818, dated May 8, 2019, 20 pages.
Park, "Bioreactive Components in Bovine Milk," in Bioactive Components in Milk and Dairy Products, Wiley-Blackwell, Danvers, MA, pp. 15-42, 2009.
Park, "Rheological characteristics of goat and sheep milk," Small Ruminant Res. 68(1-2):73-87, 2007.
Posati et al., "Composition of foods: dairy and egg products: raw, processed, and prepared," Agricultural Handbook—U.S. Dept. of Agriculture (USA), 1976, No. 8-1, 158 pages.
Rocha et al. "Expression and secretions of recombinant Bovine β-lactoglobulin in *Saccharomyces ceevisiae* and Kluveromyces lactis," Biochem. J., Feb. 1996, 313:927-932.
Rosmaninho et al., "The effect of citrate on calcium phosphate deposition from simulated milk ultrafiltrate (SMUF)," J. Food Engineering 77(3):379-387, 2006.
Saito et al., "Secretion of Glycosylated a-Lacatalbumin in Yeast *Pichia pastori*," Jol. of Biochemistry, Jul. 2002, 132:77-82.
Saunois et al., "The Global Methane Budget 2000-2017" Earth Syst. Sci. Data, 12:1561-1623, 2020.
Simons et al., "Overproduction of bovine beta-casein in *Escherichia coli* and engineering of its main chymosin cleavage site," Protein Eng. 6(7):763-770, 1993.
Smouse, "A Laboratory Continuous Deodorizer," Inform, 1997, 8:1176-1181.
Sood et al., "Colloidal Calcium Phosphate in the Reconstituted Milk Micelle May Direct Wild-type Recombinant Human [beta]-Casein to Fold Like the Native Protein", Journal of Protein Chemistry, Kluwer Academic Publishers-Plenum Publishers, NE, vol. 24, No. 6, pp. 379-384, 2005.
store.alishan.jp [online], "Dairy Free Margarine," Jul. 25, 2022, retrieved on Aug. 21, 2023, retrieved from URL<https://store.alishan.jp/en/product/dairy-freemargarine>, 10 pages (with English translation).
stuff.co.nz, [online], "Milk made in laboratories to hit shelves," Jul. 12, 2014, retrieved on Sep. 3, 2021, retrieved from URL<https://www.stuff.co.nz/business/10258565/Milk-made-in-laboratories-to-hit-shelves>,3 pages.
Su et al, "Heterologous gene expression in filamentous fungi", Adv Appl Microbiol., 81: 1-61, 2012.
Third Declaration by Dr. Tonya Schoenfuss, PH.D, in Australian Patent Application No. 2015305271, dated Jun. 14, 2021, 20 pages.
Third Party Submission Under 37 C.F.R. § 1.290 and Concise Description of Relevance filed in U.S. Appl. No. 15/505,557 on Feb. 1, 2019, 46 pages.
Third Party Submission Under 37 C.F.R. § 1.290 Concise Description of Relevance filed in U.S. Appl. No. 15/505,557 on Feb. 1, 2019, 10 pages.
Third Party Submission Under 37 C.F.R. § 1.290 Concise Description of Relevance filed in U.S. Appl. No. 15/505,557 on Oct. 24, 2018, 13 pages.
Third Party Submission Under 37 C.F.R. § 1.290 Concise Description of Relevance filed in U.S. Appl. No. 15/505,557 on Oct. 24, 2018, 3 pages.
Totsuka et al., "Expression and Secretion of Bovine 13-lactoglobulin in *Saccharomyces cerevisiae*," Agric. Biol. Chem., 54 (12) 3111-3116, 1990.
Viaene et al., "Efficient expression of bovine x-lactalbumin in *Saccharomyces cerevisiae*", Eur. J. Bichem., 202, 471-477, 1991.
Ward et al., "An inducible expression system for the production of human lactoferrin in Aspergillus nidulans" Gene, Aug. 1992, 122: 219-223.
Ward et al., "Production of Biologically Active Recombinant Human Lactoferrin in Aspergillus Oryzae," Nature Biotechnology, Aug. 1992, 10:784-789.
Wilson et al., "Expression of recombinant wild type and mutant β-Lactoglobulins in the yeast *Pichia pastoris*," International. Jol. of Food Sci and Tech., Oct. 1999, 34:445-450.
wired.com, [online], "Cow milk without the cow is coming to change food forever," Apr. 15, 2015, retrieved on Sep. 3, 2021 from URL<https://www.wired.com/2015/04/diy-biotech-vegan-cheese/>, 7 pages.
Written Opinion of the International Searching Authority for PCT/US2015/046428, mailed Feb. 5, 2016, 10 pages.
Yu et al., "The Modification and Analysis of Vegetable Oil for Cheese Making," J. Am. Oil. Chem. Soc., 2000, 77:911-915.
Zhang et al., "Fermentation Strategies for Recombinant Protein Expression in the Methylotrophic Yeast Pichia pastoris," Biotechnol. Bioprocess Eng., 2000, 5:275-287.
Zhu, "Mammalian cell protein expression for biopharmaceutical production," Biotechnol. Adv. 30(5):1158-1170, 2012.

COMPOSITIONS COMPRISING A CASEIN AND METHODS OF PRODUCING THE SAME

CROSS-REFERENCE TO RELATED APPLICATION

This application is a continuation of U.S. patent application Ser. No. 17/081,167, filed Oct. 27, 2020, which is a continuation of U.S. patent application Ser. No. 15/505,557, filed Feb. 21, 2017 (issued as U.S. Pat. No. 11,076,615), which is a national stage application filed under 35 U.S.C. § 371 of International Patent Application No. PCT/US2015/046428, filed Aug. 21, 2015, which claims priority to U.S. Provisional Patent Application Ser. No. 62/040,393, filed on Aug. 21, 2014, the entire contents of which are incorporated by reference.

SEQUENCE LISTING

This application contains a Sequence Listing that has been submitted electronically as an XML file named "42233-0004007 ST26 SL.XML." The XML file, created on Jul. 31, 2023, is 221,908 bytes in size. The material in the XML file is hereby incorporated by reference in its entirety.

FIELD OF THE INVENTION

The invention is directed to dairy substitutes, methods of manufacturing the same, and compositions comprising animal-free milk fats and proteins for food applications, such as milk, butter, cheese, yogurt, and cream.

BACKGROUND OF THE INVENTION

The global dairy market is estimated at $500 billion with an average annual growth rate of 4%. Bovine milk attributes to a significant portion of the market whereas plant-based alternatives account for $1 billion in the US and an estimated $700 million is estimated for lactose-intolerant milk. Bovine milk is known to have four specific caseins, α-s1-casein, α-s2-casein, β-casein, and κ-casein. Mammal- or mammalian-produced milk is a very complex fluid that includes several thousand components (e.g., if all triglycerides are identified). Mammal- or mammalin-produced milk includes water, variety of different lipids, sugar, a variety of different proteins, and a variety of different inorganic salts and compounds (see, e.g., Boland and Thompson (Eds), Milk Proteins from Expression to Food, Academic Press, 2014). Although mammal-produced milk, such as bovine milk, is considered by many to be an ideal source of nutrition, various milk alternatives to mammal- or mammalian-produced milk (e.g., bovine milk), such as plant- or nut-based milks, e.g., soy, almond, or coconut milk, have been pursued for reasons related to mammal- or mammalian-produced milk's allergenicity, lactose intolerance of certain components, personal preference, and the perceived environmental benefits of a reduced dairy industry.

For example, the environmental impact resulting from dairy effluent can result in significant levels of nitrate which has the potential to contaminate groundwater. Groundwater forms the main source of water supply for many towns and farms where surface water supplies are limited. In the US, half the population relies completely or partially on groundwater, and similar figures are available for Europe (see, e.g., the Victoria State Government Department of Environment and Primary Industries website at www.depi.vic.gov.au/agriculture-and-food/dairy/managing-effluent/dairy-effluent-protecting-groundwater). The presence of foodborne pathogens in milk is due to direct contact with contaminated sources in the dairy farm environment and to excretion from the udder of an infected animal. Outbreaks of disease in humans have been traced to the consumption of unpasteurized milk and have also been traced back to pasteurized milk. The major contaminants usually encountered in milk and milk products include pesticide residues, heavy metals, and aflatoxin M1 (Awasthi et al., *Indian J. Public Health* 56:95-99, 2012).

Existing dairy milk alternatives, such as soy, almond, or coconut milk fall short both in flavor and in functionality; moreover, a large part of the industrial and cultural significance of dairy milk stems from its usefulness in derivative products, such as cheese, yogurt, cream, or butter. Non-dairy plant-based milks, while addressing environmental and health concerns (and while providing adequate flavor for a small segment of the population), almost universally fail to form such derivative products when subjected to the same processes used for dairy milk.

What is needed, therefore, is a dairy substitute or composition that has desirable flavor and performance characteristics, e.g., a composition that replicates dairy flavors, minimizes foodborne pathogens, and has a lower environmental impact in production, while retaining the ability to be used for derivative or downstream applications of dairy milk and while providing a similar nutritional profile as a mammal- or mammalian-produced milk.

SUMMARY OF THE INVENTION

The present invention is based on the discovery that only a subset of components in mammal-produced milk can be used to generate a composition that has a similar flavor, a similar appearance, a similar nutritional value, a similar aroma, and a similar mouth feel of mammal-produced milk.

Provided herein are compositions including: about 0.3 g/L to about 1.1 g/L casein protein; about 1.25 g/L to about 4.9 g/L β-casein protein; a final total concentration of one or more lipids of about 0 weight % to about 45 weight %; a final total concentration of one or more flavor compounds of about 0.01 weight % to about 6 weight %; a final total concentration of about 0.1 weight % to about 6 weight % of one or more sweetening agents; and a final total concentration of ash of about 0.15 weight % to about 1.5 weight %, where the composition does not include an animal-derived component.

Also provided are compositions that include: about 0.3 g/L to about 1.1 g/L κ-casein protein; about 1.25 g/L to about 4.9 g/L β-casein protein; a final total concentration of one or more lipids of about 0 weight % to about 45 weight %; a final total concentration of one or more flavor compounds of about 0.01 weight % to about 6 weight %; a final total concentration of about 0.1 weight % to about 6 weight % of one or more sweetening agents; and a final total concentration of ash of about 0.15 weight % to about 1.5 weight %, where the composition: does not include at least one component found in a mammal-produced milk; includes at least one component not present in a mammal-produced milk; and/or includes a higher or lower concentration of at least one component as compared to the concentration of the at least one component in a mammal-produced milk. In some embodiments of these compositions, the composition includes a higher concentration of at least one component selected from the group of: calcium, phosphate, B complex vitamins, vitamin A, vitamin D, vitamin E, and vitamin K, as compared to the concentration of the one or more components in a mammal-produced milk. In some embodiments of these compositions, the composition does not include at least one component found in a mammal-produced milk selected from the group of: lactose, bacteria, mycobacteria, allergens, viruses, prions, yeast, growth hormones, leukocytes, antibiotics, heavy metals, immunoglobulins, lactoferrin, lactoperoxidase, and lipase. In some embodiments of these compositions, wherein the composition includes at least one component not present in a mammal-produced milk selected from the group of an artificial sweetener, a plant-derived lipid, a β-casein protein that is non-glycosylated or has a non-mammalian glycosylation pattern, and a κ-casein protein that is non-glycosylated or has a non-mammalian glycosylation pattern.

Also provided are compositions including: about 0.3 g/L to about 1.1 g/L κ-casein protein that is unglycosylated or has a non-mammalian glycosylation pattern; about 1.25 g/L to about 4.9 g/L β-casein protein that is unglycosylated or has a non-mammalian glycosylation pattern; a final total concentration of one or more lipids of about 0 weight % to about 45 weight %; a final total concentration of one or more flavor compounds of about 0.01 weight % to about 6 weight %; a final total concentration of about 0.1 weight % to about 6 weight % of one or more sweetening agents; and a final total concentration of ash of about 0.15 weight % to about 1.5 weight %.

Also provided are composition including a micelle including a κ-casein protein and a β-casein protein, where the micelle has a diameter of about 50 nm to about 350 nm, and the κ-casein protein and the β-casein protein are unglycosylated or have a non-mammalian glycosylation pattern. In some embodiments of these methods, the compositions include a final concentration of micelles of about 2.0 weight % to about 6 weight %. In some embodiments of these compositions, the ratio of the β-casein protein to the κ-casein protein in the micelle is about 3.5:1 to about 5.5:1 (e.g., about 4:1 to about 5:1). In some embodiments of these methods, the composition further includes: a final total concentration of one or more lipids of about 0 weight % to about 45 weight %; a final total concentration of one or more flavor compounds of about 0.01 weight % to about 6 weight %; a final total concentration of about 0.1 weight % to about 6 weight % of one or more sweetening agents; and a final total concentration of ash of about 0.15 weight % to about 1.5 weight %.

In some embodiments of any of the compositions described herein, the composition comprises about 0.27 weight % to about 0.75 weight % κ-casein protein and about 1.23 weight % to about 3.27 weight % β-casein. In some embodiments of any of the compositions described herein, the final total concentration of one or more lipids of about 0 weight % to about 4.5 weight %.

In some embodiments of any of the compositions described herein, the one or more lipids are selected from the group consisting of: sunflower oil, coconut oil, tributyrin, mono- and di-glycerides, free fatty acids, and phospholipids. In some embodiments of any of the compositions described herein, the composition includes one of more of: a final concentration of sunflower oil of about 1 weight % to about 28 weight %; a final concentration of coconut oil of about 0.5 weight % to about 14 weight %; a final concentration of tributyrin of about 0.05 weight to about 1.0 weight %; a final total concentration of monoglycerides and diglycerides of about 0.08 weight % to about 1.2 weight %; a final total concentration of free fatty acids of about 0.02 weight % to about 0.28 weight %; and a final total concentration of phospholipids of about 0.02 weight % to about 0.3 weight percent. In some embodiments of any of the compositions described herein, the free fatty acids comprise at least one fatty acid selected from the group of: butyric acid, caproic acid, caprylic acid, and capric acid. In some embodiments of any of the compositions described herein, the phospholipids are soy lecithin phospholipids, sunflower lecithin phospholipids, cotton lecithin phospholipids, or rapeseed lecithin phospholipids. In some embodiments of any of the compositions described herein, the monoglycerides and diglycerides are plant-derived monoglycerides and diglycerides, or are bacteria-derived monoglycerides and diglycerides.

In some embodiments of any of the compositions described herein, the flavor compounds include at least one flavor compound selected from the group consisting of: δ-decalactone, ethyl butyrate, 2-furyl methyl ketone, 2,3-pentanedione, γ-undecalactone, and δ-undecalactone. In some embodiments of any of the compositions described herein, the one or more sweetening agents is a saccharide. In some embodiments of any of the compositions described herein, the saccharide is selected from the group consisting of: glucose, mannose, maltose, fructose, galactose, lactose, sucrose, monatin, and tagatose. In some embodiments of any of the compositions described herein, the one or more sweetening agents is an artificial sweetener. In some embodiments of any of the compositions described herein, the artificial sweetener is selected from the group of: stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, and P-4000.

In some embodiments of any of the compositions described herein, the ash includes one or more of: calcium, phosphorus, potassium, sodium, citrate, and chloride. In some embodiments of any of the compositions described herein, the ash comprises one or more (e.g., one, two, or three) of $CaCl_2$), $KH_2PO_4$, and $Na_3$ citrate. In some embodiments of any of the compositions described herein, the $CaCl_2$) has a final concentration of about 0.05 g/L to about 0.2 g/L; the $KH_2PO_4$ has a final concentration of about 0.2 g/L to about 0.4 g/L; and the $Na_3$ citrate has a final concentration of about 0.1 g/L to about 0.3 g/L.

In some embodiments of any of the compositions described herein, the κ-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein. In some embodiments of any of the compositions described herein, the β-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein.

In some embodiments of any of the compositions described herein, the composition further includes: a final concentration of α-lactalbumin protein of about 0.4 g/L weight % to about 2.5 weight %; and/or a final concentration of β-lactoglobulin protein of about 2.5 weight % to about 4.5 weight %. In some embodiments of any of the methods described herein, the α-lactalbumin protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-lactalbumin protein. In some embodiments of any of the compositions described herein, the β-lactoglobulin protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-lactoglobulin protein.

In some embodiments of any of the compositions described herein, the composition further includes: a final concentration of α-S1-casein protein of about 11 weight % to about 16 weight %; and/or a final concentration of α-S2-casein protein of about 2 weight % to about 5 weight %. In some embodiments of any of the compositions described herein, the α-S1-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S1-casein protein; and/or the α-S2-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S2-casein protein.

In some embodiments of any of the compositions described herein, the composition further includes one or more of: serum albumin, lactoferrin, and transferrin. In some embodiments of any of the compositions described herein, the serum albumin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth serum albumin; the lactoferrin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth lactoferrin; and/or the transferrin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth transferrin protein.

Some embodiments of any of the compositions described herein, further include one or more color balancing agents. In some embodiments of any of the compositions described herein, the one or more color balancing agents is β-carotene or annatto. In some embodiments of any of the compositions described herein, the composition has a pH of about 6.2 to about 7.2 (e.g., about 6.2 to about 6.8).

Also provided are compositions including: a mammalian-produced milk or a processed mammal-produced milk; and one or both of a κ-casein protein that is unglycosylated or has an non-mammalian glycosylation pattern, and a β-casein protein that is unglycosylated or has an non-mammalian glycosylation pattern. In some embodiments of these methods, the final concentration of the κ-casein protein that is unglycosylated or has a non-mammalian glycosylation pattern in the composition is 0.02 weight % to about 3.0 weight %. In some embodiments of these methods, the final concentration of the β-casein protein that is unglycosylated or has a non-mammalian glycosylation pattern in the composition is 0.02 weight % to about 3.0 weight %. In some embodiments of these methods, the final concentration of the κ-casein protein that is unglycosylated and/or has a non-mammalian glycosylation pattern in the composition is about 0.02 weight % to about 0.6 weight %; and the final concentration of the β-casein that is unglycosylated and/or has a non-mammalian glycosylation pattern in the composition is about 0.02 weight % to about 2.5 weight %.

Also provided are powder compositions that include: a final concentration of κ-casein protein of about 3.6 weight % to about 5.4 weight %; a final concentration of β-casein protein of about 16.3 weight % to about 24.5 weight %; a final concentration of a sweetening agent of about 35 weight % to about 40 weight %; a final concentration of one or more lipids of about 25 weight % to about 30 weight %; a final concentration of ash of about 5 weight % to about 7 weight %; and a final concentration of water of about 2 weight % to about 5 weight %, where the κ-casein protein is an unglycosylated and/or has a non-mammalian glycosylation pattern, and/or the β-casein protein is an unglycosylated and/or has a non-mammalian glycosylation pattern.

Also provided are nucleic acids that include: a promoter; a sequence encoding a signal sequence; a sequence encoding a milk protein; and a yeast termination sequence, where the promoter is operably linked to the signal sequence, the signal sequence is operably linked to the sequence encoding the milk protein, and the terminal sequence is operably linked to the sequence encoding the milk protein. In some embodiments of these nucleic acids, the promoter is a constitutive promoter. In some embodiments of these nucleic acids, the promoter is an inducible promoter. In some embodiments of these nucleic acids, the signal sequence is a signal sequence from the encoded milk protein or a different milk protein, or is a signal sequence from a yeast mating factor. In some embodiments of these nucleic acids, the encoded milk protein is selected from the group consisting of: β-casein, κ-casein, α-S1-casein, α-S2-casein, α-lactalbumin, β-lactoglobulin, lactoferrin, or transferrin. In some embodiments of these nucleic acids, the nucleic comprises a bacterial origin of replication. In some embodiments of these nucleic acids, the nucleic acid further includes a selection marker. In some embodiments of these nucleic acids, the selection marker is an antibiotic resistance gene.

Some embodiments of these nucleic acids further include: an additional promoter sequence; an additional sequence encoding a signal sequence; a sequence encoding an additional milk protein; and an additional yeast termination sequence, where the additional promoter sequence is operably linked to the additional sequence encoding a signal sequence, the sequence encoding the signal sequence is operably linked to the sequence encoding the additional milk protein, and the sequence encoding the additional milk protein is operably linked to the additional yeast terminal sequence.

Also provided are host cells that include any of the nucleic acids described herein. In some embodiments of these host cells, the host cell is a yeast strain (e.g., a *Kluyveromyces* sp., *Pichia* sp., *Saccharomyces* sp., *Tetrahymena* sp., *Yarrowia* sp., *Hansenula* sp., *Blastobotrys* sp., *Candida* sp., *Zygosaccharomyces* sp., or *Debaryomyces* sp.).

Also provided herein are methods of producing a recombinant milk protein that is unglycosylated or has a non-mammalian glycosylation pattern, the method including: culturing any of the host cells described herein in a culture medium under conditions sufficient to allow for secretion of the milk protein that is unglycosylated or has a non-mammalian glycosylation pattern; and harvesting the milk protein that is unglycosylated or has a non-mammalian glycosylation pattern from the culture medium.

Also provided are methods of producing a micelle including a β-casein that is unglycosylated or has a non-mammalian glycosylation pattern and a κ-casein that is unglycosylated or has a non-mammalian glycosylation pattern, that include: culturing any of the host cells provided herein in a culture medium under conditions sufficient to allow for release of the micelle from the host cell, where the host cell includes nucleic acid including a sequence that encodes a β-casein and a sequence that encodes a κ-casein.

Also provided are methods of supplementing a mammal-produced milk that include: providing a mammalian-produced milk or a processed mammalian-produced milk; and mixing into the milk at least one of: a β-casein protein that is unglycosylated or has a non-mammalian glycosylation pattern; a κ-casein protein that is unglycosylated or has a non-mammalian glycosylation pattern; and a micelle including a β-casein protein that is unglycosylated or has a non-mammalian glycosylation pattern, and a κ-casein protein that is unglycosylated or has a non-mammalian glycosylation pattern.

Also provided are methods of producing a composition that include: sonicating a liquid including a protein mixture comprising β-casein protein and casein κ protein, or comprising micelles comprising β-casein protein and κ-casein protein; mixing ash into the liquid; adding to the liquid a mixture of one or more lipids, one or more flavor compounds, and one or more color balancing agents, and sonicating the liquid; and adding to the liquid one or more sweetening agents, thereby producing the composition. In some embodiments of these methods, the β-casein protein is unglycosylated or has a non-mammalian glycosylation pattern, and/or the κ-casein protein is unglycosylated or has a non-mammalian glycosylation pattern. In some embodiments of these methods, the ash includes one or more of: calcium, phosphorus, potassium, sodium, citrate, and chloride. In some embodiments of these methods, the ash added includes one or more (e.g., one, two, or three) of $CaCl_2$), $KH_2PO_4$, and $Na_3$ citrate. In some embodiments of these methods, the one or more lipids comprises at least one of: sunflower oil, coconut oil, tributyrin, mono- and di-glycerides, free fatty acids, and phospholipids. In some embodiments of these methods, the free fatty acids comprise at least one fatty acid selected from the group of: butyric acid, caproic acid, caprylic acid, and capric acid. In some embodiments of these methods, the phospholipids are soy lecithin phospholipids, sunflower lecithin phospholipids, cotton lecithin phospholipids, or rapeseed lecithin phospholipids. In some embodiments of these methods, the monoglycerides and diglycerides are plant-derived monoglycerides and diglycerides, or are bacteria-derived monoglycerides and diglycerides. In some embodiments of these methods, the flavor compounds include at least one flavor compound selected from the group consisting of: δ-decalactone, ethyl butyrate, 2-furyl methyl ketone, 2,3-pentanedione, γ-undecalactone, and δ-undecalactone. In some embodiments of these methods, the one or more coloring balancing agent is β-carotene or annatto. In some embodiments of these methods, the one or more sweetening agents is a saccharide. In some embodiments of these methods, the saccharide is selected from the group consisting of: glucose, mannose, maltose, fructose, galactose, lactose, sucrose, monatin, and tagatose. In some embodiments of these methods, the one or more sweetening agents is an artificial sweetener. In some embodiments of these methods, the artificial sweetener is selected from the group consisting of: stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, and P-4000. In some embodiments of these methods, the pH of the liquid is between about 6.2 and about 7.4 (e.g., about 6.4 to about 6.8). In some embodiments of these methods, the β-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein; and/or the κ-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein. In some embodiments of these methods, the protein mixture further includes one or more proteins selected from the group of: α-lactalbumin, β-lactoglobulin, α-S1-casein, α-S2-casein, lactoferrin, transferrin, and serum albumin.

Also provided is a composition produced by any of the methods described herein.

Also provided is a method of making butter, cheese, caseinate, or yogurt that include: providing any of the compositions described herein; and producing the butter, cheese, caseinate, or yogurt using any of the compositions described herein as a starting material.

Also provided are kits that include: (a) a mixture of one or more milk proteins, one or more fats, and one or flavor compounds; and (b) a mixture of ash and at least one sweetening agent. In some embodiments of these kits, the one or more milk proteins are selected from the group of: β-casein, κ-casein, α-lactalbumin, β-lactoglobulin, α-S1-casein, α-S2-casein, lactoferrin, transferrin, and serum albumin. In some embodiments of these kits, the one or more milk proteins are cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth milk proteins. In some embodiments of these kits, the one or more fats are selected from the group consisting of: sunflower oil, coconut oil, tributyrin, mono- and di-glycerides, free fatty acids, and phospholipids. In some embodiments of these kits, the free fatty acids include at least one fatty acid selected from the group of: butyric acid, caproic acid, caprylic acid, and capric acid. In some embodiments of these kits, the phospholipids are soy lecithin phospholipids, sunflower lecithin phospholipids, cotton lecithin phospholipids, or rapeseed lecithin phospholipids. In some embodiments of these kits, the monoglycerides and diglycerides are plant-derived monoglycerides and diglycerides, or are bacteria-derived monoglycerides and diglycerides. In some embodiments of these kits, the flavor compounds comprise at least one flavor compound selected from the group consisting of: δ-decalactone, ethyl butyrate, 2-furyl methyl ketone, 2,3-pentanedione, γ-undecalactone, and δ-undecalactone. In some embodiments of these kits, the mixture in (a) further includes one or more color balancing agent. In some embodiments of these kits, the one or more color balancing agent is β-carotene or annatto. In some embodiments of these kits, the one or more sweetening agents is a saccharide (e.g., a saccharide selected from the group of: glucose, mannose, maltose, fructose, galactose, lactose, sucrose, monatin, and tagatose). In some embodiments of these kits, the one or more sweetening agents is an artificial sweetener (e.g., an artificial sweetener selected from the group of: stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, and P-4000). In some embodiments of any of these kits, the ash includes one or more of: calcium, phosphorus, potassium, sodium, citrate, and chloride. In some embodiments of these kits, the ash includes one or more (e.g., one, two, or three) of $CaCl_2$), $KH_2PO_4$, and $Na_3$ citrate. Some embodiments of these kits further include instructions for making any of the compositions described herein.

Also provided are kits that include at least one of the nucleic acids described herein.

Also provided herein are dairy substitute food products including one or more isolated milk protein components, fats, carbohydrates, and ash. In some embodiments of these dairy substitute food products, the food product is non-animal derived. In some embodiments of these substitute food product, the food product includes milk, butter, cheese, caseinare, yogurt, and cream. In some embodiments of these dairy substitute food products, the isolated milk protein components include casein and whey proteins. In some embodiments of these dairy substitute food products, the casein protein further includes alpha-s1, alpha-s2, beta, and kappa-casein. In some embodiments of these dairy substitute food products, the casein protein further includes alpha-s1, beta, and kappa. In some embodiments of these dairy substitute food products, the casein protein further includes components for micelle formation. In some embodiments of these dairy substitute food products, the casein protein exhibits curdling properties at pH 4.0-6.0. In some embodiments of these dairy substitute food products, the casein protein is at least or equal to 2.5% (w/v) and less than or equal to 10% (w/v). In some embodiments of these dairy substitute food products, the whey protein further includes beta-lactoglobulin and alpha-lactalbumin. In some embodiments of these dairy substitute food products, the whey protein forms a polymer matrix gel. In some embodiments of these dairy substitute food products, the whey protein is at least 0.1% (w/v) and less than or equal to 1% (w/v). In some embodiments of these dairy substitute food products, the one or more milk protein components is isolated from microbes. In some embodiments of any of these dairy substitute food products, the one or more milk protein components is isolated from recombinant microbes. In some embodiments of these dairy substitute food products, the one or more milk protein components is synthesized in eukaryotic microbes. In some embodiments of these dairy substitute food products, the eukaryotic microbes include yeast. In some embodiments of these dairy substitute food products, the yeast include *Kleuyveromyces* sp., *Pichia* sp., *Saccharomyces* sp. and *Tetrahymena* sp.

In some embodiments of these substitute food products, the fats include triglycerides. In some embodiments of these dairy substitute food products, the fats comprise high-oleic oil. In some embodiments of these dairy substitute food products, the high-oleic oil further includes one or more of monounsaturates, oleic, linoleic, linolenic and saturates. In some embodiments of these dairy substitute food products, the fats comprise short chain fatty acids. In some embodiments of these dairy substitute food products, the short chain fatty acids include butanoic, hexanoic, octanoic, and decanoic acids. In some embodiments of these dairy substitute food products, one or more of the fats comprised trans-esterified fatty acids. In some embodiments of these dairy substitute food products, one or more of the fats are isolated from plants. In some embodiments of these dairy substitute food products, the plant is selected from one or more of the following: sunflower, corn, olive, soy, peanut, walnut, almond, sesame, cottonseed, canola, safflower, flax seed, palm, palm kernel, palm fruit, coconut, babassu, shea butter, mango butter, cocoa butter, wheat germ and rice bran oil. In some embodiments of these dairy substitute food products, the sugars comprise of galactose, sucrose, glucose, fructose and maltose. In some embodiments of these dairy substitute food products, the dairy substitute food product is essentially free of lactose. In some embodiments of these dairy substitute food products, the ash includes minerals. In some embodiments of these dairy substitute food products, the minerals further include one or more of the following: sodium, potassium, calcium, magnesium, phosphorus, iron, copper, zinc, chloride, manganese, selenium, iodine, retinol, carotene, vitamins, vitamin D, vitamin E, vitamin B12, thiamin and riboflavin. In some embodiments of these dairy substitute food products, the ash includes anions. In some embodiments of these dairy substitute food products, the minerals further include one or more of the following: phosphate, citrate, sulfate, carbonate, and chloride.

Also provided are methods of making a dairy substitute food product including the step of contacting one or more isolated milk protein components, interesterified fats, carbohydrates and ash. Some embodiments of these methods, further include the step of isolating one or more milk protein components is from a lower eukaryote.

Also provided are methods of altering a flavor profile of a dairy substitute product that include modulating a combination of fatty acids in a mixture including milk protein components, carbohydrates, and ash. In some embodiments of these methods, the step of modulating includes triglyceride comprising three oleic acids and short-chain triglyceride comprising butyric, one hexanoic, and one octanoic acid. In some embodiments of these methods, the step of modulating comprises increasing or decreasing one or more fatty acids comprising butyric acid, caprioc acid, caprylic acid, and capric acid. In some embodiments of these methods, the flavor profile of a dairy substitute product mimics the flavor profile of one or more dairy product. In some embodiments of these methods, the flavor profile of one or more dairy food product includes bovine milk, goat milk, soy milk, almond milk and coconut milk. In some embodiments of these methods, the flavor profile includes one or more sensory impressions selected from: buttery, nutty, sweet, sour, fruity, floral, bitter, woody, earthy, beany, spicy, metallic, sweet, musty, oily and vinegary.

Disclosed herein are methods and compositions to produce dairy substitutes. In some embodiments, methods and compositions are provided for a dairy substitute food product comprising one or more isolated milk protein components, fats, carbohydrates and ash. In certain embodiments, methods and compositions are provided for dairy substitute composition comprising casein protein and whey protein wherein the composition is essentially free of animal products and wherein the casein protein to whey protein are in a preferred (w/v) ratio. In certain other embodiments, methods are provided to modulate a flavor profile of a dairy substitute food product comprising modulating a fatty acid content in a mixture comprising milk protein components, fats, carbohydrates, and ash. Preferred steps of modulating comprises increasing or decreasing one or more fatty acids comprising butyric acid, caproic acid, caprylic acid, and capric acid. In additional embodiments, methods and compositions of the present invention provide milk protein components and fats in a desired (w/v) ratio.

In various aspects, the methods and compositions of the present invention provide for dairy substitutes that still retain their functional characteristics and organoleptic properties. In some embodiments, the core functionalities can be, but are not limited to achieving a nutritional profile similar to a conventional dairy product, and replicates one or more, if not all, of the core functionalities thereof.

In other embodiments, the core functionalities can be, but are not limited to replicating sensory characteristics that are identical or similar to the traditional dairy-based products, which include but are not limited to taste, appearance, handling and mouthfeel, desired density, structure, texture, elasticity, springiness, coagulation, binding, leavening, aeration, foaming, creaminess, and emulsification.

Preferred methods and compositions provide dairy substitute products such as milk, butter, cheese, yogurt, and cream. Provided herein are formulations for a non-dairy milk substitute comprising (3.3%) one or more isolated milk protein components, (4.0%) fats, (2.4%) carbohydrates and (0.7%) ash (w/v). Varying the fat content through modulating triglyceride levels and the fatty acid composition of the triglycerides enhances the flavor profile of the non-dairy milk substitute.

Advantages in the methods and dairy substitute compositions include reduction or removal of antibiotic residues, heavy metals, bacteria and adulterations commonly found in natural dairy products as well as reducing environmental impact.

Accordingly, certain aspects of the present invention provide animal-free dairy substitute that has desirable flavor characteristics, e.g., replicates dairy flavors, minimizes foodborne pathogens and has a lower environmental impact, while retaining the downstream applications of dairy milk.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, dairy processing, biochemistry, enzymology, molecular and cellular biology, microbiology, genetics and protein and nucleic acid chemistry and hybridization described herein are those well-known and commonly used in the art.

Methods and materials are described herein for use in the present invention; other, suitable methods and materials known in the art can also be used. The materials, methods, and examples are illustrative only and not intended to be limiting.

All publications, patents, patent applications, sequences, database entries, and other references mentioned herein are incorporated by reference to the same extent as if each individual publication, patent, patent application, sequence, database entry, or other reference was specifically and individually indicated to be incorporated by reference. In case of conflict, the present specification, including definitions, will control.

Other features and advantages of the invention will be apparent from the following detailed description and figures, and from the claims.

The terminology and description used herein is for the purpose of describing particular embodiments only and is not intended to limit the invention. As used herein, the singular forms "a," "an," and "the" can be intended to include the plural forms as well, unless the context clearly indicates otherwise. The terms "including," "includes," "having," "has," "with," or variants thereof are intended to be inclusive in a manner similar to the term "comprising".

An "isolated" RNA, DNA or a mixed polymer is one which is substantially separated from other cellular components that naturally accompany the native polynucleotide in its natural host cell, e.g., ribosomes, polymerases, and genomic sequences with which it is naturally associated.

As used herein, an "isolated" organic molecule (e.g., a fatty acid or a SCFA) is one which is substantially separated from the cellular components (membrane lipids, chromosomes, proteins) of the host cell from which it originated. As used herein, the term "isolated" with respect to protein indicates that the preparation of protein is at least 60% pure, e.g., greater than 65%, 70%, 75%, 80%, 85%, 90%, 95%, or 99% pure. The term does not require that the biomolecule has been separated from all other chemicals, although certain isolated biomolecules may be purified to near homogeneity.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, or double-stranded, or circular.

The term "SCFA" is abbreviated for short-chain fatty acids, the term "HOSO" is abbreviated for high oleic sunflower oil, "SCTG" is abbreviated for short-chain triglycerides.

The term "milk protein component" refers to proteins or protein equivalents and variants found in milk such as casein, whey or the combination of casein and whey, including their subunits, which are derived from various sources and as further defined herein.

The term "milk protein" means a protein that is found in a mammal-produced milk or a protein having a sequence that is at least 80% identical (e.g., at least 85%, at least 90%, at least 95%, at least 96%, at least 97%, at least 98%, or at least 99% identical) to the sequence of a protein that is found in a mammal-produced milk. Non-limiting examples of milk proteins include: β-casein, κ-casein, α-S1-casein, α-S2-casein, α-lactalbumin, β-lactoglobulin, lactoferrin, transferrin, and serum albumin. Additional milk proteins are known in the art.

The term "casein protein" is art-known and represents a family of proteins that is present in mammal-produced milk and is capable of self-assembling with other proteins in the family to form micelles and/or precipitate out of an aqueous solution at an acidic pH. Non-limiting examples of casein proteins include: β-casein, κ-casein, α-S1-casein, and α-S2-casein. Non-limiting examples of sequences for casein protein from different mammals are provided herein. Additional sequences for other mammalian caseins are known in the art.

The term "mammal-produced milk" is art known and means a milk produced by a mammal.

The term "processed mammal-produced milk" means a mammal-produced milk that is processed using one or more steps known in the dairy industry (e.g., homogenization, pasteurization, irradiation, or supplementation).

The term "mammal-derived component" means a molecule or compound (e.g., a protein, a lipid, or a nucleic acid) obtained from the body of a mammal or a molecule obtained from a fluid or solid produced by a mammal.

The term "component of milk" or "milk component" is a molecule, compound, element, or an ion present in a mammal-produced milk.

The term "non-mammalian glycosylation pattern" means one of a difference in one or more location(s) of glycosylation in a protein, and/or a difference in the amount of and/or type of glycosylation at one or more location(s) in a protein produced and post-translational modified in a non-mammalian cell (e.g., a yeast cell, an insect cell, or a bacterial cell) as compared to a reference protein (e.g., the same protein produced and post-translationally modified in a mammalian cell, e.g., a CHO cell, a MEK cell, or a mammalian udder cell).

The term "lipids" means one or more molecules (e.g., biomolecules) that include a fatty acyl group (e.g., saturated or unsaturated acyl chains). For example, the term lipids includes oils, phospholipids, free fatty acids, phospholipids, monoglycerides, diglycerides, and triglycerides. Non-limiting examples of lipids are described herein. Additional examples of lipids are known in the art.

The term "plant-derived lipid" means a lipid obtained from and/or produced by a plant (e.g., monocot or dicot).

The term "sweetening agent" means a saccharide (e.g., a monosaccharide, a disaccharide, or a polysaccharide) or an artificial sweetener (e.g., a small molecule artificial sweetener or a protein artificial sweetener) that, when added to a composition, makes the composition taste sweet when ingested by a mammal, such as a human. Non-limiting examples of sweetening agents are described herein. Additional examples of sweetening agents are known in the art.

The term "ash" is an art-known term and represents one or more ions, elements, minerals, and/or compounds that can be found in a mammal-produced milk. Non-limiting ions, elements, minerals, and compounds that are found in a mammal-produced milk are described herein. Additional ions, elements, minerals, and compounds that are found in a mammal-produced milk are also known in the art.

The term "color balancing agent" or "coloring agent" means an agent added to a composition to modulate the color of the composition, e.g., to make the color of the composition appear more similar to a mammalian-produced milk. Non-limiting examples of color balancing agents or coloring agents include β-carotene and annatto. Other examples of coloring balancing agents are known in the art. A color balancing agent or a coloring agent can be produced by or obtained from a plant.

The term "micelle" means is a generally (or roughly) spherical supramolecular structure that exists as a dispersion within a composition. A micelle can have, e.g., a surface that is composed of a charged outer layer. A micelle can encapsulate one or more biomolecules. For example, a micelle can encapsulate two or more proteins (e.g., a β-casein protein and a κ-casein protein). A micelle can have diameter of between about 10 nm and about 350 nm. Additional aspects and characteristics of micelles are known in the art.

The phrase "concentration of a component in a mammal-produced milk" means the concentration of a component in the milk produced by a mammal or the mean concentration of a component in milk produced by a population of mammals of the same species.

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

Deletion: The removal of one or more nucleotides from a nucleic acid molecule or one or more amino acids from a protein, the regions on either side being joined together.

Knock-Out: A gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "synthetic milk substitute" refers to a composition that resembles, is similar to, is to equivalent to, or is nearly identical to a dairy milk.

The term "flavor" refers to the taste and/or the aroma of a food or drink.

The term "recombinant" is an art known-term. When referring to a nucleic acid (e.g., a gene), the term "recombinant" can be used, e.g., to describe a nucleic acid that has been removed from its naturally occurring environment, a nucleic acid that is not associated with all or a portion of a nucleic acid abutting or proximal to the nucleic acid when it is found in nature, a nucleic acid that is operatively linked to a nucleic acid which it is not linked to in nature, or a nucleic acid that does not occur in nature. The term "recombinant" can be used, e.g., to describe cloned DNA isolates, or a nucleic acid including a chemically-synthesized nucleotide analog. When "recombinant" is used to describe a protein, it can refer to, e.g., a protein that is produced in a cell of a different species or type, as compared to the species or type of cell that produces the protein in nature.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion, or a point mutation introduced artificially, e.g., by human intervention. A "recombinant nucleic acid" also includes a nucleic acid integrated into a host cell chromosome at a heterologous site and a nucleic acid construct present as an episome.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap, or Bestfit, which are programs in Wisconsin Package Version 10.0, Genetics Computer Group (GCG), Madison, Wis. FASTA provides alignments and percent sequence identity of the regions of the best overlap between the query and search sequences. See, e.g., Pearson, *Methods Enzymol.* 183:63-98, 1990 (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410, 1990; Gish and States, *Nature Genet.* 3:266-272, 1993; Madden et al., *Meth. Enzymol.* 266:131-141, 1996; Altschul et al., *Nucleic Acids Res.* 25:3389-3402, 1997; Zhang and Madden, *Genome Res.* 7:649-656, 1997, especially blastp or tblastn (Altschul et al., *Nucleic Acids Res.* 25:3389-3402, 1997.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y., page 9.51, 1989, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Examples of modified nucleotides are described in Malyshev et al., *Nature* 509:385-388, 2014; and Li et al., *J. Am. Chem. Soc.* 136:826-829, 2014. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted, or changed compared to a reference nucleic acid sequence. A single alteration may be made at a locus (a point mutation) or multiple nucleotides may be inserted, deleted, or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique* 1:11-15, 1989, and Caldwell and Joyce, *PCR Methods Applic.* 2:28-33, 1992); and "oligonucleotide-directed mutagenesis" (a process which enables the generation of site-specific mutations in any cloned DNA segment of interest; see, e.g., Reidhaar-Olson and Sauer, *Science* 241: 53-57, 1988).

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

Promoters useful for expressing the recombinant genes described herein include both constitutive and inducible/repressible promoters. Examples of inducible/repressible promoters include galactose-inducible promoters (e.g., PLAC4-PBI). Where multiple recombinant genes are expressed in an engineered yeast, the different genes can be controlled by different promoters or by identical promoters in separate operons, or the expression of two or more genes may be controlled by a single promoter as part of an operon.

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operably linked. Expression control sequences are sequences which control the transcription, post-transcriptional events, and translation of nucleic acid sequences. Expression control sequences include appropriate transcription initiation, termination, promoter and enhancer sequences; efficient RNA processing signals, such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "transfect", "transfection", "transfecting," and the like refer to the introduction of a heterologous nucleic acid into eukaryote cells, both higher and lower eukaryote cells. Historically, the term "transformation" has been used to describe the introduction of a nucleic acid into a yeast or fungal cell; however, herein the term "transfection" is used to refer to the introduction of a nucleic acid into any eukaryote cell, including yeast and fungal cells.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Preferred host cells are yeasts and fungi.

The term "yeast and filamentous fungi" include, but are not limited to any *Kluyveromyces* sp., such as *Kluyveromyces lactis, Kluyveromyces marxianus, Saccharomyces* sp., such as *Saccharomyces cerevisiae, Pichia* sp., such as *Pichia pastoris, Pichia finlandica, Pichia trehalophila, Pichia koclamae, Pichia membranaefaciens, Pichia minuta* (*Ogataea minuta, Pichia lindneri*), *Pichia opuntiae, Pichia thermotolerans, Pichia salictaria, Pichia guercuum, Pichia pijperi, Pichia stiptis, Pichia methanolica, Hansenula polymorpha, Candida albicans*, any *Aspergillus* sp., such as *Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens*, and *Neurospora crassa.*

As used herein, the term "predominantly" or variations thereof will be understood to mean, for instance, a) in the context of fats the amount of a particular fatty acid composition relative to the total amount of fatty acid composition; b) in the context of protein the amount of a particular protein composition (e.g., β-casein) relative to the total amount of protein composition (e.g., α-, β-, and κ-casein).

The term "about," "approximately," or "similar to" means within an acceptable error range for the particular value as determined by one of ordinary skill in the art, which can depend in part on how the value is measured or determined, or on the limitations of the measurement system. It should be understood that all ranges and quantities described below are approximations and are not intended to limit the invention. Where ranges and numbers are used these can be approximate to include statistical ranges or measurement errors or variation. In some embodiments, for instance, measurements could be plus or minus 10%.

The phrase "essentially free of" is used to indicate the indicated component, if present, is present in an amount that does not contribute, or contributes only in a de minimus fashion, to the properties of the composition. In various embodiments, where a composition is essentially free of a particular component, the component is present in less than a functional amount. In various embodiments, the component may be present in trace amounts. Particular limits will vary depending on the nature of the component, but may be, for example, selected from less than 10% by weight, less than 9% by weight, less than 8% by weight, less than 7% by weight, less than 6% by weight, less than 5% by weight, less than 4% by weight, less than 3% by weight, less than 2% by weight, less than 1% by weight, or less than 0.5% by weight.

As used herein, the term "essentially free of" a particular carbohydrate, such as lactose is used to indicate that the food composition is substantially devoid of carbohydrate residues. Expressed in terms of purity, essentially free means that the amount of carbohydrate residues do not exceed 10%, and preferably is below 5%, more preferably below 1%, most preferably below 0.5%, wherein the percentages are by weight or by mole percent. Thus, substantially all of the carbohydrate residues in a food composition according to the present invention are free of, for example, lactose.

Unless indicated otherwise, percentage (%) of ingredients refer to total % by weight.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

DETAILED DESCRIPTION OF THE INVENTION

Figure 1:
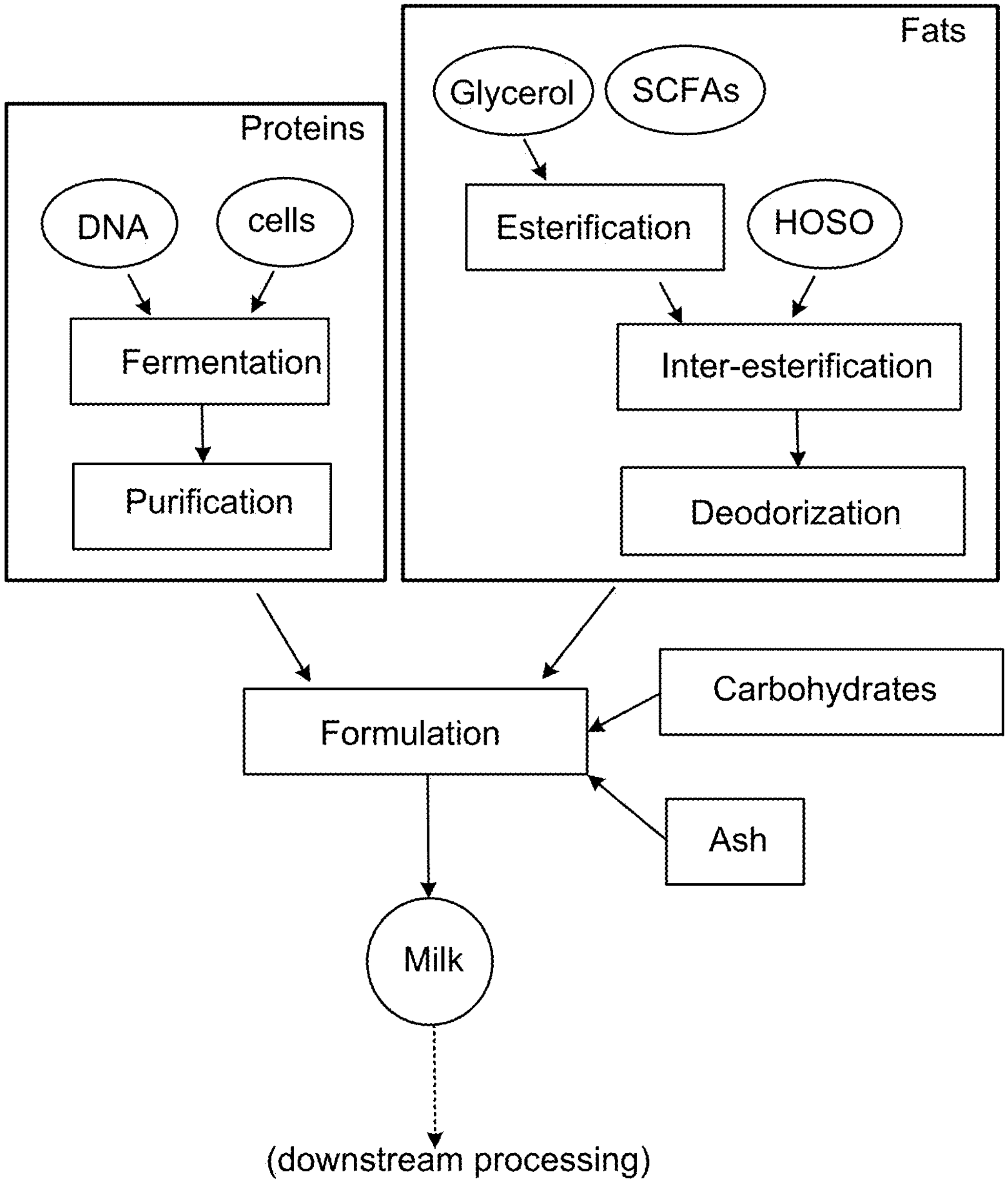
FIG. 1 represents a flow diagram representative of an exemplary process to produce synthetic milk substitute.

The invention is based on the discovery that only a few components present in a mammal-produced milk provide for the texture and taste of a mammal-produced milk, and the development of compositions that have a similar taste, aroma, and mouth feel as compared to a mammal-produced milk. In view of this discovery, provided herein are such compositions, methods of making the compositions, and kits including these compositions and mixtures useful for making these compositions.

The compositions provided herein provide for compositions that have a similar taste, mouth feel, aroma, and nutritional value as compared to a mammal-produced milk, but lack one or more of the components of a mammal-produced milk that may be considered to be undesirable (e.g., allergens, lactose, antibiotics, hormones (e.g., stress hormones and/or growth hormones), heavy metals, bacteria (e.g., *E. coli*), viruses, and prions). The compositions provided herein also have an improved shelf-life as compared to mammal-produced milk, and can have an improved aroma profile as compared to a mammal-produced milk.

Also provided herein are methods and compositions for dairy substitute food product comprising one or more isolated milk protein components, fats, carbohydrates and ash. In certain aspects the methods and compositions comprise milk or milk-like protein equivalents. Preferably, the milk protein component is essentially free of impurities. In some embodiments, the milk protein component comprises microbially derived or produced casein, whey or a combination thereof. More preferably, a method is provided to introduce an engineered nucleic acid sequence encoding one or more milk protein components. Even more preferably, the milk protein component is not animal derived. In other preferred embodiments, the recombinant milk protein component is modified to express the same phosphate groups or lack phosphate groups and/or carbohydrate groups attached to the casein proteins. By having recombinant β-casein and κ-casein having the same phosphate groups as the same proteins present in a mammal-produced milk, the recombinant β-casein and the recombinant κ-casein are able to form micelles.

The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y., 1989; Ausubel et al., Current Protocols in Molecular Biology, Greene Publishing Associates, 1992, and Supplements to 2002); Harlow and Lane, Antibodies: A Laboratory Manual, Cold Spring Harbor Laboratory Press, Cold Spring Harbor, N.Y., 1990; Taylor and Drickamer, Introduction to Glycobiology, Oxford Univ. Press, 2003; Worthington Enzyme Manual, Worthington Biochemical Corp., Freehold, N.J.; Handbook of Biochemistry: Section A Proteins, Vol I, CRC Press, 1976; Handbook of Biochemistry: Section A Proteins, Vol II, CRC Press, 1976; Essentials of Glycobiology, Cold Spring Harbor Laboratory Press, 1999.

Exemplary materials and methods for use in any of the methods and compositions are described below, and can be used in any combination. Additional materials and methods that can be used in any of the methods and compositions are also known in the art.

Casein Proteins

Casein proteins include a variety of different proteins found in mammalian milk. Non-limiting examples of casein proteins include: β-casein, κ-casein, α-S2-casein, and α-S1-casein.

As an alternative to obtaining casein proteins from mammals or mammal-produced milk for us in dairy product manufacture, the present invention provides methods and composition for the production of recombinant casein proteins. In various aspects of the present invention, methods and compositions are provided for non-animal derived casein that has similar solubility and similar turbidity, and heat stability suitable for incorporation into various food products. Preferably, the non-animal derived casein has excellent solubility similar turbidity and heat stability suitable for incorporation into various dairy substitute products. Additionally, further characterization of the protein includes less or no aggregation or precipitation during such heat treatment and is suitable for procedures such as pasteurization, concentration, etc.

Difference in function of the non-animal derived casein in milk can be characterized in terms of viscosity of the liquid; the ability of the proteins to withstand heat; the ability of the proteins to form micelles; and the ability of the proteins to hold different minerals & vitamins.

B-Casein

The primary structure of human β-casein as determined by Greenberg et al. (*J. Biol. Chem.* 259:5132-5138, 1984) was shown to be a phosphorylated protein with phosphorylation sites at specific seryl and threonyl residues located near the amino terminus. A comparison of human and bovine β-caseins showed 47% identity.

Non-limiting examples of β-casein proteins are SEQ ID Nos: 25, 27, 29, 31, 33, 35, 36, 38, 40, 42, 44, and 46. Non-limiting examples of nucleic acid sequences encoding a β-casein protein are SEQ ID NOs: 26, 28, 30, 32, 34, 37, 39, 41, 43, 45, 47, and 144. A β-casein protein can be a β-casein protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein. Additional sequences for different β-casein proteins and nucleic acids encoding different β-casein proteins are known in the art.

A β-casein protein can also be a proteins that is at least 50% (e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5%) identical to a wildtype β-casein protein (e.g., SEQ ID Nos: 25, 27, 29, 31, 33, 35, 36, 38, 40, 42, 44, or 46). A nucleic acid encoding a β-casein protein can encode a protein that is at least 50% (e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5%) identical to a wildtype β-casein protein (e.g., SEQ ID Nos: 25, 27, 29, 31, 33, 35, 36, 38, 40, 42, 44, or 46).

Methods known for isolating β-casein from genetically engineered bacterial cells typically involve precipitating the β-casein from a supernatant derived from lysed or fractionated cells. For example, Simons, et al., *Protein Eng.* 6: 763-770 (1993), used genetically engineered *E. coli* to express bovine β-casein. The protein, which accumulated in the periplasmic spaces of the bacteria, was released into a cell suspension by osmotic shock. After centrifugation of the suspension, the β-casein in the pellet was resuspended in a cold water wash and centrifuged again. The β-casein, present in the supernatant, was precipitated by acidification with acetic acid, filtered, and further purified by HPLC. Similarly, Hansson, et al., *Protein Express. Purif.* 4:373-381, 1993, used genetically engineered *E. coli* to express β-casein. The β-casein, present in a cell lysate, was precipitated with ammonium sulfate, dissolved in ethanolamine and 6M urea, and further purified by ion-exchange chromatography. See, e.g., U.S. Pat. No. 6,121,421.

Additionally, methods for isolating recombinantly produced β-casein in yeast that are simpler and more effective than known techniques are also known. Choi et al., *J. Agric. Food Chem.* 49(4):1761-1766, 2001. Expression and purification of glycosylated bovine β-casein (L70S/P71S) in *Pichia pastoris*, resulted in the observation that the majority of bovine β-casein was not being hyperglycosylated in *P. pastoris*, and its molecular weight was estimated to be 33.6 kDa. Glycosylated bovine β-casein was normally phosphorylated to the same degree as native bovine β-casein.

K-Casein

Kappa-casein is both phosphorylated and glycosylated. The sequence of human κ-casein was determined by Brignon et al. (Fed. Eur. Biol. Soc. Lett. 188:48-54, 1985). See, e.g., U.S. Pat. No. 5,710,044.

Non-limiting examples of κ-casein proteins are SEQ ID Nos: 1, 3, 5, 7, 9, 11, 13, 15, 17, 19, 21, and 23. Non-limiting examples of nucleic acid sequences encoding a κ-casein protein are SEQ ID NOs: 2, 4, 6, 8, 10, 12, 14, 16, 18, 20, 22, 24, and 148. A κ-casein protein can be a κ-casein protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein. Additional sequences for different κ-casein proteins and nucleic acids encoding different κ-casein proteins are known in the art.

A κ-casein protein can also be a proteins that is at least 50% (e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5%) identical to a wildtype κ-casein protein (e.g., SEQ ID Nos: 1, 3, 5, 7, 9, 11, 13, 15, 17, 19, 21, or 23). A nucleic acid encoding a κ-casein protein can encode a protein that is at least 50% (e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5%) identical to a wildtype κ-casein protein (e.g., SEQ ID Nos: 1, 3, 5, 7, 9, 11, 13, 15, 17, 19, 21, or 23).

α-S1-Casein

Non-limiting examples of α-S1-casein proteins are SEQ ID Nos: 48, 50, 52, 54, 56, 57, 59, 61, 63, 64, 66, 68, 70, 72, 74, and 76. Non-limiting examples of nucleic acid sequences encoding an α-S1-casein protein are SEQ ID NOs: 49, 51, 53, 55, 58, 60, 62, 65, 67, 69, 71, 73, 75, 77, and 147. A α-S1-casein protein can be an α-S1-casein protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S1-casein protein. Additional sequences for different α-S1-casein proteins and nucleic acids encoding different α-S1-casein proteins are known in the art.

An α-S1-casein protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-S1-casein protein (e.g., SEQ ID Nos: 48, 50, 52, 54, 56, 57, 59, 61, 63, 64, 66, 68, 70, 72, 74, or 76). A nucleic acid encoding an α-S1-casein protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-S1-casein protein (e.g., SEQ ID Nos: 48, 50, 52, 54, 56, 57, 59, 61, 63, 64, 66, 68, 70, 72, 74, or 76).

α-S2-Casein

Non-limiting examples of α-S2-casein proteins are SEQ ID Nos: 78, 80, 82, 84, 86, 88, and 90. Non-limiting examples of nucleic acid sequences encoding an α-S2-casein protein are SEQ ID NOs: 79, 81, 83, 85, 87, 89, 91, 145, and 146. A α-S2-casein protein can be an α-S2-casein protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S2-casein protein. Additional sequences for different α-S2-casein proteins and nucleic acids encoding different α-S2-casein proteins are known in the art.

An α-S2-casein protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-S2-casein protein (e.g., SEQ ID Nos: 78, 80, 82, 84, 86, 88, or 90). A nucleic acid encoding an α-S2-casein protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-S2-casein protein (e.g., SEQ ID Nos: 78, 80, 82, 84, 86, 88, or 90).

Micelles Including Casein Proteins

In bovine milk, casein or casein micelles usually makes up 2.5% of the entire mixture in suspension. If sufficient casein is not present the micelles, which are very important for the optimum behavior of milk, will not form. Too much protein does not go into solution properly resulting in an undesirable mixture. The casein micelle can include water and salts—mainly calcium and phosphorous. Casein micelles are easily separated and removed by centrifugation. Separation from whey is easily done by precipitating casein with an acid to lower the pH to around 4.6.

In some embodiments, a micelle can include a β-casein protein (e.g., any of the β-casein proteins described herein) and κ-casein protein (e.g., any of the κ-casein proteins described herein). In some examples, the ratio of β-casein protein to κ-casein protein in the micelle is about 2.0:1 to about 5.5:1, 2.0:1 to about 5.0:1, 2.0:1 to about 4.5:1, about 2.0:1 to about 4.0:1, about 2.0:1 to about 3.5:1, about 2.0:1 to about 3.0:1, about 2.0:1 to about 2.5:1, about 2.5:1 to about 5.0:1, about 2.5:1 to about 4.5:1, about 2.5:1 to about 4.0:1, about 2.5:1 to about 3.5:1, about 2.5:1 to about 3.0:1, 3.0:1 to about 5.0:1, about 3.0:1 to about 4.5:1, about 3.0:1 to about 4.0:1, about 3.0:1 to about 3.5:1, about 3.5:1 to about 5.0:1, about 3.5:1 to about 4.5:1, about 3.5:1 to about 4.0:1, about 4.0:1 to about 5.0:1, about 4.0:1 to about 4.5:1, or about 4.5:1 to about 5.0:1.

In some examples, the micelle has a diameter (or a population of micelles have an average diameter) of about 20 nm to about 350 nm, about 320 nm, about 300 nm, about 280 nm, about 260 nm, about 240 nm, about 220 nm, about 200 nm, about 180 nm, about 160 nm, about 140 nm, about 120 nm, about 100 nm, about 80 nm, about 60 nm, or about 40 nm; about 40 nm to about 350 nm, about 340 nm, about 320 nm, about 300 nm, about 280 nm, about 260 nm, about 240 nm, about 220 nm, about 200 nm, about 180 nm, about 160 nm, about 140 nm, about 120 nm, about 100 nm, about 80 nm, or about 60 nm; about 60 nm to about 350 nm, about 340 nm, about 320 nm, about 300 nm, about 280 nm, about 260 nm, about 240 nm, about 220 nm, about 200 nm, about 180 nm, about 160 nm, about 140 nm, about 120 nm, or about 100 nm; about 80 nm to about 350 nm, about 340 nm, about 320 nm, about 300 nm, about 280 nm, about 260 nm, about 240 nm, about 220 nm, about 200 nm, about 180 nm, about 160 nm, about 140 nm, about 120 nm, or about 100 nm; about 100 nm to about 350 nm, about 340 nm, about 320 nm, about 300 nm, about 280 nm, about 260 nm, about 240 nm, about 220 nm, about 200 nm, about 180 nm, about 160 nm, about 140 nm, or about 120 nm; about 120 nm to about 350 nm, about 340 nm, about 320 nm, about 300 nm, about 280 nm, about 260 nm, about 240 nm, about 220 nm, about 200 nm, about 180 nm, about 160 nm, or about 140 nm; about 140 nm to about 350 nm, about 340 nm, about 320 nm, about 300 nm, about 280 nm, about 260 nm, about 240 nm, about 220 nm, about 200 nm, about 180 nm, or about 160 nm; about 160 nm to about 350 nm, about 340 nm, about 320 nm, about 300 nm, about 280 nm, about 260 nm, about 240 nm, about 220 nm, about 200 nm, or about 180 nm; about 180 nm to about 350 nm, about 340 nm, about 320 nm, about 300 nm, about 280 nm, about 260 nm, about 240 nm, about 220 nm, or about 200 nm; about 200 nm to about 350 nm, about 340 nm, about 320 nm, about 300 nm, about 280 nm, about 260 nm, about 240 nm, or about 220 nm; about 220 nm to about 350 nm, about 340 nm, about 320 nm, about 300 nm, about 280 nm, about 260 nm, or about 240 nm; about 240 nm to about 350 nm, about 340 nm, about 320 nm, about 300 nm, about 280 nm, or about 260 nm; about 260 nm to about 350 nm, about 340 nm, about 320 nm, about 300 nm, or about 280 nm; about 280 nm to about 350 nm, about 340 nm, about 320 nm, or about 300 nm; about 300 nm to about 350 nm or about 325 nm; or about 325 nm to about 350 nm.

Whey Proteins

Whey is commonly known as the by-product of cheese and is also known to be one cause for milk allergies. A typical whey composition comprises a mixture of β-lactoglobulin, α-lactalbumin, serum albumin, immunoglobulins, lactoferrin, and transferrin. Whey proteins do not contain phosphorus, and remain in solution at low pH whereas casein proteins do not. In one embodiment, a select combination of whey proteins comprising β-lactoglobulin and α-lactalbumin are used as the primary component or at least a part of the milk protein component or composition. Non-limiting examples of different whey proteins are provided below.

α-Lactalbumin

Non-limiting examples of α-lactalbumin proteins are SEQ ID Nos: 92, 94, 96, and 98. Non-limiting examples of nucleic acid sequences encoding an α-lactalbumin protein are SEQ ID NOs: 93, 95, 97, 99, and 157. An α-lactalbumin protein can be an α-lactalbumin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-lactalbumin protein. Additional sequences for different α-lactalbumin proteins and nucleic acids encoding different α-lactalbumin proteins are known in the art.

An α-lactalbumin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-lactalbumin protein (e.g., SEQ ID Nos: 92, 94, 96, or 98). A nucleic acid encoding an α-lactalbumin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-lactalbumin protein (e.g., SEQ ID Nos: 92, 94, 96, or 98).

β-Lactoglobulin

Non-limiting examples of β-lactoglobulin proteins are SEQ ID Nos: 100, 102, 104, and 106. Non-limiting examples of nucleic acid sequences encoding a β-lactoglobulin protein are SEQ ID NOs: 101, 103, 105, 107, and 143. A β-lactoglobulin protein can be a β-lactoglobulin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-lactoglobulin protein. Additional sequences for different β-lactoglobulin proteins and nucleic acids encoding different β-lactoglobulin proteins are known in the art.

A β-lactoglobulin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype β-lactoglobulin protein (e.g., SEQ ID Nos: 100, 102, 104, or 106). A nucleic acid encoding a β-lactoglobulin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype β-lactoglobulin protein (e.g., SEQ ID Nos: 100, 102, 104, or 106).

Lactoferrin

Non-limiting examples of lactoferrin proteins are SEQ ID Nos: 108, 110, 112, and 114. Non-limiting examples of nucleic acid sequences encoding a lactoferrin protein are SEQ ID NOs: 109, 111, 113, and 115. A lactoferrin protein can be a lactoferrin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth lactoferrin protein. Additional sequences for different lactoferrin proteins and nucleic acids encoding different lactoferrin proteins are known in the art.

A lactoferrin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype lactoferrin protein (e.g., SEQ ID Nos: 108, 110, 112, or 114). A nucleic acid encoding a lactoferrin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype lactoferrin protein (e.g., SEQ ID Nos: 108, 110, 112, or 114).

Transferrin

Non-limiting examples of transferrin proteins are SEQ ID Nos: 116 and 118. Non-limiting examples of nucleic acid sequences encoding a transferrin protein are SEQ ID NOs: 117 and 119. A transferrin protein can be a transferrin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth transferrin protein. Additional sequences for different transferrin proteins and nucleic acids encoding different transferrin proteins are known in the art.

A transferrin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype transferrin protein (e.g., SEQ ID Nos: 116 or 118). A nucleic acid encoding a transferrin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype transferrin protein (e.g., SEQ ID Nos: 116 or 118).

Serum Albumin

Non-limiting examples of serum albumin proteins are SEQ ID Nos: 120, 122, 124, and 126. Non-limiting examples of nucleic acid sequences encoding a serum albumin protein are SEQ ID NOs: 121, 123, 125, and 127. A serum albumin protein can be a serum albumin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth serum albumin protein. Additional sequences for different serum albumin proteins and nucleic acids encoding different serum albumin proteins are known in the art.

A serum albumin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype serum albumin protein (e.g., SEQ ID Nos: 20, 122, 124, or 126). A nucleic acid encoding a serum albumin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype serum albumin protein (e.g., SEQ ID Nos: 20, 122, 124, or 126).

Lipids in Mammal-Produced Milk

Milk fat contains approximately 400 different fatty acids, which makes it the most complex of all natural fats. The milk fatty acids are derived almost equally from two sources, the feed and the microbial activity in the rumen of the cow and the lipids in bovine milk are mainly present in globules as an oil-in-water emulsion. Fat is present in all natural dairy products and is critical for sensory characteristics such as flavor, mouthfeel and consistency. In addition, fats provide nutrition and health benefits. The milk fat consists mainly of triglycerides, approximately 98%, while other milk lipids are diacylglycerol (about 2% of the lipid fraction), cholesterol (less than 0.5%), phospholipids (about 1%) and free fatty acids (FFA) (about 0.1%) Jensen R G, Newburg D S. Bovine milk lipids, Handbook of milk composition. Jensen R G London: Academic Press; 1995. 543-75. In addition, there are trace amounts of ether lipids, hydrocarbons, fat-soluble vitamins, flavor compounds and compounds introduced by the feed (Lindmark Mansson H., Food & Nutrition Research 2008. DOI: 10.3402/fnr.v52i0.1821)

Milk fat triglycerides are synthesized from more than 400 different fatty acids, which makes milk fat the most complex of all natural fats. Nearly all fatty acids in milk are present in trace quantities and only about 15 acids at the 1% level or higher. Many factors are associated with the variations in the amount and fatty acid composition of bovine milk lipids. They may be of animal origin, i.e. related to genetics (breed and selection), stage of lactation, mastitis and ruminal fermentation, or they may be feed-related factors, i.e. related to fibre and energy intake, dietary fats, and seasonal and regional effects. The fatty acids in the milk fat are arranged in the triglycerides in accordance with a pattern that appears to be universal among ruminants. The percent unsaturated fatty acids (e.g., oleic and linolenic) in goats do not differ from the average found for cow's milk. A major difference between the milk fat of the goat and the cow is the percentage distribution among specific short chain fatty acids. Goats have an appreciably higher proportion of capric, caprylic and caproic acids. The high amounts of these specific fatty acids are responsible for the characteristic flavor and odor associated with goat's milk. John C. Bruhn, F S T, UC Davis, Davis, CA 95616-8598; Seewww.drinc.ucdavis.edu/goat1.htm; www.ncbi.nlm.nih.gov/pmc/articles/PMC2596709/#_ffn_sectitle; Food Nutr Res. 2008; 52: 10.3402/fnr.v52i0.1821. Published online Jun. 11, 2008. doi: 10.3402/fnr. v52i0.1821.

The milk fatty acids are derived almost equally from two sources, the feed and the microbial activity in the rumen of the cow. The fatty acid synthesizing system in the mammary gland of the cow produces fatty acids with even number of carbons of 4-16 carbons in length and accounts for approximately 60 and 45% of the fatty acids on a molar and weight basis, respectively. This de novo synthesis in the mammary gland is of the 4:0-14:0 acids together with about half of the 16:0 from acetate and β-hydroxybutyrate. Acetate and butyric acid are generated in the rumen by fermentation of feed components. The butyric acid is converted to β-hydroxybutyrate during absorption through the rumen epithelium.

Medium- and long-chain fatty acids, but mainly 18:0, may be desaturated in the mammary gland to form the corresponding monosaturated acids.

Fatty acids are not randomly esterified at the three positions of the triacylglycerol molecule (MacGibbon A H K, Taylor M W. Composition and structure of bovine milk lipidsAdvanced dairy chemistry. Fox PFMcSweeney PLHNew York: Springer; 2006. 1-42.). The short-chain acids butyric (4:0) and caproic (6:0) are esterified almost entirely at sn-3. Medium-chain fatty acids (8:0-14:0) as well as 16:0 are preferentially esterified at positions sn-1 and sn-2. Stearic acid (18:0) is selectively placed at position sn-1, whereas oleic acid (18:1) shows preference for positions sn-1 and sn-3 (Lindmark 2008).

Milk replacers with a fat component formulated to selected fatty acid profiles exist, however, such triglycerides are not interesterified into long-chain monounsaturated fatty acid triglycerides such as found in vegetable oils. U.S. Patent Appl. No. 20140147548 discloses milk replacers for young animals with by adding medium chain triglyceride, specifically caproic, caprylic, capric and lauric fatty acid or a combination thereof.

Lipids in the Present Compositions

The lipids in any of the compositions or used in any of the methods described herein can include: one or more fats, one or more oils, one or more monoglycerides, diglycerides, and/or triglycerides, one or more free fatty acids, and one or more phospholipids. Exemplary oils, monoglycerides, diglycerides, free fatty acids, and phospholipids are described below. Additional examples of fats, oils, monoglycerides, diglycerides, triglycerides, free fatty acids, and phospholipids are known in the art.

Oils

Oils used in the present compositions or methods can include, e.g., plant-derived oils. Non-limiting examples of plant-based oils include sunflower oil, coconut oil, peanut oil, corn oil, cottonseed oil, olive oil, palm oil, rapeseed oil, safflower oil, sesame oil, soybean oil, almond oil, beech nut oil, brazil nut oil, cashew oil, hazelnut oil, macadamia nut oil, mongongo nut oil, pecan oil, pine nut oil, pistachio nut oil, walnut oil, and avocado oil.

Monoglycerides and Diglycerides

Monoglycerides and diglycerides that can be used in the present invention can be plant-derived monoglycerides and diglycerides. For example, monoglycerides and diglycerides can be derived from sunflowers, coconuts, peanuts, cottonseed, olives, palm, rapeseed, safflowers, sesame seed, soybeans, almonds, beech nuts, brazil nuts, cashews, hazelnuts, macadameia nuts, mongongo nuts, pecans, pine nuts, pistachios, walnuts, and avocados. The monoglycerides and diglycerides can include the acyl chain of any of the free fatty acids listed herein. Additional examples of monoglycerides and diglycerides are known in the art.

Free Fatty Acids

The compositions described herein can include and the methods described herein can include the use of one or more free fatty acids. Non-limiting examples of free fatty acids include butyric acid, caproic acid, caprylic acid, and capric acid. Additional examples of fatty acids include lauric acid, myristic acid, palmitic acid, stearic acid, arachidic acid, behenic acid, lignoceric acid, cerotic acid, myristoleic acid, pamitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, omega-3 fatty acids, and omega-6 fatty acids. In some examples, the free fatty acid is saturated. In some examples, the free fatty acid is unsaturated. In some embodiments, the free fatty acids are not derived from or produced by a mammal. Additional examples of free fatty acids are known in the art.

Phospholipids

The compositions described herein and the methods described herein can include the use of one or more phospholipids. Non-limiting examples of phospholipids include lecithin phospholipids (e.g., soy lecithin phospholipids, sunflower lecithin phospholipids, cotton lecithin phospholipids, rapeseed lecithin phospholipids. rice bran lecithin phospholipids, and corn lecithin phospholipids). In some embodiments, the phospholipids are not derived from or produced by a mammal. Additional aspects of phospholipids are known in the art.

Flavor Compounds

Any of the compositions or methods described herein can include or include the use of one or more different flavor compounds. Non-limiting examples of flavor compounds include δ-decalactone, ethyl butyrate, 2-furyl methyl ketone, 2,3-pentanedione, γ-undecalactone, and δ-undecalactone. Additional examples of flavor compounds include artificial flavors, e.g., chocolate, coffee, strawberry, almond, hazelnut, vanilla, green tea, Irish cream, and coconut flavoring. Additional examples of flavor compounds are known in the art.

Ash

Any of the compositions or methods described herein can include or include the use of ash. Ash can, e.g., include one or more (two, three, four, five, six, seven, eight, nine, ten, eleven, twelve, thirteen, fourteen fifteen, sixteen, seventeen, eighteen, nineteen, or twenty) of: calcium, phosphorous, potassium, sodium, citrate, chloride, phosphate, magnesium, iron, molybdenum, manganese, copper, thiamin (vitamin B1), riboflavin (vitamin B2), niacin (vitamin B3), pantothenic acid (vitamin B5), vitamin B6 (pyridoxine), vitamin B12 (cobalamin), vitamin C, folate, vitamins A, vitamin D, vitamin E, and vitamin K. In some examples, the ash includes one or more (two or three) of $CaCl_2$), $KH_2PO_4$, and $Na_3$ citrate. Ash can be provided as a powder or as a solution. Additional components in and aspects of ash are known in the art. In some embodiments, the ash is not derived from or produced by mammal.

Color Balancing Agents

A variety of different color balancing agents are known in the art. For example, a color balancing agent can be a compound from obtained from a plant (e.g., a monocot or a dicot). In some examples, the color balancing agent is a synthetic compound. In some examples, the color balancing agent is not obtained from or produced by a mammal or a mammalian cell. Non-limiting examples of color balancing agents include β-carotene and annatto.

Sweetening Agents

A sweetening agent can be a saccharide (e.g., a monosaccharide, a disaccharide, or a polysaccharide) or an artificial sweetener. Non-limiting examples of sweetening agents that are saccharides include glucose, mannose, maltose, fructose, galactose, lactose, sucrose, monatin, and tagatose. Additional examples of saccharides that can be used as a sweetening agent in any of the compositions or methods described herein are known in the art.

Non-limiting examples of sweetening agents that are artificial sweeteners include stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, and P-4000. Additional artificial sweeteners that can be used as sweetening agents in any of the compositions or methods described herein are known in the art.

Compositions

Provided herein are compositions including: about 0.3 g/L to about 1.1 g/L (e.g., about 0.3 g/L to about 1.0 g/L, about 0.3 g/L to about 0.9 g/L, about 0.3 g/L to about 0.8 g/L, about 0.3 g/L to about 0.7 g/L, about 0.3 g/L to about 0.6 g/L, about 0.3 g/L to about 0.5 g/L, about 0.3 g/L to about 0.4 g/L, about 0.4 g/L to about 1.1 g/L, about 0.4 g/L to about 1.0 g/L, about 0.4 g/L to about 0.9 g/L, about 0.4 g/L to about 0.8 g/L, about 0.4 g/L to about 0.7 g/L, about 0.4 g/L to about 0.6 g/L, about 0.4 g/L to about 0.5 g/L, about 0.5 g/L to about 1.1 g/L, about 0.5 g/L to about 1.0 g/L, about 0.5 g/L to about 0.9 g/L, about 0.5 g/L to about 0.8 g/L, about 0.5 g/L to about 0.7 g/L, about 0.5 g/L to about 0.6 g/L, about 0.6 g/L to about 1.1 g/L, about 0.6 g/L to about 1.0 g/L, about 0.6 g/L to about 0.9 g/L, about 0.6 g/L to about 0.8 g/L, about 0.6 g/L to about 0.7 g/L, about 0.7 g/L to about 1.1 g/L, about 0.7 g/L to about 1.0 g/L, about 0.7 g/L to about 0.9 g/L, about 0.7 g/L to about 0.8 g/L, about 0.8 g/L to about 1.1 g/L, about 0.8 g/L to about 1.0 g/L, about 0.8 g/L to about 0.9 g/L, about 0.9 g/L to about 1.1 g/L, about 0.9 g/L to about 1.0 g/L, about 1.0 g/L to about 1.1 g/L, or about 0.27 weight % to about 0.75 weight %) κ-casein protein (e.g., any of the κ-casein proteins described herein); about 1.25 g/L to about 4.9 g/L (e.g., about 1.25 g/L to about 4.6 g/L, about 1.25 g/L to about 4.4 g/L, about 1.25 g/L to about 4.2 g/L, about 1.25 g/L to about 4.0 g/L, about 1.25 g/L to about 3.8 g/L, about 1.25 g/L to about 3.6 g/L, about 1.25 g/L to about 3.4 g/L, about 1.25 g/L to about 3.2 g/L, about 1.25 g/L to about 3.0 g/L, about 1.25 g/L to about 2.8 g/L, about 1.25 g/L to about 2.6 g/L, about 1.25 g/L to about 2.4 g/L, about 1.25 g/L to about 2.2 g/L, about 1.25 g/L to about 2.0 g/L, about 1.25 g/L to about 1.8 g/L, about 1.25 g/L to about 1.6 g/L, about 1.25 g/L to about 1.4 g/L, about 1.4 g/L to about 4.9 g/L, about 1.4 g/L to about 4.6 g/L, about 1.4 g/L to about 4.4 g/L, about 1.4 g/L to about 4.2 g/L, about 1.4 g/L to about 4.0 g/L, about 1.4 g/L to about 3.8 g/L, about 1.4 g/L to about 3.6 g/L, about 1.4 g/L to about 3.4 g/L, about 1.4 g/L to about 3.2 g/L, about 1.4 g/L to about 3.0 g/L, about 1.4 g/L to about 2.8 g/L, 1.4 g/L to about 2.6 g/L, about 1.4 g/L to about 2.4 g/L, about 1.4 g/L to about 2.2 g/L, about 1.4 g/L to about 2.0 g/L, about 1.4 g/L to about 1.8 g/L, about 1.4 g/L to about 1.6 g/L, about 1.6 g/L to about 4.9 g/L, about 1.6 g/L to about 4.6 g/L, about 1.6 g/L to about 4.4 g/L, about 1.6 g/L to about 4.2 g/L, about 1.6 g/L to about 4.0 g/L, about 1.6 g/L to about 3.8 g/L, about 1.6 g/L to about 3.6 g/L, about 1.6 g/L to about 3.4 g/L, about 1.6 g/L to about 3.2 g/L, about 1.6 g/L to about 3.0 g/L, about 1.6 g/L to about 2.8 g/L, 1.6 g/L to about 2.6 g/L, about 1.6 g/L to about 2.4 g/L, about 1.6 g/L to about 2.2 g/L, about 1.6 g/L to about 2.0 g/L, about 1.6 g/L to about 1.8 g/L, about 1.8 g/L to about 4.9 g/L, about 1.8 g/L to about 4.6 g/L, about 1.8 g/L to about 4.4 g/L, about 1.8 g/L to about 4.2 g/L, about 1.8 g/L to about 4.0 g/L, about 1.8 g/L to about 3.8 g/L, about 1.8 g/L to about 3.6 g/L, about 1.8 g/L to about 3.4 g/L, about 1.8 g/L to about 3.2 g/L, about 1.8 g/L to about 3.0 g/L, about 1.8 g/L to about 2.8 g/L, 1.8 g/L to about 2.6 g/L, about 1.8 g/L to about 2.4 g/L, about 1.8 g/L to about 2.2 g/L, about 1.8 g/L to about 2.0 g/L, about 2.0 g/L to about 4.9 g/L, about 2.0 g/L to about 4.6 g/L, about 2.0 g/L to about 4.4 g/L, about 2.0 g/L to about 4.2 g/L, about 2.0 g/L to about 4.0 g/L, about 2.0 g/L to about 3.8 g/L, about 2.0 g/L to about 3.6 g/L, about 2.0 g/L to about 3.4 g/L, about 2.0 g/L to about 3.2 g/L, about 2.0 g/L to about 3.0 g/L, about 2.0 g/L to about 2.8 g/L, 2.0 g/L to about 2.6 g/L, about 2.0 g/L to about 2.4 g/L, about 2.0 g/L to about 2.2 g/L, about 2.2 g/L to about 4.9 g/L, about 2.2 g/L to about 4.6 g/L, about 2.2 g/L to about 4.4 g/L, about 2.2 g/L to about 4.2 g/L, about 2.2 g/L to about 4.0 g/L, about 2.2 g/L to about 3.8 g/L, about 2.2 g/L to about 3.6 g/L, about 2.2 g/L to about 3.4 g/L, about 2.2 g/L to about 3.2 g/L, about 2.2 g/L to about 3.0 g/L, about 2.2 g/L to about 2.8 g/L, 2.2 g/L to about 2.6 g/L, about 2.2 g/L to about 2.4 g/L, about 2.4 g/L to about 4.9 g/L, about 2.4 g/L to about 4.6 g/L, about 2.4 g/L to about 4.4 g/L, about 2.4 g/L to about 4.2 g/L, about 2.4 g/L to about 4.0 g/L, about 2.4 g/L to about 3.8 g/L, about 2.4 g/L to about 3.6 g/L, about 2.4 g/L to about 3.4 g/L, about 2.4 g/L to about 3.2 g/L, about 2.4 g/L to about 3.0 g/L, about 2.4 g/L to about 2.8 g/L, 2.4 g/L to about 2.6 g/L, about 2.6 g/L to about 4.9 g/L, about 2.6 g/L to about 4.6 g/L, about 2.6 g/L to about 4.4 g/L, about 2.6 g/L to about 4.2 g/L, about 2.6 g/L to about 4.0 g/L, about 2.6 g/L to about 3.8 g/L, about 2.6 g/L to about 3.6 g/L, about 2.6 g/L to about 3.4 g/L, about 2.6 g/L to about 3.2 g/L, about 2.6 g/L to about 3.0 g/L, about 2.6 g/L to about 2.8 g/L, about 2.8 g/L to about 4.9 g/L, about 2.8 g/L to about 4.6 g/L, about 2.8 g/L to about 4.4 g/L, about 2.8 g/L to about 4.2 g/L, about 2.8 g/L to about 4.0 g/L, about 2.8 g/L to about 3.8 g/L, about 2.8 g/L to about 3.6 g/L, about 2.8 g/L to about 3.4 g/L, about 2.8 g/L to about 3.2 g/L, about 2.8 g/L to about 3.0 g/L, about 3.0 g/L to about 4.9 g/L, about 3.0 g/L to about 4.6 g/L, about 3.0 g/L to about 4.4 g/L, about 3.0 g/L to about 4.2 g/L, about 3.0 g/L to about 4.0 g/L, about 3.0 g/L to about 3.8 g/L, about 3.0 g/L to about 3.6 g/L, about 3.0 g/L to about 3.4 g/L, about 3.0 g/L to about 3.2 g/L, about 3.2 g/L to about 4.9 g/L, about 3.2 g/L to about 4.6 g/L, about 3.2 g/L to about 4.4 g/L, about 3.2 g/L to about 4.2 g/L, about 3.2 g/L to about 4.0 g/L, about 3.2 g/L to about 3.8 g/L, about 3.2 g/L to about 3.6 g/L, about 3.2 g/L to about 3.4 g/L, about 3.4 g/L to about 4.9 g/L, about 3.4 g/L to about 4.6 g/L, about 3.4 g/L to about 4.4 g/L, about 3.4 g/L to about 4.2 g/L, about 3.4 g/L to about 4.0 g/L, about 3.4 g/L to about 3.8 g/L, about 3.4 g/L to about 3.6 g/L, about 3.6 g/L to about 4.9 g/L, about 3.6 g/L to about 4.6 g/L, about 3.6 g/L to about 4.4 g/L, about 3.6 g/L to about 4.2 g/L, about 3.6 g/L to about 4.0 g/L, about 3.6 g/L to about 3.8 g/L, about 3.8 g/L to about 4.9 g/L, about 3.8 g/L to about 4.6 g/L, about 3.8 g/L to about 4.4 g/L, about 3.8 g/L to about 4.2 g/L, about 3.8 g/L to about 4.0 g/L, about 4.0 g/L to about 4.9 g/L, about 4.0 g/L to about 4.6 g/L, about 4.0 g/L to about 4.4 g/L, about 4.0 g/L to about 4.2 g/L, about 4.2 g/L to about 4.9 g/L, about 4.2 g/L to about 4.6 g/L, about 4.2 g/L to about 4.4 g/L, about 4.4 g/L to about 4.9 g/L, about 4.4 g/L to about 4.6 g/L, about 4.6 g/L to about 4.9 g/L, or about 1.23 weight % to about 3.27 weight %) β-casein protein (e.g., any of the β-casein proteins described herein); a final total concentration of one or more lipids (e.g., any one or more of the lipids described herein) of about 0 weight % to about 45 weight % (e.g., 0 weight %; about 0 weight % to about 4.5 weight %; about 0.5 weight % to about 40 weight %, about 35 weight %, about 30 weight %, about 25 weight %, about 20 weight %, about 15 weight %, about 10 weight %, about 8 weight %, about 6 weight %, about 5 weight %, about 4 weight %, about 3 weight %, about 2 weight %, or about 1 weight %; about 1.0 weight % to about 40 weight %, about 35 weight %, about 30 weight %, about 25 weight %, about 20 weight %, about 15 weight %, about 10 weight %, about 8 weight %, about 6 weight %, about 5 weight %, about 4 weight %, about 3 weight %, or about 2 weight %; about 2 weight % to about 40 weight %, about 35 weight %, about 30 weight %, about 25 weight %, about 20 weight %, about 15 weight %, about 10 weight %, about 8 weight %, about 6 weight %, about 5 weight %, about 4 weight %, or about 3 weight %; about 3 weight % to about 40 weight %, about 35 weight %, about 30 weight %, about 25 weight %, about 20 weight %, about 15 weight %, about 10 weight %, about 8 weight %, about 6 weight %, about 5 weight %, or about 4 weight %; about 4 weight % to about 40 weight %, about 35 weight %, about 30 weight %, about 25 weight %, about 20 weight %, about 15 weight %, about 10 weight %, about 8 weight %, about 6 weight %, or about 5 weight %; about 5 weight % to about 40 weight %, about 35 weight %, about 30 weight %, about 25 weight %, about 20 weight %, about 15 weight %, about 10 weight %, about 8 weight %, or about 6 weight %; about 6 weight % to about 40 weight %, about 35 weight %, about 30 weight %, about 25 weight %, about 20 weight %, about 15 weight %, about 10 weight %, or about 8 weight %; about 8 weight % to about 40 weight %, about 35 weight %, about 30 weight %, about 25 weight %, about 20 weight %, about 15 weight %, or about 10 weight %; about 10 weight % to about 40 weight %, about 35 weight %, about 30 weight %, about 25 weight %, about 20 weight %, or about 15 weight %; about 15 weight % to about 40 weight %, about 35 weight %, about 30 weight %, about 25 weight %, or about 20 weight %; about 20 weight % to about 40 weight %, about 35 weight %, about 30 weight %, or about 25 weight %; about 25 weight % to about 40 weight %, about 35 weight %, or about 30 weight %; about 30 weight % to about 40 weight %, or about 35 weight %; or about 35 weight % to about 40 weight %); a final total concentration of one or more flavor compounds (e.g., any of one or more of the flavor compounds described herein) of about 0.01 weight % to about 6 weight % (e.g., about 0.1 weight % to about 5.5 weight %, about 5.0 weight %, about 4.5 weight %, about 4.0 weight %, about 3.5 weight %, about 3.0 weight %, about 2.5 weight %, about 2.0 weight %, about 1.5 weight %, about 1.0 weight %, or about 0.5 weight %; about 0.5 weight % to about 6 weight %, about 5.5 weight %, about 5.0 weight %, about 4.5 weight %, about 4.0 weight %, about 3.5 weight %, about 3.0 weight %, about 2.5 weight %, about 2.0 weight %, about 1.5 weight %, or about 1.0 weight %; about 1.0 weight % to about 6.0 weight %, about 5.5 weight %, about 5.0 weight %, about 4.5 weight %, about 4.0 weight %, about 3.5 weight %, about 3.0 weight %, about 2.5 weight %, about 2.0 weight %, or about 1.5 weight %; about 1.5 weight % to about 6.0 weight %, about 5.5 weight %, about 5.0 weight %, about 4.5 weight %, about 4.0 weight %, about 3.5 weight %, about 3.0 weight %, about 2.5 weight %, or about 2.0 weight %; about 2.0 weight % to about 6.0 weight %, about 5.5 weight %, about 5.0 weight %, about 4.5 weight %, about 4.0 weight %, about 3.5 weight %, about 3.0 weight %, or about 2.5 weight %; about 2.5 weight % to about 6.0 weight %, about 5.5 weight %, about 5.0 weight %, about 4.5 weight %, about 4.0 weight %, about 3.5 weight %, or about 3.0 weight %; about 3.0 weight % to about 6.0 weight %, about 5.5 weight %, about 5.0 weight %, about 4.5 weight %, about 4.0 weight %, or about 3.5 weight %; about 3.5 weight % to about 6.0 weight %, about 5.5 weight %, about 5.0 weight %, about 4.5 weight %, or about 4.0 weight %; about 4.0 weight % to about 6.0 weight %, about 5.5 weight %, about 5.0 weight %, about 4.5 weight %; about 4.5 weight % to about 6.0 weight %, about 5.5 weight %, or about 5.0 weight %; about 5.0 weight % to about 6.0 weight % or about 5.5 weight %; or about 5.5 weight % to about 6.0 weight %); a final total concentration of about 0.1 weight % to about 6 weight % (e.g., about 0.1 weight % to about 5.5 weight %, about 5.0 weight %, about 4.5 weight %, about 4.0 weight %, about 3.5 weight %, about 3.0 weight %, about 2.5 weight %, about 2.0 weight %, about 1.5 weight %, about 1.0 weight %, or about 0.5 weight %; about 0.5 weight % to about 6.0 weight %, about 5.5 weight %, about 5.0 weight %, about 4.5 weight %, about 4.0 weight %, about 3.5 weight %, about 3.0 weight %, about 2.5 weight %, about 2.0 weight %, about 1.5 weight %, or about 1.0 weight %; about 1.0 weight % to about 6.0 weight %, about 5.5 weight %, about 5.0 weight %, about 4.5 weight %, about 4.0 weight %, about 3.5 weight %, about 3.0 weight %, about 2.5 weight %, about 2.0 weight %, or about 1.5 weight %; about 1.5 weight % to about 6.0 weight %, about 5.5 weight %, about 5.0 weight %, about 4.5 weight %, about 4.0 weight %, about 3.5 weight %, about 3.0 weight %, about 2.5 weight %, or about 2.0 weight %; about 2.0 weight % to about 6.0 weight %, about 5.5 weight %, about 5.0 weight %, about 4.5 weight %, about 4.0 weight %, about 3.5 weight %, about 3.0 weight %, or about 2.5 weight %; about 2.5 weight % to about 6.0 weight %, about 5.5 weight %, about 5.0 weight %, about 4.5 weight %, about 4.0 weight %, about 3.5 weight %, or about 3.0 weight %; about 3.0 weight % to about 6.0 weight %, about 5.5 weight %, about 5.0 weight %, about 4.5 weight %, about 4.0 weight %, or about 3.5 weight %; about 3.5 weight % to about 6.0 weight %, about 5.5 weight %, about 5.0 weight %, about 4.5 weight %, or about 4.0 weight %; about 4.0 weight % to about 6.0 weight %, about 5.5 weight %, about 5.0 weight %, or about 4.5 weight %; about 4.5 weight % to about 6.0 weight %, about 5.5 weight %, or about 5.0 weight %; about 5.0 weight % to about 6.0 weight %, or about 5.5 weight %; or about 5.5 weight % to about 6.0 weight %) of one or more sweetening agents (e.g., any one or more of the sweetening agents described herein); and a final total concentration of ash of about 0.15 weight % to about 1.5 weight % (e.g., about 0.15 weight % to about 1.4 weight %, about 1.3 weight %, about 1.2 weight %, about 1.1 weight %, about 1.0 weight %, about 0.9 weight %, about 0.8 weight %, about 0.6 weight %, about 0.5 weight %, about 0.4 weight %, about 0.3 weight %, or about 0.2 weight %; about 0.2 weight % to about 1.5 weight %, about 1.4 weight %, about 1.3 weight %, about 1.2 weight %, about 1.1 weight %, about 1.0 weight %, about 0.9 weight %, about 0.8 weight %, about 0.6 weight %, about 0.5 weight %, about 0.4 weight %, or about 0.3 weight %; about 0.3 weight % to about 1.5 weight %, about 1.4 weight %, about 1.3 weight %, about 1.2 weight %, about 1.1 weight %, about 1.0 weight %, about 0.9 weight %, about 0.8 weight %, about 0.6 weight %, about 0.5 weight %, or about 0.4 weight %; about 0.4 weight % to about 1.5 weight %, about 1.4 weight %, about 1.3 weight %, about 1.2 weight %, about 1.1 weight %, about 1.0 weight %, about 0.9 weight %, about 0.8 weight %, about 0.6 weight %, or about 0.5 weight %; about 0.5 weight % to about 1.5 weight %, about 1.4 weight %, about 1.3 weight %, about 1.2 weight %, about 1.1 weight %, about 1.0 weight %, about 0.9 weight %, about 0.8 weight %, or about 0.6 weight %; about 0.6 weight % to about 1.5 weight %, about 1.4 weight %, about 1.3 weight %, about 1.2 weight %, about 1.1 weight %, about 1.0 weight %, about 0.9 weight %, or about 0.8 weight %; about 0.8 weight % to about 1.4 weight %, about 1.3 weight %, about 1.2 weight %, about 1.1 weight %, about 1.0 weight %, or about 0.9 weight %; about 0.9 weight % to about 1.5 weight %, about 1.4 weight %, about 1.3 weight %, about 1.2 weight %, about 1.1 weight %, or about 1.0 weight %; about 1.0 weight % to about 1.5 weight %, about 1.4 weight %, about 1.3 weight %, about 1.2 weight %, or about 1.1 weight %; about 1.1 weight % to about 1.5 weight %, about 1.4 weight %, about 1.3 weight %, or about 1.2 weight %; about 1.2 weight % to about 1.5 weight %, about 1.4 weight %, or about 1.3 weight %; about 1.3 weight % to about 1.5 weight % or about 1.4 weight %; or about 1.4 weight % to about 1.5 weight %), where the composition does not comprise an animal-derived component.

Also provided are compositions including: about 0.3 g/L to about 1.1 g/L (e.g., any of the subranges of about 0.3 g/L to about 1.1 g/L described in the above paragraph) κ-casein protein (e.g., any of the κ-casein proteins described herein); about 1.25 g/L to about 4.9 g/L (e.g., any of the subranges of about 1.25 g/L to about 4.9 g/L described in the above paragraph) β-casein protein (e.g., any of the β-casein proteins described herein); a final total concentration of one or more lipids (e.g., any of the one or more lipids described herein) of about 0 weight % to about 45 weight % (e.g., any of the subranges of about 0 weight % to about 45 weight % described in the above paragraph); a final total concentration of one or more flavor compounds (e.g., any of the one or more flavor compounds described herein) of about 0.01 weight % to about 6 weight % (e.g., any of the subranges of about 0.01 weight % to about 6 weight % described in the above paragraph); a final total concentration of about 0.1 weight % to about 6 weight % (e.g., any of the subranges of about 0.1 weight % to about 6 weight % described herein) of one or more sweetening agents (e.g., any one or more sweetening agents described herein); and a final total concentration of ash (e.g., any of the exemplary ash described herein) of about 0.15 weight % to about 1.5 weight % (e.g., any of the subranges of about 0.15 weight % to about 1.5 weight % described in the above paragraph), where: the composition: does not include at least one component found in a mammal-produced milk; includes at least one component not present in a mammal-produced milk; and/or includes a higher or lower concentration of at least one component as compared to the concentration of the at least one component in a mammal-produced milk. In some examples of these compositions, the composition includes a higher concentration of at least one component selected from the group of: calcium, phosphate, B complex vitamins, vitamin A, vitamin D, vitamin E, and vitamin K, as compared to the concentration of the one or more components in a mammal-produced milk. In some embodiments of these compositions, the composition does not include at least one component found in a mammal-produced milk selected from the group of: lactose, bacteria, mycobacteria, allergens, viruses, prions, yeast, growth hormones, leukocytes, antibiotics, heavy metals, immunoglobulins, lactoferrin, lactoperoxidase, and lipase. In some examples of these compositions, the composition includes at least one component not present in a mammal-produced milk selected from the group of an artificial sweetener, a plant-derived lipid, a β-casein protein that is non-glycosylated or has a non-mammalian glycosylation pattern, and a κ-casein protein that is non-glycosylated or has a non-mammalian glycosylation pattern.

Also provided are compositions including: about 0.3 g/L to about 1.1 g/L (e.g., any of the subranges of about 0.3 g/L to about 1.1 g/L described in this section) κ-casein protein (e.g., any of the κ-casein proteins described herein) that is unglycosylated or has a non-mammalian glycosylation pattern; about 1.25 g/L to about 4.9 g/L (e.g., any of the subranges of about 1.25 g/L to about 4.9 g/L described in this section) β-casein protein (e.g., any of the β-casein proteins described herein) that is unglycosylated or has a non-mammalian glycosylation pattern; a final total concentration of one or more lipids (e.g., any of the one or more lipids described herein) of about 0 weight % to about 45 weight % (e.g., any of the subranges of about 0 weight % to about 45 weight % described in this section); a final total concentration of one or more flavor compounds (e.g., any of the one or more flavor compounds described herein) of about 0.01 weight % to about 6 weight % (e.g., any of the subranges of about 0.01 weight % to about 6 weight % described in this section); a final total concentration of about 0.1 weight % to about 6 weight % (e.g., any of the subranges of about 0.1 weight % to about 6 weight % described in this section) of one or more sweetening agents (e.g., any of the one or more sweetening agents described herein); and a final total concentration of ash (e.g., any of the ash described herein) of about 0.15 weight % to about 1.5 weight % (e.g., any of the subranges of about 0.15 weight % to about 1.5 weight % described in this section).

Also provided are compositions including a micelle including a κ-casein protein (e.g., any of the κ-casein proteins described herein) and a β-casein protein (e.g., any of the β-casein proteins described herein), where the micelle has a diameter of about 50 nm to about 350 nm (e.g., any of the subranges of the diameter of a micelle described herein), and the κ-casein protein and the β-casein protein are unglycosylated or have a non-mammalian glycosylation pattern. In some embodiments, the composition includes a final concentration of micelles of about 2.0 weight % to about 6 weight % (e.g., about 2.0 weight % to about 5.5 weight %, about 5.0 weight %, about 4.5 weight %, about 4.0 weight %, about 3.5 weight %, about 3.0 weight %, or about 2.5 weight %; about 2.5 weight % to about 6.0 weight %, about 5.5 weight %, about 5.0 weight %, about 4.5 weight %, about 4.0 weight %, about 3.5 weight %, or about 3.0 weight %; about 3.0 weight % to about 6.0 weight %, about 5.5 weight %, about 5.0 weight %, about 4.5 weight %, about 4.0 weight %, or about 3.5 weight %; about 3.5 weight % to about 6.0 weight %, about 5.5 weight %, about 5.0 weight %, about 4.5 weight %, about 4.0 weight %, or about 3.5 weight %; about 3.5 weight % to about 6.0 weight %, about 5.5 weight %, about 5.0 weight %, about 4.5 weight %, or about 4.0 weight %; about 4.5 weight % to about 6.0 weight %, about 5.5 weight %, about 5.0 weight %, about 4.5 weight %, or about 4.0 weight %; about 4.0 weight % to about 6.0 weight %, about 5.5 weight %, about 5.0 weight %, or about 4.5 weight %; about 4.5 weight % to about 5.5 weight %, or about 5.0 weight %; about 5.0 weight % to about 6.0 weight % or 5.5 weight %; or about 5.5 weight % to about 6.0 weight %). In some embodiments of these compositions, the ratio of the β-casein protein to the κ-casein protein in the micelle is about 2.0:1 to about 5.5:1 (e.g., any of the subranges of the ratios about 2.0:1 to about 5.5:1 described for the micelle herein). In some embodiments, these compositions further include: a final total concentration of one or more lipids (e.g., any of the one or more lipids described herein) of about 0 weight % to about 45 weight % (e.g., any of the subranges of about 0 weight % to about 45 weight percent described in this section); a final total concentration of one or more flavor compounds (e.g., any of the one or more flavor compounds described herein) of about 0.01 weight % to about 6 weight % (e.g., any of the subranges of 0.01 weight % to about 6 weight % described in this section); a final total concentration of about 0.1 weight % to about 6 weight % (e.g., any of the subranges of about 0.1 weight % to about 6 weight % described in this section) of one or more sweetening agents (e.g., any one or more of the sweetening agents described herein); and a final total concentration of ash (e.g., any of the ash described herein) of about 0.15 weight % to about 1.5 weight % (e.g., any of the subranges of about 0.15 weight % to about 1.5 weight % described in this section).

In some embodiments of any of the compositions described herein, the one or more lipids are selected from the group consisting of: sunflower oil, coconut oil, tributyrin, mono- and di-glycerides, free fatty acids, and phospholipids. Some examples of any of the compositions described herein further include one or more of: a final concentration of sunflower oil of about 1 weight % to about 28 weight % (e.g., about 1 weight % to about 26 weight %, about 24 weight %, about 22 weight %, about 20 weight %, about 18 weight %, about 16 weight %, about 14 weight %, about 12 weight %, about 10 weight %, about 8 weight %, about 6 weight %, about 4 weight %, or about 2 weight %; about 2 weight % to about 28 weight %, about 26 weight %, about 24 weight %, about 22 weight %, about 20 weight %, about 18 weight %, about 16 weight %, about 14 weight %, about 12 weight %, about 10 weight %, about 8 weight %, about 6 weight %, or about 4 weight %; about 4 weight % to about 28 weight %, about 26 weight %, about 24 weight %, about 22 weight %, about 20 weight %, about 18 weight %, about 16 weight %, about 14 weight %, about 12 weight %, about 10 weight %, about 8 weight %, or about 6 weight %; about 6 weight % to about 28 weight %, about 26 weight %, about 24 weight %, about 22 weight %, about 20 weight %, about 18 weight %, about 16 weight %, about 14 weight %, about 12 weight %, about 10 weight %, or about 8 weight %; about 8 weight 25% to about 28 weight %, about 26 weight %, about 24 weight %, about 22 weight %, about 20 weight %, about 18 weight %, about 16 weight %, about 14 weight %, about 12 weight %, or about 10 weight %; about 10 weight % to about 28 weight %, about 26 weight %, about 24 weight %, about 22 weight %, about 20 weight %, about 18 weight %, about 16 weight %, about 14 weight %, or about 12 weight %; about 12 weight % to about 28 weight %, about 26 weight %, about 24 weight %, about 22 weight %, about 20 weight %, about 18 weight %, about 16 weight %, or about 14 weight %; about 14 weight % to about 28 weight %, about 26 weight %, about 24 weight %, about 22 weight %, about 20 weight %, about 18 weight %, or about 16 weight %; about 16 weight % to about 28 weight %, about 26 weight %, about 24 weight %, about 22 weight %, about 20 weight %, about 18 weight %; about 18 weight % to about 28 weight %, about 26 weight %, about 24 weight %, about 22 weight %, or about 20 weight %; about 20 weight % to about 28 weight %, about 26 weight %, about 24 weight %, about 22 weight %; about 22 weight % to about 28 weight %, about 26 weight %, about 24 weight %; about 24 weight % to about 28 weight % or about 26 weight %; or about 28 weight % to about 30 weight %); a final concentration of coconut oil of about 0.5 weight % to about 14 weight % (e.g., about 0.5 weight % to about 12 weight %, about 10 weight %, about 8 weight %, about 6 weight %, about 4 weight %, about 2 weight %, or about 1 weight %; about 1 weight % to about 14 weight %, about 12 weight %, about 10 weight %, about 8 weight %, about 6 weight %, about 4 weight %, or about 2 weight %; about 2 weight % to about 12 weight %, about 10 weight %, about 8 weight %, about 6 weight %, or about 4 weight %; about 4 weight % to about 14 weight %, about 12 weight %, about 10 weight %, about 8 weight %, or about 6 weight %; about 6 weight % to about 14 weight %, about 12 weight %, about 10 weight %, or about 8 weight %; about 8 weight % to about 14 weight %, about 12 weight %, or about 10 weight %; about 10 weight % to about 14 weight % or 12 weight %; or about 12 weight % to about 14 weight %); a final concentration of tributyrin of about 0.05 weight to about 1.0 weight % (e.g., between about 0.05 weight % to about 0.9 weight %, about 0.8 weight %, about 0.7 weight %, about 0.6 weight %, about 0.5 weight %, about 0.4 weight %, about 0.3 weight %, or about 0.2 weight %; 0.1 weight % to about 1.0 weight %, about 0.9 weight %, about 0.8 weight %, about 0.7 weight %, about 0.6 weight %, about 0.5 weight %, about 0.4 weight %, about 0.3 weight %, or about 0.2 weight %; about 0.2 weight % to about 1.0 weight %, about 0.9 weight %, about 0.8 weight %, about 0.7 weight %, about 0.6 weight %, about 0.5 weight %, or about 0.4 weight %; about 0.4 weight % to about 1.0 weight %, about 0.9 weight %, about 0.8 weight %, about 0.7 weight %, about 0.6 weight %, or about 0.5 weight %; about 0.5 weight % to about 1.0 weight %, about 0.9 weight %, about 0.8 weight %, about 0.7 weight %, or about 0.6 weight %; about 0.6 weight % to about 1.0 weight %, about 0.9 weight %, about 0.8 weight %, or about 0.7 weight %; about 0.7 weight % to about 1.0 weight %, about 0.9 weight %, or about 0.8 weight %; about 0.8 weight % to about 1.0 weight % or about 0.9 weight %; or about 0.9 weight % to about 1.0 weight %); a final total concentration of monoglycerides and diglycerides (e.g., any one or more of the monoglycerides or diglycerides described herein) of about 0.08 weight % to about 1.2 weight % (e.g., 0.08 weight % to about 1.0 weight %, about 0.8 weight %, about 0.6 weight %, about 0.4 weight %, or about 0.2 weight %; about 0.2 weight % to about 1.2 weight %, about 1.0 weight %, about 0.8 weight %, about 0.6 weight %, or about 0.4 weight %; about 0.4 weight % to about 1.2 weight %, about 1.0 weight %, about 0.8 weight %, or about 0.6 weight %; about 0.6 weight % to about 1.2 weight %, about 1.0 weight %, or about 0.8 weight %; about 0.8 weight % to about 1.2 weight % or about 1.0 weight %; or about 1.0 weight % to about 1.2 weight %); and a final total concentration of free fatty acids of about 0.02 weight % to about 0.28 weight %; and a final total concentration of phospholipids (e.g., any one or more of the phospholipids described herein) of about 0.02 weight % to about 0.3 weight % (e.g., about 0.02 weight % to about 0.25 weight %, about 0.20 weight %, about 0.15 weight %, or about 0.10 weight %; about 0.05 weight % to about 0.3 weight %, about 0.25 weight %, about 0.20 weight %, about 0.15 weight %, or about 0.10 weight %; about 0.10 weight % to about 0.30 weight %, about 0.25 weight %, about 0.20 weight %, or about 0.15 weight %; about 0.15 weight % to about 0.30 weight %, about 0.25 weight %, or about 0.20 weight %; about 0.20 weight 20% to about 0.30 weight % or about 0.25 weight %; or about 0.25 weight % to about 0.30 weight %).

In some embodiments of any of the compositions, the free fatty acids include at least one (e.g., two, three, or four) fatty acid selected from the group of: butyric acid, caproic acid, caprylic acid, and capric acid. In some embodiments of any of the compositions, the phospholipids are soy lecithin phospholipids, sunflower lecithin phospholipids, cotton lecithin phospholipids, or rapeseed lecithin phospholipids. In some examples of any of the compositions described herein, the flavor compounds include at least one flavor compound selected from the group of: δ-decalactone, ethyl butyrate, 2-furyl methyl ketone, 2,3-pentanedione, γ-undecalactone, and δ-undecalactone. In some embodiments of any of the compositions described herein, the one or more sweetening agents is a saccharide (e.g., glucose, mannose, maltose, fructose, galactose, lactose, sucrose, monatin, or tagatose). In some examples of any of the compositions described herein, the one or more sweetening agents is an artificial sweetener (e.g., stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, or P-4000).

In some examples of any of the compositions described herein, the ash includes one or more (e.g., two, three, four, five, or six) of: calcium, phosphorus, potassium, sodium, citrate, and chloride. In some embodiments of any of the compositions described herein, the ash comprises one or more (e.g., two or three) of $CaCl_2$), $KH_2PO_4$, and $Na_3$ citrate. Some embodiments of the compositions described herein include: a final concentration of $CaCl_2$) of about 0.05 g/L to about 0.2 g/L (e.g., about 0.05 g/L to about 0.15 g/L, about 0.05 g/L to about 0.10 g/L, about 0.10 g/L to about 0.20 g/L, about 0.10 g/L to about 0.15 g/L, or about 0.15 g/L to about 0.2 g/L); a final concentration of $KH_2PO_4$ of about 0.2 g/L to about 0.4 g/L (e.g., about 0.2 g/L to about 0.35 g/L, about 0.2 g/L to about 0.30 g/L, about 0.2 g/L to about 0.25 g/L, about 0.25 g/L to about 0.4 g/L, about 0.25 g/L to about 0.30 g/L, about 0.30 g/L to about 0.40 g/L, or about 0.30 g/L to about 0.35 g/L, or about 0.35 g/L to about 0.40 g/L); and/or a final concentration of $Na_3$ citrate of about 0.1 g/L to about 0.3 g/L (e.g., 0.1 g/L to about 0.25 g/L, about 0.1 g/L to about 0.20 g/L, about 0.1 g/L to about 0.15 g/L, about 0.15 g/L to about 0.30 g/L, about 0.15 g/L to about 0.25 g/L, about 0.15 g/L to about 0.20 g/L, about 0.20 g/L to about 0.30 g/L, about 0.20 g/L to about 0.25 g/L, or about 0.25 g/L to about 0.30 g/L).

In any of the composition described herein, the κ-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein. In any of the compositions described herein, the β-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein.

In some examples of any of the compositions described herein can further include: a final concentration of α-lactalbumin protein (e.g., any of the α-lactalbumin proteins described herein) of about 0.4 weight % to about 2.5 weight % (e.g., about 0.4 weight % to about 2.0 weight %, about 1.5 weight %, or about 1.0 weight %; about 1.0 weight % to about 2.5 weight %, about 2.0 weight %, or about 1.5 weight %, about 1.5 weight % to about 2.5 weight % or 2.0 weight %; or about 2.0 weight % to about 2.5 weight %), and/or a final concentration of β-lactoglobulin protein (e.g., any of the β-lactoglobulin proteins described herein) of about 2.5 weight % to about 4.5 weight %. In some embodiments of any of the compositions described herein, the α-lactalbumin protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-lactalbumin protein. In some embodiments of any of the compositions described herein, the β-lactoglobulin protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-lactoglobulin protein.

Some embodiments of any of the compositions described herein further include: a final concentration of α-S1-casein protein (e.g., any of the α-S1-casein proteins described herein) of about 11 weight % to about 16 weight % (e.g., about 11 weight % to about 15 weight %, about 14 weight %, about 13 weight %, or about 12 weight %; about 12 weight % to about 16 weight %, about 15 weight %, about 14 weight %, or about 13 weight %; about 13 weight % to about 16 weight %, about 15 weight %, or about 14 weight %; about 14 weight % to about 16 weight % or 15 weight %; or about 15 weight % to about 16 weight %); and/or a final concentration of α-S2-casein protein (e.g., any of the α-S2-casein proteins described herein) of about 2 weight % to about 5 weight % (e.g., about 2 weight % to about 4.5 weight %, about 4.0 weight %, about 3.5 weight %, about 3.0 weight %, or about 2.5 weight %; about 2.5 weight % to about 5.0 weight %, about 4.5 weight %, about 4.0 weight %, about 3.5 weight %, or about 3.0 weight %; about 3.0 weight % to about 5.0 weight %, about 4.5 weight %, about 4.0 weight %, or about 3.5 weight %; about 3.5 weight % to about 5 weight %, about 4.5 weight %, or about 4.0 weight %; about 4.0 weight % to about 5.0 weight % or 4.5 weight %; or about 4.5 weight % to about 5.0 weight %).

In some examples of any of the compositions described herein, the α-S1-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S1-casein protein; and/or the α-S2-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S2-casein protein.

Some examples of any of the compositions described herein further include one or more (e.g., two or three) of serum albumin (e.g., any of the serum albumin proteins described herein), lactoferrin (e.g., any of the lactoferrin proteins described herein), and transferrin (e.g., any of the transferrin proteins described herein). In some examples of any of the compositions described herein, the serum albumin can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth serum albumin; the lactoferrin can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth lactoferrin; and/or the transferrin can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth transferrin protein.

In some examples of any of the compositions described herein, the composition further includes one or more color balancing agents (e.g., any of the coloring agents described herein, e.g., β-carotene or annatto).

Any of the compositions described herein can have a pH of about 6.2 to about 7.2 (e.g., about 6.2 to about 7.0, about 6.2 to about 6.8, about 6.2 to about 6.6, about 6.2 to about 6.4, about 6.4 to about 7.2, about 6.4 to about 7.0, about 6.4 to about 6.8, about 6.4 to about 6.6, about 6.6 to about 7.2, about 6.6 to about 7.0, about 6.6 to about 6.8, about 6.8 to about 7.2, about 6.8 to about 7.0, or about 7.0 to about 7.2).

In various embodiments, the milk protein components comprise about 0.5% about 1%, about 1.5%, about 2%, about 2.5%, about 3%, about 3.5%, about 4%, about 4.5%, about 5%, about 6% milk protein by dry weight or total weight. In some embodiments, the compositions can comprise about 0.5-2.5%, about 1-2%, about 2-3%, or about 4-10% protein by dry weight or total weight. In particular embodiments, the compositions can comprise about 10-15% protein by dry weight or total weight.

A wide range of caseins including casein with substantial homology to the wildtype casein, variants, mutants of casein are expressed and incorporated as a component of milk protein.

Dry Compositions

Also provided are powder compositions including: a final concentration of κ-casein protein (e.g., any of the α-casein proteins described herein) of about 3.6 weight % to about 5.4 weight % (e.g., about 3.6 weight % to about 5.2 weight %, about 5.0 weight %, about 4.8 weight %, about 4.6 weight %, about 4.4 weight %, about 4.2 weight %, about 4.0 weight %, or about 3.8 weight %; about 3.8 weight % to about 5.4 weight %, about 5.2 weight %, about 5.0 weight %, about 4.8 weight %, about 4.6 weight %, about 4.4 weight %, about 4.2 weight %, or about 4.0 weight %; about 4.0 weight % to about 5.4 weight %, about 5.2 weight %, about 5.0 weight %, about 4.8 weight %, about 4.6 weight %, about 4.4 weight %, or about 4.2 weight %; about 4.2 weight % to about 5.2 weight %, about 5.2 weight %, about 5.0 weight %, about 4.8 weight %, about 4.6 weight %, or about 4.4 weight %; about 4.8 weight % to about 5.4 weight %, about 5.2 weight %, or about 5.0 weight %; about 5.0 weight % to about 5.4 weight % or about 5.2 weight %; or about 5.2 weight % to about 5.4 weight %); a final concentration of β-casein protein (e.g., any of the β-casein proteins described herein) of about 16.3 weight % to about 24.5 weight %; 16.3 weight % to about 22 weight %, about 20 weight %, or about 18 weight %; about 18 weight % to about 24.5 weight %, about 22 weight %, or about 20 weight %; about 20 weight % to about 24.5 weight % to about 22 weight %; or about 22 weight % to about 24.5 weight %); a final concentration of a sweetening agent (e.g., any one or more of the sweetening agents described herein) of about 35 weight % to about 40 weight % (e.g, about 35 weight % to about 39 weight %, about 38 weight %, about 37 weight %, or about 36 weight %; about 36 weight % to about 40 weight %, about 39 weight %, about 38 weight %, or about 37 weight %; about 37 weight % to about 40 weight %, about 39 weight %, or about 38 weight %; about 38 weight % to about 40 weight % or 39 weight %; or about 39 weight % to about 40 weight %); a final concentration of one or more lipids (e.g., any of the one or more lipids described herein) of about 25 weight % to about 30 weight % (e.g., about 25 weight % to about 29 weight %, about 28 weight %, about 27 weight %, or about 26 weight %; about 26 weight % to about 30 weight %, about 29 weight %, about 28 weight %, or about 27 weight %; about 27 weight % to about 30 weight %, about 29 weight %, or about 28 weight %; about 28 weight % to about 30 weight % or about 29 weight %; or about 29 weight % to about 30 weight %); a final concentration of ash (e.g., any of the ash described herein) of about 5 weight % to about 7 weight % (e.g., about 5 weight % to about 6.5 weight %, about 6.0 weight %, or about 5.5 weight %; about 5.5 weight % to about 7.0 weight %, about 6.5 weight %, or about 6.0 weight %; about 6.0 weight % to about 7.0 weight % or about 6.5 weight %; or about 6.5 weight % to about 7.0 weight %); and a final concentration of water of about 2 weight % to about 5 weight % (e.g., about 2 weight % to about 4 weight or about 3 weight %; about 3 weight % to about 5 weight % or about 4 weight %; or about 4 weight % to about 5 weight %), where the κ-casein protein is an unglycosylated and/or has a non-mammalian glycosylation pattern, and/or the β-casein protein is an unglycosylated and/or has a non-mammalian glycosylation pattern.

Any of the powder compositions can contain any of the components described in any of the compositions described herein (e.g., one or more of any of the color matching agents, α-S1-casein proteins, α-S2-casein proteins, α-lactalbumin proteins, β-lactoglobulin proteins, lactoferrin proteins, transferrin proteins, and serum albumin protein described herein at any of the concentrations described herein for each component, respectively).

Supplemented Milk Compositions

Also provided herein are compositions including: a mammalian-produced milk or a processed mammal-produced milk; and one or more (e.g., two or three) of a κ-casein protein that is unglycosylated or has an non-mammalian glycosylation pattern; a β-casein protein that is unglycosylated or has an non-mammalian glycosylation pattern; or a micelle including a κ-casein protein that is unglycosylated or has an non-mammalian glycosylation pattern and a β-casein protein that is unglycosylated or has an non-mammalian glycosylation pattern.

In some examples, the composition includes a mammal-produced milk or a processed mammalian-produced milk and a κ-casein protein that is unglycosylated or has a non-mammalian glycosylation pattern. In some examples, the composition includes a mammal-produced milk or a processed mammalian-produced milk and a β-casein protein that is unglycosylated or has a non-mammalian glycosylation pattern. In other examples, the composition includes a mammal-produced milk or a processed mammalian-produced milk and a micelle including a κ-casein protein that is unglycosylated or has a non-mammalian glycosylation pattern and a β-casein protein that is unglycosylated or has a non-mammalian glycosylation pattern.

In some examples, the final concentration of the κ-casein protein that is unglycosylated or has a non-mammalian glycosylation pattern or the final concentration of the β-casein protein that is unglycosylated or has a non-mammalian glycosylation pattern in the composition is: 0.02 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, about 0.2 weight %, or about 0.1 weight %; about 0.1 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, or about 0.2 weight %; about 0.2 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, or about 0.4 weight %; about 0.8 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, or about 1.0 weight %; about 1.0 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, or about 1.2 weight %; about 1.2 weight % to about 3.0 weight %, about 2.8 weight %, about 2.6 weight %, about 2.4 weight %, about 2.2 weight %, about 2.0 weight %, about 1.8 weight %, about 1.6 weight %, or about 1.4 weight %; about 1.4 weight % to about 3.0 weight %, about 2.8 weight %, about 2.6 weight %, about 2.4 weight %, about 2.2 weight %, about 2.0 weight %, about 1.8 weight %, or about 1.6 weight %; about 1.6 weight % to about 3.0 weight %, about 2.8 weight %, about 2.6 weight %, about 2.4 weight %, about 2.2 weight %, about 2.0 weight %, or about 1.8 weight %; about 1.8 weight % to about 3.0 weight %, about 2.8 weight %, about 2.6 weight %, about 2.4 weight %, about 2.2 weight %, or about 2.0 weight %; about 2.0 weight % to about 3.0 weight %, about 2.8 weight %, about 2.6 weight %, about 2.4 weight %, or about 2.2 weight %; about 2.2 weight % to about 3.0 weight %, about 2.8 weight %, about 2.6 weight %, or about 2.4 weight %; about 2.4 weight % to about 3.0 weight %, about 2.8 weight %, or about 2.6 weight %; about 2.6 weight % to about 3.0 weight % or about 2.8 weight %; or about 2.8 weight % to about 3.0 weight % (of the final composition).

In some compositions, the final concentration of the κ-casein protein that is unglycosylated and/or has a non-mammalian glycosylation pattern in the composition is about 0.02 weight % to about 0.6 weight % (e.g., about 0.02 weight % to about 0.5 weight %, about 0.02 weight % to about 0.4 weight %, about 0.02 weight % to about 0.3 weight %, about 0.02 weight % to about 0.2 weight %, about 0.02 weight % to about 0.1 weight %, about 0.1 weight % to about 0.5 weight %, about 0.1 weight %, to about 0.4 weight %, about 0.1 weight % to about 0.3 weight %, about 0.1 weight % to about 0.2 weight %, about 0.2 weight % to about 0.5 weight %, about 0.2 weight % to about 0.4 weight %, about 0.2 weight % to about 0.3 weight %, about 0.3 weight % to about 0.5 weight %, about 0.3 weight % to about 0.4 weight %, or about 0.4 weight % to about 0.5 weight %); and the final concentration of β-casein that is unglycosylated and/or has a non-mammalian glycosylation pattern in the composition is about 0.02 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, or about 0.2 weight %; about 0.2 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, or about 0.4 weight %; about 0.4 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, or about 0.6 weight %; about 0.6 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, or about 0.8 weight %; about 0.8 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, or about 1.0 weight %; about 1.0 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, or about 1.2 weight %; about 1.2 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, or about 1.4 weight %; about 1.4 weight % to about 4.0 weight %, about 3.8 weight %, about 3.6 weight %, about 3.4 weight %, about 3.2 weight %, about 3.0 weight %, about 2.8 weight %, about 2.6 weight 10%, about 2.4 weight %, about 2.2 weight %, about 2.0 weight %, about 1.8 weight %, or about 1.6 weight %; about 1.6 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, or about 1.8 weight %; about 1.8 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, or about 2.0 weight %; about 1.8 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, or about 2.0 weight %; about 2.0 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, or about 2.2 weight %; about 2.2 weight % to about 4.0 weight %, about 3.8 weight %, about 3.6 weight %, about 3.4 weight %, about 3.2 weight %, about 3.0 weight %, about 2.8 weight %, about 2.6 weight %, or about 2.4 weight %; about 2.4 weight % to about 4.0 weight %, about 3.8 weight %, about 3.6 weight %, about 3.4 weight %, about 3.2 weight %, about 3.0 weight %, about 2.8 weight %, or about 2.6 weight %; about 2.6 weight % to about 4.0 weight %, about 3.8 weight %, about 3.6 weight %, about 3.4 weight %, about 3.2 weight %, about 3.0 weight %, or about 2.8 weight %; about 2.8 weight % to about 4.0 weight %, about 3.8 weight %, about 3.6 weight %, about 3.4 weight %, about 3.2 weight %, or about 3.0 weight %; about 3.0 weight % to about 4.0 weight %, about 3.8 weight %, about 3.6 weight %, about 3.4 weight %, or about 3.2 weight %; about 3.2 weight % to about 4.0 weight %, about 3.8 weight %, about 3.6 weight %, or about 3.4 weight %; about 3.4 weight % to about 4.0 weight %, about 3.8 weight %, or about 3.6 weight %; about 3.6 weight % to about 4.0 weight % or about 3.8 weight %; or about 3.8 weight % to about 4.0 weight %.

In some examples, the final concentration of micelles including a κ-casein protein that is unglycosylated or has an non-mammalian glycosylation pattern and a β-casein protein that is unglycosylated or has an non-mammalian glycosylation pattern in the composition is: 0.02 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, about 0.2 weight %, or about 0.1 weight %; about 0.1 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, or about 0.2 weight %; about 0.2 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, or about 0.4 weight %; about 0.8 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, or about 1.0 weight %; about 1.0 weight % to about 3.0 weight %, about 2.8 weight %, about 2.6 weight %, about 2.4 weight %, about 2.2 weight 25%, about 2.0 weight %, about 1.8 weight %, about 1.6 weight %, about 1.4 weight %, or about 1.2 weight %; about 1.2 weight % to about 3.0 weight %, about 2.8 weight %, about 2.6 weight %, about 2.4 weight %, about 2.2 weight %, about 2.0 weight %, about 1.8 weight %, about 1.6 weight %, or about 1.4 weight %; about 1.4 weight % to about 3.0 weight %, about 2.8 weight %, about 2.6 weight %, about 2.4 weight %, about 2.2 weight %, about 2.0 weight %, about 1.8 weight %, or about 1.6 weight %; about 1.6 weight % to about 3.0 weight %, about 2.8 weight %, about 2.6 weight %, about 2.4 weight %, about 2.2 weight %, about 2.0 weight %, or about 1.8 weight %; about 1.8 weight % to about 3.0 weight %, about 2.8 weight %, about 2.6 weight %, about 2.4 weight %, about 2.2 weight %, or about 2.0 weight %; about 2.0 weight % to about 3.0 weight %, about 2.8 weight %, about 2.6 weight %, about 2.4 weight %, or about 2.2 weight %; about 2.2 weight % to about 3.0 weight %, about 2.8 weight %, about 2.6 weight %, or about 2.4 weight %; about 2.4 weight % to about 3.0 weight %, about 2.8 weight %, or about 2.6 weight %; about 2.6 weight % to about 3.0 weight % or about 2.8 weight %; or about 2.8 weight % to about 3.0 weight % (of the final composition).

Nucleic Acids and Vectors

Also provided are nucleic acids (e.g., vectors) that include: a promoter (e.g., a yeast, bacterial, or a mammalian promoter); a sequence encoding a signal sequence; a sequence encoding a milk protein (e.g., any of the exemplary sequences described herein); and a yeast termination sequence, where the promoter is operably linked to the signal sequence, the signal sequence is operably linked to the sequence encoding the milk protein, and the terminal sequence is operably linked to the sequence encoding the milk protein. In some examples of these nucleic acids, the promoter is a constitutive promoter or an inducible promoter. Non-limiting examples of promoters are described herein. Additional promoters that can be used in these nucleic acids are known in the art.

The signal sequence in any of the vectors described herein can be a signal sequence from the encoded milk protein or a different milk protein, or is a signal sequence from a yeast mating factor (e.g., any alpha mating factor). In some examples, the encoded milk protein is selected from the group of: β-casein (e.g., any of the β-casein proteins described herein), κ-casein (e.g., any of the κ-casein proteins described herein), α-S1-casein (e.g., any of the α-S1-casein proteins described herein), α-S2-casein (e.g., any of the α-S2-casein proteins described herein), α-lactalbumin (e.g., any of the α-lactalbumin proteins described herein), β-lactoglobulin (e.g., any of the β-lactoglobulin proteins described herein), lactoferrin (e.g., any of the lactoferrin proteins described herein), or transferrin (e.g., any of the transferrin proteins described herein). Additional signal sequences that can be used in the present vectors are known in the art.

Any of the nucleic acids described herein can further include a bacterial origin of replication. Any of the nucleic acids described herein can further include a selection marker (e.g., an antibiotic resistance gene). The sequences of bacterial origin of replication are known in the art. Non-limiting examples of antibiotic resistance genes are described herein. Additional examples of resistance genes are known in the art.

Non-limiting examples of termination sequences are described herein. Additional examples of termination sequences are known in the art.

Some embodiments of the nucleic acids provided herein further include: an additional promoter sequence (e.g., any of the exemplary promoters described herein); an additional sequence encoding a signal sequence (e.g., any of the exemplary signal sequences described herein); a sequence encoding an additional milk protein (e.g., any of the exemplary sequences encoding a milk protein described herein); and an additional yeast termination sequence (e.g. any of the exemplary yeast termination sequences described herein), where the additional promoter sequence is operably linked to the additional sequence encoding a signal sequence, the sequence encoding the signal sequence is operably linked to the sequence encoding the additional milk protein, and the sequence encoding the additional milk protein is operably linked to the additional yeast terminal sequence. The additional milk protein can be, e.g., β-casein (e.g., any of the β-casein proteins described herein), κ-casein (e.g., any of the κ-casein proteins described herein), α-S1-casein (e.g., any of the α-S1-casein proteins described herein), α-S2-casein (e.g., any of the α-S2-casein proteins described herein), α-lactalbumin (e.g., any of the α-lactalbumin proteins described herein), β-lactoglobulin (e.g., any of the β-lactoglobulin proteins described herein), lactoferrin (e.g., any of the lactoferrin proteins described herein), or transferrin (e.g., any of the transferrin proteins described herein). In some embodiments, the nucleic acid includes a sequence encoding a β-casein and a sequence encoding a κ-casein. The promoter and the additional promoter can be the same or different. The yeast termination sequence and the additional yeast terminal sequence can be the same or different. The signal sequence and the additional signal sequence can be the same or different.

The present invention also encompasses a vector containing the isolated DNA sequence encoding casein or whey polypeptide and host cells comprising the vector. The vector may further comprise an isolated DNA sequence comprising a nucleotide sequence encoding a casein, wherein the nucleotide sequence is operably linked to a promoter, a nucleotide sequence encoding an alpha mating factor, or a variant thereof, a nucleotide sequence encoding a bacterial resistance marker and a transcription terminator. One or more of suitable promoters are utilized for expression of the genes encoding casein or whey proteins may be any promoter which is functional in the host cell and is able to elicit expression of the product encoded by the gene. Suitable promoters include, for example, PLAC4-PBI, T7, Ptac, Pgal, λPL, λPR, bla, spa, Adh, CYC, TDH3, ADH1 and CLB1.

Introducing Nucleic Acids into a Cell

Methods of introducing nucleic acids (e.g., any of the nucleic acids described herein) into a cell to generate a host cell are well-known in the art. Non-limiting examples of techniques that can be used to introduce a nucleic acid into a cell include: calcium phosphate transfection, dendrimer transfection, liposome transfection (e.g., cationic liposome transfection), cationic polymer transfection, electroporation, cell squeezing, sonoporation, optical transfection, protoplast fusion, impalefection, hyrodynamic delivery, gene gun, magnetofection, and viral transduction.

One skilled in the art would be able to select one or more suitable techniques for introducing the nucleic acids into a cell based on the knowledge in the art that certain techniques for introducing a nucleic acid into a cell work better for different types of host cells. Exemplary methods for introducing a nucleic acid into a yeast cell are described in Kawai et al., *Bioeng. Bugs* 1:395-403, 2010.

Host Cells

Also provided herein a host cells including any of the nucleic acids (e.g., vectors) described herein. In some examples, the nucleic acid described herein is stably integrated within the genome (e.g., a chromosome) of the host cell. In other examples, the nucleic acid described herein is not stably integrated within the genome of the host cell.

In some embodiments, the host cell is a yeast strain or a bacterial strain. In some embodiments, the host cell can be, e.g., a yeast strain selected from the group of: a *Kluyveromyces* sp., *Pichia* sp., *Saccharomyces* sp., *Tetrahymena* sp., *Yarrowia* sp., *Hansenula* sp., *Blastobotrys* sp., *Candida* sp., *Zygosaccharomyces* sp., and *Debaryomyces* sp. Additional non-limiting examples of yeast strains that can be used as the host cell are *Kluyveromyces lactis, Kluyveromyces marxianus, Saccharomyces cerevisiae*, and *Pichia pastoris*. Additional species of yeast strains that can be used as host cells are known in the art.

In some examples, the host cell can be a protozoa, such as, e.g., *Tetrahymena thermophile, T. hegewischi, T. hyperangularis, T. malaccensis, T. pigmentosa, T. pyriformis*, and *T. vorax*.

It is an object of the invention to isolate milk protein components by recombinantly expressing them in any of the host cells provided herein.

Methods of Producing a Recombinant Milk Protein and Methods of Making a Micelle

Also provided are methods of producing a recombinant milk protein (e.g., one or more of any of the milk proteins described herein) that is unglycosylated or has a non-mammalian glycosylation pattern that include: culturing any of the host cells described herein in a culture medium under conditions sufficient to allow for secretion of the milk protein that is unglycosylated or has a non-mammalian glycosylation pattern; and harvesting the milk protein that is unglycosylated or has a non-mammalian glycosylation pattern from the culture medium. Suitable culture medium for use in these methods are known in the art. Culture conditions sufficient to allow for secretion of a milk protein are also known in the art. The host cells used in these methods can be any of the host cells described herein. The host cells can include any of the nucleic acids described herein. The recombinant milk protein produced can be one or more of: β-casein (e.g., any of the β-casein proteins described herein), κ-casein (e.g., any of the κ-casein proteins described herein), α-S1-casein (e.g., any of the α-S1 caseins described herein), α-S2-casein (e.g., any of the α-S2-caseins described herein), α-lactalbumin (e.g., any of the α-lactalbumin proteins described herein), β-lactoglobulin (e.g., any of the β-lactoglobulin proteins described herein), lactoferrin (e.g., any of the lactoferrin proteins described herein), transferrin (e.g., any of the transferrin proteins described herein), and serum albumin (e.g., any of the serum albumin proteins described herein). Some of these methods further include isolating (e.g., purifying) the recombinant milk protein from the culture medium. Methods of isolating (e.g., purifying) a recombinant milk protein from a liquid are well-known in the art. Exemplary methods for isolating (e.g., purifying) recombinant milk proteins are described in Imafidon et al., *Crit. Rev. Food Sci. Nutrition* 37:663-669, 1997).

Also provided are methods of producing a micelle including a β-casein (e.g., any of the β-casein proteins described herein) that is unglycosylated or has a non-mammalian glycosylation pattern and a κ-casein (e.g., any of the κ-casein proteins described herein) that is unglycosylated or has a non-mammalian glycosylation pattern, that include: culturing any of the host cells described herein in a culture medium under conditions sufficient to allow for release of the micelle from the host cell, where the host cell comprises nucleic acid including a sequence that encodes a β-casein and a sequence that encodes a κ-casein; and harvesting the micelle from the culture medium. Suitable culture medium for use in these methods are known in the art. The host cells used in these methods can be any of the host cells described herein. The host cells can include any of the nucleic acids described herein. The micelles produced can be any of the micelles described herein (and can have any of the physical characteristics of micelles described herein). Some of these methods further include isolating (e.g., purifying) the micelle from the culture medium. Methods of isolating (e.g., purifying) a micelle from a liquid are well-known in the art (e.g., ultracentrifigation).

Exemplary details of culturing yeast host cells are described in Idiris et al., *Appl. Microbiol. Biotechnol.* 86:403-417, 2010; Zhang et al., *Biotechnol. Bioprocess. Eng.* 5:275-287, 2000; Zhu, *Biotechnol. Adv.* 30:1158-1170, 2012; Li et al., *MAbs* 2:466-477, 2010.

It is an object of the invention to express one or more different forms of casein for application into various types of dairy substitute products. Casein subunits such as α-s1-casein, α-s2-casein, β-casein and κ-casein differ by one or more amino acid changes. In certain embodiments, the methods and compositions comprise incorporation of bovine casein such as α-s1-casein, α-s2-casein, β-casein and κ-casein. In other embodiments, the methods and compositions comprise incorporation of human casein such as β-casein and κ-casein. See U.S. Pat. No. 5,942,274. In alternative embodiments, casein is selected from one or more following sources including but not limited to: bovine, human, buffalo, camel, goat, sheep, horse, dolphin, whale, mountain goat and pig.

Also provided are methods for producing the milk protein components that can include, e.g., using a plasmid or construct of the invention as described in Example 1. This method comprises preparing the plasmid of interest, inserting the plasmid into an appropriate host cell, culturing the host cell for a suitable time and under suitable conditions such that the protein of interest is expressed, and then purifying the protein.

Proteins can be separated on the basis of their molecular weight, for example, by size exclusion chromatography, ultrafiltration through membranes, or density centrifugation. In some embodiments, the proteins can be separated based on their surface charge, for example, by isoelectric precipitation, anion exchange chromatography, or cation exchange chromatography. Proteins also can be separated on the basis of their solubility, for example, by ammonium sulfate precipitation, isoelectric precipitation, surfactants, detergents or solvent extraction. Proteins also can be separated by their affinity to another molecule, using, for example, hydrophobic interaction chromatography, reactive dyes, or hydroxyapatite. Affinity chromatography also can include using antibodies having specific binding affinity for the protein, nickel NTA for His-tagged recombinant proteins, lectins to bind to sugar moieties on a glycoprotein, or other molecules which specifically binds the protein.

Generally, centrifugation at an optimum pH yields purification efficiency >95%. Isoelectric point for the native caseins and whey proteins are known. In nature, the pH is 4.91 for bovine α-s1-casein, pH 4.1 for bovine α-s2-casein, pH 4.5 for bovine β-casein, pH 4.1 for bovine κ-casein, pH 4.2 for bovine α-lactalbumin, and pH 5.2 for bovine β-lactoglobulin. The recombinantly produced casein and whey can differ in terms of its phosphate groups and sugar groups. Other methods for protein purification include membrane filtration to remove any potential bacteria or contaminants, followed by lyophilization for protein isolation.

Preferably, the methods and compositions provide for a production cost that is competitive at or below $1,000/kg, $500/kg, $10/kg, $1.0/kg, $0.10/kg, $0.010/kg or $0.0010/kg of milk protein component. In more preferred embodiments, the cost is below $0.009, $0.007, $0.006, $0.005/kg of milk protein component.

Methods of Supplementing a Mammal-Produced Milk

Also provided herein are methods of supplementing a mammal-produced milk that include providing a mammalian-produced milk or a processed mammalian-produced milk; and mixing into the milk at least one of: a β-casein protein (e.g., any of the β-casein proteins described herein) that is unglycosylated or has a non-mammalian glycosylation pattern; a κ-casein protein (e.g., any of the κ-casein proteins described herein) that is unglycosylated or has a non-mammalian glycosylation pattern; and a micelle (e.g., any of the micelles described herein) comprising a β-casein protein (e.g., any of the β-casein proteins described herein) that is unglycosylated or has a non-mammalian glycosylation pattern, and a κ-casein protein (e.g., any of the casein proteins described herein) that is unglycosylated or has a non-mammalian glycosylation pattern.

One or more of the β-casein protein, the κ-casein protein, and the micelles can be mixed into the milk to achieve any of the exemplary final concentrations of the β-casein protein, the κ-casein protein, and the micelles in a composition described in the section called "Supplemented Milk Compositions" herein. Methods of mixing are well known in the art. As one of skill in the art can appreciate, additional components described herein can also be mixed into the milk (e.g., any component described herein without limitation).

Methods of Making a Composition

Also provided are methods of producing a composition that include: sonicating a liquid including a protein mixture comprising β-casein protein (e.g., any of the β-casein proteins described herein) and casein κ protein (e.g., any of the κ-casein proteins described herein), or including micelles comprising β-casein protein (e.g., any of the β-casein proteins described herein) and κ-casein protein (e.g., any of the κ-casein proteins described herein); mixing ash (e.g., any of the ash described herein) into the liquid; adding to the liquid a mixture of one or more lipids (e.g., any of the one or more liquids described herein), one or more flavor compounds (e.g., any of the one or more flavor compounds described herein), and one or more color balancing agents (e.g., any of the one or more color balancing agents described herein), and sonicating the liquid; and adding to the liquid one or more sweetening agents (e.g., one or more of any of the sweetening agents described herein), thereby producing the composition.

In some examples of these methods, the β-casein protein is unglycosylated or has a non-mammalian glycosylation pattern, and/or the κ-casein protein is unglycosylated or has a non-mammalian glycosylation pattern. In some examples of these methods, the ash includes one or more of: calcium, phosphorus, potassium, sodium, citrate, and chloride. In some examples of any of these methods, the ash added includes one or more (e.g., two or three) of $CaCl_2$), $KH_2PO_4$, and $Na_3$ citrate.

In some examples of these methods, the one or more lipids comprises at least one (e.g., two, three, four, five, six, or seven) of: sunflower oil, coconut oil, tributyrin, mono- and di-glycerides, free fatty acids, and phospholipids. In some examples of these methods, the free fatty acids comprise at least one fatty acid selected from the group of: butyric acid, caproic acid, caprylic acid, and capric acid. In some examples of these methods, the phospholipids are soy lecithin phospholipids, sunflower lecithin phospholipids, cotton lecithin phospholipids, or rapeseed lecithin phospholipids. In some embodiments of these methods, the flavor compounds include at least one (e.g., two, three, four, five, or six) flavor compound selected from the group of: δ-decalactone, ethyl butyrate, 2-furyl methyl ketone, 2,3-pentanedione, γ-undecalactone, and δ-undecalactone.

In some examples of these methods, the one or more coloring balancing agent is β-carotene or annatto. In some embodiments of these methods, the one or more sweetening agents is a saccharide (e.g., glucose, mannose, maltose, fructose, galactose, lactose, sucrose, monatin, or tagatose) or an artificial sweetener (e.g., stevia, aspartame, cyclamate, saccharin, sucralose, mogrosides, brazzein, curculin, erythritol, glycyrrhizin, inulin, isomalt, lacititol, mabinlin, malitiol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, or P-4000).

The pH of the resulting composition can be between about pH 6.2 and about pH 7.4 (e.g., about 6.2 to about 7.2; about 6.2 to about 7.0, about 6.2 to about 6.8, about 6.2 to about 6.6, about 6.2 to about 6.4, about 6.4 to about 7.2, about 6.4 to about 7.0, about 6.4 to about 6.8, about 6.4 to about 6.6, about 6.6 to about 7.2, about 6.6 to about 7.0, about 6.6 to about 6.8, about 6.8 to about 7.2, about 6.8 to about 7.0, or about 7.0 to about 7.2).

In any of these methods, the β-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein; and/or the κ-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein.

In some embodiments of these methods, the protein mixture further comprises one or more proteins selected from the group of: α-lactalbumin (e.g., any of the α-lactalbumin proteins described herein), β-lactoglobulin (e.g., any of the β-lactoglobulin proteins described herein), α-S1-casein (e.g., any of the α-S1-casein proteins described herein), α-S2-casein (e.g., any of the α-S2-casein proteins described herein), lactoferrin (e.g., any of the lactoferrin proteins described herein), transferrin (e.g., any of the transferrin proteins described herein), and serum albumin (e.g., any of the serum albumin proteins described herein).

As one of skill in the art can appreciate, the amount of each component used in these methods can be calculated in order to produce any of the compositions described herein.

Methods of Making Butter, Cheese, Caseinate, or Yogurt

Also provided herein are methods of making butter, cheese, caseinate, or yogurt that include providing any of the compositions provided herein; and producing the butter, cheese, caseinate, or yogurt using any of the composition provided herein as a starting material.

Methods for making butter, cheese, caseinate, or yogurt are well-known in the art. See, e.g., Scott, Cheesemaking Practice, Kluwer Academic/Plenum Publishers, New York, NY, 1998; U.S. Pat. No. 4,360,535 (which describes methods of making creams); U.S 285,878 (which described methods of making butter);

Kits

Also provided are kits that include: (a) a mixture of one or more milk proteins (e.g., any of the milk proteins described herein, including any one or more of the β-casein proteins, κ-casein proteins, α-S1-proteins, α-S2-proteins, α-lactalbumin proteins, β-lactoglobulin proteins, lactoferrin proteins, transferrin proteins, and serum albumin proteins described herein), one or more lipids (e.g., any of one or more of the lipids described herein), and one or flavor compounds (e.g., any one or more of the flavor compounds described herein); and (b) a mixture of ash (e.g., any of the ash described herein) and at least one sweetening agent (e.g., any one or more of the sweetening agents described herein). In some examples of these kits, the one or more milk proteins are cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth milk proteins.

In some examples of these kits, the one or more fats are selected from the group of: sunflower oil, coconut oil, tributyrin, mono- and di-glycerides, free fatty acids, and phospholipids. The fatty acids present in the kit can include at least one fatty acid selected from the group of: butyric acid, caproic acid, caprylic acid, and capric acid. The phospholipids in the kit can be soy lecithin phospholipids, sunflower lecithin phospholipids, cotton lecithin phospholipids, or rapeseed lecithin phospholipids.

The flavor compounds in the kit can include at least one flavor compound selected from the group of: δ-decalactone, ethyl butyrate, 2-furyl methyl ketone, 2,3-pentanedione, γ-undecalactone, and δ-undecalactone.

In some embodiments of the kit, the mixture in (a) further includes one or more color balancing agent (e.g., any of the color balancing agents described herein, e.g., β-carotene or annatto).

In some examples of the kits, the one or more sweetening agents is a saccharide (e.g., glucose, mannose, maltose, fructose, galactose, lactose, sucrose, monatin, or tagatose) or an artificial sweetener (e.g., stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, or P-4000).

The kits can include an ash including one or more of: calcium, phosphorus, potassium, sodium, citrate, and chloride. In some examples, the ash in the kit includes one or more (e.g., two or three) of $CaCl_2$), $KH_2PO_4$, and $Na_3$ citrate.

In some embodiments of the kits, the mixture in (a) is provided in a light-sealed and airtight package (e.g., a metal foil, e.g., an aluminum foil), and/or the mixture in (b) is provided in an airtight package (e.g., a sealed plastic bag).

Some examples of the kits further include instructions for making any of the compositions described herein.

Also provided herein are kits including at least one nucleic acid described herein.

Modulating Flavor Profiles

Sensory impressions such as "feed," "barny," or "unclean," are described as flavor descriptions that are absorbed from the food ingested by the cow and from the odours in its surroundings. Others develop through microbial action due to growth of bacteria in large numbers. Chemical changes can also take place through enzyme action, contact with metals (such as copper), or exposure to sunlight or strong fluorescent light. Quality-control directors are constantly striving to avoid off-flavors in milk and other dairy foods. It is, therefore, an object of the invention to reduce, eliminate or even mask the undesirable flavors and odor of various dairy products.

In certain preferred aspects of the present invention, varying the fat content can alter the flavors and odor of various dairy substitute products. For example, increasing the butyric acid content can change a flavor profile of a non-dairy cheese to a flavor profile similar to parmesan cheese. In other embodiments, modulating the triglycerides such caproic, capric, and/or caprylic acid results in a flavor profile similar to goat cheese. Accordingly, modulating the triglycerides with the ratios of fatty acid components provides different flavor profiles that can be fine-tuned to resemble those of various desirable dairy-food products.

Similarly, the methods and compositions provide for minimizing one or more undesirable aromas by modulating various triglycerides incorporated into the dairy substitute products.

In certain aspects flavor profile is modulated by incorporating synthetic short-chain triglycerides combined with plant-based oils e.g., sunflower oil, in desired combinations. For example a mixture of [C18 C18 C6] and [C18 C6 C18] provides a different flavor profile than a mixture of [C18 C4 C4] and [C18 C10 C10].

Dairy Substitute Products

A wide variety of dairy substitute products can be made using the methods and compositions of the present invention. Such products include without limitation, milk, whole milk, buttermilk, skim milk, infant formula, condensed milk, dried milk, evaporated milk, butter, clarified butter, cream and various types of cheese.

The dairy substitute products can also be incorporated into various food applications as a replacement for dairy products, which include the following ice cream, frozen custard, frozen yogurt, cookies, cakes, cottage cheese, cream cheese, crème fraiche, curds and yogurt.

In certain aspects, the present invention provides one or more subunits of casein selected from α-s1-casein, α-s2-casein, β-casein and κ-casein for the milk protein component in a dairy substitute product. A select combination of casein subunits are used as the primary or at least a part of the milk protein component. In preferred embodiments, the casein composition comprises the following amounts of casein subunits such that about 12-15 g/L α-s1-casein, about 3-4 g/L α-s2-casein, about 9-11 g/L β-casein and about 2-4 g/L κ-casein represent the total casein in a synthetic milk product.

In various embodiments, the casein compositions can comprise about 0.5% about 1%, about 1.5%, about 2%, about 2.5%, about 3%, about 3.5%, about 4%, about 4.5%, about 5%, about 6%, protein by dry weight or total weight. In some embodiments, the casein compositions can comprise about 0.5-2.5%, about 1-2%, about 2-3%, or about 4-10% casein protein by dry weight or total weight. In particular embodiments, the casein compositions can comprise about 1.5-10% protein by dry weight or total weight.

In certain aspects, the methods and compositions of the dairy substitute products are essentially free of one or more serum proteins. Serum proteins typically comprise, among other proteins, enzymes, hormones, growth factors, nutrient transporters and disease resistance factors. In additional embodiments, the methods and compositions of the dairy substitute products are essentially free of one or more immunoglobulins, which may induce an undesirable immune response.

In some embodiments, whey compositions can comprise about 0.001%, about 0.05%, about 0.1%, about 0.5%, about 1%, about 1.5%, about 2%, about 2.5%, about 3%, about 3.5%, about 4% whey protein by dry weight or total weight. In some embodiments, the compositions can comprise about 0.1-1%, about 1-2%, about 2-3%, or about 0.1-2.3% protein by dry weight or total weight. In particular embodiments, the compositions can comprise about 10-15% protein by dry weight or total weight.

In various embodiments, carbohydrates are incorporated into the dairy substitute products. These carbohydrates provide a bland sweetness to the flavor profile of the product and additionally serve as a fast-acting energy and nutrition source. Carbohydrates include but are not limited to sugars such as galactose, sucrose, glucose, fructose and maltose. Dairy-free sources of sugars include but are not limited to sugar beet and other plants such as celery, basil, honey, cherries, corn, spinach, plums, kiwis and peas.

Lactose intolerance is common for many milk consumers. Accordingly, in preferred embodiments, carbohydrates such as lactose are omitted from the dairy substitute composition. In preferred embodiments, methods and compositions of the dairy substitute composition essentially free of lactose.

In some embodiments, the carbohydrate compositions can comprise about 1%, about 1.5%, about 2%, about 2.5%, about 3%, about 3.5%, about 4%, about 4.5%, about 5% carbohydrate by dry weight or total weight. In some embodiments, the compositions can comprise about 1-3%, about 2-4%, or about 10-30% carbohydrate by dry weight or total weight. In particular embodiments, the compositions can comprise about 2-5% carbohydrate by dry weight or total weight.

Ash attributes to the structure and stability of casein micelles. Ash is important for holding the emulsion that is milk or cream together. The calcium and phosphate present in the ash interact with the fat globules and the casein micelles to maintain an emulsified mixture.

The ash also affects the sensory characteristics such as mouthfeel, consistency, and to a certain extent, the flavor of the milk.

In some embodiments, the ash compositions can comprise about 0.1%, about 0.2%, about 0.3%, about 0.4%, about 0.5%, about 0.6%, about 0.7%, about 0.8%, about 0.9%, about 1%, about 2% or about 3% ash by dry weight or total weight. In some embodiments, the compositions can comprise about 0.1-0.3%, about 0.5-0.7%, about 0.7-1%, or about 1-2% ash by dry weight or total weight. In particular embodiments, the compositions can comprise about 0.6-0.8% protein by dry weight or total weight.

Additional ingredients for various animal-free dairy products include vitamins, flavoring agents, natural or artificial sweeteners, coloring agents, salt, pH adjustment agents, binders, buffers, stabilizers, essential amino acids, anti-caking agents, anti-foaming agents, and mixtures thereof.

In some embodiments, the remaining ingredient compositions can comprise about 0%, about 0.01%, about 0.1%, about 0.5%, about 1%, about 2%, about 3%, about 4% or about 5% additives by dry weight or total weight. In some embodiments, the compositions can comprise about 0.001-0.01%, about 0.01-1%, about 0.01-2%, or about 1-5% additives by dry weight or total weight. In particular embodiments, the compositions can comprise about 0-10% additives by dry weight or total weight.

In some aspects, the present invention provides methods and compositions for dairy substitutes with fat comprising varying levels of triglyceride content. In preferred embodiments, isolated triglycerides from various plant sources are incorporated with milk protein components, carbohydrates and ash. It is an object of the present invention to modulate the fatty acids isolated in plants and transesterified in a dairy substitute to resemble the percentage of fatty acids found in natural dairy products, and/or to develop novel flavor profiles with improved flavor not found in nature. In some embodiments, modulating specific short-to-medium chain fatty acids including but not limited to s butyric, capric, caprylic, caproic and lauric acids provides the desired flavor profile in a dairy substitute.

In some embodiments, the fat compositions in synthetic milk comprises about 0%, about 1%, about 2%, about 3%, about 3.5%, about 4% fat by dry weight or total weight. In some embodiments, the compositions can comprise about 1-2%, about 2-3%, about 3-4% fat by dry weight or total weight. In particular embodiments, the compositions can comprise about 3-4% fat by dry weight or total weight. In alternative embodiments, fat compositions in cream can comprise about 10%, about 20%, about 30%, about 40%, about 50% or even 60%. Preferably, fat compositions in cream is typically about 40 to about 50%.

In some aspects, the short-chain triglycerides are combined with longer chain oil to produce transesterified fatty acid esters. Preferably, the longer chain oils are selected from: sunflower, corn, olive, soy, peanut, walnut, almond, sesame, cottonseed, canola, safflower, flax seed, palm, palm kernel, palm fruit, coconut, babassu, shea butter, mango butter, cocoa butter, wheat germ and rice bran oil. More preferably, the longer chain oils comprise engineered sunflower varieties, which overexpress oleic acid by 400%.

Longer chain oil can also provide to the flavor profile, for example, reduce or even remove sharpness and mellow out the overall flavor profile of the desired end product.

In some embodiments, the fat component of the dairy substitute comprises select triglycerides that are transesterified into longer chain oil such as high-oleic sunflower oil (Example 2). It is contemplated that the same four short chain fatty acids give milk and derivative products such as cheese their particular flavors such as robustness and richness. Various combinations of triglycerides and longer chain oils are incorporated to create a number of different flavor profiles. In one embodiment, triglyceride with three oleic acids and synthetic short-chain triglyceride with, in this case, one butyric, one hexanoic, and one octanoic acid, yields a desired synthetic "milk fat" triglyceride. Additional embodiments include incorporating various short-chain triglycerides to tune slightly different flavor profiles, for instance, short-chain triglyceride comprising hexanoic acid; short-chain triglyceride comprising hexanoic acid and butyric acid; short-chain triglyceride comprising hexanoic acid and decanoic acid. Accordingly, methods and compositions provide for various combinations of synthetic short-chain triglycerides with the sunflower oil triglycerides resulting in different flavor profiles.

Synthetic Milk

An exemplary embodiment of synthetic milk formulation comprising microbially derived proteins of the present invention is illustrated in Example 4. For example, the present formulation incorporates all four subunits of bovine casein: α-s1-casein, α-s2-casein, β-casein and κ-casein and two whey proteins α-lactalbumin and β-lactoglobulin as the predominant milk protein components in the formulation. The exemplary synthetic milk formulation further comprises plant-based interesterified fats as shown in FIG. 1. Additional components include carbohydrates and ash. The resulting milk substitute exhibits characteristics that looks, functions, tastes, smells, and feels like natural milk. As one of key facets of the present invention, modifying the formulations for synthetic milk can exhibit different sensory impressions such as flavoring by modulating the oil content, namely the types of triglycerides added to mimic milk of different flavors.

As described in Young W. Park, Bioactive Components in Milk and Dairy Products, Technology Engineering, pp 60, 2009, sterols are a minor fraction of total lipids in milk, the main sterol being cholesterol (300 mg/100 g fat, equivalent to 10 mg/100 mL bovine milk) (Park et al., *Small Rumin. Res.* 68: 88-113, 2007). Goat milk has been shown to contain less cholesterol than other milk but generally contains higher total fat than cow milk. See, Posati et al., 1976. Composition of Foods. Agric. Handbook No. 8-1. ARS, USDA, Washington, D.C., 1976; Jenness, *J. Dairy Sci.* 63:1605-1630, 1980; and Juarez et al., Intl. Dairy Fed. Bull. No. 202. pp. 54-67, 1986, have shown that goat milk has greater palmitic and oleic acid fractions than cows. Cholesterol content was significantly varied among different breeds and most cholesterol in goat milk was in free state, with only a small fraction in ester form 52 mg/100 g fat. See, e.g., Arora et al., Ind. J. Dairy Sci. 29: 191.

In certain embodiments, the methods and composition of the present invention provide synthetic milk product that has less cholesterol, or is cholesterol free or has the same cholesterol content in comparison to the dairy milk by modulating the oil content, namely the types of triglycerides. In other embodiments, the amount of saturated and unsaturated fats is also modulated in dairy substitutes to at least less or the same amount of fats in comparison to the dairy milk. In preferred embodiments the synthetic milk product of the present invention is very low in saturated fat but smells and tastes like dairy milk. The long chain fatty acids, which are typically saturated fatty acids in milk, are instead monounsaturated acids such as oleic acid, in the preferred embodiments of the invention.

The present invention may not require or at least minimizes pasteurization, as each component can be rendered sterile separately, before combining through the formulation process. In other embodiments of the invention, synthetic milk product of the present invention can undergo pasteurization.

Homogenization is optional for the methods and compositions of the present invention as is the case for natural milk.

When sold as a standalone liquid beverage, the synthetic milk product of the present invention can be sold in homogenized form.

Differences between the milk substitute of the present invention with dairy milk include flavor, nutritional value and storage stability. Flavorings can be adjusted to a desired sensory impression based on triglycerides as well as other natural or artificial flavors that can impart in blandness or sharpness or a different aroma such as cow, goat, coconut, almond or soy.

Synthetic Cheese

In other aspects of the present invention, methods and compositions comprising one or more isolated milk protein components, fats, carbohydrates and ash are provided to produce various types of cheese products. Generally, the cheese is made from the milk protein components of the present invention. One or more sensory impressions are incorporated into the cheese product through modulating the triglycerides. Accordingly, cheese with desired organoleptic characteristics with distinct appearance, aroma, taste and texture can be produced. For some cheese varieties, in addition to modulating the triglycerides, one or more bacteria is employed in the cheese making process for fermentation where fermentative products and by-products such as lactic acid, carbon dioxide, alcohols, aldehydes and ketones are produced. Types of cheese include whey cheese such as ricotta and mozzarella, semi-soft cheese include Havarti and Munster, medium-hard cheese such as Swiss and Jarlsberg, hard cheese such as Cheddar and soft ripened cheese such as Brie and Camembert.

Synthetic Cream

Directly usable cream substitutes should preferably comprise from about 50 to 90% by weight water, and more preferably from about 65 to 80% by weight water, with the base being dispersed within the water. The base for a substitute cream should advantageously contain (all percentages computed using the total weight of the base taken as 100%) from about 22 to 87% by weight carbohydrate (more preferably from about 30 to 64%), from about 12 to 70% by weight of particulate fat (most preferably from about 28 to 60%), and from about 0.4 to 8% by weight of a selected emulsifier or group thereof (most preferably from about 1 to 4%).

In preferred embodiments, the products of the invention are stable in aqueous emulsion. As used herein, a dried, liquid fat-containing non-dairy food product is said to be "stable" when the following minimum criteria are met: reconstituted emulsion stability, whitening capability, oiling or oil separation, feathering-precipitation. See U.S. Pat. No. 4,310,561.

Synthetic Butter

Commercial butter is 80-82% milk fat, 16-17% water, and 1-2% milk solids other than fat (sometimes referred to as curd).

Advantages of Dairy Substitute Products or the Compositions Provided Herein

Desirable advantages of the present invention are environmental in nature such as 8 times more energy efficient, 260 times more water efficient than conventional milk product. Other environmental advantages include less water usage than conventional milk production, which is estimated to be about 1000 L/L and reduced land usage for conventional milk production typically requires grazing, crop land, ability to reduce the 600 billion kg of carbon dioxide per year that is emitted from conventional milk production. The present invention also provides reduction or elimination of costs of feed, operations, labor, animal and marketing. Preferably, substantially reduce feed cost by a factor of 8.

Advantages in food safety include reduction or removal of antibiotic residues, heavy metals, bacteria, adulterations. Accordingly, certain aspects of the present invention provide animal-free milk that is bacteria-free, requires no pasteurization or cold shipping yet has an increased shelf-life and exhibit a number of characteristics such as taste, appearance, handling and mouth feel properties which are identical or at least closely similar to their traditional dairy counterparts. Preferably, the dairy substitute products are essentially free of bacteria such as *Brucella, Camplyobacter, Listeria, Mycobacterium, Salmonella, Shigella, Yersinia, Giardia* and noroviruses, and, thus are safer for consumption. Further advantage include minimal or no pasteurization and/or homogenization. More preferably, the dairy substitute is shelf stable for relatively long periods (e.g., at least three weeks and preferably longer) for production and distribution. Even more preferably, the dairy substitute products has a lower environmental impact.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods.

EXAMPLES

Example 1

Vectors

Protein sequences bovine α-S1 casein (UniProt accession #P02662), bovine α-2 casein (UniProt accession #P02663), bovine β-casein (UniProt accession #P02666), bovine κ-casein (UniProt accession #P02668), bovine α-lactalbumin (UniProt accession #B6V3I5) and bovine β-lactoglobulin (UniProt accession #P02754) were obtained on Uniprot.org and altered with the following changes: removed 15 or 21-residue signal peptide from N-terminal end; added XhoI (CTC GAG) endonuclease recognition sequence and KEX endopeptidase recognition sequence (AAA AGA) to 5' end of DNA; and added SalI (GTC GAC) endonuclease recognition sequence to 3' end of DNA. An additional combination sequence was made by combining the sequences for the four caseins in the order shown above, separating each sequence with the following DNA phrase:

```
                                          (SEQ ID NO: 128)
GGC TCA GGA TCA GGG TCG AAA AGA GGC TCA GGA TCA
GGG TCG.
```

Here the non-underlined segments encode a $(GS)_6$ linker sequence for adequate posttranslational spacing and accessibility to the KEX protease, and the underlined segment encodes the KEX endopeptidase sequence which cleaves the proteins apart post-translation. As above, the entire cassette is flanked on the 5' end by XhoI and on the 3' end by SalI for ligation into pKLAC2 (New England Biolabs, Beverly, MA). DNA was synthesized by either Gen9, Inc. (Cambridge, MA) or IDT (Coralville, IA). The plasmid used had, among other things, a multiple cloning site, a Lac promoter, an Acetamide based reporter gene and the alpha-mating factor gene, used as a fusion protein for secretion of exogenous proteins.

Yeast Transfection

Transfection of the yeast was accomplished by thawing a tube of 0.5 mL competent cells containing 25% glycerol on ice and adding 0.62 mL yeast transfection reagent. The mixture was then warmed at 30° C. for 30 minutes, heat shocked at 37° C. for 1 hour. The cells were then pelleted at 7000 rpm & washed twice with 1.0 mL of YPGal medium. The cell mixture was then transferred to a sterile culture tube and incubated at 30° C. for 3 hours, with constant shaking at 300 rpm. The cell mixture was then transferred to a sterile 1.5 mL microcentrifuge tube and pelleted the cells at 7000 rpm for 2 minutes, and resuspended in 1 mL sterile 1×PBS. 10, 50 and 100 μL of the cell suspension was placed into separate fresh sterile 1.5 mL microcentrifuge tubes each containing 50 μL of sterile deionized water. Tubes were mixed briefly and spread onto separate yeast carbon base agar (YCB Agar) plates containing 5 mM acetamide for selection. Plates were then incubated, inverted, at 30° C. for 4 days until colonies form. 15 individual colonies were then streaked onto fresh YCB Agar plates containing 5 mM acetamide and incubated at 30° C. for 2 days.

DNA encoding alpha-lactalbumin and beta-lactoglobulin, two key whey proteins, was designed in-house and ordered for synthesis from IDT and was transfected into competent *K. lactis* cells from the New England Biolabs kit (Catalog #E1000S) according to the vendor-supplied protocol.

High-Throughput Transfectant Selection

From each YCB Agar plate, once the colonies had grown sufficiently, each of the 30 plates was tested for successful integration of the vector plasmid. This was followed by PCR analysis of each plate to test for special cells with multiple integrants of the vector. Once isolated, the highest producing individual culture was used for scale up. This process can be iterated with successively higher concentrations of selective pressure in order to force colonies to develop higher copy numbers of our engineered plasmid.

Five transfection events were performed and plated on 5 separate plates consisting of nitrogen-free yeast carbon base medium. (Any observed growth on these plates therefore implied successful uptake of the plasmid, if not uptake of the exogenous DNA itself). Of these 5 plates, 100% showed positive growth. 30 individual colonies from the 5 plates were chosen for scale-up, and each was grown in a separate YCB agar plate to create a homozygous culture plate to allow for easy characterization and management. After a 3 day growth period, a single colony from each plate was initially added to a 10 ml glass culture tube, containing 2 ml YPGal media, to test for protein expression. After a growth period of two days, the cells were pelleted out and the supernatant was run on an SDS PAGE gel to check for protein expression. The strains which provided the best protein expression were scaled up to a 10 ml, 100 ml, 500 ml, and ultimately 1 L culture vessel. From each whey protein, two liters of culture were grown. Approximately one gram of protein was harvested from the total, suggesting a non-optimized yield/productivity of 0.5 g/L.

Scale-Up in 1 L Shake Flask Culture

Cultures are scaled up and seeded in a 1 L shake flask at split ratios of at least 1:10. Prior to seeding, inoculation flasks are grown for 24 hours in production media without acetamide supplementation. On the starting day of a fed-batch production run, the reactor is charged with 90% of the target starting volume and heated to the run temperature. For now, the temperature is set at 30° C. in order to save on energy costs associated with heating the reactor. Additional parameters can be explored in the process optimization phase. When the reactor reaches 30° C., the inoculation flask is added to the reaction vessel dropwise using a peristaltic pump. The reactor is maintained using vendor supplied software at a target pH. Twice daily samples are taken of the reactor broth in order to quantify the amount of glucose and electrolyte usage by the cells, and as a doublecheck for the reactor's pH and dissolved gas measurements. After each measurement, bolus glucose is added to maintain a target glucose concentration 10% to start, although this may also be altered in process development. When cells reach maximum density, protein production is triggered by the addition of galactose, which triggers the promoter on our pKLAC2 plasmid. Galactose is supplemented until the end of the run. Optimum run length can be determined in process development as well, but is set as a 5-day fedbatch. After a full run, yeast cells are removed from the reactor and the proteins are purified as discussed below.

Casein Protein Purification

The following casein proteins α-s1 casein, α-s2casein, and β-casein are inherently hydrophobic, which precipitate out when secreted from the yeast and come into contact with water. Purification from the reactor media involves collection of the protein from the surface of the media, followed by drying to isolate pure protein. Kappa-casein is inherently hydrophilic and purification of the κ-caseins involves the change in pH of the solution to 4.6, followed by centrifugation at 10,000 rcf. Combined casein cassette works the same way as κ-casein.

Whey Protein Purification

Alpha-lactalbumin: The isoelectric point of alpha-lactalbumin is 4.2. When the pH of the bioreactor media solution is lowered to 4.2, the solubility of the protein is at its lowest. This knocks the protein out of solution and allows for collection by centrifugation. Beta-lactoglobulin: Similar to the purification of the alpha-lactalbumin, the pH of the solution is lowered to 5.2 the isoelectric point of beta-lactoglobulin. This neutralizes the charge of the protein and allows its collection by centrifugation at 14,000 rcf.

Protein Purification

Figure 2A:
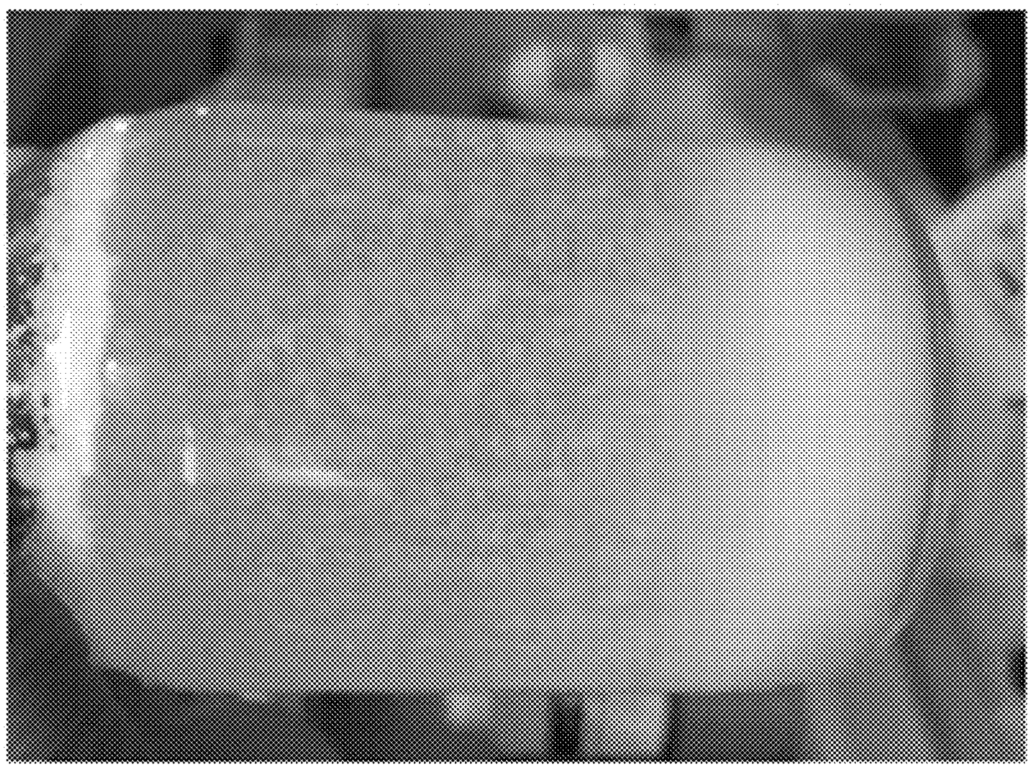
FIG. 2A represents a picture depicting precipitate of an exemplary milk protein component.
Figure 2B:
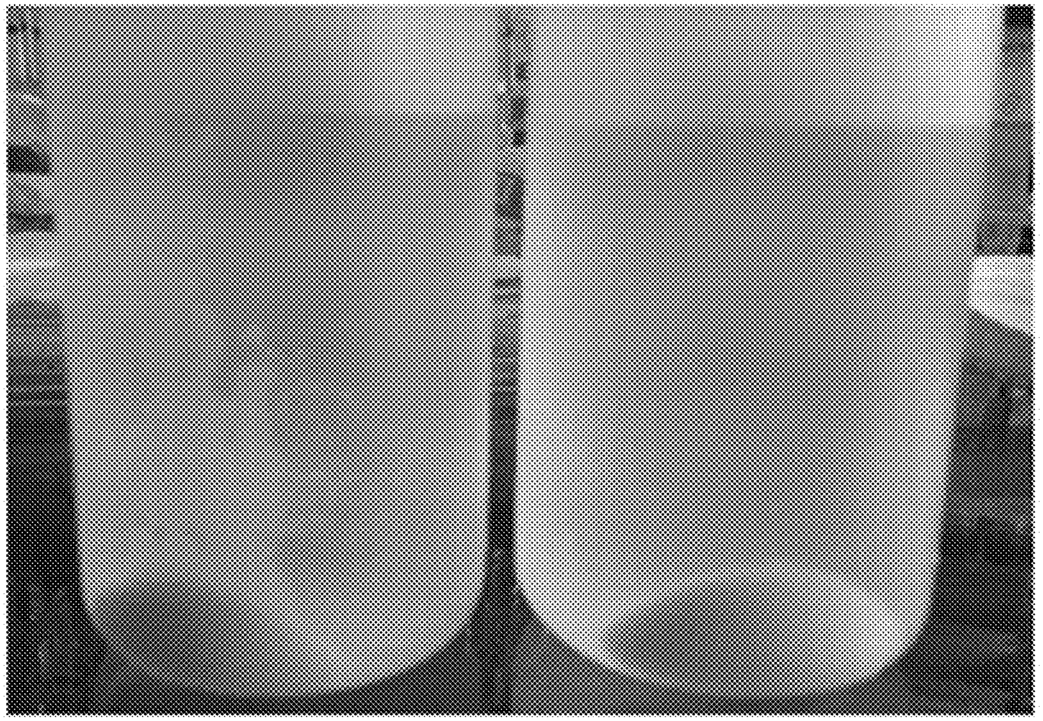
FIG. 2B represents a picture depicting a pellet of an exemplary milk protein component.

The 2 L of culture media was spun at 3,000 g in a floor centrifuge to pellet out the yeast cells. The pellet was discarded, and the supernatant was transferred into a new vessel & the pH of the solution was lowered to 4.2 for the alpha-lactalbumin and 5.2 for the beta-lactoglobulin (FIG. 2A). This was followed by incubation of the supernatant at 35° C. for 30 mins in a shaker flask, centrifugation at 14,000 g in a floor centrifuge to pellet out the protein mixture (FIG. 2B).

Protein Characterization

Figure 3:
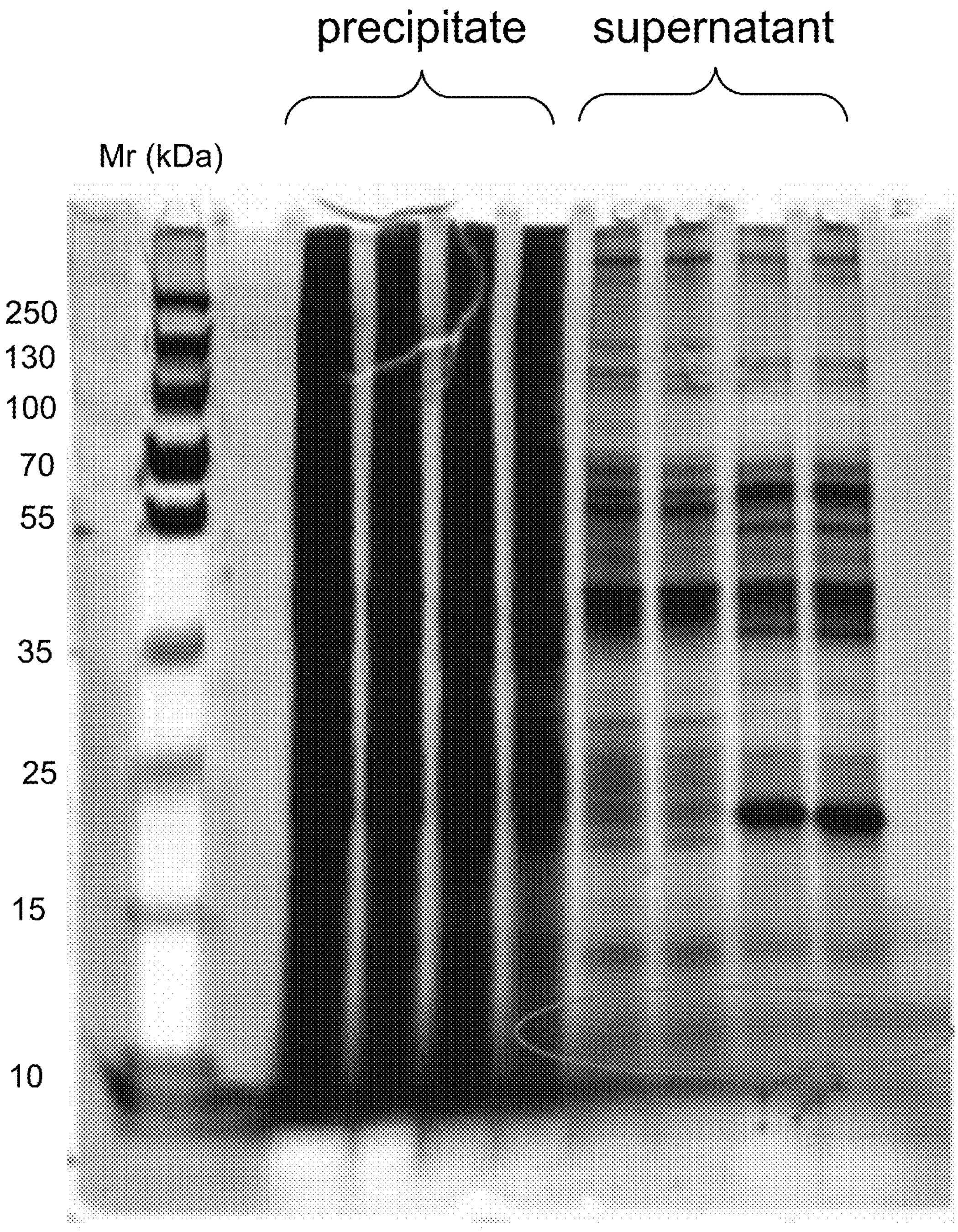
FIG. 3 represents an image of a silver stain SDS-PAGE gel to visualize the milk protein components.

After separation of the protein by centrifugation, the solid pellet and the supernatant solution were run on a 14% SDA-PAGE gel to check for protein expression. A positive band was observed at 14 kDa and at 18 kDa (FIG. 3), which correlates to the size of alpha-lactalbumin and beta-lactoglobulin of bovine origin, respectively. Further characterization is done to confirm equivalence in terms of primary sequence, glycosylation and phosphorylation.

Example 2

Triglyceride Synthesis

Milk fat triglycerides were made by transesterifying short-chain triglycerides into high oleic sunflower oil, the oil from a custom engineered variant of sunflowers which express the following ratios of fatty acid esters as described in Table 1:

TABLE 1

| Fatty Acids | Sunflower† | NuSun Mid-Oleic Sunflower‡ | High-Oliec Sunflower† |
|---|---|---|---|
| C6:0 | ND | ND | ND |
| C8:0 | ND | ND | ND |
| C10:0 | ND | ND | ND |
| C12:0 | ND-0.1 | ND | ND |
| C14:0 | ND-0.2 | 0.4-0.8 | ND-0.1 |
| C16:0 | 2.0-7.6 | 4.0-5.5 | 2.6-5.0 |
| C16:1 | ND-0.3 | ND-0.05 | ND-0.1 |
| C17:0 | ND-0.2 | ND-0.06 | ND-0.1 |
| C17:1 | ND-0.1 | ND-0.06 | ND-0.1 |
| C18:0 | 1.0-6.5 | 2.1-5.0 | 2.9-6.2 |
| C18:1 | 14-29.4 | 43.1-71.8 | 75-90.7 |
| C18:2 | 48.3-74.0 | 18.7-45.3 | 2.1-17.0 |
| C18:3 | ND-0.3 | ND-0.1 | ND-0.3 |
| C20:0 | 0.1-0.5 | 0.2-0.4 | 0.2-0.5 |
| C20:1 | ND-0.3 | 0.2-0.3 | 0.1-0.5 |
| C20:2 | ND | ND | ND |
| C22:0 | 0.3-1.5 | 0.6-1.1 | 0.5-1.6 |
| C22:1 | ND-0.3 | ND | ND-0.3 |
| C22:2 | ND-0.3 | ND-0.09 | ND |
| C24:0 | ND-0.5 | 0.3-0.4 | ND-0.5 |
| C24:1 | ND | ND | ND |

ND = not detectable (ND defined as <0.05%)
†From Codex Alimentarius (2001)
‡From Table 3 www.sunflowernsa.com/uploads/resources/51/warner_.pdf

Short-Chain Triglyceride Preparation

The short-chain fatty acids which are principally responsible for rich flavor in milk and cream are the molecules with even numbers of carbons between 4 and 10, and are mixed in the following ratios as described in Table 2:

TABLE 2

Table 1. Fatty acid composition expressed as percent by weight of total fatty acids in Swedish dairy milk in 2001, given as weighted means with standard deviations (SD) and as the minimum and maximum weighted means. The estimation of the weighted mean values was based on the proportion of milk delivered to each dairy or dairy company at each sampling occasion (seven dairies at four sampling occasions during 2001). The lowest and highest values observed and p-values for geographical and seasonal variation are also given

| Fatty acid | Weighted mean 2001 | SD | Lowest value observed | Highest value observed | Seasonal variation |
|---|---|---|---|---|---|
| 4:0 | 4.4 | 0.1 | 4.0 | 5.1 | n.s. |
| 6:0 | 2.4 | 0.1 | 2.1 | 2.9 | n.s. |
| 8:0 | 1.4 | 0.1 | 1.2 | 1.9 | n.s. |
| 10:0 | 2.7 | 0.2 | 2.4 | 3.5 | * |
| 12:0 | 3.3 | 0.2 | 3.0 | 4.1 | ** |
| 14:0 | 10.9 | 0.5 | 10.0 | 12.1 | *** |
| 15:0 | 0.9 | 0.0 | 0.8 | 1.1 | n.s. |
| 16:0 | 30.6 | 0.9 | 28.7 | 34.1 | ** |
| 17:0 | 0.4 | 0.0 | 0.4 | 0.5 | ** |
| 18:0 | 12.2 | 0.4 | 10.3 | 13.3 | n.s. |
| 20:0 | 0.2 | 0.0 | 0.2 | 0.2 | n.s. |
| Saturated fatty acids total | 69.4 | 1.7 | 67.1 | 74.4 | *** |
| 10:1 | 0.3 | 0.0 | 0.2 | 0.4 | n.s. |
| 14:1 | 0.8 | 0.4 | 0.4 | 1.3 | ** |
| 16:1 | 1.0 | 0.0 | 0.9 | 1.8 | n.s. |
| 17:1 | 0.1 | 0.0 | <0.1 | 0.3 | n.s. |
| 18:1 | 22.8 | 1.0 | 19.7 | 24.7 | *** |
| Mono-unsaturated fatty acids, cis, total | 25.0 | 1.0 | 22.2 | 26.7 | ** |

TABLE 2-continued

Table 1. Fatty acid composition expressed as percent by weight of total fatty acids in Swedish dairy milk in 2001, given as weighted means with standard deviations (SD) and as the minimum and maximum weighted means. The estimation of the weighted mean values was based on the proportion of milk delivered to each dairy or dairy company at each sampling occasion (seven dairies at four sampling occasions during 2001). The lowest and highest values observed and p-values for geographical and seasonal variation are also given

| Fatty acid | Weighted mean 2001 | SD | Lowest value observed | Highest value observed | Seasonal variation |
|---|---|---|---|---|---|
| 18:2 | 1.6 | 0.1 | 1.4 | 1.8 | n.s. |
| 18:3 | 0.7 | 0.0 | 0.6 | 0.9 | ** |
| Poly-unsaturated fatty acids, cis, total | 2.3 | 0.1 | 2.0 | 2.5 | n.s. |
| 16:1t | 0.4 | 0.1 | 0.3 | 0.4 | *** |
| 18:1t | 2.1 | 0.7 | 2.0 | 3.3 | *** |
| 18:2t | 0.2 | 0.0 | 0.1 | 0.5 | n.s. |
| Trans fatty acids total | 2.7 | 0.7 | 0.6 | 3.9 | *** |
| CLA | 0.4 | 0.1 | 0.3 | 0.5 | *** |

n.s.: Not significant; *$p < 0.05$; $p < 0.01$; *$p < 0.001$.
www.ncbi.nlm.nih.gov/pmc/articles/PMC2596709/pdf/FNR-52-1821.pdf

TABLE 3

| Chain Length | Names | Mass Fraction in Mixture (%) |
|---|---|---|
| 4 | Butanoic/butyric acid | 40 |
| 6 | Hexanoic/caproic acid | 26 |
| 8 | Octanoic/caprylic acid | 11 |
| 10 | Decanoic/capric acid | 22 |

The fractions in Table 3 are based upon the relative prevalence of these species in cow's milk, but can be altered during process development both in order to design a better tasting product and in order to design milks of other species, such as buffalo or goat. Short-chain fatty acids in the mass ratios shown above are combined with toluene, paratoluenesulfonic acid, and glycerol in a Dean-Stark water trap, commonly used for esterification reactions in order to remove water produced in the condensation reaction. The reaction is carried out in a fume hood for several hours, until the level of water entering the water trap is observed as unchanging for more than 30 minutes. The vessel is allowed to cool and the mixture is removed from the reaction flask. The mixture is washed twice with a 5% sodium carbonate solution and five times with plain water. Brine (a 10% solution of NaCl in water) is added periodically in order to disrupt an emulsion which forms in the separating funnel. The washed mixture of short-chain triglycerides, water, toluene, and impurities is dried in a rotary evaporator at 90° C. and under a 54 mbar atmosphere for one hour, until it has proceeded well past excess in order to minimize the chance of food contamination.

Transesterification

The short-chain triglyceride mixture is combined with high-oleic sunflower oil at a volumetric ratio of 1:8. A mass of sodium methoxide equal to 1% of the oil mixture mass is added in order to catalyze the transesterification, and the reaction vessel is heated to 65° C., stirring continuously, under an inert Argon atmosphere, for six hours. A 5% acetic acid mixture is added to quench the reaction, then the oil is washed five times with deionized water and dried in a rotary evaporator for one hour at >90° C. The finished milk fat is autoclaved to ensure sterility and is thence suitable for use in milk or cream as described above.

Example 3

Milk Formulation

One non-limiting milk composition formulation is described below.

TABLE 4

| Components | % (w/v) Range | Amount (g/L) |
|---|---|---|
| Casein proteins | 1-10 | 10-100 |
| Whey proteins | 0-1 | 0-10 |
| Plant-based milk fats | 0-8 | 0-80 ml/L |
| Sugar | 0-5 | 0-50 |
| Ash | 0.1-1 | 1-10 |
| Calcium | 0.1-0.5 | 1-L |
| X (Functional additive) | 0-1 | 0-10 L |

Following Table 4, milk formulation is achieved through the following procedure, per 1 liter of milk. 26 grams of casein, 3.5 grams of whey and 5 grams of ash are combined and mixed well. 40 mL of triglycerides are thawed & heated to 55° C. Protein mixture is poured slowly into triglycerides and vortexed at high speed for five minutes. In the meantime, 3.5 grams of whey and 24 grams of galactose are added to 850 mL deionized water; mixture is heated to 37° C. Triglyceride/protein/ash mixture is moved into Waring commercial blender and blended at low speed. Whey/galactose/water mixture is poured slowly into blender; cap placed on blender. Mixture is blended at high speed for ten minutes. Deionized water is added to a final volume of 1000 mL. Milk can optionally be homogenized using existing methods. The above protocol can be altered for cream or arbitrary milk formulations by altering the ratios of solids; however, our preliminary research suggests that the presence of ash in the protein mixture and the separation of a significant proportion of the whey can greatly affect the quality of the emulsion.

Example 4

Synthetic Milk Formulation

As a preliminary proof of concept, in order to determine whether the key components of milk could be recombined to form milk, dry food-grade purified casein and research grade whey was purchased. Irish cream was obtained from a local source and pure fat was isolated from it by centrifuging the cream at 14,000 g. Finally, all minerals used were purchased from Sigma Aldrich.

Terms

C-roux=roux made by mixing casein proteins & fat together while maintaining the temperature of the mixture at 37° C.

W-roux=roux made by mixing whey proteins & fat together while maintaining the temperature of the mixture at 37° C.

CW-roux=roux made by mixing casein & whey proteins together in a mixture first, adding fat and mixing at 37° C.

TABLE 5

| Experiment | Result |
|---|---|
| Casein + Fat + Water | A pale yellow liquid with bad taste, precipitation of protein, and bad mouthfeel (watery). |
| Casein + Water + Fat | A pale yellow liquid with bad taste, precipitation of protein, and bad mouthfeel (watery). |
| (Casein + Fat) to make a roux. roux + Water | A pale yellow liquid with average taste and bad mouthfeel (watery). Low protein precipitation was observed. |

Hypothesized that the bad mouthfeel (e.g., wateriness) was due to the lack of whey protein.

TABLE 6

| Experiment | Result |
|---|---|
| Casein + Whey + Fat + Water | Pale yellow-white liquid with bad taste, precipitation of protein, and bad mouthfeel. |
| C-roux + Whey + Water | Pale yellow-white liquid with average taste, low precipitation of protein, and bad mouthfeel |
| W-roux + Casein + Water | Pale yellow-white liquid with average taste, low precipitation of protein, and bad mouthfeel. |
| CW-roux + Water | Pale yellow-white liquid with average taste and bad mouthfeel. Zero protein precipitation. |

Hypothesized that bad mouth feel was because of bad casein micelle formation, that addition of Ca would allow the micelle to reform.

TABLE 7

| Experiment | Result |
|---|---|
| CW-roux + Water + Calcium phosphate (optimum amount of Ca was figured out by trial & error) | White liquid with normal mouth feel. Zero protein precipitation. Average taste |

To improve taste, different sugars were added in different concentrations to the above mixture.

TABLE 8

| Sugar | 2.4% | 3.0% | 3.6% | 4.2% | 4.8% |
|---|---|---|---|---|---|
| Glucose | Good | Too Sweet | Too Sweet | Too Sweet | Too Sweet |
| Galactose | Bland | Excellent | Average | Excellent | Too Sweet |
| Sucrose | Bad | Bad | Bad | Bad | Bad |
| Maltose | Bland | Excellent | Excellent | Too Sweet | Too Sweet |

All additional ions found in cow milk was incorporated to recreate the ionic environment found in nature.

Reference: R. Rosmaninho, L. F. Melo/Journal of Food Engineering 73 (2006) 379-387

TABLE 9

| Reagent | Composition (mM) |
|---|---|
| $KH_2PO_4$ | 11.60 |
| $K_3$ Citrate $H_2O^a$ | 3.7 |
| $Na_3$ Citrate $2H_2O$ | 6.1 |
| $K_2SO_4$ | 1.03 |
| $K_2CO_3$ | 2.17 |

TABLE 9-continued

| Reagent | Composition (mM) |
|---|---|
| KCL | 8.0 |
| $CaCL_2 \cdot 2H_2O$ | 8.98 |

End result was a liquid which was bright white in color, likely because the ionic environment kept the solids present in milk from joining together and increased the overall refractive index of the solution. Taste was excellent, but it had an average mouthfeel (e.g., a certain amount of chalkiness was observed in the liquid). Exact mineral composition as described in Table 9 can provide excellent mouthfeel.

Milk Fat Synthesis

Synthetic milk fat was made by interesterifying short-chain fatty acids among the large-chain fatty acids present in high-oleic sunflower oil triglycerides. The four short-chains used were:

- 40% C4: Butyric acid. found in milk, especially goat, sheep and buffalo milk, butter, Parmesan cheese, and as a product of anaerobic fermentation (including in the colon and as body odor). It has an unpleasant smell and acrid taste, with a sweetish aftertaste (similar to ether). Butyric acid is present in, and is the main distinctive smell of, human vomit.
- 26% C6: Caproic acid. a colorless oily liquid with an odor that is fatty, cheesy, waxy, and like that of goats or other barnyard animals.
- 11% C8: Caprylic acid. It is an oily liquid that is minimally soluble in water with a slightly unpleasant rancid-like smell and taste.
- 22% C10: Capric acid. Not much said about the flavor, and with longer carbon chains you start to get less flavors. This is in coconut oil so it is not a milk fat flavor per se as much as the other ones.

Iterations include lauric acid (C12), as it is present at 2.9% of total fatty acid content in cow's milk (Beare-Rogers, J.; Dieffenbacher, A.; Holm, J. V. (2001). "Lexicon of lipid nutrition (IUPAC Technical Report)". Pure and Applied Chemistry 73 (4): 685-744. doi:10.1351/pac200173040685.)

The following procedure as described Yu et al., The modification an analysis of vegetable oil for cheese making. *J. Am. Oil Chem. Soc.,* 77:911 (2000) was followed in, at quarter of the amounts specified below:

A mixture of butyric, caproic, caprylic, and capric acids (Sigma Chemical Co., St. Louis, MO) at the same ratios found for a milk fat sample [see above] and totaling 7.26 mol, 21.42 g of p-toluenesulfonic acid (Sigma Chemical Co.), 2.305 mol of glycerol (Sigma Chemical Co.), and 458 mL of toluene (Fisher Scientific) was refluxed with a Dean-Stark water trap for 6 h. The reaction was considered complete when no more water dripped into the trap. The SCTG were washed once with 5% sodium carbonate solution and several times with water. Then, the SCTG were heated at 85° C. in a rotary evaporator to remove water and toluene.

SCTG from both commercial and natural sources are interesterified with HOSO (Trisun 80, RBD; AC Humko, Memphis, TN) at a SCTG/HOSO ratio of 1:8.82 in order to produce a fat that has the same percentage of SCFA as that of milk fat. SCTG from the commercial source are also interesterified at a SCTG/HOSO ratio of 1:7.19 to produce a fat that has a level of SCFA equal to 120% of that in milk fat. Sodium methoxide (Aldrich Chemical Company, St. Louis, MO) is used as a catalyst at 0.5% of total oil weight. The reaction is carried out at 65° C. under nitrogen with stirring for 6 h. Next, 5% acetic acid (Fisher Scientific) is added to neutralize the catalyst, and the oil is then washed several times with distilled water and dried on a rotary evaporator for 30 min at 90° C.

A pilot-scale continuous deodorizer similar to the one described by Smouse (Smouse, T. H., A Laboratory Continuous Deodorizer, inform 8:1176-1181 (1997).) is used to deodorize the interesterified oils. The oil flow rate is 600 mL/h, the column temperature is 180° C., pressure at 0.5 Torr, and the steam rate 12.6 mL/h. Each batch of deodorized oil is tasted by to ensure the flavor. The deodorized oil is stored at 4° C. until used for cheese making.

Example 5

Modulation of Fatty Acids

Sunflower oil triglycerides with three oleic acids are transesterified with four short chain fatty acids containing one butyric acid, one hexanoic acid, and one octanoic acid as part of the fat composition in a mixture of synthetic milk product. This array or combination of fat is expected to result in a synthetic milk fat providing its rich flavor as compared to natural dairy milk. The ability to control the composition of one or more triglycerides is likely to enhance or change flavor profiles of synthetic dairy products. Accordingly, a matrix of long-chain and short-chain can yield in flavor profiles including, but not limited to, multiple aromatic compounds associated with buttery, nutty, sweet, sour, fruity, floral, bitter, woody, earthy, beany, spicy, metallic, sweet, musty, oily and vinegary sensory impressions. Additionally, increase in texture such as creaminess, improvements in melting characteristics or tolerance and increase in stretching ability relative to a corresponding dairy product can be exhibited.

Example 6. Recombinant Production of Milk Proteins

Alpha-lactalbumin, β-lactoglobulin, α-S1-casein, α-Ω-casein, β-casein, and κ-casein were produced in recombinant yeast strain (*Pichia pastoris*) strains. As the glycosylation enzymes in yeast are different than mammalian cells, the proteins producted by the yeast will either be non-glucosylated or have a non-mammalian glycosylation pattern. The produced proteins can be used as a component in any of the compositions described herein.

Plasmids

Plasmids were constructed for the expression of each protein. Each plasmid included the following components: an inducible promoter (e.g., AOX1 promoter) or a constuitive (GAP promoter or PGK promoter) promoter, for each protein being expressed; a sequence encoding a signal peptide for each protein being expressed, derived either from the native bovine protein sequence or one from a yeast protein sequence (alpha mating factor or OST1); a sequence encoding the milk protein(s) to be expressed; a yeast transcription terminator sequence (e.g., AOX1, AOD, or CYC1) for each protein being expressed; a bacterial origin of replication from pUC19 to enable replication of the plasmid in *E. coli*; and a selectable marker cassette (e.g., kanR or zeocinR) to enable selection in bacteria and yeast with antibiotics.

The different plasmids used to produce the different proteins are listed in Table 10 below.

TABLE 10

| Expression Plasmids (SEQ ID NO) | | | | | | | | | |
|---|---|---|---|---|---|---|---|---|---|
| Plasmid name | Select marker | Prom 1 | Signal peptide 1 | ORF 1 | Terminat 1 | Prom 2 | Signal pept 2 | ORF 2 | Term 2 |
| pJAG-nat-LAA | Amp (bacteria), G418 (yeast) (159)[1] | P_AOX1 (153) | SP_lactalbumin (156) | α-lactalbumin (157) | TT_AOX1 (158) | | | | |
| pJAG-MFa-LAA | Ampicillin (bacteria), G418 (yeast) (159) | P_AOX1 (153) | SP_MFa (154) | α-lactalbumin (157) | TT_AOX1 (158) | | | | |
| pJAG-OST-LAA | Ampicillin (bacteria), G418 (yeast) (159) | P_AOX1 (153) | SP_OST (155) | α-lactalbumin (157) | TT_AOX1 (158) | | | | |
| pLH37 | Zeocin (151) | P_AOX1 (129) | SP_MFαT (132) | β-lactoglobulin (143) | TT_AOX1 (149) | | | | |
| pLH0044 | Zeocin (151) | P_GAP1 (130) | SP_MFαT (132) | β-lactoglobulin (143) | TT_AOX1 (149) | | | | |
| pLH0045 | Zeocin (151) | P_PGK1 (131) | SP_MFalphaT (132) | β-lactoglobulin (143) | TT_AOX1 (149) | | | | |
| pLH46 | Zeocin (151) | P_GAP1 (130) | SP_β_casein (135) | β-casein (144) | TT_CYC1 (150) | P_PGK1 (131) | SP_αS1_casein (137) | αS1-casein (147) | TT_AOX1 (149) |
| pLH47 | Kanamycin (bacteria), G418 (yeast) (152) | P_GAP1 (130) | SP_αS2_casein (133) | αS2-casein (145) | TT_CYC1 (150) | P_PGK1 (131) | SP_κcasein (138) | κ-casein (148) | TT_AOX1 (149) |
| pLH48 | Zeocin (151) | P_GAP1 (130) | SP_OST (134) | β-casein (144) | TT_CYC1 (150) | P_PGK1 (131) | SP_OST (134) | αS1-casein (147) | TT_AOX1 (149) |
| pLH49 | Kanamycin (bacteria), G418 (yeast) (152) | P_GAP1 (130) | SP_OST (136) | αS2-casein (145) 5 | TT_CYC1 (150) | P_PGK1 (131) | SP_OST (134) | κ-casein (148) | TT_AOX1 (149) |
| pLH50 | Zeocin (151) | P_GAP1 (130) | SP_OST (136) | β-casein (144) | TT_CYC1 (150) | P_PGK1 (131) | SP_αS1_casein (137) | αS1-casein (147) | TT_AOX1 (149) |
| pLH51 | Zeocin (151) | P_GAP1 (130) | SP_β_casein (135) | β-casein (144) | TT_CYC1 (150) | P_PGK1 (131) | SP_OST (134) | αS1-casein (147) | TT_AOX1 (149) |
| pLH52 | Kanamycin (bacteria), G418 (yeast) (152) | P_GAP1 (130) | SP_αS2 casein (133) | αS2-casein K113E (146) | TT_CYC1 (150) | P_PGK1 (131) | SP κ_casein (138) | κ-casein (148) | TT_AOX1 (149) |
| pLH53 | Kanamycin (bacteria), G418 (yeast) (152) | P_GAP1 (130) | SP_OST (136) | αS2-casein K113E (146) | TT_CYC1 (150) | P_PGK1 (131) | SP_OST (134) | κ-casein (148) | TT_AOX1 (149) |
| pLH54 | Kanamycin (bacteria), G418 (yeast) (152) | P_GAP1 (130) | SP_OST (136) | αS2-casein (145) | TT_CYC1 (150) | P_PGK1 (131) | SP_κ_casein (138) | κ-casein (148) | TT_AOX1 (149) |
| pLH55 | Kanamycin (bacteria), G418 (yeast) (152) 5 | P_GAP1 (130) | SP_αS2 casein (133) | αS2-casein (145) | TT_CYC1 (150) | P_PGK1 (131) | SP_OST1 (134) | κ-casein (148) | TT_AOX1 (149) |

(Synthetic)

SEQ ID NO: 159

```
ATGGGTAAGGAAAAGACTCACGTTTCCAGACCAAGATTGAACTCTAACA
TGGACGCTGACTTGTACGGTTACAAGTGGGCTAGAGACAACGTTGGTCA
ATCTGGTGCTACTATTTACAGATTGTACGGTAAGCCAGACGCTCCAGAG
TTGTTCTTGAAGCACGGTAAGGGTTCTGTTGCTAACGACGTTACTGACG
AGATGGTTAGATTGAACTGGTTGACTGAGTTCATGCCATTGCCAACTAT
TAAGCACTTCATTAGAACTCCAGACGACGCTTGGTTGTTGACTACTGCT
ATTCCAGGTAAGACTGCTTTCCAAGTTTTGGAGGAGTACCCAGACTCTG
GTGAGAACATTGTTGACGCTTTGGCTGTTTTCTTGAGAAGATTGCACTC
TATTCCAGTTTGTAACTGTCCATTCAACTCTGACAGAGTTTTCAGATTG
GCTCAAGCTCAATCCAGAATGAACAACGGTTTGGTTGACGCTTCTGACT
TCGACGACGAGAGAAACGGTTGGCCAGTTGAGCAAGTTTGGAAGGAGAT
GCACAAGTTGTTGCCATTCTCTCCAGACTCTGTTGTTACTCACGGTGAC
TTCTCTTTGGACAACTTGATTTTCGACGAGGGTAAGTTGATTGGTTGTA
TTGACGTTGGTAGAGTTGGTATTGCTGACAGATACCAAGACTTGGCTAT
TTTGTGGAACTGTTTGGGTGAGTTCTCTCCATCTTTGCAAAAGAGATTG
TTCCAAAAGTACGGTATTGACAACCCAGACATGAACAAGTTGCAATTCC
ACTTGATGTTGGACGAGTTCTTCTAA
```

These plasmids were then integrated into wildtype *P. pastoris* for expression. The production of the proteins was detected by SDS-PAGE, ELISA, and Western blot.

Alpha-Lactalbumin

Strain Construction

Three plasmids were created, placing the expression of bovine alpha-lactalbumin (bvLAA) under the control of the methanol-induced promoter $P_{AOX1}$, with either the native LAA signal peptide (pJAG-nat-LAA), the full length alpha mating factor signal peptide (pJAG-aMF-LAA), or the OST1 signal peptide (pJAG-OST-LAA).

Prior to transformation, 20 μg each plasmid was linearized by digestion with the restriction enzyme SacI. The digested plasmids were then concentrated by ethanol precipitation, and resuspended in 10 μl distilled water.

Competent *Pichia pastoris* cells were prepared as follows: A culture of *P. pastoris* was grown to log phase (OD600~1.0) in YPD media (10 g/L yeast extract, 20 g/L peptone, 20 g/L dextrose). A 1.5 mL aliquot was harvested by centrifugation, then resuspended in 1 mL of a 1:1 mixture of YPD+20 mM HEPES (pH 8):1M lithium acetate. After adding 10 μL 1 M dithiothreitol, the cells were incubated for 15 min at 30° C. in a shaker at 300 rpm. The cells were pelleted by centrifugation and washed three times in 1 mL ice cold 1 M sorbitol. After the final wash, the cells were resuspended in 50 μL 1 M sorbitol.

The cells were combined with the linearized plasmid DNA in a chilled 2 mm electroporation cuvette, and subjected to a 1.5 kV pulse (25 μF, 200Ω). The cells were transferred to a culture tube with 200 μL cold 1:1 YPD:1 M sorbitol, and allowed to recover for 2 hours at 30° C. (300 rpm). Finally, the cells were plated onto YPD agar plates containing zeocin and grown for two days at 30° C.

Protein Expression

Colonies were picked from the agar plates and grown in 750 μL BMD1% (0.2M Potassium Phosphate buffer, 13.4 g/l Yeast Nitrogen Base, 0.4 mg/ml biotin, 1.1% glucose) at 30° C., 300 rpm. After 48 hours, 900 μL of culture was used to inoculate 750 μL BMM2 (0.2M Potassium Phosphate buffer, 13.4 g/l Yeast Nitrogen Base, 0.4 mg/ml Biotin, 1% methanol). After 24 hours, 150 μL BMM10 (BMM10: 0.2M Potassium Phosphate buffer, 13.4 g/l Yeast Nitrogen Base, 0.4 mg/ml Biotin, 5% methanol), and samples were harvested for analysis after one additional day.

Analysis

Protein expression was analyzed in samples of culture that were centrifuged to remove the cell mass. The clarified supernatant was then evaluated by SDS-PAGE, ELISA, and western blot.

Figure 4:
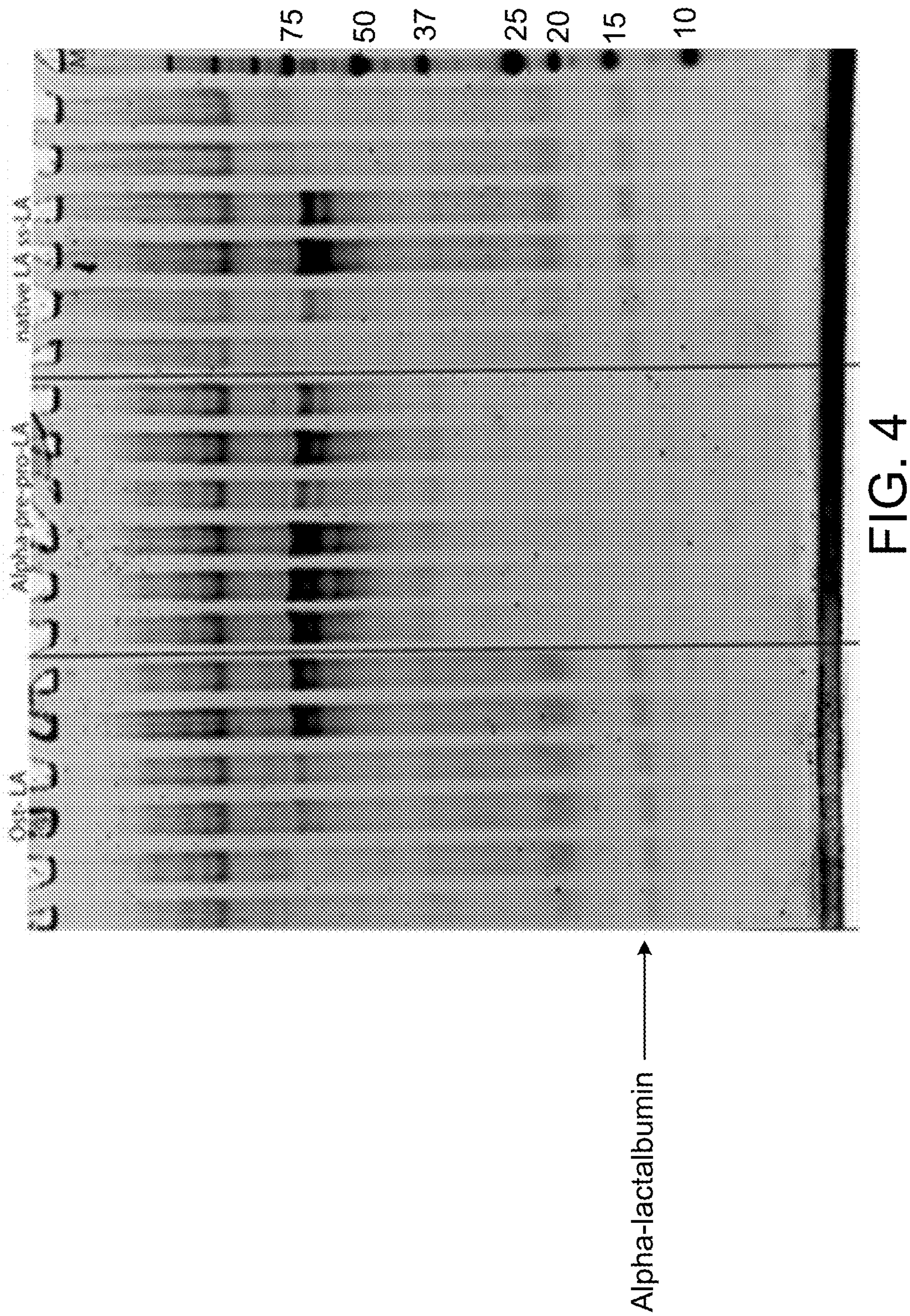
FIG. 4 is a SYPRO Ruby-stained SDS-PAGE gel showing the levels of secretion of α-lactalbumin mediated by the OST signal sequence, the native α-lactalbumin signal sequence, and the α mating factor signal sequence as described in Example 6.

To visualize total protein via SDS-PAGE, cell-free supernatant was treated with SDS-PAGE sample buffer, boiled, and run on a 10% polyacrylamide gel. The gel was stained with SYPRO Ruby stain (Life Technologies). The resulting gel shows that secretion of α-lactalbumin occurs using the OST1 or the native lactalbumin signal peptide (FIG. 4).

Figure 5:
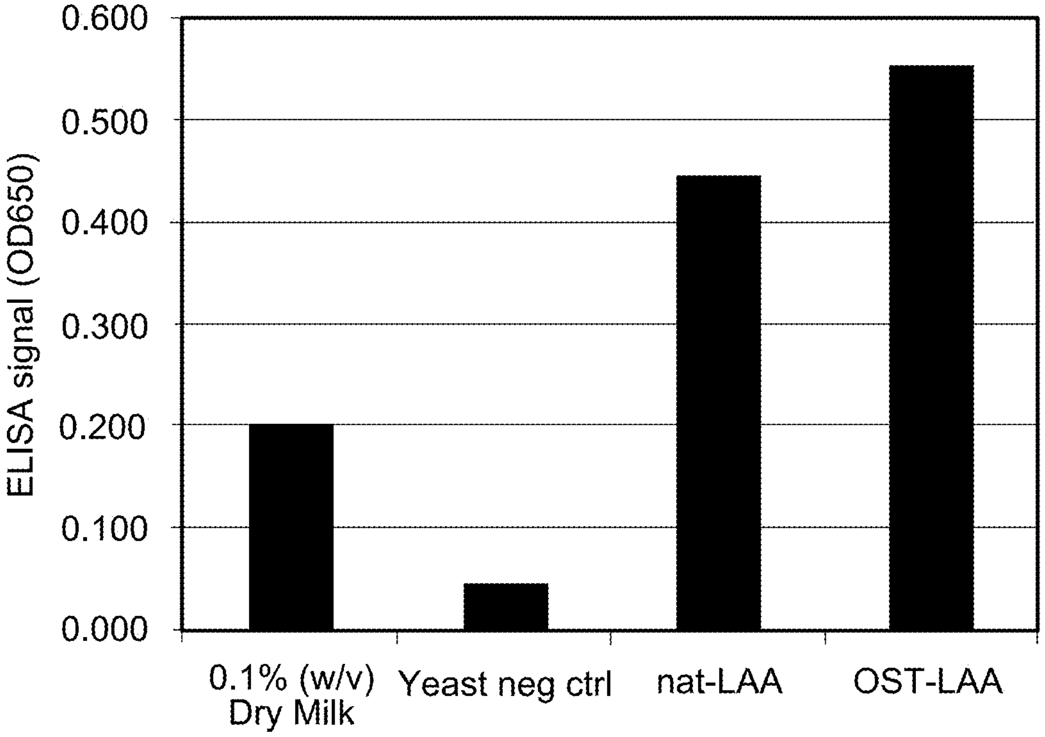
FIG. 5 is shows the levels of secretion of α-lactalbumin by wildtype yeast cells or yeast cells expressing α-lactalbumin using the native α-lactalbumin signal peptide or a OST1 signal peptide (as determined by an ELISA assay as described in Example 6).

To measure protein titers via ELISA, 25 μL of each sample were placed in a half-area 96 well microtiter plate, and allowed to bind overnight at 4° C. After removing the samples, the binding surface was blocked by filling each well with 1% (w/v) bovine serum albumin (BSA) dissolved in Tris Buffered Saline (50 mM Tris, pH 7.6, 150 mM NaCl) and incubating for 1 hour at room temperature. The samples were then incubated for 1.5 hr in primary antibody that was diluted in 1% BSA/TBS+0.1% (v/v) Tween-20. Following three washes in TBS+Tween, the samples were incubated with secondary antibody conjugated with horseradish peroxidase (HRP) for an additional hour. After three final washes in TBS+Tween, a chromogenic substrate (TMB Single Solution, Life Technologies) was added, and the absorbance at 650 nm was measured. The resulting data show that α-lactalbumin was secreted using the native α-lactalbumin signal peptide or the OST1 signal peptide (FIG. 5).

To analyze samples via Western blot, one volume of sample was combined with an equal volume of SDS-PAGE sample buffer and run on a 10% polyacrylamide gel. The proteins were transferred to a nitrocellulose membrane, which was blocked by treating with 1% BSA/TBS for 1 hr. After incubating for 1.5 hr with primary antibody diluted in 1% BSA/TBS+Tween, the blot was washed three times in TBS+Tween. The blot was then incubated with secondary antibody conjugated with horseradish peroxidase (HRP) for an additional hour. After three final washes in TBS+Tween, a chromogenic substrate (1-Step Ultra TMB Blotting Solution, Thermo Fisher) was added. After staining was completed, the blot was washed in distilled water.

Beta-Lactoglobulin

Strain Constructions

Three plasmids were assembled, placing the expression of bovine beta-lactoglobulin (bvLGB) under the control of either a methanol-induced promoter ($P_{AOX1}$ in pLH37) or one of two constitutive promoters ($P_{GAP}$ in pLH44, or $P_{PGK}$ in pLH45).

Prior to transformation, 20 μg pLH37 was linearized by digestion with the restriction enzyme SacI. The same amounts of pLH44 and pLH45 were linearized with the enzyme ApaLI. The digested plasmids were then concentrated by ethanol precipitation, and resuspended in 10 μl distilled water.

Competent *Pichia pastoris* cells were prepared as follows: A culture of *P. pastoris* was grown to log phase (OD600~1.0) in YPD media (10 g/L yeast extract, 20 g/L peptone, 20 g/L dextrose). A 1.5 mL aliquot was harvested by centrifugation, then resuspended in 1 mL of a 1:1 mixture of YPD+20 mM HEPES (pH 8):1M lithium acetate. After adding 10 μL 1 M dithiothreitol, the cells were incubated for 15 min at 30° C. in a shaker at 300 rpm. The cells were pelleted by centrifugation and washed three times in 1 mL ice cold 1 M sorbitol. After the final wash, the cells were resuspended in 50 μL 1 M sorbitol.

The cells were combined with the linearized plasmid DNA in a chilled 2 mm electroporation cuvette, and subjected to a 1.5 kV pulse (25 μF, 200Ω). The cells were transferred to a culture tube with 200 μL cold 1:1 YPD:1 M sorbitol, and allowed to recover for 2 hours at 30° C. (300 rpm). Finally, the cells were plated onto YPD agar plates containing zeocin and grown for two days at 30° C.

Protein Expression

To evaluate expression in clones transformed with the plasmid containing a methanol-inducible promoter (pLH37), individual clones were grown in 750 μL BMD1% (0.2M Potassium Phosphate buffer, 13.4 g/l Yeast Nitrogen Base, 0.4 mg/ml biotin, 1.1% glucose) at 30° C., 300 rpm. After 48 hours, 900 μL of culture was used to inoculate 750 μL BMM2 (0.2M Potassium Phosphate buffer, 13.4 g/l Yeast Nitrogen Base, 0.4 mg/ml Biotin, 1% methanol). After 24 hours, 150 μL BMM10 (BMM10: 0.2M Potassium Phosphate buffer, 13.4 g/l Yeast Nitrogen Base, 0.4 mg/ml Biotin, 5% methanol), and samples were harvested for analysis after one additional day.

To evaluate expression in clones transformed with a plasmid supporting constitutive expression (pLH44 or pLH45), individual clones were grown overnight in PG media (20 g/L peptone, 2% glycerol) at 30° C. with shaking at 300 rpm. The cultures were diluted 1:10 in minimal sulfate media:

| |
|---|
| Glucose 20 g/L |
| Calcium Chloride (CaCl2) 1 g/L |
| Sodium phosphate (Na2PO4) 24 g/L |
| Potassium sulfate (K2SO4) 18.2 g/L |
| Magnesium sulfate (MgSO4—7H2O) 14.9 g/L |
| Ammonium sulfate (NH4)2SO4 9 g/L |
| EDTA (Ethylenediaminetetraacetic acid) 65.25 mg/L |
| FeSO4—7H2O (Iron Sulfate heptahydrate) 12.18 g/L |
| ZnSO4—7H2O (Zinc sulfate heptahydrate) 25.0125 g/L |
| CaCl2—2H2O (Calcium chloride dihydrate) 12.615 g/L |
| CuSO4—5H2O (Copper sulfate pentahydrate) 2.175 g/L |
| NaMoO4—2H2O (Sodium molybdate dihydrate) 2.088 g/L |
| CoCl2—6H2O (Cobalt chloride hexahydrate) 2.0445 g/L |
| MnCl2—4H2O (Manganese chloride tetrahydrate) 1.392 g/L |
| Biotin 0.2175 g/L |

After 48 hours, samples were harvested for analysis.

Analysis

Protein expression was analyzed in samples of culture that were centrifuged to remove the cell mass. The clarified supernatant was then evaluated by ELISA and Western blot.

Figure 6:
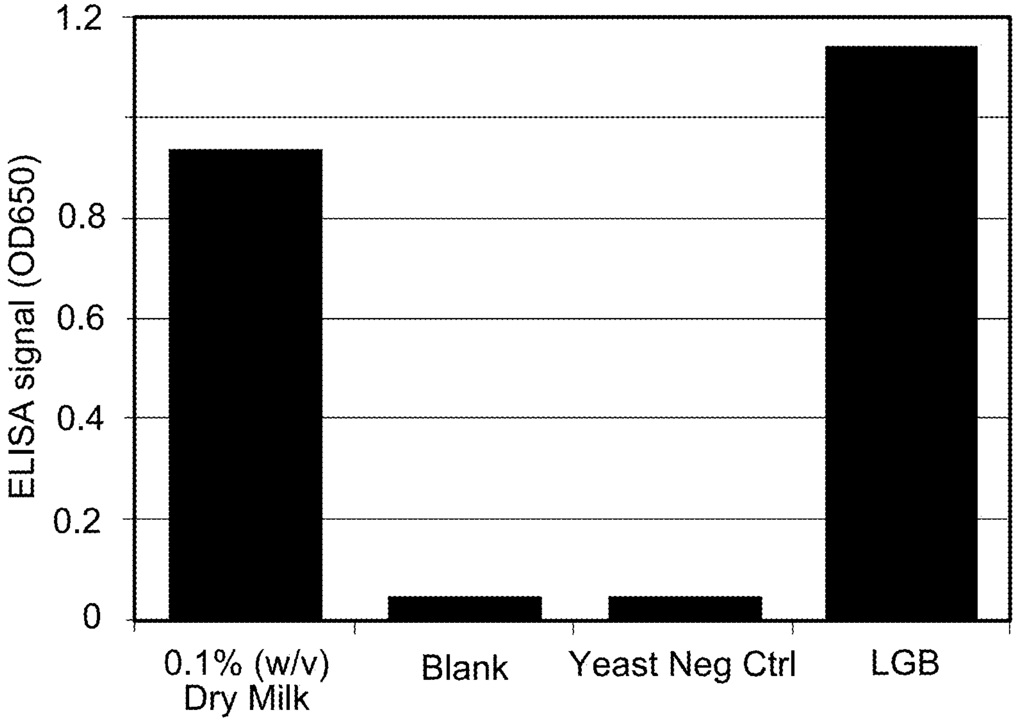
FIG. 6 is shows the levels of secretion of β-lactoglobulin by wildtype yeast cells and yeast cells including a vector as described in Example 6 (using SDS-PAGE).

To measure protein titers via ELISA, 25 μL of each sample were placed in a half-area 96 well microtiter plate, and allowed to bind overnight at 4° C. After removing the samples, the binding surface was blocked by filling each well with 1% (w/v) bovine serum albumin (BSA) dissolved in Tris Buffered Saline (50 mM Tris, pH 7.6, 150 mM NaCl) and incubating for 1 hour at room temperature. The samples were then incubated for 1.5 hr in primary antibody that was diluted in 1% BSA/TBS+0.1% (v/v) Tween-20. Following three washes in TBS+Tween, the samples were incubated with secondary antibody conjugated with horseradish peroxidase (HRP) for an additional hour. After three final washes in TBS+Tween, a chromogenic substrate (TMB Single Solution, Life Technologies) was added, and the absorbance at 650 nm was measured. The resulting data show the secretion of β-lactoglobulin (FIG. 6).

Figure 7:
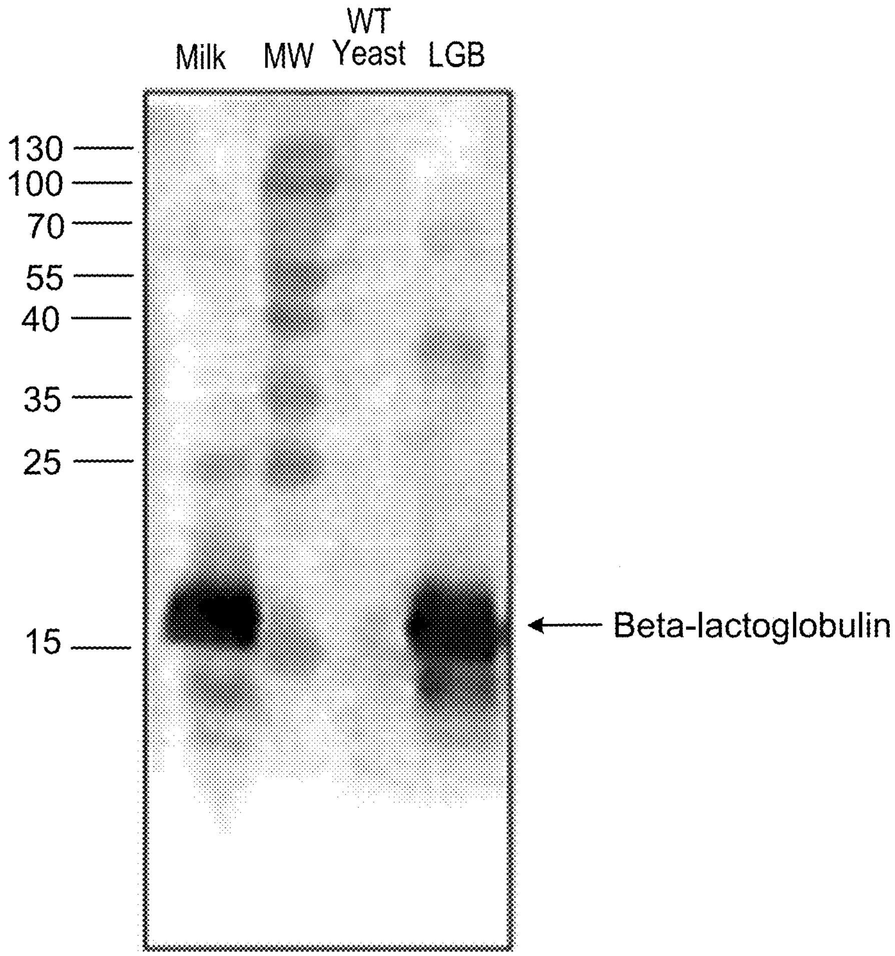
FIG. 7 is a Western blot showing the level of secretion of β-lactoglobulin from wildtype yeast and yeast cells including a vector as described in Example 6.

To analyze samples via western blot, one volume of sample was combined with an equal volume of SDS-PAGE sample buffer and run on a 10% polyacrylamide gel. The proteins were transferred to a nitrocellulose membrane, which was blocked by treating with 1% BSA/TBS for 1 hr. After incubating for 1.5 hr with primary antibody diluted in 1% BSA/TBS+Tween, the blot was washed three times in TBS+Tween. The blot was then incubated with secondary antibody conjugated with horseradish peroxidase (HRP) for an additional hour. After three final washes in TBS+Tween, a chromogenic substrate (1-Step Ultra TMB Blotting Solution, Thermo Fisher) was added. After staining was completed, the blot was washed in distilled water. The resulting Western blot shows that β-lactoglobulin was secreted from the recombinant yeast (FIG. 7).

Bovine Caseins

Dual expression plasmids were built, to support expression of α-S1-casein with β-casein in one plasmid, and α-S2-casein with kappa-casein in another plasmid. These pairings were chosen because the molar ratio of α-S1:α-S2:0:x in fluid milk is approximately 5.5: 1.5: 4.0: 1.5; it is therefore desirable to have a similar number of copies of α-S1-casein and beta-casein, and a similar number of copies of α-S2-casein and kappa-casein.

Beta-casein and α-S2-casein were placed under the control of the constitutive $P_{GAP}$ promoter in their respective plasmids, while α-S1-casein and κ-casein were placed under the control of the constitutive $P_{PGK}$ promoter.

In order to direct the proteins into the secretory pathway, the proteins were expressed with either their native signal peptide (pLH46 and pLH47), or the OST1 signal peptide (pLH48 and pLH49). In addition, plasmids were made in which one protein was expressed with its native signal peptide, and the other protein with the OST1 signal peptide:

pLH0050 OST1-beta, native-α-S1 pLH0051 native-β, OST1-α-S1 pLH0054 OST1-α-S2, native-κ pLH0055 native-α-S2, OST1-κ

To generate strains expressing all four casein proteins, yeast cells were first transformed with the plasmid encoding beta-casein and α-S1-casein. Prior to transformation, 20 μg of each plasmid was linearized with the enzyme ApaLI. The digested plasmids were then concentrated by ethanol precipitation, and resuspended in 10 μl distilled water.

Competent *Pichia pastoris* cells were prepared as follows: A culture of *P. pastoris* was grown to log phase (OD600~1.0) in YPD media (10 g/L yeast extract, 20 g/L peptone, 20 g/L dextrose). A 1.5 mL aliquot was harvested by centrifugation, then resuspended in 1 mL of a 1:1 mixture of YPD+20 mM HEPES (pH 8):1M lithium acetate. After adding 10 μL 1 M dithiothreitol, the cells were incubated for 15 min at 30° C. in a shaker at 300 rpm. The cells were pelleted by centrifugation and washed three times in 1 mL ice cold 1 M sorbitol. After the final wash, the cells were resuspended in 50 μL 1 M sorbitol.

The cells were combined with the linearized plasmid DNA in a chilled 2 mm electroporation cuvette, and subjected to a 1.5 kV pulse (25 μF, 200Ω). The cells were transferred to a culture tube with 200 μL cold 1:1 YPD:1 M sorbitol, and allowed to recover for 2 hours at 30° C. (300 rpm). Finally, the cells were plated onto PG agar (20 g/L peptone, 2% (v/v) glycerol, 2% agar) plates containing zeocin and grown for two days at 30° C.

Six clones from the beta+alphaS1 plates were then grown in culture, and made competent for DNA uptake using the procedure described above. They were then transformed with the linearized alphaS2+kappa plasmids, and grown for two days at 30° C. on PG plates containing G418.

Expression

To evaluate the production of bovine casein proteins, five clones expressing casein and a wildtype yeast negative control were grown overnight in PG media (20 g/L peptone, 2% glycerol) at 30° C. with shaking at 300 rpm. All five of the casein-expressing clones expressed alphaS2- and κ-casein with the respective native casein signal peptides. Clones sLH115, 116, 117, and 118 expressed β-casein and α-S1-casein with the respective native signal peptides; clone sLH122 expressed beta-casein and α-S1-casein with the OST1 signal peptide. The cultures were diluted 1:10 in minimal sulfate media:

| |
|---|
| Glucose 20 g/L |
| Calcium Chloride (CaCl2) 1 g/L |
| Sodium phosphate (Na2PO4) 24 g/L |
| Potassium sulfate (K2SO4) 18.2 g/L |
| Magnesium sulfate (MgSO4—7H2O) 14.9 g/L |
| Ammonium sulfate (NH4)2SO4 9 g/L |
| EDTA (Ethylenediaminetetraacetic acid) 65.25 mg/L |
| FeSO4—7H2O (Iron Sulfate heptahydrate) 12.18 g/L |
| ZnSO4—7H2O (Zinc sulfate heptahydrate) 25.0125 g/L |
| CaCl2—2H2O (Calcium chloride dihydrate) 12.615 g/L |
| CuSO4—5H2O (Copper sulfate pentahydrate) 2.175 g/L |
| NaMoO4—2H2O (Sodium molybdate dihydrate) 2.088 g/L |
| CoCl2—6H2O (Cobalt chloride hexahydrate) 2.0445 g/L |
| MnCl2—4H2O (Manganese chloride tetrahydrate) 1.392 g/L |
| Biotin 0.2175 g/L |

After 48 hours, samples were harvested for analysis.

Analysis

Protein expression was analyzed in samples of culture that were centrifuged to remove the cell mass. The clarified supernatant was then evaluated by ELISA and western blot.

Figure 8:
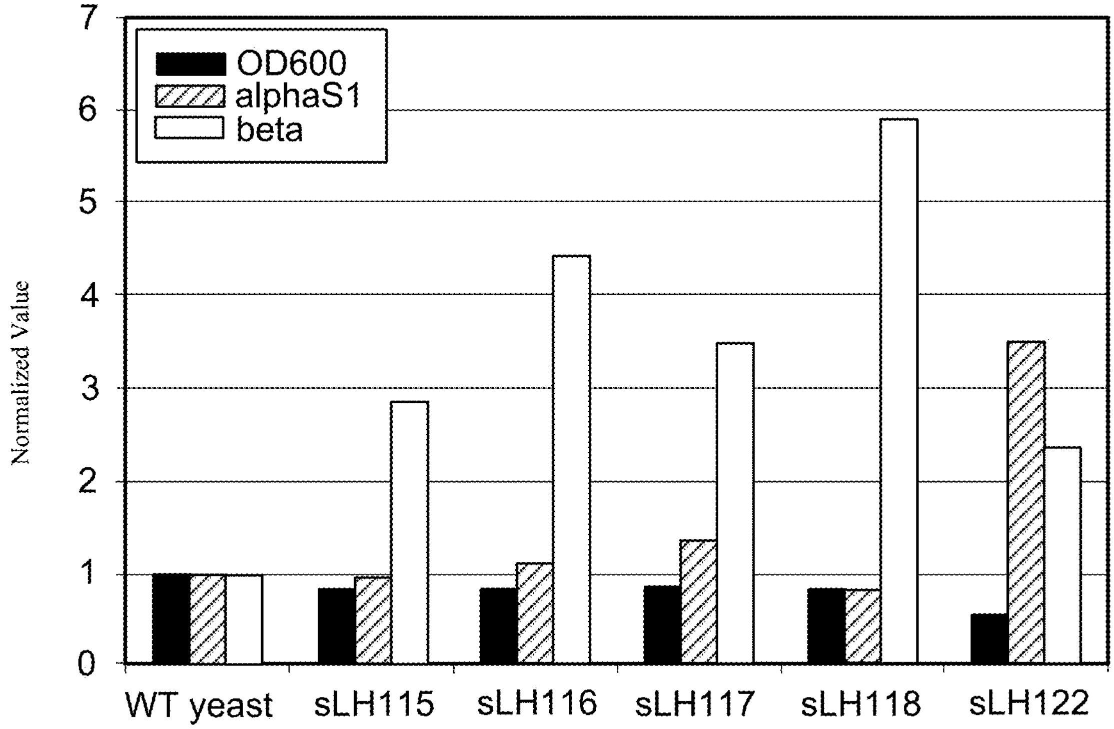
FIG. 8 is a graph showing the level of secreted β-casein and secreted α-S1-casein produced by wildtype yeast and yeast cells including the vectors described in Example 6.

To measure protein titers via ELISA, 25 μL of each sample were placed in a half-area 96 well microtiter plate, and allowed to bind overnight at 4° C. After removing the samples, the binding surface was blocked by filling each well with 1% (w/v) bovine serum albumin (BSA) dissolved in Tris Buffered Saline (50 mM Tris, pH 7.6, 150 mM NaCl) and incubating for 1 hour at room temperature. The samples were then incubated for 1.5 hr in primary antibody that was diluted in 1% BSA/TBS+0.1% (v/v) Tween-20. Following three washes in TBS+Tween, the samples were incubated with secondary antibody conjugated with horseradish peroxidase (HRP) for an additional hour. After three final washes in TBS+Tween, a chromogenic substrate (TMB Single Solution, Life Technologies) was added, and the absorbance at 650 nm was measured. The ELISA data show that the different yeast strains can secrete α-S1 casein and β-casein into the culture medium (FIG. 8).

To analyze samples via western blot, one volume of sample was combined with an equal volume of SDS-PAGE sample buffer and run on a 10% polyacrylamide gel. The proteins were transferred to a nitrocellulose membrane, which was blocked by treating with 1% BSA/TBS for 1 hr. After incubating for 1.5 hr with primary antibody diluted in 1% BSA/TBS+Tween, the blot was washed three times in TBS+Tween. The blot was then incubated with secondary antibody conjugated with horseradish peroxidase (HRP) for an additional hour. After three final washes in TBS+Tween, a chromogenic substrate (1-Step Ultra TMB Blotting Solution, Thermo Fisher) was added. After staining was completed, the blot was washed in distilled water.

The data in this Example show that the different expression vectors described herein can be used to generate transgenic yeast strains that secrete the different milk proteins.

Example 7. Method of Making a Composition

An exemplary composition described herein was generated using the specific method described below. A schematic diagram of this method is shown in FIG. 9.

To prepare the milk product, laboratory equipment such as mixers, stirring plates, and sonicators are employed. For large scale production, standard fluid milk processing equipment should be used.

Figure 9:
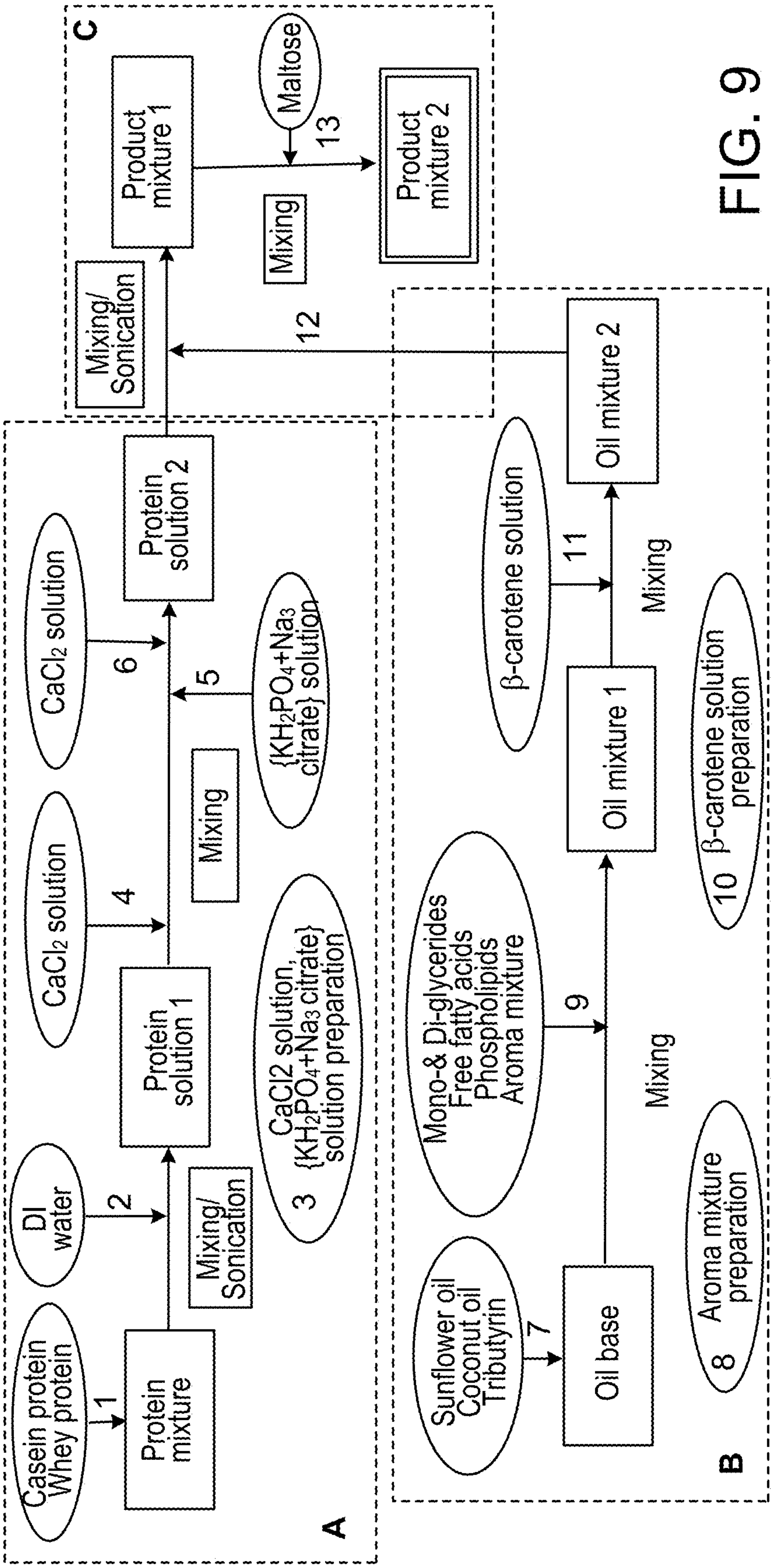
FIG. 9 is a schematic showing the steps in the process described in Example 7.

As FIG. 9 shows, there are three main components to this method of making a composition. These steps include:

A. Preparation of the protein solution

B. Preparation of the oil mixture

C. Reconstitution of the milk solids

In step A, powdered micellar casein protein and whey protein are combined and blended (step 1) and subsequently mixed with deionized (DI) water (step 2) to obtain the protein solution 1. Typically, this contains 2.8% powered micellar casein, 0.7% powered whey protein, and 85.5% water in this solution. The mixing vessel is covered to prevent evaporation of water. This mixing is performed by mixers, stirring plates, or a sonicator in a sufficient period of time (approximately 30 minutes). This mixing time ensures all proteins are dispersed in the water. The mixing speed has been optimized as medium which provides enough force to disperse the proteins and avoids the entrapment of air in the solution. The water content can be adjusted according to the usage of other ingredients.

In step 3, separate solutions of $CaCl_2$), $KH_2PO_4$, and $Na_3$ citrate in water are the mineral sources utilized to prepare similar mineral profile as native bovine milk. In a typical instance, $CaCl_2$) solution concentration is 0.1 g/mL, $KH_2PO_4$ is 0.27 g/mL, and $Na_3$ citrate solution is 0.21 g/ml $Na_3$ citrate. The water used to prepare $KH_2PO_4$ with $Na_3$ citrate solution is usually warm to make sure the complete dissolution of $KH_2PO_4$. During the mixing of protein solution 1, 0.015% $CaCl_2$) is added slowly (step 4). The volume of $CaCl_2$) solution used is adjusted according to the weight percent of $CaCl_2$) needed. The mixing continues for approximately 30 minutes to allow the complete interaction between proteins and Ca' ions. Subsequently, 0.27% $KH_2PO_4$ and 0.21% $Na_3$ citrate are divided to 5 portions and each portion is added slowly into the mixing solution at an interval time of 5 to 10 minutes (step 5). 0.085% $CaCl_2$) is divided to 4 portions and each portion is added slowly into the mixing solution at an interval time of 5-10 minutes (step 6). The mixing continues for at least 30 minutes, preferably 1-2 hours, to obtain the protein solution 2.

In the process B, low speed mixing is sufficient to achieve the homogeneous mixing of different oil ingredients. The percent of each component used below for preparing the oil mixture 1 is based on the total oil mixture 1 weight. Initially, 65% sunflower oil, 29% coconut oil, and 2% tributyrin are mixed together form the oil base (step 7). The sunflower oil and coconut oil is deodorized to prevent an unwanted aroma. The combination of sunflower oil, coconut oil, and tributyrin can mimic a similar fatty acid profile as the native milk. The oil base ingredient and its content can be adjusted according to different needs (different types of products). The aroma mixture is prepared by mixing different the aroma components in the sunflower oil (step 8). The compounds used to mimic the aroma contain, but are not limited to ethyl butyrate, δ-decalactone, 2-furyl methyl ketone, 2,3-pentanedione, γ-undecalactone, δ-undecalactone, acetoin, furfuryl alcohol, furfural, 2-methylfurfural, and 2-methylpyrazine. Their contents can be adjusted by different applications and preference. 2.5% mono- and di-glycerides, 0.6% free fatty acids, 0.5% phospholipids, and 0.4% aroma mixture are added to prepare the oil mixture 1 with mixing (step 9). In a typical instance, free fatty acids contain 0.15% butyric acid and 0.45% hexanoic acid. Soy lecithin is used as the phospholipid source. Soy lecithin is readily available and is inexpensive. A β-carotene solution is prepared in sunflower oil at a concentration of 0.5 mg/g (step 10). 4% of oil mixture 1 and 0.06% the β-carotene solution are mixed together to obtain the oil mixture 2 (step 11). The usage of β-carotene is adjusted to achieve different color levels of the milk. The usage of oil mixture 1 can also be adjusted according to different milk product applications.

In the process C, oil mixture 2 is added slowly to protein solution 2 and mixed thoroughly to prepare product mixture 1 (step 12). The mixing can be performed by mixers or sonicators. In a typical instance, oil mixture 2 and protein solution 2 are mixed under medium to high speed to ensure sure the oil is uniformly dispersed in the aqueous solution. Subsequently, sonication is applied to break down the oil globules into smaller size, which leads to an increase of their stability in the solution. It is necessary to prevent the entrapment of air bubbles in the solution during mixing. A mixing time of least 20 minutes is utilized to stir the oil mixture 2 into the aqueous solution and allow the thorough dispersion. A 4% maltose solution is added into product mixture 1 and was mixed continuously for an additional 30 minutes to yield product mixture 2 (step 13). The sweetness can be adjusted by the sugar content according to different applications. The source of the sugar can also be adjusted according to requests. Extra DI water may be required to make up the final total weight to 100%.

No intensive homogenization, pasteurization, and sterilization is included in this process. However, it will be necessary to apply these steps to prepare the product mixture in the process C for a scale-up production.

Equipment Used

Mixer: IKA-Labortechnik RW16 Basic, speed level (4-6)

Tip sonicator: Qsonica Model CL-188, Amplitude 70%

Water bath sonicator: Bransonic Model 1510R-MT

Example 8. Example Formulations

Example formulations compositions that have a similar taste and texture profile as whole milk, cream, high protein milk, fat-free milk, and sugar-free milk are provided in Tables 11-15 below.

As can be appreciated in the art, the compositions listed in Tables 11-15 are made by making the necessary modifications to the process described in Example 7.

TABLE 11

| Composition like Whole Milk Total Sample Weight 100 g | | | |
|---|---|---|---|
| | Wt % | Amount in Section | Weight Percent in 100 g Sample |
| Protein Component 3 g | | | |
| Micellular Casein | 80% | 2.4 g | 2.40% |
| Whey Protein | 20% | 0.6 g | 0.60% |

TABLE 11-continued

| Composition like Whole Milk Total Sample Weight 100 g | | | |
|---|---|---|---|
| | Wt % | Amount in Section | Weight Percent in 100 g Sample |
| Fat 3.9 g | | | |
| Sunflower Oill | 65% | 2.54 g | 2.54% |
| Coconut Oil | 29% | 1.13 g | 1.13% |
| Tributyrin | 2% | 0.08 g | 0.08% |
| Mono and Di Glycerides | 2.50% | 0.098 g | 0.098% |
| Free fatty acids (butyric and hexanoic acid | 0.60% | 0.023 g | 0.023% |
| Phospholipids | 0.50% | 0.020 g | 0.02% |
| Aroma Compounds 0.4% | 0.40% | 0.016 g | 0.016% |
| Minerals 0.54 g | | | |
| Calcium | | 0.1005 g | 0.1005% |
| Phosphores | | 0.09 g | 0.090% |
| Potassium | | 0.078 g | 0.078% |
| Sodium | | 0.0545 g | 0.0545% |
| Citrate | | 0.1493 g | 0.1493% |
| Chloride | | 0.064 g | 0.064% |
| Sugar 4 g | | | |
| Maltose | | 4 g | 4% |
| Water | | 88.56 g | 88.56% |

Aroma Compounds List
δ-Decalactone
Ethyl butyrate
2-furyl methyl ketone
2,3-pentanedione
γ-Undecalactone
δ-Undecalactone

TABLE 12

| Composition like Cream Total Sample Weight 100 g | | | |
|---|---|---|---|
| | Wt % | Amount in Section | Weight Percent in 100 g Sample |
| Protein Component 3 g | | | |
| Micellular Casein | 80% | 2.4 g | 2.40% |
| Whey Protein | 20% | 0.6 g | 0.60% |
| Fat 40 g | | | |
| Sunflower Oil | 65% | 26 g | 26.0% |
| Coconut Oil | 29% | 11.6 g | 11.6% |
| Tributyrin | 2% | 0.8 g | 0.8% |
| Mono and Di Glycerides | 2.50% | 1 g | 1.0% |
| Free fatty acids (butyric and hexanoic acid) | 0.60% | 0.24 g | 0.24% |
| Phospholipids | 0.50% | 0.2 g | 0.2% |
| Aroma Compounds 0.4% | 0.40% | 0.16 g | 0.16% |
| Minerals 0.54 g | | | |
| Calcium | | 0.1005 g | 0.1005% |
| Phosphorus | | 0.09 g | 0.090% |
| Potassium | | 0.078 g | 0.078% |
| Sodium | | 0.0545 g | 0.0545% |
| Citrate | | 0.1493 g | 0.1493% |
| Chloride | | 0.064 g | 0.064% |
| Sugar 4 g | | | |
| Maltose | | 4 g | 4% |
| Water | | 52.46 g | 52.46% |

Aroma Compounds List
δ-Decalactone
Ethyl butyrate
2-furyl methyl ketone
2,3-pentanedione
γ-Undecalactone
δ-Undecalactone

TABLE 13

| Composition like Protein Rich Milk<br>Total Sample Weight 100 g | Wt % | Amount in Section | Weight Percent in 100 g Sample |
|---|---|---|---|
| Protein Component 6 g | | | |
| Micellular Casein | 80% | 4.8 g | 4.80% |
| Whey Protein | 20% | 1.2 g | 1.20% |
| Fat 3.9 g | | | |
| Sunflower Oil | 65% | 2.54 g | 2.54% |
| Coconut Oil | 29% | 1.13 g | 1.13% |
| Tributyrin | 2% | 0.08 g | 0.08% |
| Mono and Di Glycerides | 2.50% | 0.098 g | 0.098% |
| Free fatty acids (butyric and hexanoic acid) | 0.60% | 0.023 g | 0.023% |
| Phospholipids | 0.50% | 0.020 g | 0.02% |
| Aroma Compounds 0.4% | 0.40% | 0.016 g | 0.016% |
| Minerals 0.54 g | | | |
| Calcium | | 0.1005 g | 0.1005% |
| Phosphorus | | 0.09 g | 0.090% |
| Potassium | | 0.078 g | 0.078% |
| Sodium | | 0.0545 g | 0.0545% |
| Citrate | | 0.1493 g | 0.1493% |
| Chloride | | 0.064 g | 0.064% |
| Sugar 4 g | | | |
| Maltose | | 4 g | 4% |
| Water | | 85.56 g | 85.56% |

Aroma Compounds List
δ-Decalactone
Ethyl butyrate
2-furyl methyl ketone
2,3-pentanedione
γ-Undecalactone
δ-Undecalactone

TABLE 14

| Composition like Fat-Free Milk<br>Total Sample Weight 100 g | Wt % | Amount in Section | Weight Percent in 100 g Sample |
|---|---|---|---|
| Protein Component 3 g | | | |
| Micellular Casein | 80% | 2.4 g | 2.40% |
| Whey Protein | 20% | 0.6 g | 0.60% |
| Minerals 0.54 g | | | |
| Calcium | | 0.1005 g | 0.1005% |
| Phosphorus | | 0.09 g | 0.090% |
| Potassium | | 0.078 g | 0.078% |
| Sodium | | 0.0545 g | 0.0545% |
| Citrate | | 0.1493 g | 0.1493% |
| Chloride | | 0.064 g | 0.064% |
| Sugar 4 g | | | |
| Maltose | | 4 g | 4% |
| Water | | 92.46 g | 92.46% |

Aroma Compounds List
δ-Decalactone
Ethyl butyrate
2-furyl methyl ketone
2,3-pentanedione
γ-Undecalactone
δ-Undecalactone

TABLE 15

| Composition like Sugar Free Milk<br>Total Sample Weight 100 g | Wt % | Amount in Section | Weight Percent in 100 g Sample |
|---|---|---|---|
| Protein Component 3 g | | | |
| Micellular Casein | 80% | 2.4 g | 2.40% |
| Whey Protein | 20% | 0.6 g | 0.60% |
| Fat 3.9 g | | | |
| Sunflower Oil | 65% | 2.54 g | 2.54% |
| Coconut Oil | 29% | 1.13 g | 1.13% |
| Tributyrin | 2% | 0.08 g | 0.08% |
| Mono and Di Glycerides | 2.50% | 0.098 g | 0.098% |
| Free fatty acids (butyric and hexanoic acid) | 0.60% | 0.023 g | 0.023% |
| Phospholipids | 0.50% | 0.020 g | 0.02% |
| Aroma Compounds 0.4% | 0.40% | 0.016 g | 0.016% |
| Minerals 0.54 g | | | |
| Calcium | | 0.1005 g | 0.1005% |
| Phosphorus | | 0.09 g | 0.090% |
| Potassium | | 0.078 g | 0.078% |
| Sodium | | 0.0545 g | 0.0545% |
| Citrate | | 0.1493 g | 0.1493% |
| Chloride | | 0.064 g | 0.064% |
| Sugar 4 g | | | |
| Stevia | | 4 g | 4% |
| Water | | 88.56 g | 88.56% |

Aroma Compounds List
δ-Decalactone
Ethyl butyrate
2-furyl methyl ketone
2,3-pentanedione
γ-Undecalactone
δ-Undecalactone

Example 9. Exemplary Composition

Figure 10:
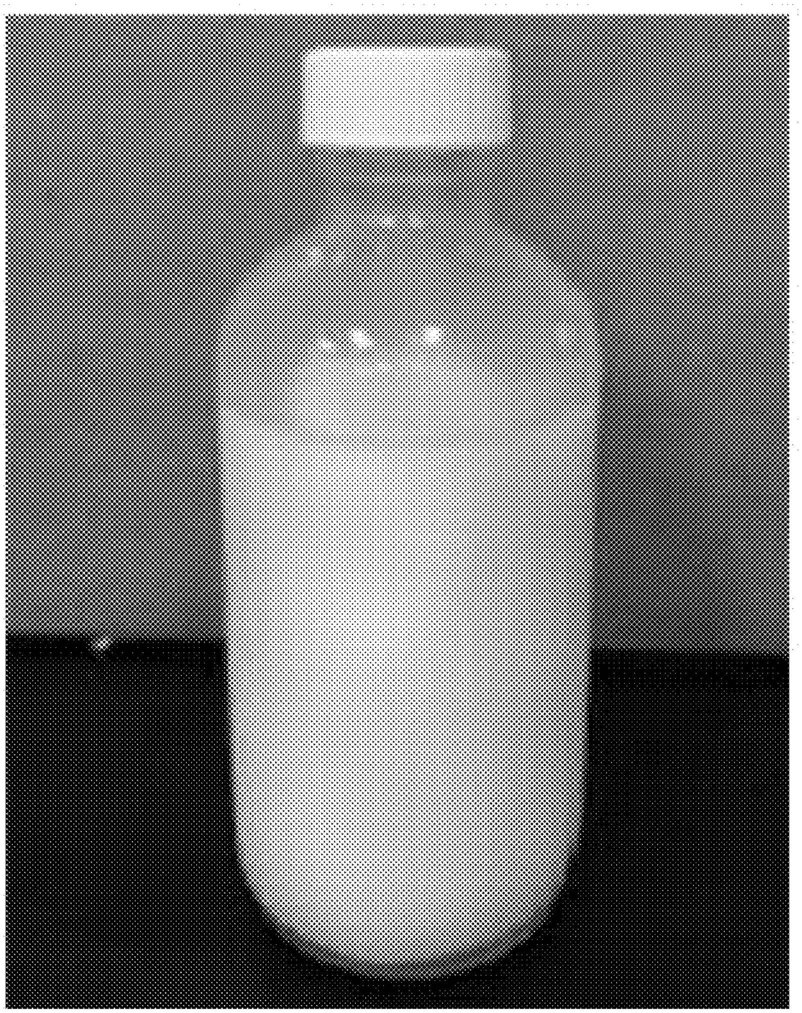
FIG. 10 is an image of a composition made by a method described herein.

An exemplary composition made by the presently described methods is shown in FIG. 10. The composition in FIG. 10 has a similar look (color), viscosity, foaming property, flavor, and nutritional value as a mammal-produced milk. The composition shown in FIG. 10 comprises mammal-derived proteins.

What is claimed is:

1. A substitute dairy food composition, wherein:

(a) the substitute dairy food composition comprises one or more identified recombinant milk proteins;

(b) the substitute dairy food composition is essentially free of milk proteins other than the one or more identified recombinant milk proteins;

(c) the one or more identified recombinant milk proteins are:

i. a recombinant a-lactalbumin protein, ii. a recombinant a-lactalbumin protein and a recombinant κ-casein protein, or iii. a recombinant a-lactalbumin protein and a recombinant β-casein protein; and (d) the one or more identified recombinant milk proteins confer on the substitute dairy food composition one or more characteristics of a dairy product.

2. The substitute dairy food composition of claim 1, wherein at least one of the one or more identified recombinant milk proteins comprises an amino acid sequence that is at least 80% identical to an amino acid sequence of a cow milk protein, a sheep milk protein, a horse milk protein, a goat milk protein, or a human milk protein.

3. The substitute dairy food composition of claim 1, wherein the recombinant α-lactalbumin protein comprises an amino acid sequence that is at least 90% identical to an amino acid sequence of a human milk α-lactalbumin protein.

4. The substitute dairy food composition of claim 1, wherein at least one of the one or more identified recombinant milk proteins is produced by a fungal cell or a bacterial cell.

5. The substitute dairy food composition of claim 4, wherein the fungal cell is from a genus selected from the group consisting of: *Saccharomyces, Kluyveromyces, Pichia, Tetrahymena, Yarrowia, Hansenula, Blastobotrys, Zygosaccharomyces, Debravomyces, Aspergillus, Candida, Trichoderma, Chrysosporium, Fusarium*, and *Neurospora*.

6. The substitute dairy food composition of claim 3, wherein the recombinant α-lactalbumin protein is produced by a fungal cell from genus *Aspergillus* or *Trichoderma*.

7. The substitute dairy food composition of claim 1, wherein the substitute dairy food composition is selected from the group consisting of a substitute ice cream, a substitute cream, a substitute milk, a substitute cream cheese, a substitute cottage cheese, a substitute yogurt, a substitute cheese, a substitute crème fraiche, a substitute buttermilk, a substitute butter, a substitute frozen custard, a substitute curd, a nutritional supplement composition, and an infant formula.

8. The substitute dairy food composition of claim 1, wherein the substitute dairy food composition is a powder.

9. A supplemented dairy food composition, wherein:

(a) the supplemented dairy food composition comprises a mammalian-produced milk or a mammal-produced dairy food;

(b) the supplemented dairy food composition comprises one or more identified recombinant milk proteins;

(c) the one or more identified recombinant milk proteins are:

i. a recombinant α-lactalbumin protein, ii. a recombinant α-lactalbumin protein and a recombinant-casein protein, or iii. a recombinant α-lactalbumin protein and a recombinant β-casein protein; and (d) the one or more identified recombinant milk proteins confer on the supplemented dairy food composition one or more characteristics of a dairy product; and (e) the supplemented dairy food composition is essentially free of native milk proteins.

10. The supplemented dairy food composition of claim 9, wherein at least one of the one or more identified recombinant milk proteins comprises an amino acid sequence that is at least 80% identical to an amino acid sequence of a cow milk protein, a sheep milk protein, a horse milk protein, a goat milk protein, or a human milk protein.

11. The supplemented dairy food composition of claim 9, wherein the recombinant α-lactalbumin protein comprises an amino acid sequence that is at least 90% identical to an amino acid sequence of a human milk α-lactalbumin protein.

12. The supplemented dairy food composition of claim 9, wherein at least one of the one or more identified recombinant milk proteins is produced by a fungal cell or a bacterial cell.

13. The supplemented dairy food composition of claim 12, wherein the fungal cell is from a genus selected from the group consisting of: *Saccharomyces, Kluyveromyces, Pichia, Tetrahymena, Yarrowia, Hansenula, Blastobotrys, Zygosaccharomyces, Debravomyces, Aspergillus, Candida, Trichoderma, Chrysosporium, Fusarium*, and *Neurospora*.

14. The supplemented dairy food composition of claim 9, wherein the mammalian-produced milk or the mammal-produced dairy food is selected from the group consisting of: an ice cream composition, a milk composition, a yoghurt composition, a cream composition, a cheese composition, a frozen custard composition, a crème fraiche composition, a curd composition, a cottage cheese composition, a cream cheese composition, a buttermilk composition, and a caseinate composition.

15. An infant formula, wherein the infant formula comprises a recombinant α-lactalbumin protein; and wherein the infant formula is essentially free of native milk proteins.

16. The infant formula of claim 15, wherein the recombinant α-lactalbumin protein comprises an amino acid sequence that is at least 80% identical to an amino acid sequence of a cow milk protein, a sheep milk protein, a horse milk protein, a goat milk protein, or a human milk protein.

17. The infant formula of claim 15, wherein the recombinant α-lactalbumin protein comprises an amino acid sequence that is at least 90% identical to an amino acid sequence of a human α-lactalbumin protein.

18. The infant formula of claim 15, wherein the recombinant α-lactalbumin protein is produced by a fungal cell or a bacterial cell.

19. The infant formula of claim 18, wherein the fungal cell is from a genus selected from the group consisting of:

*Saccharomyces, Kluyveromyces, Pichia, Tetrahymena, Yarrowia, Hansenula, Blastobotrys, Zygosaccharomyces, Debravomyces, Aspergillus, Candida, Trichoderma, Chrysosporium, Fusarium*, and *Neurospora*.

20. The infant formula of claim 17, wherein the recombinant α-lactalbumin protein is produced by a fungal cell from genus *Aspergillus* or *Trichoderma*.

* * * * *

SEQUENCE LISTING

```
Sequence total quantity: 159
SEQ ID NO: 1           moltype = AA  length = 190
FEATURE                Location/Qualifiers
source                 1..190
                       mol_type = protein
                       organism = Bos taurus
SEQUENCE: 1
MMKSFFLVVT ILALTLPFLG AQEQNQEQPI RCEKDERFFS DKIAKYIPIQ YVLSRYPSYG  60
LNYYQQKPVA LINNQFLPYP YYAKPAAVRS PAQILQWQVL SNTVPAKSCQ AQPTTMARHP  120
HPHLSFMAIP PKKNQDKTEI PTINTIASGE PTSTPTIEAV ESTVATLEAS PEVIESPPEI  180
NTVQVTSTAV                                                        190

SEQ ID NO: 2           moltype = DNA  length = 573
FEATURE                Location/Qualifiers
source                 1..573
                       mol_type = genomic DNA
                       organism = Bos taurus
SEQUENCE: 2
atgatgaaga gtttttcct agttgtgact atcctagcat taaccctgcc atttttgggt  60
gcccaagagc aaaaccaaga acaaccaata cgctgtgaga aagatgaaag attcttcagt  120
gacaaaatag ccaaatatat cccaatccag tatgtgctga gtaggtatcc tagttatgga  180
ctcaattact accaacagaa accagttgca ctaattaata atcaatttct gccataccca  240
tattatgcaa agccagctgc agttaggtca cctgcccaaa ttcttcaatg gcaagttttg  300
tcaaatactg tgcctgccaa gtcctgccaa gcccagccaa ccaccatggc acgtcaccca  360
cacccacatt tatcatttat ggccattcca ccaaagaaaa atcaggataa aacagaaatc  420
cctaccatca ataccattgc tagtggtgag cctacaagta cacctaccat cgaagcagta  480
gagagcactg tagctactct agaagcttct ccagaagtta ctgagagccc acctgagatc  540
aacacagtcc aagttacttc aaccgcggtc taa                              573

SEQ ID NO: 3           moltype = AA  length = 192
FEATURE                Location/Qualifiers
source                 1..192
                       mol_type = protein
                       organism = Capra hircus
SEQUENCE: 3
MMKSFFLVVT ILALTLPFLG AQEQNQEQPI CCEKDERFFD DKIAKYIPIQ YVLSRYPSYG  60
LNYYQQRPVA LINNQFLPYP YYAKPVAVRS PAQTLQWQVL PNTVPAKSCQ DQPTTLARHP  120
HPHLSFMAIP PKKDQDKTEV PAINTIASAE PTVHSTPTTE AIVNTVDNPE ASSESIASAS  180
ETNTAQVTST EV                                                     192

SEQ ID NO: 4           moltype = DNA  length = 579
FEATURE                Location/Qualifiers
source                 1..579
                       mol_type = genomic DNA
                       organism = Capra hircus
SEQUENCE: 4
atgatgaaga gtttttcct agttgtgact atcctggcat taaccctgcc atttttgggt  60
gcccaggagc aaaaccagga acagccgata tgctgtgaga aagatgaaag attcttcgat  120
gacaaaatag ccaaatatat cccaattcag tatgtgctga gtaggtatcc tagttatgga  180
ctcaattact atcaacagag accagttgca ctaattaata atcaatttct gccataccca  240
tattatgcaa agccagttgc agttaggtca cctgcccaaa ctcttcaatg gcaagttttg  300
ccaaatactg tgcctgccaa gtcctgccaa gaccagccaa ctaccctggc acgtcaccca  360
cacccacatt tatcatttat ggccattcca ccaaagaaag atcaggataa aacagaagtc  420
cctgccatca ataccattgc tagtgctgag cctacagtac acagtacacc taccaccgaa  480
gcaatagtga acactgtaga taatccagaa gcttcctcag aatcgattgc gagtgcatct  540
gagaccaaca cagcccaagt tacttcaacc gaggtctaa                        579

SEQ ID NO: 5           moltype = AA  length = 182
FEATURE                Location/Qualifiers
source                 1..182
                       mol_type = protein
                       organism = Felis catus
SEQUENCE: 5
MKTFFLVVNI LALTLPFLGA QVQNQEQPTC RENDERLLNQ KTAKYIPVHY VLSNYPHYEP  60
SYYPHKPAVP VNNQYMPYPY YAKPVAVRPH VQIPQWQVLP NTYTPTVVRH PHLPASFIAI  120
PPKKIQDKTG NPTINTIATA ELTLTPTTEP IVNTVVTTEA SSEFTITSTP ETTTVPVAST  180
MV                                                                182

SEQ ID NO: 6           moltype = DNA  length = 549
FEATURE                Location/Qualifiers
source                 1..549
                       mol_type = genomic DNA
                       organism = Felis catus
SEQUENCE: 6
atgaagactt ttttcctagt tgtgaatatc cttgcattaa ccttgccatt tttgggtgca  60
caggtgcaaa accaagaaca accaacttgc cgtgaaaatg atgaaagatt gcttaatcag  120
aaaactgcca agtatatccc agttcattat gtactgagta actatcctca ctatgagccc  180
agttactacc cgcataaacc agctgtacca gttaataatc aatatatgcc ctatccatat  240
```

```
tatgcaaaac cagttgcagt taggccacat gtccaaattc ctcagtggca agtcctgcca  300
aatacctaca cacccactgt ggtacgtcac ccacacctac ctgcgtcatt tattgccatt  360
cccccaaaga aaattcagga taagacaggc aaccctacca tcaataccat tgctactgct  420
gagcttacac ttactcctac cactgaacca atagtgaaca ctgtagtcac tacagaagca  480
tcctcagaat tcaccatcac aagcacacct gagactacca cagttccagt ggcttcaacc  540
atggtctaa                                                           549

SEQ ID NO: 7           moltype = AA  length = 196
FEATURE                Location/Qualifiers
source                 1..196
                       mol_type = protein
                       organism = Homo sapiens
SEQUENCE: 7
MRANANVADA QSAIMKSFLL VVNALALTLP FLAVEVQNQK QPACHENDER PFYQKTAPYV  60
PMYYVPNSYP YYGTNLYQRR PAIAINNPYV PRTYYANPAV VRPHAQIPQR QYLPNSHPPT  120
VVRRPNLHPS FIAIPPKKIQ DKIIIPTINT IATVEPTPAP ATEPTVDSVV TPEAFSESII  180
TSTPETTTVA VTPPTA                                                   196

SEQ ID NO: 8           moltype = DNA  length = 591
FEATURE                Location/Qualifiers
source                 1..591
                       mol_type = genomic DNA
                       organism = Homo sapiens
SEQUENCE: 8
atgagggcaa atgcaaatgt agctgatgcg caaagtgcaa taatgaagag ttttcttcta  60
gttgtcaatg ccctggcatt aaccctgcct tttttggctg tggaggttca aaaccagaaa  120
caaccagcat gccatgagaa tgatgaaaga ccattctatc agaaaacagc tccatatgtc  180
ccaatgtatt atgtgccaaa tagctatcct tattatggaa ccaatttgta ccaacgtaga  240
ccagctatag caattaataa tccatatgtg cctcgcacat attatgcaaa cccagctgta  300
gttaggccac atgcccaaat tcctcagcgg caatacctgc caaatagcca cccacccact  360
gtggtacgtc gcccaaacct gcatccatca tttattgcca tccccccaaa gaaaattcag  420
gataaaataa tcatccctac catcaatacc attgctactg ttgaacctac accagctcct  480
gccactgaac caacggtgga cagtgtagtc actccagaag ctttttcaga gtccatcatc  540
acgagcaccc ctgagacaac cacagttgca gttactccac ctacggcata a            591

SEQ ID NO: 9           moltype = AA  length = 178
FEATURE                Location/Qualifiers
source                 1..178
                       mol_type = protein
                       organism = Loxodonta Africana
SEQUENCE: 9
MKGFLLVVNI LLLPLPFLAA EVQNQEESRC LEKDERWFCQ KAVKYIPNDY VLKSYYRYEP  60
NYNQFRAAVP INNPYLIYLY PAKQVAVRPH TQIPQWQVPS NIYPSPSVPH TYLKPPFIVI  120
PPKKTQDKPI IPPTGTVASI EATVEPKVNT VVNAEASSEF IATNTPEATT VPVISPQI    178

SEQ ID NO: 10          moltype = DNA  length = 537
FEATURE                Location/Qualifiers
source                 1..537
                       mol_type = genomic DNA
                       organism = Loxodonta Africana
SEQUENCE: 10
atgaagggct ttctcttggt tgtgaacatc ctgttgttac ctttgccctt tttggctgca  60
gaggtgcaaa accaggagga gtcaagatgc cttgagaaag atgaaagatg gttctgtcag  120
aaagcagtca aatatattcc aaatgattat gtgctgaaga gctattatcg ttatgaacca  180
aattataacc aatttagggc agctgtacca atcaataatc catacctaat ttacctatat  240
cctgctaaac aggttgcagt taggccacat acacaaattc cgcaatggca agttccatca  300
aatatctacc catctccatc agtacctcac acatacctca aaccaccatt tattgtcatt  360
cccccaaaga aaactcagga taaacctata atccctccca ccggcaccgt tgcttctatt  420
gaagctaccg ttgagcctaa ggtgaacact gtcgtcaatg ctgaagcttc ctcagagttc  480
attgccacaa atacacctga ggctaccaca gtcccagtta tttcacccca gatctaa      537

SEQ ID NO: 11          moltype = AA  length = 175
FEATURE                Location/Qualifiers
source                 1..175
                       mol_type = protein
                       organism = Mammuthus primigenius
SEQUENCE: 11
MKGFLLVVNI LLLPLFLAAE VQNQEESRCL EKDERWFCQK AVKYIPNDYV LKSYYRYEPN  60
YNQFRAAVPI NNPYLIYLYP AKQVAVRPHT QIQWQVPSNI YPSPSVPHTY LKPPFIIPPK  120
KTQDKPIIPP TGTVASIEAT VEPKVNTVVN AEASSEFIAT NTPEATTVPV ISPQI       175

SEQ ID NO: 12          moltype = DNA  length = 546
FEATURE                Location/Qualifiers
source                 1..546
                       mol_type = genomic DNA
                       organism = Mammathus primigenius
SEQUENCE: 12
atgatgaagg gctttctctt ggttgtgaac atcctgttgt tacctttggc ctttttggct  60
gcagaggtgc aaaaccagga ggagtcaaga agctgttgcc ttgagaaaga tgaaagatgg  120
```

-continued

```
ttctgtcaga aagcagtcaa atatattcca aatgattatg tgctgaagag ctattatcgt  180
tatgaaccaa attataacca atttagggca gctgtaccaa tcaataatcc atacctaatt  240
tacctatatc ctgctaaaca ggttgcagtt aggccacata cacaaattct gcaatggcaa  300
gttccatcaa atatctaccc atctccatca gtacctcaca catacctcaa accaccattt  360
attgccattc ccccaaagaa aactcaggat aaacctataa tccctcccac cggcaccgtt  420
gcttctattg aagctaccgt tgagcctaag gtgaacactg tcgtcaatgc tgaagcttcc  480
tcagagttca ttgccacaaa tacacctgag gctaccacag tcccagttat ttcaccccag  540
atctaa                                                              546

SEQ ID NO: 13          moltype = AA  length = 180
FEATURE                Location/Qualifiers
source                 1..180
                       mol_type = protein
                       organism = Oryctolagus cuniculus
SEQUENCE: 13
MMKHFLLVVN ILAVTLPFLA ADIQNQEQTT CRENEERLFH QVTAPYIPVH YVMNRYPQYE  60
PSYYLRRQAV PTLNPFMLNP YYVKPIVFKP NVQVPHWQIL PNIHQPKVGR HSHPFFMAIL  120
PNKMQDKAVT PTTNTIAAVE PTPIPTTEPV VSTEVIAEAS PELIISPETT TEATAASAAA  180

SEQ ID NO: 14          moltype = DNA  length = 543
FEATURE                Location/Qualifiers
source                 1..543
                       mol_type = genomic DNA
                       organism = Oryctolagus cuniculus
SEQUENCE: 14
atgatgaagc attttcttct agttgtgaac atcctggcag taaccttgcc ttttttggct  60
gcagacatac aaaaccagga acagacaacg tgccgtgaga atgaggaaag actgttccac  120
caggttacag ctccatatat cccagttcac tatgtgatga acagatatcc tcaatacgaa  180
cccagctact acctgcgcag acaagctgtt ccaactctta atccatttat gcttaaccca  240
tattatgtaa aaccaattgt atttaagcca aatgtccaag ttcctcactg gcaaatcctg  300
ccaaatatcc accagccaaa agtgggacgt cactcacatc catttttat ggccattctc  360
ccgaataaaa tgcaggataa agcagtcacc cccaccacca acaccattgc tgctgtggag  420
cctaccccga ttcctaccac tgagccagtg gtgagcactg aagtgattgc agaggcttcc  480
ccagagctca tcatcagccc tgagactacc acggaagcaa ctgctgcatc agcggcagca  540
tga                                                                 543

SEQ ID NO: 15          moltype = AA  length = 192
FEATURE                Location/Qualifiers
source                 1..192
                       mol_type = protein
                       organism = Ovis aries
SEQUENCE: 15
MMKSFFLVVT ILALTLPFLG AQEQNQEQRI CCEKDERFFD DKIAKYIPIQ YVLSRYPSYG  60
LNYYQQRPVA LINNQFLPYP YYAKPVAVRS PAQTLQWQVL PNAVPAKSCQ DQPTAMARHP  120
HPHLSFMAIP PKKDQDKTEI PAINTIASAE PTVHSTPTTE AVVNAVDNPE ASSESIASAP  180
ETNTAQVTST EV                                                       192

SEQ ID NO: 16          moltype = DNA  length = 579
FEATURE                Location/Qualifiers
source                 1..579
                       mol_type = genomic DNA
                       organism = Ovis aries
SEQUENCE: 16
atgatgaaga gttttttcct agttgtgact atcctggcat taaccctgcc atttttgggt  60
gcccaggagc aaaaccaaga acaacgaata tgctgtgaga aagatgaaag attcttcgat  120
gacaaaatag ccaaatatat cccaattcag tatgtgctga gtaggtatcc tagttatgga  180
ctcaattact accaacagag accagttgca ctaattaata atcaatttct gccataccca  240
tattatgcga agccagttgc agttaggtca cctgcccaaa ctcttcaatg gcaagttttg  300
ccaaatgctg tgcctgccaa gtcctgccaa gaccagccaa ctgccatggc acgtcaccca  360
cacccacatt tatcatttat ggccattcca ccaaagaaag atcaggataa aacagaaatc  420
cctgccatca ataccattgc tagtgctgag cctacagtac acagtacacc taccaccgaa  480
gcagtagtga acgctgtaga taatccagaa gcttcctcag aatcgattgc gagtgcacct  540
gagaccaaca cagcccaagt tacttcaacc gaggtctaa                          579

SEQ ID NO: 17          moltype = AA  length = 181
FEATURE                Location/Qualifiers
source                 1..181
                       mol_type = protein
                       organism = Physeter catodon
SEQUENCE: 17
MKSFLLVVTI LALTLPFLSA EGQNQEQSTR CENDERLFNK KTVKYIPIHY VLSRYPSYGL  60
NYYQHRPVAL INNQFMPYLY YAKPVVVSPH AQIPQWQFLP NIHPPTLAHH PHPRPSFTAI  120
PPKKTQDKTA IPIINTIATV EPTLIPTTEP IVNTVVTPEA SSEFITSTPE TTTVQVASPV  180
A                                                                   181

SEQ ID NO: 18          moltype = DNA  length = 546
FEATURE                Location/Qualifiers
source                 1..546
                       mol_type = genomic DNA
```

```
                         organism = Physeter catodon
SEQUENCE: 18
atgaagagtt ttttactagt tgtgactatc ctggcattaa ccctgccttt tttgagtgca  60
gaggggcaaa accaggaaca atcaacacgc tgtgagaatg atgaaagatt gttcaataaa  120
aaaacagtaa aatatatccc aattcattat gtgctgagta ggtatcctag ttatggactc  180
aattactacc agcacagacc agttgcacta attaataacc aatttatgcc atacctatat  240
tatgcaaagc cagttgtagt tagcccacat gcccaaattc ctcaatggca attcctgcca  300
aatatccacc cacctactct ggcacatcac ccacacccac gtccatcatt tactgccatc  360
ccaccaaaga aaactcagga taaaacagca atccctatca tcaataccat tgctactgtt  420
gagcctacac ttatacctac cactgaacca atagtgaaca ctgtagttac tccagaagct  480
tcctcagaat tcatcacgag tacacctgag accaccacag tccaagttgc ttcacctgtg  540
gcctaa                                                              546

SEQ ID NO: 19            moltype = AA  length = 165
FEATURE                  Location/Qualifiers
source                   1..165
                         mol_type = protein
                         organism = Tachyglossus aculeatus
SEQUENCE: 19
MKTLLLVGGI LVMTVCFSAA EDEEWKKVDY SESEERWLRL KRQPSFPFSF QGKPERNIPR  60
PYYPRPFLNI PRPYTINPEH QFAYVFPNLK FQIPSVFPFP LEFLPPPYPF VHPIYYGPQT  120
STPPRNPTVT SQTPQPPVHS SANTPESATA APVTATPMAQ TPLQP                  165

SEQ ID NO: 20            moltype = DNA  length = 498
FEATURE                  Location/Qualifiers
source                   1..498
                         mol_type = genomic DNA
                         organism = Tachyglossus aculeatus
SEQUENCE: 20
atgaagactc tactactggt tggaggtatc ctggttatga ccgtttgctt ctccgcggca  60
gaggacgagg aatggaaaaa ggttgattac agcgagagtg aagaaagatg gttgaggctg  120
aagcgccagc caagctttcc ctttagcttc caaggcaaac ctgagagaaa catcccacgt  180
ccttattacc ctcgaccatt tctaaatatt ccccgcccct acacgattaa ccctgagcac  240
caattcgcct atgtttttcc caacttgaag ttccaaatcc caagtgtatt tccatttccc  300
ctggaattcc tcccaccttt ctatcccttt gttcatccca tctattatgg ccctcaaacc  360
tcaacccctc ccagaaatcc caccgtgacc agccaaactc cacagccccc tgtccattcc  420
tccgccaata ccccggagtc tgctactgct gcccccgtga ctgctacccc catggcccaa  480
actcccctcc aaccttaa                                                 498

SEQ ID NO: 21            moltype = AA  length = 178
FEATURE                  Location/Qualifiers
source                   1..178
                         mol_type = protein
                         organism = Trichosurus Vulpecula
SEQUENCE: 21
MKVLFLTVHI LAVMVCFSTA DLDWEKWPCD KQNERQSELR QQPLRRSPVQ YVYTPYTHQS  60
YVPVIYPPRA YVRHPYFSRV AWQKPYPSYM PLLPSIYPWS VVSRNLHPAF AFNPPHYAQL  120
PVPSSPTNSP TTTIQTTNIP ITNPTSTIVT PAVSSKSAAT EDSAAAAMLT SPTAAQMA    178

SEQ ID NO: 22            moltype = DNA  length = 537
FEATURE                  Location/Qualifiers
source                   1..537
                         mol_type = genomic DNA
                         organism = Trichosurus Vulpecula
SEQUENCE: 22
atgaaggtcc tattcttgac tgtgcatatt ctggcagtaa tggtgtgctt ctcaactgct  60
gacttggact gggaaaaatg gccttgcgat aagcaaaatg aaagacagtc tgagctgaga  120
caacagccac tcagacggtc ccctgtccaa tatgtctaca ccccatatac acatcaatca  180
tacgtgccag tcatttatcc accaagggca tatgtacgtc atccatattt ctctagagta  240
gcatggcaga aaccatatcc ctcctatatg ccactgctgc ccagtatcta cccttggtct  300
gtggtttcta gaaacctaca ccctgcattc gcttttaatc cccctcatta tgcccagctt  360
ccagtaccat caagtccaac caacagcccc acaactacca ttcagactac aaacattccc  420
atcactaacc ccacaagcac tatagtcacc ccagctgtct cctccaagtc tgcggccaca  480
gaggatagcg cagctgctgc aatgttgact tccccaaccg ctgctcagat ggcataa     537

SEQ ID NO: 23            moltype = AA  length = 178
FEATURE                  Location/Qualifiers
source                   1..178
                         mol_type = protein
                         organism = Monodelphis domestica
SEQUENCE: 23
MKVLFLIGHI LLAMVCFSTA ELDWRKWPCE KQMERPSELE QQPPGQPPVQ DVYTRYTRQI  60
YVPILYAPKT SIQYPYFSKL AWQRPYAAYI PLLSSRYPWP VIPRSPHPSF AFNPPQYARV  120
PAPSGPTSSP AAPMETTTIP STSTVAATVT PDATSKFVTT EYSTTATIPT SPIPEQQP    178

SEQ ID NO: 24            moltype = DNA  length = 537
FEATURE                  Location/Qualifiers
source                   1..537
                         mol_type = genomic DNA
```

```
                          organism = Monodelphis domestica
SEQUENCE: 24
atgaaggtcc tgttcttgat tgggcatatt ctgttggcaa tggtgtgctt ctctactgct  60
gaactggact ggaggaaatg gccttgcgag aagcaaatgg aaagaccatc ggagctggaa  120
caacagccac ccggacagcc ccctgtccaa gacgtctaca cccgatacac ccgtcagatc  180
tacgtaccca tcttgtatgc acccaagact tccatccagt atccatattt ctctaagcta  240
gcctggcaga gaccatatgc tgcctacata ccactgctgt ccagtcgcta cccgtggcct  300
gtgattccta gaagcccaca cccttccttc gcttttaatc ccccacaata tgcccgggtt  360
ccagccccat caggtcctac cagcagcccc gcagctccca tggagactac aaccattccc  420
agcacgagca ccgtagctgc gactgtcacc cccgacgcca cttctaaatt tgtaaccacc  480
gagtatagca caactgcaac aatcccaact tccccaatcc ctgaacagca accatga     537

SEQ ID NO: 25             moltype = AA  length = 224
FEATURE                   Location/Qualifiers
source                    1..224
                          mol_type = protein
                          organism = Bos taurus
SEQUENCE: 25
MKVLILACLV ALALARELEE LNVPGEIVES LSSSEESITR INKKIEKFQS EEQQQTEDEL  60
QDKIHPFAQT QSLVYPFPGP IPNSLPQNIP PLTQTPVVVP PFLQPEVMGV SKVKEAMAPK  120
HKEMPFPKYP VEPFTESQSL TLTDVENLHL PLPLLQSWMH QPHQPLPPTV MFPPQSVLSL  180
SQSKVLPVPQ KAVPYPQRDM PIQAFLLYQE PVLGPVRGPF PIIV                  224

SEQ ID NO: 26             moltype = DNA  length = 780
FEATURE                   Location/Qualifiers
source                    1..780
                          mol_type = genomic DNA
                          organism = Bos taurus
SEQUENCE: 26
atgccattaa atactatata taaacaacca caaaatcaga tcattatcca ttcagctcct  60
ccttcacttc ttgtcctcta ctttggaaaa aaggaattga gagccatgaa ggtcctcatc  120
cttgcctgcc tggtggctct ggcccttgca agagagctgg aagaactcaa tgtacctggt  180
gagattgtgg aaagcctttc aagcagtgag gaatctatta cacgcatcaa taagaaaatt  240
gagaagtttc agagtgagga acagcagcaa acagaggatg aactccagga taaaatccac  300
ccctttgccc agacacagtc tctagtctat cccttccctg ggcccatccc taacagcctc  360
ccacaaaaca tccctcctct tactcaaacc cctgtggtgg tgccgccttt ccttcagcct  420
gaagtaatgg gagtctccaa agtgaaggag gctatggctc ctaagcacaa agaaatgccc  480
ttccctaaat atccagttga gccctttact gaaagccaga gcctgactct cactgatgtt  540
gaaaatctgc accttcctct gcctctgctc cagtcttgga tgcaccagcc tcaccagcct  600
cttcctccaa ctgtcatgtt tcctcctcag tccgtgctgt ccctttctca gtccaaagtc  660
ctgcctgttc cccagaaagc agtgccctat ccccagagag atatgcccat tcaggccttt  720
ctgctgtacc aggagcctgt actcggtcct gtccggggac ccttccctat tattgtctaa  780

SEQ ID NO: 27             moltype = AA  length = 222
FEATURE                   Location/Qualifiers
source                    1..222
                          mol_type = protein
                          organism = Capra hircus
SEQUENCE: 27
MKVLILACLV ALAIAREQEE LNVVGETVES LSSSEESITH INKKIEKFQS EEQQQTEDEL  60
QDKIHPFAQA QSLVYPFTGP IPNSLPQNIL PLTQTPVVVP PFLQPEIMGV PKVKETMVPK  120
HKEMPFPKYP VEPFTESQSL TLTDVEKLHL PLPLVQSWMH QPPQPLSPTV MFPPQSVLSL  180
SQPKVLPVPQ KAVPQRDMPI QAFLLYQEPV LGPVRGPFPI LV                    222

SEQ ID NO: 28             moltype = DNA  length = 669
FEATURE                   Location/Qualifiers
source                    1..669
                          mol_type = genomic DNA
                          organism = Capra hircus
SEQUENCE: 28
atgaaggtcc tcatccttgc ctgtctggtg gctctggcca ttgcaagaga gcaggaagaa  60
ctcaatgtag tcggtgagac tgtggaaagc ctttcaagca gtgaggaatc tattacacac  120
atcaataaga aaattgagaa gtttcaaagt gaggaacaac agcaaacaga ggatgaactc  180
caggataaaa tccacccctt tgcccaggca cagtctctag tctatccctt cactgggccc  240
atccctaaca gcctcccaca aaacatcctg cctcttactc aaacccctgt ggtggtgccg  300
cctttccttc agcctgaaat aatgggagtc cccaaagtga aggagactat ggttcctaag  360
cacaaagaaa tgcccttccc taaatatcca gttgagccct ttactgaaag ccagagcctg  420
actctcactg atgttgaaaa gctgcacctt cctctgcctc tggtccagtc ttggatgcac  480
cagcctcccc agcctctttc tccaaccgtc atgtttcctc ctcagtccgt gctgtccctt  540
tctcagccca aagttctgcc tgttccccag aaagtagtgc cccagagaga tatgcccatc  600
caggcctttc tgctgtacca ggagcctgta cttggtcctg tccggggacc cttccctatt  660
cttgtctaa                                                         669

SEQ ID NO: 29             moltype = AA  length = 244
FEATURE                   Location/Qualifiers
source                    1..244
                          mol_type = protein
                          organism = Felis catus
SEQUENCE: 29
```

```
MKVLILACLL ALALAREKEE LTVSTETVES LSSSEESITH INKQKLENLK REEQQQRQEE  60
RQNKIHPVFQ PQPLVYPYAE PIPYPVLPQN ILPLAQPAMV LPFLQPEIME IPKVKETIFP  120
RRKVMPILKS PVVPSLDSQI VNLPDLESLH LPLPLPLSLL QPLMHQIPQP LPQTTMLPPQ  180
PLLSIPQPKV MPFPQQIVPY LQRDMPVQTL LLYQDATREA QPVTAPAYNP VIVSPNLIIP  240
LSHL                                                              244

SEQ ID NO: 30          moltype = DNA  length = 735
FEATURE                Location/Qualifiers
source                 1..735
                       mol_type = genomic DNA
                       organism = Felis catus
SEQUENCE: 30
atgaaggtcc tcatcctcgc ctgcctgctg gctcttgctc ttgcaagaga gaaggaagaa  60
ctcactgtat ccactgagac tgtggaaagt ctttcaagca gtgaggaatc tattacacac  120
atcaacaagc agaaacttga gaatcttaaa cgtgaggagc agcagcagag acaggaggaa  180
cgccagaata aaatccaccc cgttttccag ccacagcctc tagtctatcc ttatgctgag  240
cccattcctt accctgttct tccacagaac atccttcccc ttgctcagcc tgctatggtg  300
ctgcctttcc ttcagcctga aataatggaa atccccaaag ttaaggagac catctttccc  360
aggcgcaaag tgatgcccat tctgaaatct ccagtagtgc cctctttgga cagccaaatc  420
gtgaatctcc ctgatcttga aagtctgcac ttgcctctgc ctctgcctct gtctctactc  480
cagcccctga tgcaccagat cccccagcct cttcctcaga ctaccatgct tcctcctcag  540
ccactgctgt ccatcccaca gcccaaagtc atgccttttc cccagcaaat tgtgccctac  600
ctccagagag acatgcccgt gcaaacccta ctgctgtacc aggatgccac ccgtgaggcc  660
caacctgtga ctgccccagc ttacaatcct gttattgtaa gtccaaactt aataattccg  720
ctgtctcact tatga                                                  735

SEQ ID NO: 31          moltype = AA  length = 225
FEATURE                Location/Qualifiers
source                 1..225
                       mol_type = protein
                       organism = Homo sapiens
SEQUENCE: 31
MKVLILACLV ALALARETIE SLSSSEESIT EYKKVEKVKH EDQQQGEDEH QDKIYPSFQP  60
QPLIYPFVEP IPYGFLPQNI LPLAQPAVVL PVPQPEIMEV PKAKDTVYTK GRVMPVLKSP  120
TIPFFDPQIP KLTDLENLHL PLPLLQPLMQ QVPQPIPQTL ALPPQPLWSV PQPKVLPIPQ  180
QVVPYPQRAV PVQALLLNQE LLLNPTHQIY PVTQPLAPVH NPISV                 225

SEQ ID NO: 32          moltype = DNA  length = 678
FEATURE                Location/Qualifiers
source                 1..678
                       mol_type = genomic DNA
                       organism = Homo sapiens
SEQUENCE: 32
atgaaggtcc tcatcctcgc ctgcctggtg gctcttgctc ttgcaaggga gaccatagaa  60
agcctttcaa gcagtgagga atctattaca gaatacaaga aagttgagaa ggttaaacat  120
gaggaccagc agcaaggaga ggatgaacac caggataaaa tctacccctc tttccagcca  180
cagcctctga tctatccatt cgttgaacct atcccctatg gttttcttcc acaaaacatt  240
ctgcctcttg ctcagcctgc tgtggtgctg cctgtccctc agcctgaaat aatggaagtc  300
cctaaagcta aagacactgt ctacactaag ggcagagtga tgcctgtcct taaatctcca  360
acgataccct tttttgaccc tcaaatccca aaactcactg atcttgaaaa tctgcatctt  420
cctctgcctc tgctccagcc cttgatgcag caggtccctc agcctattcc tcagactctt  480
gcacttcccc ctcagcccct gtggtctgtt cctcagccca aagtcctgcc tatcccccag  540
caagtggtgc cctaccctca gagagctgtg cctgttcaag cccttctgct caaccaagaa  600
cttctactta accccaccca ccagatctac cctgtgactc agccacttgc cccagttcat  660
aaccccatta gtgtctaa                                               678

SEQ ID NO: 33          moltype = AA  length = 263
FEATURE                Location/Qualifiers
source                 1..263
                       mol_type = protein
                       organism = Loxodonta Africana
SEQUENCE: 33
MKVFILACLV AFALGRETVE NLSSSEIRQF YSEQKPEGVK HEEQQREDEH QNKIQPLFQP  60
QPLVYPFAEP IPYTVFPPNA IPLAQPIVVL PFPQPEVKQL PEAKEITFPR QKLMSFLKSP  120
VMPFFDPQIP NLGTDLENLH LPLPLLQPLR HQLHQPLAQT PVLPLPLSLP KVLPVPQQVI  180
PYPQRGRPIQ NLQLYEEPLL DPTRKIYPVA QPLAPVYNPV AYMIGIPCCS TLLTYLHQSS  240
RSQYPIQNKL GYLIAMPKKV RPT                                         263

SEQ ID NO: 34          moltype = DNA  length = 792
FEATURE                Location/Qualifiers
source                 1..792
                       mol_type = genomic DNA
                       organism = Loxodonta Africana
SEQUENCE: 34
atgaaggtct tcatccttgc ctgcctggtg gcttttgctc ttggaagaga gactgtagaa  60
aatctttcaa gcagtgagat aagacaattt tattcagagc aaaaacctga gggagttaag  120
catgaggaac agcaaagaga ggatgaacat cagaataaaa tccagcccct tttccagcca  180
cagcctctag tctatccttt cgctgagccc attccttata ctgtctttcc accaaacgcc  240
attcctcttg ctcagcctat tgtggtgctg cctttccctc agcctgaagt aaagcaactc  300
```

```
cctgaagcta aagaaatcac ctttcctagg caaaaattga tgtccttcct taagtctcca  360
gtaatgccct tttttgatcc ccagatccca aatcttggga ccgatcttga aaatctgcac  420
cttcctctgc ctctgctcca gcccttaaga caccagctcc accagcctct tgctcagact  480
ccagtgcttc ctcttcctct atccttgccc aaagtcctgc ccgttcccca gcaggtgata  540
ccctatcccc agagaggtag acccatccaa aaccttcaac tgtacgaaga gcctctactt  600
gacccaaccc gtaagatcta cccagtggct caaccacttg ctccagttta taaccctgtt  660
gcttacatga taggtattcc ctgttgctca acattgctca catacttaca ccagagcagt  720
aggagccagt atcccatcca gaataaactg ggttacttaa tagcaatgcc aaagaaagta  780
cgacctacat ga                                                      792

SEQ ID NO: 35          moltype = AA  length = 302
FEATURE                Location/Qualifiers
source                 1..302
                       mol_type = protein
                       organism = Macropus eugenii
SEQUENCE: 35
MKLLILTCLV ALGFARPMVE KISESEEYVN EVPEKRLKRR FPVKNEHQVE INHHLRPESE  60
MMSLYYQPFY WSEEMRNLKM TSLPKDRRMA VLKSTVSDEV FPSLQHKSLS LPKSKVQPLS  120
RQQILTFHTL QMVPLSHKLL TTPKREMLPI YERERLPAHK RESLLAHERE SLLAHERDIL  180
VPQREMSFVP EREFLFASER VVLPEQEKEI LHNDEREVLA VHKKEILPPF EKEKVLPLLQ  240
HRVVPLPQRE IVPPFQRETL LPEEILPVNQ WELMPEVVPF DPYPFLQPVA PFYYSTELNE  300
KN                                                                 302

SEQ ID NO: 36          moltype = AA  length = 263
FEATURE                Location/Qualifiers
source                 1..263
                       mol_type = protein
                       organism = Monodelphis domestica
SEQUENCE: 36
MKLLILSCLV ALAVARPMVE KISETEEFVT VIPEQQIRRE DVPVKNERHP EINRFIPLEA  60
ETMSFYVPVY WPEEMRDAKM TSPLKEKRMT LANPIAPEEE LPHLQHKSLS LAKQRFLASL  120
RPKAAQPFYA PRMAPLPHKL FTMPKEQALP IAKRDMLSAA ELVIPAVHER VIPAIDKREP  180
LPLLAREMPA LPDKEIQQLA VPFVRRESAL PHQRAIVPVA TAAAAVRESL PLVQQEVVPP  240
IMPLDVYLVR HPEVSFYNPT EKY                                          263

SEQ ID NO: 37          moltype = DNA  length = 792
FEATURE                Location/Qualifiers
source                 1..792
                       mol_type = genomic DNA
                       organism = Monodelphis domestica
SEQUENCE: 37
atgaagctcc tcatcctcag ctgccttgtg gctcttgctg ttgccaggcc tatggtggaa  60
aagatctcag aaactgagga atttgtcacc gtcatcccgg agcaacagat caggagagag  120
gacgtcccag taaagaacga gcgtcatcct gaaatcaacc gctttattcc ccttgaagct  180
gaaacgatga gcttttacgt gcccgtttac tggcccgaag aaatgcgtga cgccaagatg  240
accagccctc taaaagagaa gagaatgacc ctcgctaacc ctattgcccc ggaggaagag  300
ctccctcacc tgcagcacaa atctctgtct ctcgctaagc aaagattcct ggcttctctt  360
cgccccaagg cggcgcagcc cttctatgcc ccaaggatgg cccctctccc tcacaaactg  420
tttaccatgc ccaaggagca ggcgctgcct attgccaaga gagacatgct gtccgccgcc  480
gagctcgtca tccctgcagt gcacgagaga gtcattccag ccattgacaa gagagagccc  540
ctgccgcttc ttgcgagaga gatgccagct cttcccgaca aagagattca acaactggct  600
gtgcccttcg tccgcagaga gagcgcgctc cctcaccaga gagccatcgt gcctgtcgcc  660
accgccgccg ccgccgtgag ggagagcctg cctctggtcc agcaggaagt cgtgcctccc  720
atcatgcctc tcgatgtcta cctggtccgc cacccagagg tcagcttcta caatcccacc  780
gagaagtact aa                                                      792

SEQ ID NO: 38          moltype = AA  length = 260
FEATURE                Location/Qualifiers
source                 1..260
                       mol_type = protein
                       organism = Mammuthus primigenius
SEQUENCE: 38
MKVFILACLV AFALGRETVE NLSSSEIRQF YSEQKPEGVK HEEQQREDEH QNKIQPLFQP  60
QPLVYPFAEP IPYTVFPPNA IPLAQPIVVL PFPQPEVQLP EAKEITFPRQ KLMSFLKSPV  120
MPFFDPQPNL GTDLENLHLP LPLLQPLRHQ LHQPLAQTPV LPLPLSLPKV LPVPQQVIPY  180
PQRGRPIQNL LYEEPLLDPT RKIYPVAQPL APVYNPVAYM IGIPCCSTLL TYLHQSSRSQ  240
YPIQNKLGYL IAMPKKVRPT                                              260

SEQ ID NO: 39          moltype = DNA  length = 717
FEATURE                Location/Qualifiers
source                 1..717
                       mol_type = genomic DNA
                       organism = Mammuthus primigenius
SEQUENCE: 39
atgaaggtct tcatccttgc ctgcctggtg gcttttgctc ttggaagaga gaaggaagaa  60
attattgtat ctactgagac tgtagaaaat ctttcaagca gtgagataag gcaattttat  120
tcagaggaat ctgttacaca agtcaacaaa caaaaacctg agggagttaa gcatgaggaa  180
cagcaaagag aggatgaaca tcagaataaa atccagcccc ttttccagcc acagcctcta  240
gtctatcctt tcgctgagcc cattccttat actgtctttc caccaaacgc cattcctctt  300
```

```
gctcagccta ttgtggtgct gcctttccct cagcctgaag taatgcaact ccctgaagct  360
aaagaaatca cctttcctag gcaaaaattg atgtccttcc ttaagtctcc agtaatgccc  420
ttttttgacc cccagatgcc aaatcttggg accgatcttg aaaatctgca ccttcctctg  480
cctctactcc agcccttaag acaccagctc caccagcctc ttgctcagac tccagtgctt  540
cctcttcctc tatccttgcc caaagtcctg cccgttcccc agcaggtgat accctatccc  600
cagagaggta gacccatcca aaaccttcca ctgtacgaag agcctctact tgacccaacc  660
cgtaagatct acccagtggc tcaaccactt gctccagttt ataaccctgt tgctgta     717

SEQ ID NO: 40          moltype = AA  length = 228
FEATURE                Location/Qualifiers
source                 1..228
                       mol_type = protein
                       organism = Oryctolagus cuniculus
SEQUENCE: 40
MKVLILACLV ALALAREKEQ LSVPTEAVGS VSSSEEITHI NKQKLETIKH VEQLLREEKL  60
QDKILPFIQS LFPFAERIPY PTLPQNILNL AQLDMLLPLL QPEIMEDPKA KETIIPKHKL  120
MPFLKSPKTV PFVDSQILNL REMKNQHLLL PQLLPFMHQV FQPFPQTPIP YPQALLSLPQ  180
SKFMPIVPQV VPYPQRDMPI QALQLFQELL FPTHQGYPVV QPIAPVNV              228

SEQ ID NO: 41          moltype = DNA  length = 687
FEATURE                Location/Qualifiers
source                 1..687
                       mol_type = genomic DNA
                       organism = Oryctolagus cuniculus
SEQUENCE: 41
atgaaggtcc tcattcttgc ctgcctggtg gctctcgctc ttgcaaggga gaaggaacaa  60
ctcagtgttc ccacagaggc tgtaggaagt gtttccagca gcgaggaaat tacacatatc  120
aacaagcaga aactcgagac gattaagcac gtggaacagc tgctaagaga ggagaaactc  180
caggataaaa tcctcccctt tattcaatca ctctttcctt ttgctgagcg catcccctac  240
cctactcttc cacagaacat cctgaacctt gctcaactcg acatgctgct acctctcctt  300
cagcctgaaa taatggaaga ccccaaggct aaagagacca ttatccctaa gcacaaactg  360
atgcccttcc ttaaatctcc aaagacggtc ccctttgttg actctcaaat tctgaatctc  420
agggagatga aaaatcaaca ccttctttg ccccagctcc tgcccttcat gcaccaggtc  480
ttccagcctt ttccccagac tcccattcca tatcctcagg ccctcctctc tcttcctcag  540
tccaaattca tgcctattgt cccacaagtg gtgccctacc ctcaaaggga catgcctatc  600
caagcccttc agctgttcca agaactgctt ttccctaccc atcaaggcta ccctgtggtt  660
caaccaatag ccccagttaa tgtctaa                                     687

SEQ ID NO: 42          moltype = AA  length = 222
FEATURE                Location/Qualifiers
source                 1..222
                       mol_type = protein
                       organism = Ovis aries
SEQUENCE: 42
MKVLILACLV ALALAREQEE LNVVGETVES LSSSEESITH INKKIEKFQS EEQQQTEDEL  60
QDKIHPFAQA QSLVYPFTGP IPNSLPQNIL PLTQTPVVVP PFLQPEIMGV PKVKETMVPK  120
HKEMPFPKYP VEPFTESQSL TLTDVEKLHL PLPLVQSWMH QPPQPLPPTV MFPPQSVLSL  180
SQPKVLPVPQ KAVPQRDMPI QAFLLYQEPV LGPVRGPFPI LV                    222

SEQ ID NO: 43          moltype = DNA  length = 669
FEATURE                Location/Qualifiers
source                 1..669
                       mol_type = genomic DNA
                       organism = Ovis aries
SEQUENCE: 43
atgaaggtcc tcatccttnc ctgtctggtg gctctggccc ttgcaagaga gcaggaagaa  60
ctcaatgtag tcggtgagac tgtggaaagc ctttcaagca gtgaggaatc tattacacac  120
atcaataaga aaattgagaa gtttcaaagt gaggaacaac agcaaacaga ggatgaactc  180
caggataaaa tccacccctt tgcccaggca cagtctctag tctatccctt cactgggccc  240
atccctaaca gcctcccaca aaacatcctg cctcttactc aaacccctgt ggtggtgccg  300
cctttccttc agcctgaaat aatgggagtc cccaaagtga aggagactat ggttcctaag  360
cacaaggaaa tgcccttccc taaatatcca gttgagccct ttactgaaag ccagagcctg  420
actctcactg atgttgaaaa gctgcacctt cctctgcctc tggtccagtc ttggatgcac  480
cagcctcccc agcctcttcc tccaaccgtc atgtttcctc ctcagtccgt gctgtccctt  540
tctcagccca aagttctgcc tgttccccag aaagcagtgc cccagagaga tatgcccatc  600
caggcctttc tgctgtacca ggagcctgta cttggtcctg tccggggacc cttccctatt  660
cttgtctaa                                                         669

SEQ ID NO: 44          moltype = AA  length = 224
FEATURE                Location/Qualifiers
source                 1..224
                       mol_type = protein
                       organism = Physeter catodon
SEQUENCE: 44
MKVLILACLL ALALAREKEE LNVSGETVKS LSSSEESVTH MNKKIGKFKH EEQQQTEDER  60
QDKIHRFSQP QPLVYSYTGP IPYPILPQNI LPLAQPPVLV PFPQPGIMEV PKAKETLLPK  120
HKEMPFPKSP VEPFIESQSL TLNDLENLHL PLPLLQSLMH QPPHPLPPTP MFPPQPLQSL  180
SQPKVLPIPQ QVVPYLQRDM PIQALLLYQE PVLGPIRGLY PVIV                  224
```

-continued

```
SEQ ID NO: 45          moltype = DNA  length = 675
FEATURE                Location/Qualifiers
source                 1..675
                       mol_type = genomic DNA
                       organism = Pyseter catodon
SEQUENCE: 45
atgaaggtcc tcatccttgc ctgcttgttg gctcttgccc ttgcaagaga gaaagaagaa  60
ctcaatgtat ccggtgagac tgtgaaaagc ctttcaagca gtgaggaatc tgttacgcac  120
atgaacaaga aaattgggaa gtttaaacat gaggaacagc agcaaacaga ggatgaacgc  180
caggataaaa tccaccgctt ttcccagcca cagcctctag tctattccta cactgggcca  240
atcccttacc ctatccttcc acaaaacatc ctgcctcttg ctcagccccc tgtgctggtg  300
cctttccctc agcctggaat aatggaagtc cccaaagcta aggagactct ccttcctaag  360
cataaagaaa tgcccttccc taaatctcca gtagagccct ttattgaaag ccagagcctg  420
actctcaatg atcttgaaaa tctgcacctt cctctgcctc tgctccagtc cttgatgcac  480
cagcctcccc atcctcttcc tcctaccccc atgtttcctc ctcagcccct gcagtccctt  540
tctcagccca aagtcctgcc tattccccag caagtggtgc cctacctcca gagagatatg  600
cccatccagg cccttctgct gtaccaggag cctgtacttg gtcctatccg gggggctctac  660
cctgttattg tctaa                                                   675

SEQ ID NO: 46          moltype = AA  length = 183
FEATURE                Location/Qualifiers
source                 1..183
                       mol_type = protein
                       organism = Tachyglossus aculeatus
SEQUENCE: 46
MKVFILACLV AVAMALPKQH SSSSSSEESD RLLVKDIPTA FSSEEHSVDP KELYEPRQSY  60
SYPWQSVRPI NTYTYPRAYQ IPAVLPMTHP QTLTYLQPQF KPEDMSISQK QIPPYVQAVV  120
MPYPQVEAIP FPGAEFMPYA QPITTPLLQP EVFSAPFYRE AVFKPVIYGL PQSQPVQKIP  180
ETD                                                                183

SEQ ID NO: 47          moltype = DNA  length = 552
FEATURE                Location/Qualifiers
source                 1..552
                       mol_type = genomic DNA
                       organism = Tachyglossus aculeatus
SEQUENCE: 47
atgaaggtct tcatcctcgc ctgcctagtg gctgttgcca tggcattgcc taaacaacac  60
agcagcagct cttccagtga ggaatctgac agactgctgg ttaaggacat tcctactgcc  120
ttctccagcg aggaacactc tgtggacccg aaggaactct acgagccccg tcagagctat  180
tcctacccat ggcaatcagt ccgtcccatc aacacctaca cttatcctcg cgcttaccaa  240
attccggctg tcctccccat gactcatcct cagaccctga cttatctcca gcctcaattc  300
aagcccgaag acatgtctat ttctcagaaa caaatcccgc cctacgtcca ggctgtagtc  360
atgccctacc cccaggttga agccattcct ttccccgggg ctgaattcat gccctacgct  420
caacccatca ccacgcctct acttcagcct gaggtcttct ccgcccccatt ctacagagag  480
gccgtcttca agccagtgat ctacggcctt cctcaatctc aaccagttca gaagatccca  540
gaaaccgact ga                                                      552

SEQ ID NO: 48          moltype = AA  length = 214
FEATURE                Location/Qualifiers
source                 1..214
                       mol_type = protein
                       organism = Bos taurus
SEQUENCE: 48
MKLLILTCLV AVALARPKHP IKHQGLPQEV LNENLLRFFV APFPEVFGKE KVNELSKDIG  60
SESTEDQAME DIKQMEAESI SSSEEIVPNS VEQKHIQKED VPSERYLGYL EQLLRLKKYK  120
VPQLEIVPNS AEERLHSMKE GIHAQQKEPM IGVNQELAYF YPELFRQFYQ LDAYPSGAWY  180
YVPLGTQYTD APSFSDIPNP IGSENSGKTT MPLW                              214

SEQ ID NO: 49          moltype = DNA  length = 645
FEATURE                Location/Qualifiers
source                 1..645
                       mol_type = genomic DNA
                       organism = Bos taurus
SEQUENCE: 49
atgaaacttc tcatccttac ctgtcttgtg gctgttgctc ttgctaggcc taaacatcct  60
atcaagcacc aaggactccc tcaagaagtc ctcaatgaaa atttactcag gtttttttgtg  120
gcaccttttc cagaagtgtt tggaaaggag aaggtcaatg aactgagcaa ggatattggg  180
agtgaatcaa ctgaggatca agccatggaa gatattaagc aaatggaagc tgaaagcatt  240
tcgtcaagtg aggaaattgt tcccaatagt gttgagcaga agcacattca aaaggaagat  300
gtgccctctg agcgttacct gggttatctg gaacagcttc tcagactgaa aaaatacaaa  360
gtaccccagc tggaaattgt tcccaatagt gctgaggaac gacttcacag tatgaaagag  420
ggaatccatg cccaacagaa agaacctatg ataggagtga atcaggaact ggcctacttc  480
taccctgagc ttttcagaca attctaccag ctggatgcct atccatctgg tgcctggtat  540
tacgttccac taggcacaca atacactgat gccccatcat tctctgacat ccctaatcct  600
attggctctg agaacagtga aaagactact atgccactgt ggtga                  645

SEQ ID NO: 50          moltype = AA  length = 222
FEATURE                Location/Qualifiers
source                 1..222
```

```
                          mol_type = protein
                          organism = Camelus dromedarius
SEQUENCE: 50
MKLLILTCLV AVALARPKYP LRYPEVFQNE PDSIEEVLNK RKILDLAVVS PIQFRQENID  60
ELKDTRNEPT EDHIMEDTER KESGSSSSEE VVSSTTEQKD ILKEDMPSQR YLEELHRLNK  120
YKLLQLEAIR DQKLIPRVKL SSHPYLEQLY RINEDNHPQL GEPVKVVTQP FPQFFQLGAS  180
PYVAWYYPPQ VMQYIAHPSS YDTPEGIASE DGGKTDVMPQ WW                    222

SEQ ID NO: 51             moltype = DNA  length = 669
FEATURE                   Location/Qualifiers
source                    1..669
                          mol_type = genomic DNA
                          organism = Camelus dromedarius
SEQUENCE: 51
atgaagcttc tcatccttac ctgccttgtg gctgttgcgc ttgccaggcc taaatatcct  60
ctcaggtacc cagaagtctt tcaaaatgaa ccagacagca tagaggaagt cctcaacaaa  120
agaaagattc ttgatttagc agtggtttca cccattcagt ttagacagga gaacatcgat  180
gaactgaagg atactaggaa cgaaccaacc gaagatcaca tcatggaaga cactgagcga  240
aaggaatctg gaagcagttc aagtgaggaa gttgtttcca gtaccactga gcagaaggac  300
attctcaagg aagatatgcc ctcccaacgc tatctggaag agcttcacag actgaacaaa  360
tacaaactac tccagctgga agctatccgt gaccagaaac ttattccaag agtgaagctg  420
tcctcccacc catatctgga acaactttac agaataaatg aggacaacca cccccaactg  480
ggggagcctg tgaaagtagt gactcagcct ttcccacaat tcttccagct tggtgcctct  540
ccctatgttg cttggtatta tcctccacaa gtcatgcaat atattgctca cccctcatcc  600
tacgacaccc ctgaaggcat tgcctctgag gacggtggaa aaaccgacgt tatgccacag  660
tggtggtga                                                         669

SEQ ID NO: 52             moltype = AA  length = 213
FEATURE                   Location/Qualifiers
source                    1..213
                          mol_type = protein
                          organism = Capra hircus
SEQUENCE: 52
MKLLILTCLV VVALARPKHP INHQGLSPEV LNENLLRFVV APFPEVFRKE NINELSKDIG  60
SESTEDQAME DAKQMKAGSS SSSEEIVPNS AQKYIQKEDV PSERYLGYLE QLLRLKKYNV  120
PQLEIVPKSA EEQLHSMKEG NPAHQKQPMI AVNQELAYFY PQLFRQFYQL DAYPSGAWYY  180
LPLGTQYTDA PSFSDIPNPI GSENSGKTTM PLW                              213

SEQ ID NO: 53             moltype = DNA  length = 642
FEATURE                   Location/Qualifiers
source                    1..642
                          mol_type = genomic DNA
                          organism = Capra hircus
SEQUENCE: 53
atgaaacttc tcatccttac ctgtcttgtg gttgttgctc ttgccaggcc taaacatcct  60
atcaatcacc aaggactctc tccagaagtc ctcaatgaaa atttactcag gtttgttgtg  120
gcgccttttc cagaagtgtt tagaaaggag aacatcaatg aactgagtaa ggatattggg  180
agtgaatcaa ctgaggatca agccatggaa gatgctaagc aaatgaaagc tggaagcagt  240
tcgtcaagtg aggaaattgt tcccaatagt gctcagaagt acattcaaaa ggaagatgtg  300
ccctctgagc gttacctggg ttatctggaa cagcttctca gactgaaaaa atacaacgtg  360
ccccagctgg aaattgttcc caaaagtgct gaggaacaac ttcacagtat gaaagaggga  420
aaccctgccc accagaaaca gcctatgata gcagtgaacc aggaactggc ctacttctac  480
cctcagcttt tcagacaatt ctaccagctg gacgcctatc catctggtgc ctggtactac  540
cttccactag gcacacaata cactgatgcc ccctcattct ctgacatccc taatcccatt  600
ggctctgaga acagtggaaa gactactatg ccactgtggt ga                    642

SEQ ID NO: 54             moltype = AA  length = 212
FEATURE                   Location/Qualifiers
source                    1..212
                          mol_type = protein
                          organism = Equus przewalskii
SEQUENCE: 54
MKLLILTCLV AVALARPKLP HRQPEIIQNK QDSREKVLKE RKFPSFALEY INELNRQREL  60
LKEKQKDEHK EYLIEDPEQQ ESSSTSSSEE VVPINTEQKR IPREDMLYQH TLEQLRRLSK  120
YNQLQLQAIH AQEQLLRMKE NSQRKPMRVV NQEQAYFYLE PFQPSYQLDV YPYAAWFHPA  180
QIMQHVAYSP FHDTAKLIAS ENSEKTDIIP EW                               212

SEQ ID NO: 55             moltype = DNA  length = 639
FEATURE                   Location/Qualifiers
source                    1..639
                          mol_type = genomic DNA
                          organism = Equus przewalskii
SEQUENCE: 55
atgaagcttc tcatccttac ctgccttgtg gctgttgctc ttgccaggcc taaacttcct  60
catagacagc cagaaatcat tcagaataaa caggacagta gagagaaagt cctcaaagaa  120
agaaagtttc ccagttttgc tctagagtac atcaatgaac tgaacaggca gagagaactt  180
ctgaaagaaa aacagaaaga tgaacacaag gaatatctca tagaagaccc tgagcaacag  240
gaatctagca gcacttcatc aagcgaggaa gttgttccca ttaacactga gcagaagcgc  300
attccaaggg aagacatgct ctaccaacac actctggaac agcttcgcag actgagcaaa  360
```

```
tacaaccaac tccagctgca agccatccat gcccaggaac aacttctcag aatgaaggaa  420
aacagccaga gaaagcctat gagagtagtg aatcaggaac aggcctactt ctaccttgag  480
cctttccaac catcctacca gcttgatgtc tatccctatg ctgcttggtt tcatcctgcg  540
caaatcatgc aacatgttgc ttactcacca ttccatgaca ctgccaaact cattgcctct  600
gagaactcgg aaaaaactga cattatacca gagtggtga                         639

SEQ ID NO: 56          moltype = AA  length = 212
FEATURE                Location/Qualifiers
source                 1..212
                       mol_type = protein
                       organism = Equus asinus africanus
SEQUENCE: 56
MKLLILTCLV AVALARPKLP HRHPEIIQNE QDSREKVLKE RKFPSFALEY INELNRQREL  60
LKEKQKDEHK EYLIEDPEQQ ESSSTSSSEE VVPINTEQKR IPREDMLYQH TLEALRRLSK  120
YNQLQLQAIY AQEQLLRMKE NSQRKPMRVV NQEQAYFYLE PFQPSYQLDV YPYAAWFHPA  180
QIMQHVAYSP FHDTAKLIAS ENSEKTDIIP EW                                212

SEQ ID NO: 57          moltype = AA  length = 212
FEATURE                Location/Qualifiers
source                 1..212
                       mol_type = protein
                       organism = Equus caballus
SEQUENCE: 57
MKLLILTCLV AVALARPKLP HRQPEIIQNE QDSREKVLKE RKFPSFALEY INELNRQREL  60
LKEKQKDEHK EYLIEDPEQQ ESSSTSSSEE VVPINTEQKR IPREDMLYQH TLEQLRRLSK  120
YNQLQLQAIH AQEQLIRMKE NSQRKPMRVV NQEQAYFYLE PFQPSYQLDV YPYAAWFHPA  180
QIMQHVAYSP FHDTAKLIAS ENSEKTDIIP EW                                212

SEQ ID NO: 58          moltype = DNA  length = 640
FEATURE                Location/Qualifiers
source                 1..640
                       mol_type = genomic DNA
                       organism = Equus caballus
SEQUENCE: 58
catgaagctt ctcatcctta cctgccttgt ggctgttgct cttgccaggc ctaaacttcc  60
tcatagacag ccagaaatca ttcagaatga acaggacagt agagagaaag tcctcaaaga  120
aagaaagttt cccagttttg ctctagagta catcaatgaa ctgaacaggc agagagaact  180
tctgaaagaa aaacagaaag atgaacacaa ggaatatctc atagaagacc ctgagcaaca  240
ggaatctagc agcacttcat caagcgagga agttgttccc attaacactg agcagaagcg  300
cattccaagg gaagacatgc tctaccaaca cactctggaa cagcttcgca gactgagcaa  360
atacaaccaa ctccagctgc aagccatcca tgcccaggaa caacttatca gaatgaagga  420
aaacagccag agaaagccta tgagagtagt gaatcaggaa caggcctact tctaccttga  480
gcctttccaa ccatcctacc agcttgatgt ctatccctat gctgcttggt ttcatcctgc  540
gcaaatcatg caacatgttg cttactcacc attccatgac actgccaaac tcattgcctc  600
tgagaactcg gaaaaaactg acattatacc agagtggtga                        640

SEQ ID NO: 59          moltype = AA  length = 125
FEATURE                Location/Qualifiers
source                 1..125
                       mol_type = protein
                       organism = Felis catus
SEQUENCE: 59
MEDPEQREIS SSSSSEEAVP NNTQQKHISK EDILSQRYLE QLHRLSKYNQ LQLEALRDQQ  60
QLRRVTENNH IQLPFQQFYQ LDAYPYAVWY YPPQVMQYIA YTPFYDVTKL TAPENAENVG  120
VVPEW                                                              125

SEQ ID NO: 60          moltype = DNA  length = 378
FEATURE                Location/Qualifiers
source                 1..378
                       mol_type = genomic DNA
                       organism = Felis catus
SEQUENCE: 60
atggaagacc ctgagcaaag ggaaattagc agcagttcat caagcgagga agctgttccc  60
aataacactc agcagaagca catttcaaag gaagatatac tctctcaacg ctatctggaa  120
cagcttcata gactgagcaa atacaaccaa ctgcaactgg aagctctccg tgaccagcaa  180
caactgcgca gagtgactga aaacaaccac atccaattgc ctttccaaca attctaccaa  240
cttgatgctt atccctatgc tgtgtggtat taccctccac aagtcatgca gtatattgct  300
tacaccacat tctatgacgt cactaaactt acggcccctg agaacgctga aaacgttggt  360
gttgtgccag agtggtag                                                378

SEQ ID NO: 61          moltype = AA  length = 185
FEATURE                Location/Qualifiers
source                 1..185
                       mol_type = protein
                       organism = Homo sapiens
SEQUENCE: 61
MRLLILTCLV AVALARPKLP LRYPERLQNP SESSEPIPLE SREEYMNGMN RQRNILREKQ  60
TDEIKDTRNE STQNCVVAEP EKMESSISSS SEEMSLSKCA EQFCRLNEYN QLQLQAVHAQ  120
EQIRRMNENS HVQVPFQQLN QLAAYPYAVW YYPQIMQYVP FPPFSDISNP TAHENYEKNN  180
```

```
VMLQW                                                         185

SEQ ID NO: 62          moltype = DNA  length = 558
FEATURE                Location/Qualifiers
source                 1..558
                       mol_type = genomic DNA
                       organism = Homo sapiens
SEQUENCE: 62
atgaggcttc tcattctcac ctgtcttgtg gctgttgctc ttgccaggcc taaacttcct  60
cttagatacc cagaacgcct tcagaatcca tcagagagca gtgagcctat accattagaa  120
tcaagagagg aatacatgaa tggtatgaac aggcagagaa acattctgag agaaaaacag  180
actgatgaaa tcaaggatac taggaatgag tctactcaga actgtgttgt ggcagagcct  240
gagaagatgg aatccagcat cagttcatcg agtgaggaaa tgtctctcag taagtgtgcg  300
gaacagtttt gtagactgaa cgaatacaac caacttcagc tgcaagctgt ccatgcccag  360
gagcaaattc gcagaatgaa tgaaaacagc catgtccaag tgcctttcca gcagctcaac  420
caacttgctg cctaccccta tgctgtttgg tactatccac aaatcatgca gtatgttcct  480
ttcccaccgt tttccgacat ctccaatccc actgctcatg aaaattatga aaaaaataac  540
gtcatgctac agtggtga                                           558

SEQ ID NO: 63          moltype = AA  length = 237
FEATURE                Location/Qualifiers
source                 1..237
                       mol_type = protein
                       organism = Macropus eugenii
SEQUENCE: 63
MKLLIFSCLV TLALARPDAL RLSIDRHFKH RELENRLNED PIPVSEASSS EESVHQLNRD  60
RRPLEKYELD KYREDLKTSS SEEFVTPSTN ERVRRQVEYN FNEEDSSASR ERKIEDFSEH  120
DRQYLRRRVE ERALNLRYLE PLYYATEPEY YYYYAYVPVS SHDIPYQQKP LSLLPAKSHY  180
LISTGLLNEP LPILRERLGR GFQSPSLLIL VLTENSNLFM GSVFYWCLQI AHPMQEI     237

SEQ ID NO: 64          moltype = AA  length = 189
FEATURE                Location/Qualifiers
source                 1..189
                       mol_type = protein
                       organism = Monodelphis domestica
SEQUENCE: 64
MKLLIFSCLV ALALARPEAL NFSARRVKHQ EAESRLNEVI IPARAVSSSE ETSQEAIEIR  60
YPLEQQVLDK AREERVRRPV EYIIEDDSSA LNERKIEDAR AYDEQYLRRP EEERAVHYRE  120
LRAFPTEARK LKAYREPYVQ PEIYYYLISV PQPMPYPDEV PLAYTYKFVV PAVNRADEAV  180
NTPVEEEKN                                                     189

SEQ ID NO: 65          moltype = DNA  length = 570
FEATURE                Location/Qualifiers
source                 1..570
                       mol_type = genomic DNA
                       organism = Monodelphis domestica
SEQUENCE: 65
atgaagctgc tcatcttctc ctgccttgtg gctcttgctc tggccaggcc agaagccctc  60
aacttctctg ctaggcgtgt taaacaccaa gaagcagaaa gccgcctgaa tgaagttatc  120
attccagcaa gagcggtttc atcaagtgag gaaacttccc aggaggcaat cgaaatcaga  180
tatcccctgg agcagcaagt actcgacaaa gccagagagg aacgtgtccg cagaccggtc  240
gagtacatca tcgaggatga ttcttctgcc ttaaatgaga gaaagattga agatgcccgt  300
gcatacgacg agcagtacct gagaagacct gaggaagaga gagctgttca ctaccgggaa  360
cttcgcgctt ttcctactga ggcaagaaaa cttaaggctt acagagaacc ctacgtgcag  420
ccagaaatct actactatct catttccgtg ccacaaccca tgccttatcc agatgaggtc  480
cctcttgctt acacctacaa attcgtagta cctgctgtca acagggcaga tgaggcagtc  540
aatacccctg tggaagagga gaagaactaa                              570

SEQ ID NO: 66          moltype = AA  length = 207
FEATURE                Location/Qualifiers
source                 1..207
                       mol_type = protein
                       organism = Microcebus murinus
SEQUENCE: 66
MKLLILTCLV AVALARPKHP LRHPELIQNQ PGSSEEILKE RKFSAIALAT PIELRQEYIN  60
ELNREQHVIT ETEQSESSSS SSSEEVASQS STEPKCALNE DVTNQCNQEQ LHRMNKYNQL  120
QLEAIHAQEQ LRRMNEYNHA QVEEPVRVVN QEQAQFYPEP FPQVYQLDAT WYYFPQNMQY  180
PSFLPSQDIA KQTSAENNEK TNVMAQW                                 207

SEQ ID NO: 67          moltype = DNA  length = 624
FEATURE                Location/Qualifiers
source                 1..624
                       mol_type = genomic DNA
                       organism = Microcebus murinus
SEQUENCE: 67
atgaagcttc tcatactcac ctgccttgtg gctgtcgctc ttgccagacc taaacatcct  60
cttagacacc cagaactcat tcaaaatcaa ccaggcagca gcgaggaaat cctcaaagaa  120
agaaagtttt cagcaattgc tctggccaca ccaatagaat taagacagga atacatcaat  180
gaactgaaca gggaacaaca tgtaataacc gagactgagc agagtgaatc tagcagcagt  240
```

```
tcatcaagcg aggaagttgc ttcccaaagc agcaccgagc caaaatgcgc tttaaatgaa  300
gatgtgacca accaatgcaa tcaggaacag cttcatagaa tgaacaaata caaccaactc  360
cagctggaag ctatccatgc tcaggagcaa cttcgcagaa tgaatgaata caaccatgct  420
caagtggaag agcccgtaag agtagtgaat caggaacagg cccaattcta ccctgagccc  480
ttccctcaag tctaccagct tgacgctact tggtactatt tcccacaaaa catgcagtac  540
ccatctttcc tgccatccca agacatcgct aagcaaactt ccgctgagaa caatgagaaa  600
actaatgtta tggcacagtg gtga                                          624

SEQ ID NO: 68          moltype = AA  length = 215
FEATURE                Location/Qualifiers
source                 1..215
                       mol_type = protein
                       organism = Oryctolagus cuniculus
SEQUENCE: 68
MKLLILTCLV ATALARHKFH LGHLKLTQEQ PESSEQEILK ERKLLRFVQT VPLELREEYV  60
NELNRQRELL REKENEEIKG TRNEVTEEHV LADRETEASI SSSSEEIVPS STKQKYVPRE  120
DLAYQPYVQQ QLLRMKERYQ IQEREPMRVV NQELAQLYLQ PFEQPYQLDA YLPAPWYYTP  180
EVMQYVLSPL FYDLVTPSAF ESAEKTDVIP EWLKN                              215

SEQ ID NO: 69          moltype = DNA  length = 648
FEATURE                Location/Qualifiers
source                 1..648
                       mol_type = genomic DNA
                       organism = Oryctolagus cuniculus
SEQUENCE: 69
atgaagcttc tcatcctcac ttgccttgtg gctactgctc ttgccaggca taaatttcat  60
ttaggacacc tgaaactcac tcaggagcag cctgagagca gtgagcagga aatcttaaaa  120
gaaagaaagc tcctcaggtt tgtccagaca gtaccactag aattaagaga ggaatatgtc  180
aatgaactga acaggcagag agaacttctg agagaaaaag agaatgagga aatcaaggga  240
actagaaatg aagtaactga ggaacatgtt ttggcagacc gtgagacaga agctagcatc  300
agctcatcaa gtgaggaaat tgttcccagc agcaccaagc agaagtacgt gccaagggaa  360
gacctggctt accaacctta cgtgcagcag cagcttctca gaatgaaaga acgctaccaa  420
atccaggaga gagagcctat gagagtggtg aatcaggaac tggctcagct ctatcttcag  480
cctttcgaac aaccctacca gcttgatgcc tatctccctg ctccttggta ctatactccg  540
gaagtgatgc agtatgttct ttccccactg ttctatgacc tcgttacacc cagtgccttt  600
gagagtgctg aaaaaactga cgttattcca gagtggttga agaattaa                648

SEQ ID NO: 70          moltype = AA  length = 214
FEATURE                Location/Qualifiers
source                 1..214
                       mol_type = protein
                       organism = Ovis aries
SEQUENCE: 70
MKLLILTCLV AVALARPKHP IKHQGLSPEV LNENLLRFVV APFPEVFRKE NINELSKDIG  60
SESIEDQAME DAKQMKAGSS SSSEEIVPNS AEQKYIQKED VPSERYLGYL EQLLRLKKYN  120
VPQLEIVPKS AEEQLHSMKE GNPAHQKQPM IAVNQELAYF YPQLFRQFYQ LDAYPSGAWY  180
YLPLGTQYTD APSFSDIPNP IGSENSGKIT MPLW                               214

SEQ ID NO: 71          moltype = DNA  length = 645
FEATURE                Location/Qualifiers
source                 1..645
                       mol_type = genomic DNA
                       organism = Ovis aries
SEQUENCE: 71
atgaaacttc tcatccttac ctgtcttgtg gctgttgctc ttgccaggcc taaacatcct  60
atcaagcacc aaggactctc tccagaagtc ctcaatgaaa atttactcag gtttgttgtg  120
gcgccttttc cagaagtgtt tagaaaggag aacatcaatg aactgagtaa ggatattggg  180
agtgaatcaa ttgaggatca agccatggaa gatgctaagc aaatgaaagc tggaagcagt  240
tcgtcaagtg aggaaattgt tcccaatagt gctgagcaga agtacattca aaaggaagat  300
gtgccctctg agcgttacct gggttatctg gaacagcttc tcagactgaa aaaatacaac  360
gtgccccagc tggaaattgt tcccaaaagt gctgaggaac aacttcatag tatgaaagag  420
ggaaaccctg cccaccagaa acagcctatg atagcagtga atcaggaact ggcctacttc  480
taccctcagc ttttcagaca attctaccag ctggacgcct atccatctgg tgcctggtat  540
taccttccac taggcacaca atacactgat gccccctcat tctctgacat ccctaatccc  600
attggctctg agaacagtgg aaagattact atgccactgt ggtga                   645

SEQ ID NO: 72          moltype = AA  length = 199
FEATURE                Location/Qualifiers
source                 1..199
                       mol_type = protein
                       organism = Physeter catodon
SEQUENCE: 72
VLTTMKLLIL TCLVTAALAK PNEPDSREPL SEQLREDHGM EDPEQRGSGS SSSSEVNRFD  60
VNSASQLENV CESLLYQEGY LSPKEVVPNG NERKHIQGED VPSERYLREP MRVVNQPFQQ  120
FYQLDVHPYA AWYYPPQVTQ YIASPSFFDI PKPIASENGG KTIMPQWCFY HMSVPNESTE  180
HSFTCCESYR NKAIDVMNA                                                199

SEQ ID NO: 73          moltype = DNA  length = 600
FEATURE                Location/Qualifiers
```

```
source                  1..600
                        mol_type = genomic DNA
                        organism = Physeter catodon
SEQUENCE: 73
gtcttgacaa ccatgaaact tctcatcctt acctgccttg tgactgctgc tcttgccaag  60
cctaatgaac cagatagcag agagccttta tcagaacagc ttagagagga tcatggcatg  120
gaagaccctg agcaaagggg gtctggcagc agttcatcaa gtgaggtaaa tcgttttgat  180
gttaattcag catcccaatt agaaaatgtt tgtgaaagct tgttgtacca ggaaggttac  240
ctgtccccta aggaagttgt tcccaatggc aatgagcgga agcacattca aggggaagat  300
gtgccctctg aacgctatct gagagagcct atgagagtag tgaatcaacc tttccaacaa  360
ttctatcagc ttgatgtcca tccttatgct gcttggtatt atcctccaca agtcacacaa  420
tatattgctt ctccatcatt cttcgacatc cctaaaccca ttgcctctga gaacggtgga  480
aaaacaatta tgccacagtg gtgcttctat catatgtcgg ttcccaacga atcaacagaa  540
cacagcttca cgtgttgtga atcctacagg aataaagcca tcgatgtaat gaatgcatga  600

SEQ ID NO: 74           moltype = AA  length = 183
FEATURE                 Location/Qualifiers
source                  1..183
                        mol_type = protein
                        organism = Tachyglossus aculeatus
SEQUENCE: 74
MKVLILACLV AFVVAMPESP SSSSSSEEAS KILTKKRVQR DQEYYLPHQE ESVSSSSSEE  60
STDRLKRRLL KDKPIFRLLK ATESSSSEES DSAIEKRILR ERQYYQQKLD ELKEYFRQFE  120
PYFYPVAYQK KEVMPYQLEY FVPQPEVYSI PQPVYRVPQE VTFPSLLHFR YAFPQSTLPI  180
ERK                                                                183

SEQ ID NO: 75           moltype = DNA  length = 552
FEATURE                 Location/Qualifiers
source                  1..552
                        mol_type = genomic DNA
                        organism = Tachyglossus aculeatus
SEQUENCE: 75
atgaaggtcc tcatcctggc ctgcctggtg gcttttgtcg tggcaatgcc tgagtcaccc  60
agcagcagtt catccagcga ggaagcttcc aaaattctga caaaaaagcg tgtccaaaga  120
gaccaagaat actaccttcc ccatcaggag gaatccgtaa gcagctcatc cagtgaggaa  180
tcgaccgatc gactcaaaag acgtctcctg aaagacaaac ccatcttccg tctcctgaag  240
gctacagaga gctcttcaag tgaggaatct gacagtgcta ttgaaaagcg tattctgagg  300
gagagacagt actatcaaca gaagctggat gaactcaaag aatattttcg tcagtttgaa  360
ccctacttct accctgtggc ttatcagaaa aaagaagtca tgccctacca gctggaatac  420
tttgttcctc aaccagaagt gtacagcatc ccccaaccag tatatagggt tcctcaagag  480
gtaaccttcc ccagtcttct ccatttccgc tacgcttttc ctcagtcaac cctccccatt  540
gagaggaagt aa                                                      552

SEQ ID NO: 76           moltype = AA  length = 230
FEATURE                 Location/Qualifiers
source                  1..230
                        mol_type = protein
                        organism = Ailuropoda melanoleuca
SEQUENCE: 76
MEIKHCPKDL KDGSLKQCTG SGHKAALSQE EQGSSAVIEH GSIPRGGNNV HRVGGVRASC  60
TLESTRRLLW MCPSEKTSVL ALTTMKVLIL TCLVAVALAR PGQAVEDPEQ RQSSSSSSE  120
EVVPSTTEQK QIPREDILNQ RYLEQLRRLS KYNQQQQETI HDQQQLRGVN ENNLLQLPFQ  180
QFYQLDAYPF AAWYYLPQIM QYIGYTPSYD IIKPIASENI ENVDVVPEWW             230

SEQ ID NO: 77           moltype = DNA  length = 693
FEATURE                 Location/Qualifiers
source                  1..693
                        mol_type = genomic DNA
                        organism = Ailuropoda melanoleuca
SEQUENCE: 77
atggaaatta aacactgtcc aaaagacctc aaagacgggt cacttaaaca gtgcacggga  60
agtggtcaca aggcagcgct aagccaggaa gagcagggaa gtagtgctgt aatagaacac  120
ggaagcattc cacgtggagg aaataacgtg catagggttg gaggagtaag agcttcatgc  180
actcttgaaa gcacaagaag attgttgtgg atgtgtcctt cagaaaagac gagtgtgctg  240
gccttgacaa ccatgaaggt tctcatcctt acctgccttg tggctgttgc tcttgccagg  300
cctggacagg ccgtggaaga ccctgagcaa aggcaatcta gcagcagttc gtcaagtgag  360
gaagttgttc ccagtaccac tgagcagaag caaattccaa gagaagacat actcaaccaa  420
cgctatctgg aacagcttcg tagactgagc aaatacaacc aacaacagca ggaaactatc  480
catgaccagc aacaacttcg cggagtgaat gaaaacaacc tcctccaact gcctttccaa  540
cagttctacc agcttgatgc ttatcccttt gctgcttggt attatcttcc acaaatcatg  600
cagtatattg gttatacacc atcctatgac atcattaaac ccattgcctc tgagaacatt  660
gaaaacgttg atgttgtgcc agagtggtgg taa                              693

SEQ ID NO: 78           moltype = AA  length = 222
FEATURE                 Location/Qualifiers
source                  1..222
                        mol_type = protein
                        organism = Bos taurus
SEQUENCE: 78
```

```
MKFFIFTCLL AVALAKNTME HVSSSEESII SQETYKQEKN MDINPSKENL CSTFCKEVVR  60
NANEEEYSIG SSSEESAEVA TEEVKITVDD KHYQKALNEI NQFYRKFPQY LQYLYQGPIV  120
LNPWDQVKRN AVPITPTLNR EQLSTSEENS KKTVDMESTE VFTKKTKLTE EEKNRLNFLK  180
KISQRYQKFA LPQYLKTVYQ HQKAMKPWIQ PKTKVIPYVR YL                    222

SEQ ID NO: 79          moltype = DNA  length = 669
FEATURE                Location/Qualifiers
source                 1..669
                       mol_type = genomic DNA
                       organism = Bos taurus
SEQUENCE: 79
atgaagttct tcatctttac ctgccttttg gctgttgccc ttgcaaagaa tacgatggaa  60
catgtctcct ccagtgagga atctatcatc tcccaggaaa catataagca ggaaaagaat  120
atggacatta atcccagcaa ggagaacctt tgctccacat tctgcaagga agttgtaagg  180
aacgcaaatg aagaggaata ttctatcggc tcatctagtg aggaatctgc tgaagttgcc  240
acagaggaag ttaagattac tgtggacgat aagcactacc agaaagcact gaatgaaatc  300
aatcagtttt atcggaagtt cccccagtat ctccagtatc tgtatcaagg tccaattgtt  360
ttgaacccat gggatcaggt taagagaaat gctgttccca ttactcccac tctgaacaga  420
gagcagctct ccaccagtga ggaaaattca aagaagaccg ttgacatgga atcaacagaa  480
gtattcacta agaaaactaa actgactgaa gaagaaaaga atcgcctaaa ttttctgaaa  540
aaaatcagcc agcgttacca gaaattcgcc ttgccccagt atctcaaaac tgtttatcag  600
catcagaaag ctatgaagcc atggattcaa cctaagacaa aggttattcc ctatgtgagg  660
tacctttaa                                                         669

SEQ ID NO: 80          moltype = AA  length = 223
FEATURE                Location/Qualifiers
source                 1..223
                       mol_type = protein
                       organism = Capra hircus
SEQUENCE: 80
MKFFIFTCLL AVALAKHKME HVSSSEEPIN IFQEIYKQEK NMAIHPRKEK LCTTSCEEVV  60
RNANEEEYSI RSSSEESAEV APEEIKITVD DKHYQKALNE INQFYQKFPQ YLQYPYQGPI  120
VLNPWDQVKR NAGPFTPTVN REQLSTSEEN SKKTIDMEST EVFTKKTKLT EEEKNRLNFL  180
KKISQYYQKF AWPQYLKTVD QHQKAMKPWT QPKTNAIPYV RYL                   223

SEQ ID NO: 81          moltype = DNA  length = 672
FEATURE                Location/Qualifiers
source                 1..672
                       mol_type = genomic DNA
                       organism = Capra hircus
SEQUENCE: 81
atgaagttct tcatttttac ctgccttttg gccgttgccc ttgcaaagca taagatggaa  60
catgtctcct ccagtgagga acctatcaat atcttccagg aaatatataa gcaggaaaag  120
aatatggcca ttcatcccag aaaggagaaa ctttgcacca catcctgtga ggaagttgta  180
aggaacgcaa atgaagagga atattctatc agatcatcta gtgaggaatc tgctgaagtt  240
gccccagagg aaattaagat tactgtggac gataagcact accagaaagc cctgaatgaa  300
atcaatcagt tttatcagaa gttcccccag tatctccagt atccgtatca aggtccaatt  360
gttttgaacc catgggatca ggttaagaga aatgctggcc cctttactcc caccgtgaac  420
agagagcagc tctccaccag tgaggaaaat tcaaagaaga ccattgatat ggaatcaaca  480
gaagtattca ctaagaaaac taaactgact gaagaagaaa agaatcgcct aaattttctg  540
aaaaaaatca gccagtatta ccagaaattt gcctggcccc agtatctcaa gactgttgat  600
cagcatcaga aagctatgaa gccatggact caacctaaga caaatgctat tccctatgtg  660
aggtaccttt aa                                                     672

SEQ ID NO: 82          moltype = AA  length = 239
FEATURE                Location/Qualifiers
source                 1..239
                       mol_type = protein
                       organism = Felis catus
SEQUENCE: 82
MSGAEAVDWE VSEKKLHICR LSRGCGVSPR VTMNFLLFTC LLAVALAKHE LKQLSSSEES  60
ATSSSSQETG DVPTDTIELT EEEKVYLNQL SKINQFYQAW NLPQYLEAYH QQHSVRNPWN  120
HIKTNGYHLF PLLEKEYLSS SEVRGFPVRT ETWHPETEIK EVQLNDEEKN YLKQLVKINQ  180
YQQKFTFPHY FQAVHPQQIA LNPWNRLKEN TYPFILTLLG SLNQFGPPDD EKGLDYFSK   239

SEQ ID NO: 83          moltype = DNA  length = 720
FEATURE                Location/Qualifiers
source                 1..720
                       mol_type = genomic DNA
                       organism = Felis catus
SEQUENCE: 83
atgtccggtg cagaggcagt ggactgggaa gttagtgaga agaagctgca catatgtcgt  60
ctttcaagag gctgcggggt cagtccccga gtaaccatga atttcctcct ctttacctgc  120
cttttggctg tggctctggc aaagcatgag ctaaagcagc tctcctccag cgaggaatct  180
gccaccagtt catctagtca ggaaactggt gatgtcccta ctgacacaat tgagctgact  240
gaggaagaaa aggtctacct caatcaactg agcaaaatca accagtttta tcaggcatgg  300
aatcttcccc agtatcttga ggcttatcat caacagcaca gtgttaggaa cccatggaat  360
cacattaaga caaatggcta tcatctattt ccccttctgg aaaaagagta cctgtcctcc  420
agtgaggtga ggggctttcc tgtgaggaca gaaacatggc atccagaaac agagattaag  480
```

```
gaagttcagc tgaatgatga agaaaagaat tacctgaaac agctggtcaa aatcaaccag  540
tatcaacaga agttcacctt cccccactat ttccaggctg ttcatccaca gcagatagct  600
ctgaaccctt ggaatcgcct taaggaaaat acttacccat tcattctcac tttgcttggt  660
tctctgaacc agtttggtcc tcctgatgat gaaaagggat tagactactt ttctaaataa  720

SEQ ID NO: 84          moltype = AA  length = 121
FEATURE                Location/Qualifiers
source                 1..121
                       mol_type = protein
                       organism = Homo sapiens
SEQUENCE: 84
MKFFIFTCLL AIALAKHESA EVSTEEVKHT VDQKHYVKQL NKINPFYQKW NFLPFLQKTE  60
LTEEEKNDQK HLNKINQYYQ FTLPQYVKAV YQYHKIMKPW KNMKTNAYQV IPTLGSLRFL  120
N                                                                 121

SEQ ID NO: 85          moltype = DNA  length = 84
FEATURE                Location/Qualifiers
source                 1..84
                       mol_type = genomic DNA
                       organism = Homo sapiens
SEQUENCE: 85
atgaagttct tcatctttac ctgccttttg gctgttgctc tggcacatca tgagataaag  60
cactcctcct cttccagtga gtaa                                        84

SEQ ID NO: 86          moltype = AA  length = 182
FEATURE                Location/Qualifiers
source                 1..182
                       mol_type = protein
                       organism = Oryctolagus cuniculus
SEQUENCE: 86
MKFFIFTCLL AVALAKPKIE QSSSEETIAV SQEVSPNLEN ICSTACEEPI KNINEVEYVE  60
VPTEIKDQEF YQKVNLLQYL QALYQYPTVM DPWTRAETKA IPFIRTMQYK QEKDATKHTS  120
QKTELTEEEK AFLKYLDEMK QYYQKFVFPQ YLKNAHHFQK TMNPWNHVKT IIYQSVPTLR  180
YL                                                                182

SEQ ID NO: 87          moltype = DNA  length = 549
FEATURE                Location/Qualifiers
source                 1..549
                       mol_type = genomic DNA
                       organism = Oryctolagus cuniculus
SEQUENCE: 87
atgaagttct tcattttcac ctgccttctg gctgttgctc tggcaaagcc taagattgag  60
caatcttcaa gtgaggaaac tattgctgtc tcccaagaag tatcccccaaa cttagaaaac  120
atttgttcta cagcctgtga ggaacccata aagaatatca atgaagtgga atacgttgaa  180
gttcccacag agataaaaga tcaggaattt tatcagaagg tgaacctcct ccagtatctc  240
caggctcttt accaatatcc cactgtcatg gacccatgga ctcgggctga gacaaaggcc  300
atccccttta ttcgcactat gcaatataag caggaaaagg atgccactaa gcataccagt  360
cagaaaaccg aactgaccga agaagaaaag gcttttctaa aatacttgga tgaaatgaaa  420
caatattatc agaagttcgt tttccccaa tacctaaaaa atgctcatca ttttcagaaa  480
actatgaacc cttggaatca tgttaagaca attatttacc aaagtgtgcc cactctgaga  540
tacttataa                                                         549

SEQ ID NO: 88          moltype = AA  length = 223
FEATURE                Location/Qualifiers
source                 1..223
                       mol_type = protein
                       organism = Ovis aries
SEQUENCE: 88
MKFFIFTCLL AVALAKHKME HVSSSEEPIN ISQEIYKQEK NMAIHPRKEK LCTTSCEEVV  60
RNADEEEYSI RSSSEESAEV APEEVKITVD DKHYQKALNE INQFYQKFPQ YLQYLYQGPI  120
VLNPWDQVKR NAGPFTPTVN REQLSTSEEN SKKTIDMEST EVFTKKTKLT EEEKNRLNFL  180
KKISQYYQKF AWPQYLKTVD QHQKAMKPWT QPKTNAIPYV RYL                   223

SEQ ID NO: 89          moltype = DNA  length = 672
FEATURE                Location/Qualifiers
source                 1..672
                       mol_type = genomic DNA
                       organism = Ovis aries
SEQUENCE: 89
atgaagttct tcatttttac ctgccttttg gccgttgccc ttgcaaagca taagatggaa  60
catgtctcct ccagtgagga acctatcaat atctcccagg aaatatataa gcaggaaaag  120
aatatggcca ttcatcccag aaaggagaaa ctttgcacca catcctgtga ggaagttgta  180
aggaacgcag atgaagagga atattctatc agatcatcta gtgaggaatc tgctgaagtt  240
gccccagagg aagttaagat tactgtggac gataagcact accagaaagc actgaatgaa  300
atcaatcagt tttatcagaa gttcccccag tacctccagt atctgtatca aggcccaatt  360
gttttgaacc catgggatca ggttaagaga aatgctggcc cctttactcc caccgtgaac  420
agagagcagc tctccaccag tgaggaaaat tcaaagaaga ccattgatat ggaatcaaca  480
gaagtattca ctaagaaaac taaactgact gaagaagaaa agaatcgcct aaattttctg  540
aaaaaaatca gccagtatta ccagaaattt gcctggcccc agtatctcaa gactgttgat  600
```

```
cagcatcaga aagctatgaa gccatggact caacctaaga caaacgctat tccctatgtg  660
aggtaccttt aa                                                      672

SEQ ID NO: 90          moltype = AA  length = 243
FEATURE                Location/Qualifiers
source                 1..243
                       mol_type = protein
                       organism = Physeter catodon
SEQUENCE: 90
MKFFLFTCLL AVALAKHEME HVSSSEESIN MFQEKYKQRK NVVLHPSKEN ICSTSCEVCI  60
DFTSVVQCEV KYSIRSSPKE TAEVPREKVK LTVEDKQYLK QLSKISQFYQ KFPQYIQALY  120
QAPTVMNPWG QVKRSAEPFI LTVSRQQLST GEENSKKTVD MESTEVLTKK TTLTEEEKNR  180
LKFLNKINQY YQKLTWPQYL KTISQYQKTV KPWNHIKTNV IPYLDYSGNP GSPYPVNPTL  240
NIP                                                                243

SEQ ID NO: 91          moltype = DNA  length = 732
FEATURE                Location/Qualifiers
source                 1..732
                       mol_type = genomic DNA
                       organism = Physeter catodon
SEQUENCE: 91
atgaagttct tcctttttac ctgccttttg gctgttgctc ttgcaaagca tgagatggaa  60
catgtctcct ccagtgagga atctatcaac atgttccagg aaaaatataa gcagagaaag  120
aatgtggtcc ttcatcccag caaggagaac atttgttcca catcctgtga ggtatgtatt  180
gatttcacat cagtagtaca atgtgaagta aaatatagta ttagatcttc ccctaaggaa  240
actgctgaag ttcccaggga gaaagttaag cttactgtgg aagataagca atacctgaaa  300
caactgagca aaatcagtca gttttatcag aagttccccc aatatatcca ggctctatat  360
caagctccaa ctgttatgaa cccatggggt caagttaaga gaagtgctga gccctttatt  420
ctcactgtga gcagacagca gctctctacc ggtgaggaaa attcaaagaa gactgttgat  480
atggaatcaa cggaagtact cactaagaaa actacattga ctgaagaaga aaagaatcgc  540
ctaaaatttc tgaacaaaat caaccaatat tatcagaaat taacctggcc ccagtatctc  600
aagactattt ctcagtatca gaaaactgtg aagccgtgga atcacattaa gacaaatgtt  660
atcccctatc tggattacag cggcaatcct ggcagtcctt acccagttaa cccaactctg  720
aatattcctt aa                                                      732

SEQ ID NO: 92          moltype = AA  length = 142
FEATURE                Location/Qualifiers
source                 1..142
                       mol_type = protein
                       organism = Bos taurus
SEQUENCE: 92
MMSFVSLLLV GILFHATQAE QLTKCEVFRE LKDLKGYGGV SLPEWVCTTF HTSGYDTQAI  60
VQNNDSTEYG LFQINNKIWC KDDQNPHSSN ICNISCDKFL DDDLTDDIMC VKKILDKVGI  120
NYWLAHKALC SEKLDQWLCE KL                                           142

SEQ ID NO: 93          moltype = DNA  length = 429
FEATURE                Location/Qualifiers
source                 1..429
                       mol_type = genomic DNA
                       organism = Bos taurus
SEQUENCE: 93
atgatgtcct ttgtctctct gctcctggta ggcatcctat tccatgccac ccaggctgaa  60
cagttaacaa aatgtgaggt gttccgggag ctgaaagact tgaagggcta cggaggtgtc  120
agtttgcctg aatgggtctg taccacgttt cataccagtg gttatgacac acaagccata  180
gtacaaaaca atgacagcac agaatatgga ctcttccaga taaataataa aatttggtgc  240
aaagacgacc agaaccctca ctcaagcaac atctgtaaca tctcctgtga caagttcctg  300
gatgatgatc ttactgatga cattatgtgt gtcaagaaga ttctggataa agtaggaatt  360
aactactggt tggcccataa agcactctgt tctgagaagc tggatcagtg gctctgtgag  420
aagttgtga                                                          429

SEQ ID NO: 94          moltype = AA  length = 142
FEATURE                Location/Qualifiers
source                 1..142
                       mol_type = protein
                       organism = Capra hircus
SEQUENCE: 94
MMSFVSLLLV GILFHATQAE QLTKCEVFQK LKDLKDYGGV SLPEWVCTAF HTSGYDTQAI  60
VQNNDSTEYG LFQINNKIWC KDDQNPHSRN ICNISCDKFL DDDLTDDIVC AKKILDKVGI  120
NYWLAHKALC SEKLDQWLCE KL                                           142

SEQ ID NO: 95          moltype = DNA  length = 735
FEATURE                Location/Qualifiers
source                 1..735
                       mol_type = genomic DNA
                       organism = Capra hircus
SEQUENCE: 95
gggggtaac caaaatgatg tcctttgtct ctctgctcct ggtaggcatc ctgttccacg  60
ccacccaggc tgaacaatta acaaaatgtg aggtgttcca gaagctgaag gacttgaagg  120
actacggagg tgtcagtttg cctgaatggg tctgtactgc atttcatacc agtggttatg  180
```

```
acacacaagc catagtacaa aacaatgaca gcacagaata tggactcttc cagataaata  240
ataaaatttg gtgcaaagac gaccagaacc ctcactcaag gaacatctgt aacatctcct  300
gtgacaagtt cctggatgat gatcttactg atgacattgt gtgtgccaag aagattctgg  360
ataaagtagg aattaactac tggttggccc ataaagcact ctgttctgag aagctggatc  420
agtggctctg tgagaagttg tgaacacctg ctgtctttgc tgcttctgtc ctctttctgt  480
tcctggaact cctctgcccc ttggctacct cgttttgctt ctttgtaccc ccttgaagct  540
aactcgtctc tgagccctgg gccctgtagt gacgatggac atgtaaggac taatctccag  600
ggatgcgtga atggtgctca ggacatttga cccttgctcg gtgcccctga tagcactttt  660
aatgcaacag tgcatattcc acttctgtcc tgaataaaag gcctgattct gaaaaaaaaa  720
aaaaaaaaaa aaaaa                                                   735

SEQ ID NO: 96           moltype = AA  length = 142
FEATURE                 Location/Qualifiers
source                  1..142
                        mol_type = protein
                        organism = Homo sapiens
SEQUENCE: 96
MRFFVPLFLV GILFPAILAK QFTKCELSQL LKDIDGYGGI ALPELICTMF HTSGYDTQAI  60
VENNESTEYG LFQISNKLWC KSSQVPQSRN ICDISCDKFL DDDITDDIMC AKKILDIKGI  120
DYWLAHKALC TEKLEQWLCE KL                                           142

SEQ ID NO: 97           moltype = DNA  length = 701
FEATURE                 Location/Qualifiers
source                  1..701
                        mol_type = genomic DNA
                        organism = Homo sapiens
SEQUENCE: 97
atgaggttct ttgtccctct gttcctggtg ggcatcctgt tccctgccat cctggccaag  60
caattcacaa aatgtgagct gtcccagctg ctgaaagaca tagatggtta tggaggcatc  120
gctttgcctg aattgatctg taccatgttt cacaccagtg gttatgacac acaagccata  180
gttgaaaaca atgaaagcac ggaatatgga ctcttccaga tcagtaataa gctttggtgc  240
aagagcagcc aggtccctca gtcaaggaac atctgtgaca tctcctgtga caagttcctg  300
gatgatgaca ttactgatga cataatgtgt gccaagaaga tcctggatat taaaggaatt  360
gactactggt tggcccataa agccctctgc actgagaagc tggaacagtg gctttgtgag  420
aagttgtgag tgtctgctgt ccttggcacc cctgcccact ccacactcct ggaatacctc  480
ttccctaatg ccacctcagt ttgtttcttt ctgttccccc aaagcttatc tgtctctgag  540
ccttgggccc tgtagtgaca tcaccgaatt cttgaagact attttccagg gatgcctgag  600
tggtgcactg agctctagac ccttactcag tgccttcgat ggcactttca ctacagcaca  660
gatttcacct ctgtcttgaa taaaggtccc actttgaagt c                      701

SEQ ID NO: 98           moltype = AA  length = 142
FEATURE                 Location/Qualifiers
source                  1..142
                        mol_type = protein
                        organism = Ovis aries
SEQUENCE: 98
MMSFVSLLLV GILFHATQAE QLTKCEAFQK LKDLKDYGGV SLPEWVCTAF HTSGYDTQAI  60
VQNNDSTEYG LFQINNKIWC KDDQNPHSRN ICNISCDKFL DDDLTDDIVC AKKILDKVGI  120
NYWLAHKALC SEKLDQWLCE KL                                           142

SEQ ID NO: 99           moltype = DNA  length = 723
FEATURE                 Location/Qualifiers
source                  1..723
                        mol_type = genomic DNA
                        organism = Ovis aries
SEQUENCE: 99
ttccaggatc ttagggggta accaaaatga tgtcctttgt ctctctgctc ctggtaggca  60
tcctattcca tgccacccag gctgaacaat taacaaaatg tgaggcgttc cagaagctga  120
aggacttgaa ggactacgga ggtgtcagtt tgcctgaatg ggtctgtacc gcatttcata  180
ccagtggtta tgacacacaa gccatagtac aaaacaatga cagcacagaa tatggactct  240
tccagataaa taataaaatt tggtgcaaag acgaccagaa ccctcactca aggaacatct  300
gtaacatctc ctgtgacaag ttcctggatg atgatcttac tgatgacatt gtgtgtgcca  360
agaagattct ggataaagta ggaattaact actggttggc ccataaagca ctctgttctg  420
agaagctgga tcagtggctc tgtgagaagt tgtgaacacc tgctgtcttt gctgcttctg  480
ccctctttct gttcctggaa ctcctctgcc ccttggctac ctcgttttgc ttctttgtac  540
cccc ttgaag ctaacttgtc tctgagccct gggccctgta gtggcgatgg acatgtaagg  600
actaatctct agggatgcat gaatggtgct cgggacattt gacccttgct cggtgcccct  660
gatagcactt ttaatgcaac agtgcatatt ccacttctgt cctgaataaa aggcctgatt  720
ctg                                                                723

SEQ ID NO: 100          moltype = AA  length = 178
FEATURE                 Location/Qualifiers
source                  1..178
                        mol_type = protein
                        organism = Bos taurus
SEQUENCE: 100
MKCLLLALAL TCGAQALIVT QTMKGLDIQK VAGTWYSLAM AASDISLLDA QSAPLRVYVE  60
ELKPTPEGDL EILLQKWEND ECAQKKIIAE KTKIPAVFKI DALNENKVLV LDTDYKKYLL  120
VCMENSAEPE QSLVCQCLVR TPEVDDEALE KFDKALKALP MHIRLSFNPT QLEEQCHI    178
```

```
SEQ ID NO: 101          moltype = DNA  length = 790
FEATURE                 Location/Qualifiers
source                  1..790
                        mol_type = genomic DNA
                        organism = Bos taurus
SEQUENCE: 101
actccactcc ctgcagagct cagaagcgtg atcccggctg cagccatgaa gtgcctcctg  60
cttgccctgg ccctcacctg tggcgcccag gccctcatcg tcacccagac catgaagggc  120
ctggatatcc agaaggtggc ggggacttgg tactccttgg ccatggcggc cagcgacatc  180
tccctgctgg acgcccagag tgcccccctg agagtgtatg tggaggagct gaagcccacc  240
cctgagggcg acctggagat cctgctgcag aaatgggaga atgatgagtg tgctcagaag  300
aagatcattg cagaaaaaac caagatccct gcggtgttca agatcgatgc cttgaacgag  360
aacaaagtcc ttgtgctgga caccgactac aaaaagtacc tgctcgtctg catggagaac  420
agtgctgagc ccgagcaaag cctggtctgc cagtgcctgg tcaggacccc ggaggtggac  480
gacgaggccc tggagaaatt cgacaaagcc ctcaaggccc tgcccatgca catccggctg  540
tccttcaacc caacccagct ggaggagcag tgccacatct aggtgagccc ctgccggcgc  600
ctctgggagc ccgggagcct tggcccctct ggggacagac gatgtcatcc ccgcctgccc  660
catcagggga ccaggaggaa ccgggaccac attcacccct cctgggaccc aggcccctcc  720
aggcccctcc tggggcctcc tgcttggggc cgctcctcct tcagcaataa aggcataaac  780
ctgtgctctc                                                         790

SEQ ID NO: 102          moltype = AA  length = 180
FEATURE                 Location/Qualifiers
source                  1..180
                        mol_type = protein
                        organism = Capra hircus
SEQUENCE: 102
MKCLLLALGL ALACGIQAII VTQTMKGLDI QKVAGTWYSL AMAASDISLL DAQSAPLRVY  60
VEELKPTPEG NLEILLQKWE NGECAQKKII AEKTKIPAVF KIDALNENKV LVLDTDYKKY  120
LLFCMENSAE PEQSLACQCL VRTPEVDKEA LEKFDKALKA LPMHIRLAFN PTQLEGQCHV  180

SEQ ID NO: 103          moltype = DNA  length = 786
FEATURE                 Location/Qualifiers
source                  1..786
                        mol_type = genomic DNA
                        organism = Capra hircus
SEQUENCE: 103
actccctgca gagctcagaa gcacgacccc agctgcagcc atgaagtgcc tcctgcttgc  60
cctgggcctg gccctcgcct gtggcatcca ggccatcatc gtcacccaga ccatgaaagg  120
cctggacatc cagaaggtgg cggggacttg gtactccttg gctatggcgg ccagcgacat  180
ctccctgctg gacgcccaga gtgcccccct gagagtgtac gtggaggagc tgaagcccac  240
ccccgagggc aacctggaga tcctgctgca gaaatgggag aacggtgagt gtgctcagaa  300
gaagattatt gcagaaaaaa ccaagatccc tgcggtgttc aagatcgatg ccttgaacga  360
gaacaaagtc cttgtgctgg acaccgacta caaaaagtac ctgctcttct gcatggaaaa  420
cagtgctgag cccgagcaaa gcctggcctg ccagtgcctg gtcaggaccc cagaggtgga  480
caaggaggcc ctggagaaat tcgacaaagc cctcaaggcc ctgcccatgc acatccggct  540
cgccttcaac ccgacccagc tggaggggca gtgccacgtc taggtgagcc cctgccggcg  600
cctctgtggg cccgggagcc ttggcccctc tggggacaga cgacgtcacc cccgcctccc  660
ccatcagggg gaccaggagg gaccgggacc acggtcacct ctcctgggac ccaggcccct  720
ccaggcccct cctgtggcct cctgctcggg gccgctcctc cttcagcaat aaaggcataa  780
acctgt                                                             786

SEQ ID NO: 104          moltype = AA  length = 181
FEATURE                 Location/Qualifiers
source                  1..181
                        mol_type = protein
                        organism = Homo sapiens
SEQUENCE: 104
MALEKGPLLL LALGLGLAGA QKALEEVPVQ PGFNAQKVEG RWLTLQLAAN HADLVSPADP  60
LRLALHSIRT RDGDVDFVL  FWKGEGVCKE TNITVHPTQL QGQYQGSFEG GSMHVCFVST  120
DYSNLILYVR FEDDEITNLW VLLARRMLED PKWLGRYLEY VEKFHLQKAP VFNIDGPCPP  180
P                                                                  181

SEQ ID NO: 105          moltype = DNA  length = 1505
FEATURE                 Location/Qualifiers
source                  1..1505
                        mol_type = genomic DNA
                        organism = Homo sapiens
SEQUENCE: 105
tccccttcc ccggagccat ggccctggag aaaggcccgc tcctgctgct ggcccttggc  60
ctgggcctgg cgggtgccca gaaggctctg gaagaggtac cggtacagcc gggcttcaat  120
gcgcagaagg tggaggggcg ctggctcacc ctgcagctgg cagccaacca cgcagacctg  180
gtctccccgg ccgacccct gaggctcgct ctccactcca tccggaccag ggacggcggg  240
gacgtggact tcgtgctgtt ctggaaggga gaaggggtgt gtaaagaaac aaacatcacc  300
gtccatccaa cccagttgca aggccagtac caaggctcat tcgagggcgg cagcatgcac  360
gtatgcttcg tcagcaccga ctacagcaac ctcattcttt acgtgcgctt tgaggatgat  420
gagatcacca acctgtgggt gctgctggcg agaagaatgc tggaggaccc caaatggctg  480
ggaagatact tggagtacgt ggagaaattc cacctgcaga aagccccggt cttcaacata  540
```

```
gatggcccat gtcccccacc ctgagcctag gtctggcggt tctggagtct tcctgcctgg  600
gcccctcacc cctctgctgc cctcagcctc ccttccacct ccttcacctt ggcttgtggc  660
ctggactgtc cccaggtccc cctggaagcc cttttgcatc tcagggactc aaggaagctc  720
cccagctgag cccaaccctg cctctctcct ggtcccctcc cctgctggga aggcctcttc  780
cctctgtgcg tctccaggtc ctgccaacca cctgccaacc aacagccaag ggccagcagt  840
gtgccccagc ctggcctgtg ggcctggagc acacccaggg tggtgaggag ggggcacatg  900
gccccctgag ctcctgcccg cagcgccaga ggcctccaaa acttatacaa tgagtggagc  960
actgtagtcc caggtgcctc cgatgcaccc ccctccccag ggctgctggg gtggccctca  1020
agtgtccttc aggaacatga ccccacggag gctgttctca gactccagct cccctccact  1080
gtgacccacc tcacctgggt ctgctgggga ccctccagag aggtggcctc catgctccgt  1140
gagcaaacgc atatgtcccc actgaggtcc aagagcccta agtgagccca gctccagacc  1200
ctgctctctg cagaagccca gcggggctgc caggtaaaca cagacagctg tacctgtgtg  1260
gcaggtgaga ccagccaacg cccactcctc ggagcccagg attctgaagg gcggcgccca  1320
cttctgcacc cggtgagcca gggctgccca tcggcagggc aggctctgag gaaattgggt  1380
cagggactca atacttgtcg tctggaactc ccaagacagg tatgtccaga ggctgccccg  1440
aaaacgcctc cagtgaggcc ttctcccccct tctccccctt ctccccccttc tccccaatct  1500
ccccc                                                              1505

SEQ ID NO: 106         moltype = AA  length = 180
FEATURE                Location/Qualifiers
source                 1..180
                       mol_type = protein
                       organism = Ovis aries
SEQUENCE: 106
MKCLLLALGL ALACGVQAII VTQTMKGLDI QKVAGTWHSL AMAASDISLL DAQSAPLRVY  60
VEELKPTPEG NLEILLQKWE NGECAQKKII AEKTKIPAVF KIDALNENKV LVLDTDYKKY  120
LLFCMENSAE PEQSLACQCL VRTPEVDNEA LEKFDKALKA LPMHIRLAFN PTQLEGQCHV  180

SEQ ID NO: 107         moltype = DNA  length = 785
FEATURE                Location/Qualifiers
source                 1..785
                       mol_type = genomic DNA
                       organism = Ovis aries
SEQUENCE: 107
ctccctgcag agttcagaag cacgacccca gctgcagcca tgaagtgcct cctgcttgcc  60
ctgggcctgg ccctcgcctg tggcgtccag gccatcatcg tcacccagac catgaaaggc  120
ctggacatcc agaaggtggc ggggacttgg cactccttgg ctatggcggc cagcgacatc  180
tccctgctgg atgcccagag tgccccccctg agagtgtacg tggaggagct gaagcccacc  240
cccgagggca acctggagat cctgctgcag aaatgggaga acggcgagtg tgctcagaag  300
aagattattg cagaaaaaac caagatccct gcggtgttca agatcgatgc cttgaatgag  360
aacaaagtcc ttgtgctgga caccgactac aaaaagtacc tgctcttctg catggaaaac  420
agtgctgagc ccgagcaaag cctggcctgc cagtgcctgg tcaggacccc ggaggtggac  480
aacgaggccc tggagaaatt cgacaaagcc ctcaaggccc tgcccatgca catccggctt  540
gccttcaacc cgacccagct ggaggggcag tgccacgtct aggtgagccc ctgccggtgc  600
ctctgggggc ccgggagcct tggctcctct ggggacagac gacgtcacca ccgccccccc  660
ccatcagggg gactagaagg gaccaggact gcagtcaccc ttcctgggac ccaggcccct  720
ccaggcccct cctggggctc ctgctctggg cagcttctcc ttcaccaata aaggcataaa  780
cctgt                                                              785

SEQ ID NO: 108         moltype = AA  length = 708
FEATURE                Location/Qualifiers
source                 1..708
                       mol_type = protein
                       organism = Bos taurus
SEQUENCE: 108
MKLFVPALLS LGALGLCLAA PRKNVRWCTI SQPEWFKCRR WQWRMKKLGA PSITCVRRAF  60
ALECIRAIAE KKADAVTLDG GMVFEAGRDP YKLRPVAAEI YGTKESPQTH YYAVAVVKKG  120
SNFQLDQLQG RKSCHTGLGR SAGWVIPMGI LRPYLSWTES LEPLQGAVAK FFSASCVPCI  180
DRQAYPNLCQ LCKGEGENQC ACSSREPYFG YSGAFKCLQD GAGDVAFVKE TTVFENLPEK  240
ADRDQYELLC LNNSRAPVDA FKECHLAQVP SHAVVARSVD GKEDLIWKLL SKAQEKFGKN  300
KSRSFQLFGS PPGQRDLLFK DSALGFLRIP SKVDSALYLG SRYLTTLKNL RETAEEVKAR  360
YTRVVWCAVG PEEQKKCQQW SQQSGQNVTC ATASTTDDCI VLVLKGEADA LNLDGGYIYT  420
AGKCGLVPVL AENRKTSKYS SLDCVLRPTE GYLAVAVVKK ANEGLTWNSL KDKKSCHTAV  480
DRTAGWNIPM GLIVNQTGSC AFDEFFSQSC APGRDPKSRL CALCAGDDQG LDKCVPNSKE  540
KYYGYTGAFR CLAEDVGDVA FVKNDTVWEN TNGESTADWA KNLNREDFRL LCLDGTRKPV  600
TEAQSCHLAV APNHAVVSRS DRAAHVKQVL LHQQALFGKN GKNCPDKFCL FKSETKNLLF  660
NDNTECLAKL GGRPTYEEYL GTEYVTAIAN LKKCSTSPLL EACAFLTR               708

SEQ ID NO: 109         moltype = DNA  length = 2357
FEATURE                Location/Qualifiers
source                 1..2357
                       mol_type = genomic DNA
                       organism = Bos taurus
SEQUENCE: 109
gcagagcctt cgttccggag tcgccccagg accccagcca tgaagctctt cgtccccgcc  60
ctgctgtccc ttggagccct tggactgtgt ctggctgccc cgaggaaaaa cgttcgatgg  120
tgtaccatct cccaacccga gtggttcaaa tgccgccgat ggcagtggag gatgaagaag  180
ctgggtgctc cctctatcac ctgtgtgagg agggcctttg ccttggaatg tatccgggcc  240
atcgcggaga aaaaggcgga tgctgtgacc ctggatggtg gcatggtgtt tgaggcgggc  300
```

```
cgggacccct acaaactgcg gccagtagca gcagagatct atgggacgaa agagtctccc  360
caaacccact attatgctgt ggccgtcgtg aagaagggca gcaactttca gctggaccag  420
ctgcaaggcc ggaagtcctg ccatacgggc cttggcaggt ccgctgggtg ggtcatccct  480
atgggaatcc ttcgcccgta cttgagctgg acagagtcac tcgagcccct ccagggagct  540
gtggctaaat tcttctctgc cagctgtgtt ccctgcattg atagacaagc ataccccaac  600
ctgtgtcaac tgtgcaaggg ggagggggag aaccagtgtg cctgctcctc ccgggaacca  660
tacttcggtt attctggtgc cttcaagtgt ctgcaggacg gggctggaga cgtggctttt  720
gttaaagaga cgacagtgtt tgagaacttg ccagagaagg ctgacaggga ccagtatgag  780
cttctctgcc tgaacaacag tcgggcgcca gtggatgcgt tcaaggagtg ccacctggcc  840
caggtccctt ctcatgctgt cgtggcccga agtgtggatg gcaaggaaga cttgatctgg  900
aagcttctca gcaaggcgca ggagaaattt ggaaaaaaca agtctcggag cttccagctc  960
tttggctctc cacccggcca gagggacctg ctgttcaaag actctgctct tgggtttttg  1020
aggatcccct cgaaggtaga ttcggcgctg taccttggct cccgctactt gaccaccttg  1080
aagaacctca gggaaactgc ggaggaggtg aaggcgcggt acaccagggt cgtgtggtgt  1140
gccgtgggac ccgaggagca gaagaagtgc cagcagtgga gccagcagag cggccagaac  1200
gtgacctgtg ccacggcgtc caccaccgac gactgcatcg tcctggtgct gaaaggggaa  1260
gcagatgccc tgaacttgga tggaggatat atctacactg cgggcaagtg tggcctggtg  1320
cctgtcctgg cagagaaccg gaaaacctcc aaatacagta gcctagattg tgtgctgaga  1380
ccaacagaag ggtaccttgc cgtggcagtt gtcaagaaag caaatgaggg gctcacatgg  1440
aattctctga aagacaagaa gtcgtgccac accgccgtgg acaggactgc aggctggaac  1500
atccccatgg gcctgatcgt caaccagaca ggctcctgcg catttgatga attctttagt  1560
cagagctgtg cccctgggcg tgacccgaaa tccagactct gtgccttgtg tgctggcgat  1620
gaccagggcc tggacaagtg tgtgcccaac tctaaggaga agtactatgg ctataccggg  1680
gctttcaggt gcctggctga ggacgttggg gacgttgcct ttgtgaaaaa cgacacagtc  1740
tgggagaaca cgaatggaga gagcactgca gactgggcta agaacttgaa tcgtgaggac  1800
ttcaggttgc tctgcctcga tggcaccagg aagcctgtga cggaggctca gagctgccac  1860
ctggcggtgg ccccgaatca cgctgtggtg tctcggagcg atagggcagc acacgtgaaa  1920
caggtgctgc tccaccagca ggctctgttt gggaaaaatg gaaaaaactg cccggacaag  1980
ttttgtttgt tcaaatctga aaccaaaaac cttctgttca atgacaacac tgagtgtctg  2040
gccaaacttg gaggcagacc aacgtatgaa gaatatttgg ggacagagta tgtcacggcc  2100
attgccaacc tgaaaaaatg ctcaacctcc ccgcttctgg aagcctgcgc cttcctgacg  2160
aggtaaagcc tgcaaagaag ctagcctgcc tccctgggcc tcagctcctc cctgctctca  2220
gccccaatct ccaggcgcga gggaccttcc tctcccttcc tgaagtcgga tttttgccaa  2280
gctcatcagt atttacaatt ccctgctgtc attttagcaa gaaataaaat tagaaatgct  2340
gttgattttc attccct                                                 2357
```

```
SEQ ID NO: 110          moltype = AA  length = 708
FEATURE                 Location/Qualifiers
source                  1..708
                        mol_type = protein
                        organism = Capra hircus
SEQUENCE: 110
MKLFVPALLS LGALGLCLAA PRKNVRWCAI SLPEWSKCYQ WQRRMRKLGA PSITCVRRTS  60
ALECIRAIAG KNADAVTLDS GMVFEAGRDP YKLRPVAAEI YGTEKSPQTH YYAVAVVKKG  120
SNFKLDQLQG QKSCHMGLGR SAGWNIPVGI LRPPLSWTES AEPLQGAVAR FFSASCVPCV  180
DGKAYPNLCQ LCKGVGENKC ACSSQEPYFG YSGAFKCLQD GAGDVAFVKE TTVFENLPEK  240
ADRDQYELLC LNNTRAPVDA FKECHLAQVP SHAVVARSVD GKENLIWELL RKAQEKFGKN  300
KSQRFQLFGS PEGRRDLLFK DSALGFVRIP SKVDSALYLG SRYLTALKNL RETAEELKAR  360
CTRVVWCAVG PEEQSKCQQW SEQSGQNVTC ATASTTDDCI ALVLKGEADA LSLGGGYIYT  420
AGKCGLVPVM AENRKSSKYS SLDCVLRPTE GYLAVAVVKK ANEGLTWNSL KGKKSCHTAV  480
DRTAGWNIPM GLIANQTGSC AFDEFFSQSC APGADPKSSL CALCAGDDQG LDKCVPNSKE  540
KYYGYTGAFR CLAEDVGDVA FVKNDTVWEN TNGESSADWA KNLNREDFRL LCLDGTTKPV  600
TEAQSCYLAV APNHAVVSRS DRAAHVEQVL LHQQALFGKN GKNCPDQFCL FKSETKNLLF  660
NDNTECLAKL GGRPTYEKYL GTEYVTAIAN LKKCSTSPLL EACAFLTR               708
```

```
SEQ ID NO: 111          moltype = DNA  length = 2411
FEATURE                 Location/Qualifiers
source                  1..2411
                        mol_type = genomic DNA
                        organism = Capra hircus
SEQUENCE: 111
agcactggat aaagggacgc agaacgaggg caggtggcag agcttcgttc cggagtcgcc  60
ccaggacccc agacatgaag ctcttcgtcc ccgccctgct gtcccttgga gcccttggac  120
tgtgtctggc tgccccgagg aaaaacgttc gatggtgtgc catctcactg ccggagtggt  180
ccaaatgcta ccaatggcag aggaggatga ggaagctggg tgctccctct atcacctgtg  240
tgaggaggac ctctgccttg gaatgtatcc gggccatcgc gggaaaaaat gcggatgctg  300
tgaccctgga tagtggcatg gtgtttgagg cgggccggga cccctacaaa ctgcggccag  360
tagcggcaga gatctatggg acagaaaaat ctccccaaac ccactattat gctgtggccg  420
tcgtgaagaa gggcagcaac tttaagctgg accagctgca aggtcagaag tcctgccaca  480
tgggccttgg caggtccgct gggtggaaca tccctgtggg aatccttcgc ccgcccttga  540
gctggacaga gtcggccgag cccctccagg gagctgtggc tagattcttc tctgccagct  600
gtgttccctg cgttgatgga aaagcgtacc ccaacctgtg tcaactgtgc aagggggtgg  660
gagagaacaa gtgtgcctgc tcctcccagg aaccatactt tggttattct ggtgccttca  720
agtgcctgca ggacggggct ggagacgtgg cttttgtcaa ggagacgaca gtgtttgaga  780
acttgccaga gaaggctgac agggaccagt atgagcttct ctgcctaaac aacactcggg  840
cgccagtgga tgcattcaag gagtgccacc tggcccaggt cccttctcat gctgttgtgg  900
cccgcagtgt ggatggcaag gagaacttga tctgggagct tctcaggaag gcacaggaga  960
agtttggaaa aaacaagtct cagcgcttcc agctctttgg ctctccagaa ggccggaggg  1020
acctgctatt caaagactct gcccttgggt ttgtgaggat cccctcaaaa gtagattcgg  1080
```

```
cgctgtacct gggctcccgt tacttgaccg ccttgaagaa cctcagggaa accgcggagg  1140
agttgaaggc gcggtgcacg cgggtcgtgt ggtgcgcggt gggacccgag gagcagagta  1200
agtgccagca gtggagcgag cagagcggcc agaacgtgac ctgtgccacg gcctccacca  1260
ccgacgactg catcgccctg gtgctgaaag gggaagcgga cgccctgagc ttgggtggag  1320
gatatatcta cactgccggc aagtgcggcc tggtgcctgt catggcagag aaccggaaat  1380
cctccaaata cagtagccta gattgtgtgc tgagaccaac ggaagggtac cttgccgtgg  1440
cagttgtcaa gaaagcaaat gaggggctca cttggaattc tctgaaaggc aagaagtcgt  1500
gccacaccgc cgtggacagg actgcaggct ggaacatccc catgggcctg atcgccaacc  1560
agacaggctc ctgcgcattt gatgaattct ttagtcagag ctgtgcccct ggggccgacc  1620
cgaaatccag cctctgtgca ttgtgtgccg gcgatgacca gggcctggac aagtgtgtgc  1680
ccaactctaa ggagaagtac tatggctaca ccggggcttt caggtgcctg gctgaggacg  1740
ttggggacgt tgcatttgtg aaaaacgaca cagtctggga gaacacaaat ggagagagct  1800
ctgcagactg ggctaagaac ttgaatcgcg aggacttcag gctgctctgc ctcgatggca  1860
ccacgaagcc tgtgacggag gctcagagct gctacctggc ggtggccccg aatcacgctg  1920
tggtgtctcg gagcgatagg gcagcgcacg tggaacaggt gctgctccac cagcaggctc  1980
tgtttgggaa aaatggaaaa aactgcccgg accagttttg tttgttcaaa tctgaaacca  2040
aaaaccttct gttcaatgac aacactgagt gtctggccaa acttggaggc agaccaacgt  2100
atgaaaaata tttggggaca gagtatgtca cggccattgc caacctgaaa aaatgctcaa  2160
cctccccgct tctggaagcc tgcgccttcc tgacgaggta aagcctgcaa agaagctagc  2220
ctgcctcccc gggcctcagc tcctccctgc tctcagcccc agtcttcagg cgcgagggac  2280
cttcctctcc cttcctgaag tcggattttt gccaagctca tcagtattca caattccctg  2340
ctgtcatctt agcaagaaat taaattagaa atgctgttga ttttcattcc ctaaaaaaaa  2400
aaaaaaaaaa a                                                       2411
```

```
SEQ ID NO: 112          moltype = AA  length = 711
FEATURE                 Location/Qualifiers
source                  1..711
                        mol_type = protein
                        organism = Homo sapiens
SEQUENCE: 112
MKLVFLVLLF LGALGLCLAG RRRRSVQWCT VSQPEATKCF QWQRNMRRVR GPPVSCIKRD  60
SPIQCIQAIA ENRADAVTLD GGFIYEAGLA PYKLRPVAAE VYGTERQPRT HYYAVAVVKK  120
GGSFQLNELQ GLKSCHTGLR RTAGWNVPIG TLRPFLNWTG PPEPIEAAVA RFFSASCVPG  180
ADKGQFPNLC RLCAGTGENK CAFSSQEPYF SYSGAFKCLR DGAGDVAFIR ESTVFEDLSD  240
EAERDEYELL CPDNTRKPVD KFKDCHLARV PSHAVVARSV NGKEDAIWNL LRQAQEKFGK  300
DKSPKFQLFG SPSGQKDLLF KDSAIGFSRV PPRIDSGLYL GSGYFTAIQN LRKSEEEVAA  360
RRARVVWCAV GEQELRKCNQ WSGLSEGSVT CSSASTTEDC IALVLKGEAD AMSLDGGYVY  420
TAGKCGLVPV LAENYKSQQS SDPDPNCVDR PVEGYLAVAV VRRSDTSLTW NSVKGKKSCH  480
TAVDRTAGWN IPMGLLFNQT GSCKFDEYFS QSCAPGSDPR SNLCALCIGD EQGENKCVPN  540
SNERYYGYTG AFRCLAENAG DVAFVKDVTV LQNTDGNNND AWAKDLKLAD FALLCLDGKR  600
KPVTEARSCH LAMAPNHAVV SRMDKVERLK QVLLHQQAKF GRNGSDCPDK FCLFQSETKN  660
LLFNDNTECL ARLHGKTTYE KYLGPQYVAG ITNLKKCSTS PLLEACEFLR K           711
```

```
SEQ ID NO: 113          moltype = DNA  length = 2259
FEATURE                 Location/Qualifiers
source                  1..2259
                        mol_type = genomic DNA
                        organism = Homo sapiens
SEQUENCE: 113
cagaccgcag acatgaaact tgtcttcctc gtcctgctgt tcctcggggc cctcggactg  60
tgtctggctg gccgtaggag aaggagtgtt cagtggtgca ccgtatccca acccgaggcc  120
acaaaatgct tccaatggca aaggaatatg agaagagtgc gtggccctcc tgtcagctgc  180
ataaagagag actcccccat ccagtgtatc caggccattg cggaaaacag ggccgatgct  240
gtgacccttg atggtggttt catatacgag gcaggcctgg ccccctacaa actgcgacct  300
gtagcggcgg aagtctacgg gaccgaaaga cagccacgaa ctcactatta tgccgtggct  360
gtggtgaaga agggcggcag ctttcagctg aacgaactgc aaggtctgaa gtcctgccac  420
acaggccttc gcaggaccgc tggatggaat gtccctatag ggacacttcg tccattcttg  480
aattggacgg gtccacctga gcccattgag gcagctgtgg ccaggttctt ctcagccagc  540
tgtgttcccg gtgcagataa aggacagttc cccaacctgt gtcgcctgtg tgcggggaca  600
ggggaaaaca aatgtgcctt ctcctcccag gaaccgtact tcagctactc tggtgccttc  660
aagtgtctga gagacggggc tggagacgtg gcttttatca gagagagcac agtgtttgag  720
gacctgtcag acgaggctga aagggacgag tatgagttac tctgcccaga caacactcgg  780
aagccagtgg acaagttcaa agactgccat ctggcccggg tcccttctca tgccgttgtg  840
gcacgaagtg tgaatggcaa ggaggatgcc atctggaatc ttctccgcca ggcacaggaa  900
aagtttggaa aggacaagtc accgaaattc cagctctttg gctcccctag tgggcagaaa  960
gatctgctgt tcaaggactc tgccattggg ttttcgaggg tgcccccgag gatagattct  1020
gggctgtacc ttggctccgg ctacttcact gccatccaga acttgaggaa aagtgaggag  1080
gaagtggctg cccggcgtgc gcgggtcgtg tggtgtgcgg tgggcgagca ggagctgcgc  1140
aagtgtaacc agtggagtgg cttgagcgaa ggcagcgtga cctgctcctc ggcctccacc  1200
acagaggact gcatcgccct ggtgctgaaa ggagaagctg atgccatgag tttggatgga  1260
ggatatgtgt acactgcagg caaatgtggt ttggtgcctg tcctggcaga gaactacaaa  1320
tcccaacaaa gcagtgaccc tgatcctaac tgtgtggata gacctgtgga aggatatctt  1380
gctgtggcgg tggttaggag atcagacact agccttacct ggaactctgt gaaaggcaag  1440
aagtcctgcc acaccgccgt ggacaggact gcaggctgga atatccccat gggcctgctc  1500
ttcaaccaga cgggctcctg caaatttgat gaatatttca gtcaaagctg tgcccctggg  1560
tctgacccga gatctaatct ctgtgctctg tgtattggcg acgagcaggg tgagaataag  1620
tgcgtgccca acagcaatga gagatactac ggctacactg ggctttccg gtgcctggct  1680
gagaatgctg gagacgttgc atttgtgaaa gatgtcactg tcttgcagaa cactgatgga  1740
aataacaatg acgcatgggc taaggatttg aagctggcag actttgcgct gctgtgcctc  1800
```

```
gatggcaaac ggaagcctgt gactgaggct agaagctgcc atcttgccat ggccccgaat  1860
catgccgtgg tgtctcggat ggataaggtg gaacgcctga aacaggtgtt gctccaccaa  1920
caggctaaat ttgggagaaa tggatctgac tgcccggaca agttttgctt attccagtct  1980
gaaaccaaaa accttctgtt caatgacaac actgagtgtc tggccagact ccatggcaaa  2040
acaacatatg aaaaatattt gggaccacag tatgtcgcag gcattactaa tctgaaaaag  2100
tgctcaacct ccccccctcct ggaagcctgt gaattcctca ggaagtaaaa ccgaagaaga  2160
tggcccagct ccccaagaaa gcctcagcca ttcactgccc ccagctcttc tccccaggtg  2220
tgttggggcc ttggctcccc tgctgaaggt ggggattgc                        2259

SEQ ID NO: 114         moltype = AA  length = 708
FEATURE                Location/Qualifiers
source                 1..708
                       mol_type = protein
                       organism = Ovis aries
SEQUENCE: 114
MKLFVPALLS LGALGLCLAA PRKNVRWCAI SPPEGSKCYQ WQRRMRKLGA PSITCVRRTS  60
ALECIRAIAG KKADAVTLDS GMVFEAGLDP YKLRPVAAEI YGTEKSPQTH YYAVAVVKKG  120
SNFQLDQLQG QKSCHMGLGR SAGWNIPMGI LRPFLSWTES AEPLQGAVAR FFSASCVPCV  180
DGKAYPNLCQ LCKGVGENKC ACSSQEPYFG YSGAFKCLQD GAGDVAFVKE TTVFENLPEK  240
ADRDQYELLC LNNTRAPVDA FKECHLAQVP SHAVVARSVD GKENLIWELL RKAQEKFGKN  300
KSQRFQLFGS PQGQKDLLFK DSALGFVRIP SKVDSALYLG SRYLTALKNL RETAEEVKAR  360
CTRVVWCAVG PEEHSKCQQW SEQSGQNVTC AMASTTDDCI ALVLKGEADA LSLDGGYIYT  420
AGKCGLVPVM AENRESSKYS SLDCVLRPTE GYLAVAVVKK ANEGLTWNSL KGKKSCHTAV  480
DRTAGWNIPM GLIANQTGSC AFDEFFSQSC APGADPKSSL CALCAGDDQG LNKCVPNSKE  540
KYYGYTGAFR CLAEDVGDVA FVKNDTVWEN TNGESSADWA KNLNREDFRL LCLDGTTKPV  600
TEAQSCYLAV APNHAVVSRS DRAAHVEQVL LHQQALFGKN GKNCPDQFCL FKSETKNLLF  660
NDNTECLAKL GGRPTYEKYL GTEYVTAIAN LKKCSTSPLL EACAFLTR              708

SEQ ID NO: 115         moltype = DNA  length = 2127
FEATURE                Location/Qualifiers
source                 1..2127
                       mol_type = genomic DNA
                       organism = Ovis aries
SEQUENCE: 115
atgaagctct tcgtccccgc cctgctgtcc cttggagccc ttggactgtg tctggctgcc  60
ccgaggaaaa acgttcgatg gtgtgccatc tcaccgccgg aggggtccaa atgctaccaa  120
tggcagagga ggatgaggaa gctgggtgct ccctctatca cctgtgtgag gaggacctct  180
gccctggaat gtatccgggc catcgcggga aaaaaggcgg atgctgtgac cctggatagt  240
ggcatggtgt ttgaggcggg cctggacccc tacaaactgc ggccagtagc ggcagagatc  300
tatgggacag aaaagtctcc ccaaacccac tattatgctg tggccgtcgt gaagaagggc  360
agcaactttc agctggacca gctgcaaggc cagaagtcct gccacatggg ccttggtagg  420
tccgctgggt ggaacatccc tatgggaatc cttcgcccgt tcttgagctg gacagagtcg  480
gccgagcccc tccagggagc tgtggctaga ttcttctctg ccagctgtgt tccctgcgtt  540
gatggaaaag cgtatcccaa cctgtgtcaa ctgtgcaagg gggtgggaga gaacaagtgt  600
gcctgctcct cccaggaacc atactttggt tattctggtg ccttcaagtg cctgcaggac  660
ggggctggag acgtggcttt tgtcaaggag acgacagtgt ttgagaactt gccagagaag  720
gctgacaggg accagtatga gcttctctgc ctaaacaaca ctcgggcgcc agtggatgca  780
ttcaaggagt gccacctggc ccaggtccct tctcatgctg ttgtggcccg cagtgtggat  840
ggcaaggaga acttgatctg ggagcttctc aggaaggcac aggagaagtt tggaaaaaac  900
aagtctcagc gcttccagct ctttggctct ccacaaggcc agaaggacct gctattcaaa  960
gactctgccc ttgggtttgt gaggatcccc tcaaaagtag attcggcgct gtacttaggc  1020
tcccgctact tgaccgcctt gaagaacctc agggaaaccg cggaagaagt gaaggcgcgg  1080
tgcactccgg tcgtgtggtg cgcggtggga ccccaggagc atagtaagtg ccagcagtgg  1140
agcgagcaga gcggccagaa cgtgacttgt gccatggcct ccaccaccga cgaatgcatc  1200
gccctggtgt tgaaagggga agcggacgcc ctgagcttgg atggaggata tatctacact  1260
gccggcaagt gtggcctggt gcctgtcatg gcagagaacc gggaatcctc caaatacagt  1320
agcctagatt gtgtgctgag accaacggaa gggtaccttg ccgtggcagt tgtcaagaaa  1380
gcaaatgagg ggctcacttg gaattctctg aaaggcaaga agtcgtgcca caccgccgtg  1440
gacaggactg caggctggaa catccccatg ggcctgatcg ccaaccagac aggctcctgc  1500
gcatttgatg aattctttag tcagagctgt gcccctgggg ccgacccgaa atccagcctc  1560
tgtgcattgt gtgccggcga tgaccagggc ctgaacaagt gtgtgcccaa ctctaaggag  1620
aagtactatg gctacaccgg ggctttcagg tgcctggctg aggacgttgg ggacgttgca  1680
tttgtgaaaa acgacacagt ctgggagaac acgaatggag agagctctgc agactgggct  1740
aagaacttga atcgcgagga cttcaggttg ctctgcctcg atggcaccac gaagcctgtg  1800
acggaggctc agagctgcta cctggcggtg gccccgaatc acgctgtggt gtctcggagc  1860
gatagggcag cacacgtgga acaggtgctg ctccaccagc aggctctgtt cgggaaaaat  1920
ggaaaaaact gcccggacca gttttgtttg ttcaaatctg aaaccaaaaa ccttctgttc  1980
aatgacaaca ctgagtgtct ggccaaactt ggaggcagac caacgtatga aaaatatttg  2040
gggacagagt atgtcacggc cattgccaac ctgaaaaaat gctcaacctc cccgcttctg  2100
gaagcctgcg ccttcctgac gaggtaa                                     2127

SEQ ID NO: 116         moltype = AA  length = 704
FEATURE                Location/Qualifiers
source                 1..704
                       mol_type = protein
                       organism = Bos taurus
SEQUENCE: 116
MRPAVRALLA CAVLGLCLAD PERTVRWCTI STHEANKCAS FRENVLRILE SGPFVSCVKK  60
TSHMDCIKAI SNNEADAVTL DGGLVYEAGL KPNNLKPVVA EFHGTKDNPQ THYYAVAVVK  120
```

```
KDTDFKLNEL RGKKSCHTGL GRSAGWNIPM AKLYKELPDP QESIQRAAAN FFSASCVPCA  180
DQSSFPKLCQ LCAGKGTDKC ACSNHEPYFG YSGAFKCLME GAGDVAFVKH STVFDNLPNP  240
EDRKNYELLC GDNTRKSVDD YQECYLAMVP SHAVVARTVG GKEDVIWELL NHAQEHFGKD  300
KPDNFQLFQS PHGKDLLFKD SADGFLKIPS KMDFELYLGY EYVTALQNLR ESKPPDSSKD  360
ECMVKWCAIG HQERTKCDRW SGFSGGAIEC ETAENTEECI AKIMKGEADA MSLDGGYLYI  420
AGKCGLVPVL AENYKTEGES CKNTPEKGYL AVAVVKTSDA NINWNNLKDK KSCHTAVDRT  480
AGWNIPMGLL YSKINNCKFD EFFSAGCAPG SPRNSSLCAL CIGSEKGTGK ECVPNSNERY  540
YGYTGAFRCL VEKGDVAFVK DQTVIQNTDG NNNEAWAKNL KKENFEVLCK DGTRKPVTDA  600
ENCHLARGPN HAVVSRKDKA TCVEKILNKQ QDDFGKSVTD CTSNFCLFQS NSKDLLFRDD  660
TKCLASIAKK TYDSYLGDDY VRAMTNLRQC STSKLLEACT FHKP                  704

SEQ ID NO: 117          moltype = DNA  length = 2584
FEATURE                 Location/Qualifiers
source                  1..2584
                        mol_type = genomic DNA
                        organism = Bos taurus
SEQUENCE: 117
gctcggccag ccccgcggga gatatagggg cgcggggagc agggaggcta cgcagaagcc  60
ggtcggtctg tgctctgcac tccacattac agaccgggga ggatgaggcc cgctgtccgc  120
gctctgttag cctgcgcggt tctggggctg tgtctggcgg accctgagag aactgtgaga  180
tggtgcacca tttcaactca tgaggccaat aagtgtgcca gttttcgtga aaatgtgctt  240
cgtatcttgg agagtggtcc ttttgtctcc tgtgtgaaga aaacctcaca catggattgc  300
atcaaggcta tctcgaataa cgaagcagat gctgtgacgt tggatggagg tttggtgtat  360
gaggcaggcc tgaagcccaa caacctgaag cctgtggtgg cagagttcca tgggacaaaa  420
gacaacccac aaactcacta ttatgctgtg gcggtggtga agaaggacac tgacttcaag  480
ctgaatgagc tcagaggcaa gaagtcctgc cacacaggcc tcggcaggtc cgctgggtgg  540
aacatcccca tgggcaaact ttataaggaa ttgcctgatc cacaggaatc aattcagaga  600
gctgcggcca acttcttctc tgccagctgt gtcccctgtg cggatcaatc atcatttccc  660
aaactctgtc aactgtgtgc ggggaaaggg acagacaagt gtgcctgctc caaccacgaa  720
ccatacttcg gctactcagg ggcctttaaa tgtctgatgg agggcgctgg ggatgtggcc  780
tttgtcaagc actcaacggt attcgacaac ctgcctaacc cagaagacag gaaaaactat  840
gagctgctct gcggggacaa cacccggaag tctgtagatg attaccaaga atgctacttg  900
gcaatggttc cttcccatgc ggttgtggct cgaactgtgg gcggcaagga ggatgtgatc  960
tgggaacttc tcaatcacgc ccaggaacat tttggcaaag ataaaccaga caatttccag  1020
cttttccaat cccctcatgg gaaggacctg ctgtttaagg actctgctga tgggttttta  1080
aagattcctt ctaagatgga ttttgagctg tacttgggat atgaatatgt cactgctctt  1140
cagaatctaa gagaaagtaa acccccggac tcctcaaagg atgagtgcat ggtgaagtgg  1200
tgtgcaattg gtcaccagga gaggacaaag tgtgatcggt ggagtgggtt cagcggcggg  1260
gcaatagagt gtgaaacagc agagaacact gaagagtgca tcgccaagat catgaaagga  1320
gaagctgatg ccatgagctt ggacggaggc tacctctaca tagcaggcaa atgtggcctg  1380
gtgcctgtcc tggcagagaa ctacaaaact gagggtgaaa gttgcaagaa cacaccagaa  1440
aaagggtatc ttgctgtagc tgtggttaaa acatcagatg ctaatatcaa ctggaacaat  1500
ctgaaagaca agaagtcctg ccacactgca gtagacagaa ccgctggctg gaacatcccc  1560
atgggtttgc tctacagcaa gattaataac tgtaaatttg atgaattttt cagcgcaggt  1620
tgtgcacctg gatctccgcg aaattccagt ctctgtgctc tgtgcattgg ctcagagaag  1680
ggtacaggaa aggagtgtgt tcccaacagc aatgaaagat actatggcta tacaggggct  1740
ttcaggtgtc tggtggagaa gggagacgtg gcctttgtga aggaccagac tgtcatacag  1800
aacactgacg gaaataataa tgaagcatgg gcaaaaaatc tgaagaagga aaattttgaa  1860
gtactatgca aagatggcac caggaaacct gtgacagatg ctgagaactg ccacctggcc  1920
cgaggcccga atcatgctgt ggtctcacgg aaagataagg caacttgtgt ggagaaaata  1980
ttaaacaaac agcaggatga ttttggaaaa tctgtaaccg actgcacgag caatttttgt  2040
ttattccaat caaattccaa ggaccttctg ttcagggatg acactaaatg tttggcttca  2100
attgcgaaaa aaacatatga ctcctactta ggggatgact acgtcagagc tatgaccaac  2160
ctgagacaat gctcaacctc aaaactcctg gaagcatgca ctttccacaa accttaaaat  2220
ccaagagtgg agccaacacc tgatggagat gggagctcat gggacccata agcttcatct  2280
ggtttcgctg gtctgagtga tttggttgcc ctcacaattt ggtggtggcg cctctgcagg  2340
acaaaataaa aataaacatt attattggtt ttatctgtta aaaaaacttc attttcccct  2400
cttaatgctt ggtctgcaac tagcccttcc ttcagagctc aagattcatt tgctctttcc  2460
cacagccaca gttcctgggt acagtccaag taggaattct ttctaaaagg ggtctgcatg  2520
gtcattttaa taaaatcaag tgtacaagga aaaaaaaaaa aaaaaaaaaa aaaaaaaaaa  2580
aaaa                                                              2584

SEQ ID NO: 118          moltype = AA  length = 698
FEATURE                 Location/Qualifiers
source                  1..698
                        mol_type = protein
                        organism = Homo sapiens
SEQUENCE: 118
MRLAVGALLV CAVLGLCLAV PDKTVRWCAV SEHEATKCQS FRDHMKSVIP SDGPSVACVK  60
KASYLDCIRA IAANEADAVT LDAGLVYDAY LAPNNLKPVV AEFYGSKEDP QTFYYAVAVV  120
KKDSGFQMNQ LRGKKSCHTG LGRSAGWNIP IGLLYCDLPE PRKPLEKAVA NFFSGSCAPC  180
ADGTDFPQLC QLCPGCGCST LNQYFGYSGA FKCLKDGAGD VAFVKHSTIF ENLANKADRD  240
QYELLCLDNT RKPVDEYKDC HLAQVPSHTV VARSMGGKED LIWELLNQAQ EHFGKDKSKE  300
FQLFSSPHGK DLLFKDSAHG FLKVPPRMDA KMYLGYEYVT AIRNLREGTC PEAPTDECKP  360
VKWCALSHHE RLKCDEWSVN SVGKIECVSA ETTEDCIAKI MNGEADAMSL DGGFVYIAGK  420
CGLVPVLAEN YNKSDNCEDT PEAGYFAVAV VKKSASDLTW DNLKGKKSCH TAVGRTAGWN  480
IPMGLLYNKI NHCRFDEFFS EGCAPGSKKD SSLCKLCMGS GLNLCEPNNK EGYYGYTGAF  540
RCLVEKGDVA FVKHQTVPQN TGGKNPDPWA KNLNEKDYEL LCLDGTRKPV EEYANCHLAR  600
APNHAVVTRK DKEACVHKIL RQQQHLFGSN VTDCSGNFCL FRSETKDLLF RDDTVCLAKL  660
```

```
HDRNTYEKYL GEEYVKAVGN LRKCSTSSLL EACTFRRP                      698

SEQ ID NO: 119          moltype = DNA  length = 2808
FEATURE                 Location/Qualifiers
source                  1..2808
                        mol_type = genomic DNA
                        organism = Homo sapiens
SEQUENCE: 119
tggcaccgag cgagccgcga tgacaatggc tgcattgtgc ttcatgtccc ttcccatcaa  60
catttctgtg ctggactcct tccactcgcg ggtcgtctcc agagctcaga aaatgaggtg  120
atcagtggga cgagtaagga aggggggttg ggagaggggc gattgggcaa cccggctgca  180
caaacacggg aggtcaaaga ttgcgcccag cccgcccagg ccgggaatgg aataaaggga  240
cgcggggcgc cggaggctgc acagaagcga gtccgactgt gctcgctgct cagcgccgca  300
cccggaagat gaggctcgcc gtgggagccc tgctggtctg cgccgtcctg gggctgtgtc  360
tggctgtccc tgataaaact gtgagatggt gtgcagtgtc ggagcatgag gccactaagt  420
gccagagttt ccgcgaccat atgaaaagcg tcattccatc cgatggtccc agtgttgctt  480
gtgtgaagaa agcctcctac cttgattgca tcagggccat tgcggcaaac gaagcggatg  540
ctgtgacact ggatgcaggt ttggtgtatg atgcttacct ggctcccaat aacctgaagc  600
ctgtggtggc agagttctat gggtcaaaag aggatccaca gactttctat tatgctgttg  660
ctgtggtgaa gaaggatagt ggcttccaga tgaaccagct tcgaggcaag aagtcctgcc  720
acacgggtct aggcaggtcc gctgggtgga acatccccat aggcttactt tactgtgact  780
tacctgagcc acgtaaacct cttgagaaag cagtggccaa tttcttctcg ggcagctgtg  840
ccccttgtgc ggatgggacg gacttccccc agctgtgtca actgtgtcca gggtgtggct  900
gctccaccct taaccaatac ttcggctact cgggagcctt caagtgtctg aaggatggtg  960
ctggggatgt ggcctttgtc aagcactcga ctatatttga gaacttggca aacaaggctg  1020
acagggacca gtatgagctg ctttgcctgg acaacacccg gaagccggta gatgaataca  1080
aggactgcca cttggcccag gtcccttctc ataccgtcgt ggcccgaagt atgggcggca  1140
aggaggactt gatctgggag cttctcaacc aggcccagga acattttggc aaagacaaat  1200
caaaagaatt ccaactattc agctctcctc atgggaagga cctgctgttt aaggactctg  1260
cccacgggtt tttaaaagtc ccccccagga tggatgccaa gatgtacctg ggctatgagt  1320
atgtcactgc catccggaat ctacgggaag gcacatgccc agaagcccca acagatgaat  1380
gcaagcctgt gaagtggtgt gcgctgagcc accacgagag gctcaagtgt gatgagtgga  1440
gtgttaacag tgtagggaaa atagagtgtg tatcagcaga gaccaccgaa gactgcatcg  1500
ccaagatcat gaatggagaa gctgatgcca tgagcttgga tggagggttt gtctacatag  1560
cgggcaagtg tggtctggtg cctgtcttgg cagaaaacta caataagagc gataattgtg  1620
aggatacacc agaggcaggg tattttgctg tagcagtggt gaagaaatca gcttctgacc  1680
tcacctggga caatctgaaa ggcaagaagt cctgccatac ggcagttggc agaaccgctg  1740
gctggaacat ccccatgggc ctgctctaca ataagatcaa ccactgcaga tttgatgaat  1800
ttttcagtga aggttgtgcc cctgggtcta agaaagactc cagtctctgt aagctgtgta  1860
tgggctcagg cctaaacctg tgtgaaccca acaacaaaga gggatactac ggctacacag  1920
gcgctttcag gtgtctggtt gagaagggag atgtggcctt tgtgaaacac cagactgtcc  1980
cacagaacac tggggggaaaa aaccctgatc catgggctaa gaatctgaat gaaaaagact  2040
atgagttgct gtgccttgat ggtaccagga aacctgtgga ggagtatgcg aactgccacc  2100
tggccagagc cccgaatcac gctgtggtca cacggaaaga taaggaagct tgcgtccaca  2160
agatattacg tcaacagcag cacctatttg gaagcaacgt aactgactgc tcgggcaact  2220
tttgtttgtt ccggtcggaa accaaggacc ttctgttcag agatgacaca gtatgtttgg  2280
ccaaacttca tgacagaaac acatatgaaa aatacttagg agaagaatat gtcaaggctg  2340
ttggtaacct gagaaaatgc tccacctcat cactcctgga agcctgcact ttccgtagac  2400
cttaaaatct cagaggtagg gctgccacca aggtgaagat gggaacgcag atgatccatg  2460
agtttgccct ggtttcactg gcccaagtgg tttgtgctaa ccacgtctgt cttcacagct  2520
ctgtgttgcc atgtgtgctg aacaaaaaat aaaaattatt attgatttta tatttcaaaa  2580
actccattct ttcctaaata ttttcaacaa aggatttctt tatgcattct gcctaaatac  2640
ctatgcaact gagcccttcc ttctcagctc aagattcgtc tggtctttcc ctacagcttt  2700
gtgtgtgcca tggccacatc tcctgggtac agttcaagga gacatctttt ctaaaagggt  2760
ctgcgtgatc attaaaatat aatcaaatgt aaaaaaaaaa aaaaaaaa           2808

SEQ ID NO: 120          moltype = AA  length = 607
FEATURE                 Location/Qualifiers
source                  1..607
                        mol_type = protein
                        organism = Bos taurus
SEQUENCE: 120
MKWVTFISLL LLFSSAYSRG VFRRDTHKSE IAHRFKDLGE EHFKGLVLIA FSQYLQQCPF  60
DEHVKLVNEL TEFAKTCVAD ESHAGCEKSL HTLFGDELCK VASLRETYGD MADCCEKQEP  120
ERNECFLSHK DDSPDLPKLK PDPNTLCDEF KADEKKFWGK YLYEIARRHP YFYAPELLYY  180
ANKYNGVFQE CCQAEDKGAC LLPKIETMRE KVLTSSARQR LRCASIQKFG ERALKAWSVA  240
RLSQKFPKAE FVEVTKLVTD LTKVHKECCH GDLLECADDR ADLAKYICDN QDTISSKLKE  300
CCDKPLLEKS HCIAEVEKDA IPENLPPLTA DFAEDKDVCK NYQEAKDAFL GSFLYEYSRR  360
HPEYAVSVLL RLAKEYEATL EECCAKDDPH ACYSTVFDKL KHLVDEPQNL IKQNCDQFEK  420
LGEYGFQNAL IVRYTRKVPQ VSTPTLVEVS RSLGKVGTRC CTKPESERMP CTEDYLSLIL  480
NRLCVLHEKT PVSEKVTKCC TESLVNRRPC FSALTPDETY VPKAFDEKLF TFHADICTLP  540
DTEKQIKKQT ALVELLKHKP KATEEQLKTV MENFVAFVDK CCAADDKEAC FAVEGPKLVV  600
STQTALA                                                        607

SEQ ID NO: 121          moltype = DNA  length = 1883
FEATURE                 Location/Qualifiers
source                  1..1883
                        mol_type = genomic DNA
                        organism = Bos taurus
```

```
SEQUENCE: 121
gtcgactttg gcacaatgaa gtgggtgact tttatttctc ttctccttct cttcagctct  60
gcttattcca ggggtgtgtt tcgtcgagat acacacaaga gtgagattgc tcatcggttt  120
aaagatttgg gagaagaaca ttttaaaggc ctggtactga ttgccttttc tcagtatctc  180
cagcagtgtc catttgatga gcatgtaaaa ttagtgaacg aactaactga gtttgcaaaa  240
acatgtgttg ctgatgagtc ccatgccggc tgtgaaaagt cacttcacac tctctttgga  300
gatgaattgt gtaaagttgc atcccttcgt gaaacctatg gtgacatggc tgactgctgt  360
gagaaacaag agcctgaaag aaatgaatgc ttcctgagcc acaaagatga tagcccagac  420
ctccctaaat tgaaaccaga ccccaatact ttgtgtgatg agtttaaggc agatgaaaag  480
aagttttggg gaaaatacct atacgaaatt gctagaagac atccctactt ttatgcacca  540
gaactccttt actatgctaa taaatataat ggagtttttc aagaatgctg ccaagctgaa  600
gataaaggtg cctgcctgct accaaagatt gaaactatga gagaaaaagt actgacttca  660
tctgccagac agagactcag gtgtgccagt attcaaaaat ttggagaaag agctttaaaa  720
gcatggtcag tagctcgcct gagccagaaa tttcccaagg ctgagtttgt agaagttacc  780
aagctagtga cagatctcac aaaagtccac aaggaatgct gccatggtga cctacttgaa  840
tgcgcagatg acagggcaga tcttgccaag tacatatgtg ataatcaaga tacaatctcc  900
agtaaactga aggaatgctg tgataagcct ttgttggaaa aatcccactg cattgctgag  960
gtagaaaaag atgccatacc tgaaaacctg cccccattaa ctgctgactt tgctgaagat  1020
aaggatgttt gcaaaaacta tcaggaagca aaagatgcct tcctgggctc gtttttgtat  1080
gaatattcaa gaaggcatcc tgaatatgct gtctcagtgc tattgagact tgccaaggaa  1140
tatgaagcca cactggagga atgctgtgcc aaagatgatc cacatgcatg ctattccaca  1200
gtgtttgaca aacttaagca tcttgtggat gagcctcaga atttaatcaa acaaaactgt  1260
gaccaattcg aaaaacttgg agagtatgga ttccaaaatg cgctcatagt tcgttacacc  1320
aggaaagtac cccaagtgtc aactccaact ctcgtggagg tttcaagaag cctaggaaaa  1380
gtgggtacta ggtgttgtac aaagccggaa tcagaaagaa tgccctgtac tgaagactat  1440
ctgagcttga tcctgaaccg gttgtgcgtg ctgcatgaga agacaccagt gagtgaaaaa  1500
gtcaccaagt gctgcacaga gtcattggtg aacagacggc catgtttctc tgctctgaca  1560
cctgatgaaa catatgtacc caaagccttt gatgagaaat tgttcacctt ccatgcagat  1620
atatgcacac ttcccgatac tgagaaacaa atcaagaaac aaactgcact tgttgagctg  1680
ttgaaacaca agcccaaggc aacagaggaa caactgaaaa ccgtcatgga gaattttgtg  1740
gcttttgtag acaagtgctg tgcagctgat gacaaagagg cctgctttgc tgtggagggt  1800
ccaaaacttg ttgtttcaac tcaaacagcc ttagcctaaa cacgacacaa ccacaggcat  1860
ctcagcctac cctgagagtc gac                                        1883

SEQ ID NO: 122         moltype = AA  length = 607
FEATURE                Location/Qualifiers
source                 1..607
                       mol_type = protein
                       organism = Capra hircus
SEQUENCE: 122
MKWVTFISLL LLFSSAYSRG VFRRDTHKSE IAHRFNDLGE ENFQGLVLIA FSQYLQQCPF  60
DEHVKLVKEL TEFAKTCVAD ESHAGCDKSL HTLFGDELCK VATLRETYGD MADCCEKQEP  120
ERNECFLKHK DDSPDLPKLK PEPDTLCAEF KADEKKFWGK YLYEVARRHP YFYAPELLYY  180
ANKYNGVFQE CCQAEDKGAC LLPKIETMRE KVLASSARQR LRCASIQKFG ERALKAWSVA  240
RLSQKFPKAD FTDVTKIVTD LTKVHKECCH GDLLECADDR ADLAKYICDH QDTLSSKLKE  300
CCDKPVLEKS HCIAEIDKDA VPENLPPLTA DFAEDKEVCK NYQEAKDVFL GSFLYEYSRR  360
HPEYAVSVLL RLAKEYEATL EDCCAKEDPH ACYATVFDKL KHLVDEPQNL IKKNCELFEK  420
HGEYGFQNAL IVRYTRKAPQ VSTPTLVEIS RSLGKVGTKC CAKPESERMP CTEDYLSLIL  480
NRLCVLHEKT PVSEKVTKCC TESLVNRRPC FSDLTLDETY VPKPFDGESF TFHADICTLP  540
DTEKQIKKQT ALVELLKHKP KATDEQLKTV MENFVAFVDK CCAADDKEGC FLLEGPKLVA  600
STQAALA                                                          607

SEQ ID NO: 123         moltype = DNA  length = 2072
FEATURE                Location/Qualifiers
source                 1..2072
                       mol_type = genomic DNA
                       organism = Capra hircus
SEQUENCE: 123
tttccctcta ttcatactat cttttctatc aaccccacaa acctttggca caatgaagtg  60
ggtgactttt atttcccttc tccttctctt cagctctgct tattccaggg gtgtgtttcg  120
tcgagataca cacaaaagtg agattgctca tcggtttaat gatttgggag aagaaaattt  180
tcaaggcctg gtgctgattg ccttttctca gtatctccag cagtgtccat ttgatgaaca  240
tgtaaaatta gtgaaggaac taactgagtt tgcaaaaaca tgtgttgctg atgagtcaca  300
tgccggttgt gataagtcac ttcacactct ctttggagat gaattgtgta aagttgcaac  360
ccttcgcgaa acctatggtg acatggccga ctgctgtgag aaacaagagc ctgaaagaaa  420
tgaatgcttc ctgaaacaca aagatgatag cccagacctc cctaaactga aaccagagcc  480
cgatactttg tgtgccgagt ttaaggcaga tgaaaagaag ttttggggaa aatacctata  540
cgaagttgcc agaagacatc cctactttta tgcaccagaa ctcctttact atgccaataa  600
atataatgga gtttttcaag aatgctgcca agctgaagat aaaggtgcct gcctactacc  660
aaagattgaa actatgagag aaaaagtact ggcttcatct gccagacaga gactcaggtg  720
tgccagtatt caaaaattcg gagaaagagc tttaaaagca tggtcagtag ctcgcctgag  780
ccagaaattt cccaaggctg actttacaga tgttaccaag atagtgacag atctcactaa  840
ggtccacaag gagtgctgcc atggcgacct acttgaatgc gcagacgaca gggcagatct  900
tgccaagtac atatgtgatc atcaagacac actctccagt aaactgaagg aatgctgtga  960
taagcctgtg ttggaaaaat cccactgcat tgctgagata gataaagatg ccgtgcctga  1020
aaacctgccc ccattaactg ctgactttgc tgaagataag gaggtttgca aaaactatca  1080
ggaagcaaaa gacgtcttcc tgggctcgtt tttgtatgaa tattcaagaa ggcatcctga  1140
gtatgctgtc tcagtgctgt tgagacttgc caaggaatat gaagccacac tggaggactg  1200
ctgtgctaaa gaagatccac atgcatgcta tgccacagtg tttgacaaac ttaagcatct  1260
```

```
tgtggatgag cctcagaatt taatcaaaaa aaactgtgag ctatttgaaa aacatggaga  1320
gtatggattc caaaatgcgc tcatagttcg ttacaccagg aaagcacccc aagtgtcaac  1380
tccaactctg gtggagattt caagaagcct aggaaaagtg ggcactaagt gttgtgcaaa  1440
gcctgaatca gaaagaatgc cctgtaccga agactatctg agcttgatcc tgaaccggtt  1500
gtgcgtgttg cacgagaaga caccagtgag tgaaaaagtc accaagtgct gcacagagtc  1560
attggtgaac agacggccat gtttctctga tctgacactt gacgaaacat atgtacccaa  1620
acccttcgat ggtgaatctt tcaccttcca tgcagatata tgcacacttc ctgatactga  1680
gaaacaaatc aagaaacaaa ctgcacttgt tgagctgttg aaacacaagc ccaaggcaac  1740
agatgaacaa ctgaaaaccg ttatggagaa ttttgtggct tttgtagaca agtgctgcgc  1800
agctgatgac aaagaaggct gctttcttct ggagggtcca aaacttgttg cttcaactca  1860
agcagcctta gcctaaacac gacacaacca caagcatctc agcctaccct gagagtaaga  1920
cggaagaaga gaaatgaaaa ctcagagctt attcatctgt tcttcttttc tgttggtgtt  1980
aaacctacac cctctctaaa gaacataaat ttctttaaat attttgcttc ttttgtttgt  2040
gctacaatta ataaaaaatg aaaagactct aa                                2072
```

```
SEQ ID NO: 124         moltype = AA  length = 609
FEATURE                Location/Qualifiers
source                 1..609
                       mol_type = protein
                       organism = Homo sapiens
SEQUENCE: 124
MKWVTFISLL FLFSSAYSRG VFRRDAHKSE VAHRFKDLGE ENFKALVLIA FAQYLQQCPF  60
EDHVKLVNEV TEFAKTCVAD ESAENCDKSL HTLFGDKLCT VATLRETYGE MADCCAKQEP  120
ERNECFLQHK DDNPNLPRLV RPEVDVMCTA FHDNEETFLK KYLYEIARRH PYFYAPELLF  180
FAKRYKAAFT ECCQAADKAA CLLPKLDELR DEGKASSAKQ RLKCASLQKF GERAFKAWAV  240
ARLSQRFPKA EFAEVSKLVT DLTKVHTECC HGDLLECADD RADLAKYICE NQDSISSKLK  300
ECCEKPLLEK SHCIAEVEND EMPADLPSLA ADFVESKDVC KNYAEAKDVF LGMFLYEYAR  360
RHPDYSVVLL LRLAKTYKTT LEKCCAAADP HECYAKVFDE FKPLVEEPQN LIKQNCELFE  420
QLGEYKFQNA LLVRYTKKVP QVSTPTLVEV SRNLGKVGSK CCKHPEAKRM PCAEDYLSVV  480
LNQLCVLHEK TPVSDRVTKC CTESLVNRRP CFSALEVDET YVPKEFNAET FTFHADICTL  540
SEKERQIKKQ TALVELVKHK PKATKEQLKA VMDDFAAFVE KCCKADDKET CFAEEGKKLV  600
AASRAALGL                                                          609
```

```
SEQ ID NO: 125         moltype = DNA  length = 2176
FEATURE                Location/Qualifiers
source                 1..2176
                       mol_type = genomic DNA
                       organism = Homo sapiens
SEQUENCE: 125
tctcttctgt caaccccacg cgcctttggc acaatgaagt gggtaacctt tatttccctt  60
ctttttctct ttagctcggc ttattccagg ggtgtgtttc gtcgagatgc acacaagagt  120
gaggttgctc atcggtttaa agatttggga gaagaaaatt tcaaagcctt agtgttgatt  180
gcctttgctc agtatcttca gcagtgtcca tttgaagatc atgtaaaatt agtgaatgaa  240
gtaactgaat ttgcaaaaac atgtgttgct gatgagtcag ctgaaaattg tgacaaatca  300
cttcataccc tttttggaga caaattatgc acagttgcaa ctcttcgtga aacctatggt  360
gaaatggctg actgctgtgc aaaacaagaa cctgagagaa atgaatgctt cttgcaacac  420
aaagatgaca acccaaacct cccccgattg gtgagaccag aggttgatgt gatgtgcact  480
gcttttcatg acaatgaaga gacatttttg aaaaaatact tatatgaaat tgccagaaga  540
catccttact tctatgcccc ggaactcctt ttctttgcta aaaggtataa agctgctttt  600
acagaatgtt gccaagctgc tgataaggct gcctgcctgt tgccaaagct cgatgaactt  660
cgggatgaag ggaaggcttc gtctgccaaa cagaggctca agtgtgccag tctccaaaaa  720
tttggagaaa gagctttcaa agcatgggca gtagctcgcc tgagccagag atttcccaaa  780
gctgagtttg cagaagtttc caagttagtg acagatctta ccaaagtcca cacggaatgc  840
tgccatggag atctgcttga atgtgctgat gacagggcgg accttgccaa gtatatctgt  900
gaaaatcaag attcgatctc cagtaaactg aaggaatgct gtgaaaaacc tctgttggaa  960
aaatcccact gcattgccga agtggaaaat gatgagatgc ctgctgactt gccttcatta  1020
gctgctgatt ttgttgaaag taaggatgtt tgcaaaaact atgctgaggc aaaggatgtc  1080
ttcctgggca tgtttttgta tgaatatgca agaaggcatc ctgattactc tgtcgtgctg  1140
ctgctgagac ttgccaagac atataaaacc actctagaga agtgctgtgc cgctgcagat  1200
cctcatgaat gctatgccaa agtgttcgat gaatttaaac ctcttgtgga agagcctcag  1260
aatttaatca aacaaaattg tgagcttttt gagcagcttg gagagtacaa attccagaat  1320
gcgctattag ttcgttacac caagaaagta ccccaagtgt caactccaac tcttgtagag  1380
gtctcaagaa acctaggaaa agtgggcagc aaatgttgta aacatcctga agcaaaaaga  1440
atgccctgtg cagaagacta tctatccgtg gtcctgaacc agttatgtgt gttgcatgag  1500
aaaacgccag taagtgacag agtcaccaaa tgctgcacag aatccttggt gaacaggcga  1560
ccatgctttt cagctctgga agtcgatgaa acatacgttc ccaaagagtt taatgctgaa  1620
acattcacct tccatgcaga tatatgcaca ctttctgaga aggagagaca aatcaagaaa  1680
caaactgcac ttgttgagct tgtgaaacac aagcccaagg caacaaaaga gcaactgaaa  1740
gctgttatgg atgatttcgc agcttttgta gagaagtgct gcaaggctga cgataaggag  1800
acctgctttg ccgaggaggg taaaaaactt gttgctgcaa gtcgagctgc cttaggctta  1860
taacatcaca tttaaaagca tctcagccta ccatgagaat aagagaaaga aaatgaagat  1920
caaaagctta ttcatctgtt tttctttttc gttggtgtaa agccaacacc ctgtctaaaa  1980
aacataaatt tctttaatca ttttgcctct tttctctgtg cttcaattaa taaaaaatgg  2040
aaagaatcta atagagtggt acagcactgt tatttttcaa agatgtgttg ctatcctgaa  2100
aattctgtag gttctgtgga agttccagtg ttctctctta ttccacttcg gtagaggatt  2160
tctagtttct gtgggc                                                  2176
```

```
SEQ ID NO: 126         moltype = AA  length = 607
FEATURE                Location/Qualifiers
```

```
source                  1..607
                        mol_type = protein
                        organism = Ovis aries
SEQUENCE: 126
MKWVTFISLL LLFSSAYSRG VFRRDTHKSE IAHRFNDLGE ENFQGLVLIA FSQYLQQCPF  60
DEHVKLVKEL TEFAKTCVAD ESHAGCDKSL HTLFGDELCK VATLRETYGD MADCCEKQEP  120
ERNECFLNHK DDSPDLPKLK PEPDTLCAEF KADEKKFWGK YLYEVARRHP YFYAPELLYY  180
ANKYNGVFQE CCQAEDKGAC LLPKIDAMRE KVLASSARQR LRCASIQKFG ERALKAWSVA  240
RLSQKFPKAD FTDVTKIVTD LTKVHKECCH GDLLECADDR ADLAKYICDH QDALSSKLKE  300
CCDKPVLEKS HCIAEVDKDA VPENLPPLTA DFAEDKEVCK NYQEAKDVFL GSFLYEYSRR  360
HPEYAVSVLL RLAKEYEATL EDCCAKEDPH ACYATVFDKL KHLVDEPQNL IKKNCELFEK  420
HGEYGFQNAL IVRYTRKAPQ VSTPTLVEIS RSLGKVGTKC CAKPESERMP CTEDYLSLIL  480
NRLCVLHEKT PVSEKVTKCC TESLVNRRPC FSDLTLDETY VPKPFDEKFF TFHADICTLP  540
DTEKQIKKQT ALVELLKHKP KATDEQLKTV MENFVAFVDK CCAADDKEGC FVLEGPKLVA  600
STQAALA                                                           607

SEQ ID NO: 127          moltype = DNA  length = 2089
FEATURE                 Location/Qualifiers
source                  1..2089
                        mol_type = genomic DNA
                        organism = Ovis aries
SEQUENCE: 127
gaattccttt tttttctttt ctatcaaccc cacaaacctt tggcacaatg aagtgggtga  60
cttttatttc ccttctcctt ctcttcagct ctgcttattc caggggtgtg tttcgtcgag  120
atacacacaa gagtgagatt gctcatcggt ttaatgattt gggagaagaa aattttcaag  180
gcctggtgct gattgccttt tctcagtatc tccagcagtg tccatttgac gaacatgtaa  240
aattagtgaa ggagctaact gagtttgcaa aaacatgtgt tgctgatgag tcacatgccg  300
gttgtgataa gtcacttcac actctctttg gagatgaatt gtgtaaagtt gcaacccttc  360
gcgaaaccta tggtgacatg gccgactgct gtgagaaaca agagcctgaa agaaatgaat  420
gcttcctgaa tcacaaagat gatagcccag acctccctaa actgaaacca gagcccgata  480
ctttgtgtgc cgagtttaag gcagatgaaa agaagttttg gggaaaatac ctatacgaag  540
ttgccagaag acatccctac ttttatgcac cagaactcct ttactatgct aataaatata  600
atggagtttt tcaagaatgc tgccaagctg aagataaagg tgcctgccta ctaccaaaga  660
ttgacgctat gagagaaaaa gtactggctt catctgccag acagagactc aggtgtgcca  720
gtattcaaaa attcggagaa agagctttaa aagcatggtc agtagctcgc ctgagccaga  780
aatttcccaa ggctgacttt acagatgtta ccaagatagt gacagatctc actaaggtcc  840
acaaggagtg ttgccatggt gacctgcttg aatgcgcaga cgacagggca gatcttgcca  900
agtacatatg tgatcatcaa gacgcactct ccagtaaact gaaggaatgc tgtgataagc  960
ctgtgttgga aaaatcccac tgcattgctg aggtagataa agatgccgtg cctgaaaacc  1020
tgcccccatt aactgctgac tttgctgaag ataaggaggt ttgcaaaaac tatcaggaag  1080
caaaagacgt cttcctgggc tcgtttttgt atgaatattc aagaaggcat cctgagtatg  1140
ctgtctcagt gctattgaga cttgccaagg aatatgaagc cacactggag gactgctgtg  1200
ccaaagaaga tccacatgcc tgctatgcca cagtgtttga caaacttaag catcttgtgg  1260
atgagcctca gaatttaatc aaaaaaaact gtgagctatt cgaaaaacat ggagagtatg  1320
gattccaaaa tgcgctcata gttcgttaca ccaggaaagc accccaagtg tcaactccaa  1380
ctctggtgga gatttcaaga agcctaggaa aagtgggcac taagtgttgt gcaaagcctg  1440
aatcagaaag aatgccctgt accgaagact atctgagctt gatcctgaac cggttgtgcg  1500
tgttgcatga gaagacacca gtgagtgaaa aagtcaccaa gtgctgcacg gagtcattgg  1560
tgaacagacg gccatgtttc tctgatctga cacttgacga aacatatgta cccaaaccct  1620
tcgatgagaa atttttcacc ttccatgcag atatatgcac acttcctgat actgagaaac  1680
aaatcaagaa acaaactgca cttgttgagc tgttgaaaca caagcccaag gcaacagatg  1740
aacaactgaa aaccgttatg gagaattttg tggcttttgt agacaagtgc tgtgcagctg  1800
atgacaaaga aggctgcttt gttctggagg gtccaaaact tgttgcttca actcaagcag  1860
ccttagccta aacacgacac aaccacaagc atctcagcct accctgagag tgagacgaaa  1920
aaagagaaat gaaaactcag agcttattca tctgttcttc ttttcgggtg ttggtgttaa  1980
acctacaccc tctctaaaga acataaattt ctttaaatat tttgcttctt ttgtttgtgc  2040
tacaattaat aaaaaatgaa aagactctaa aaaaaaaaaa aaggaattc            2089

SEQ ID NO: 128          moltype = AA  length = 42
FEATURE                 Location/Qualifiers
source                  1..42
                        mol_type = protein
                        organism = synthetic construct
SEQUENCE: 128
GGCTCAGGAT CAGGGTCGAA AAGAGGCTCA GGATCAGGGT CG                    42

SEQ ID NO: 129          moltype = DNA  length = 943
FEATURE                 Location/Qualifiers
source                  1..943
                        mol_type = other DNA
                        organism = synthetic construct
SEQUENCE: 129
aacatccaaa gacgaaaggt tgaatgaaac ctttttgcca tccgacatcc acaggtccat  60
tctcacacat aagtgccaaa cgcaacagga ggggatacac tagcagcaga ccgttgcaaa  120
cgcaggacct ccactcctct tctcctcaac acccactttt gccatcgaaa aaccagccca  180
gttattgggc ttgattggag ctcgctcatt ccaattcctt ctattaggct actaacacca  240
tgactttatt agcctgtcta tcctggcccc cctggcgagg ttcatgtttg tttatttccg  300
aatgcaacaa gctccgcatt acacccgaac atcactccag atgagggctt tctgagtgtg  360
gggtcaaata gtttcatgtt ccccaaatgg cccaaaactg acagtttaaa cgctgtcttg  420
```

```
gaacctaata tgacaaaagc gtgatctcat ccaagatgaa ctaagtttgg ttcgttgaaa  480
tgctaacggc cagttggtca aaaagaaact tccaaaagtc ggcataccgt ttgtcttgtt  540
tggtattgat tgacgaatgc tcaaaaataa tctcattaat gcttagcgca gtctctctat  600
cgcttctgaa ccccggtgca cctgtgccga aacgcaaatg ggaaacacc cgctttttgg  660
atgattatgc attgtctcca cattgtatgc ttccaagatt ctggtgggaa tactgctgat  720
agcctaacgt tcatgatcaa aatttaactg ttctaacccc tacttgacag caatatataa  780
acagaaggaa gctgccctgt cttaaacctt ttttttatc atcattatta gcttactttc  840
ataattgcga ctggttccaa ttgacaagct tttgatttta acgactttta acgacaactt  900
gagaagatca aaaaacaact aattattgaa agaattcaaa acg                    943

SEQ ID NO: 130         moltype = DNA  length = 486
FEATURE                Location/Qualifiers
source                 1..486
                       mol_type = other DNA
                       organism = synthetic construct
SEQUENCE: 130
tttttgtaga aatgtcttgg tgtcctcgtc caatcaggta gccatctctg aaatatctgg  60
ctccgttgca actccgaacg acctgctggc aacgtaaaat tctccggggt aaaacttaaa  120
tgtggagtaa tggaaccaga aacgtctctt cccttctctc tccttccacc gcccgttacc  180
gtccctagga aattttactc tgctggagag cttcttctac ggcccccttg cagcaatgct  240
cttcccagca ttacgttgcg ggtaaaacgg aggtcgtgta cccgacctag cagcccaggg  300
atggaaaagt cccggccgtc gctggcaata atagcgggcg gacgcatgtc atgagattat  360
tggaaaccac cagaatcgaa tataaaaggc gaacaccttt cccaattttg gtttctcctg  420
acccaaagac tttaaattta atttatttgt ccctatttca atcaattgaa caactatcaa  480
aacaca                                                             486

SEQ ID NO: 131         moltype = DNA  length = 441
FEATURE                Location/Qualifiers
source                 1..441
                       mol_type = other DNA
                       organism = synthetic construct
SEQUENCE: 131
agaacggaaa ggaatatatt tactgccgat cgcattttgg cctcaaataa atcttgagct  60
tttggacata gattatatgt tctttcttgg aagctctttc agctaatagt gaagtgtttc  120
ctactaagga tcgcctccaa acgttccaac tacgggcgga ggttgcaaag aaaacgggtc  180
tctcagcgaa ttgttctcat ccatgagtga gtcctctccg tcctttcctc gcgcctggca  240
ataaagcctc cttcggagga gctccgtcta gagaataatt gctgcctttc tgactttcgg  300
actagcgcca accgcgaacc acaccaccac accatcactg tcacccgtca tagttcatcc  360
ctctctcctt ataaagcatc taataggttc cacaattgtt tgccacaaaa atctcttagc  420
atagcccaat tgattacgaa a                                            441

SEQ ID NO: 132         moltype = DNA  length = 57
FEATURE                Location/Qualifiers
source                 1..57
                       mol_type = other DNA
                       organism = synthetic construct
SEQUENCE: 132
atgaggtttc cttctatctt cacggcagtt cttttcgctg catcttccgc attggct     57

SEQ ID NO: 133         moltype = DNA  length = 45
FEATURE                Location/Qualifiers
source                 1..45
                       mol_type = other DNA
                       organism = synthetic construct
SEQUENCE: 133
atgaagttct tcatcttcac ttgtttgttg gctgttgctt tggct                  45

SEQ ID NO: 134         moltype = DNA  length = 69
FEATURE                Location/Qualifiers
source                 1..69
                       mol_type = other DNA
                       organism = synthetic construct
SEQUENCE: 134
atgagacagg tttggttctc ctggatcgtt ggtttgttct tgtgtttctt caacgtttcc  60
tccgctgct                                                          69

SEQ ID NO: 135         moltype = DNA  length = 45
FEATURE                Location/Qualifiers
source                 1..45
                       mol_type = other DNA
                       organism = synthetic construct
SEQUENCE: 135
atgaaggttt tgatcttggc ttgtttggtt gctttggctt tggct                  45

SEQ ID NO: 136         moltype = DNA  length = 69
FEATURE                Location/Qualifiers
source                 1..69
                       mol_type = other DNA
                       organism = synthetic construct
```

```
SEQUENCE: 136
atgagacagg tttggttcag ttggatagtc ggtttattcc tatgcttttt taatgtctca  60
tccgccgct                                                          69

SEQ ID NO: 137         moltype = DNA  length = 45
FEATURE                Location/Qualifiers
source                 1..45
                       mol_type = other DNA
                       organism = synthetic construct
SEQUENCE: 137
atgaagttgt tgatcttgac ttgtttggtt gctgttgctt tggct                  45

SEQ ID NO: 138         moltype = DNA  length = 63
FEATURE                Location/Qualifiers
source                 1..63
                       mol_type = other DNA
                       organism = synthetic construct
SEQUENCE: 138
atgatgaagt ccttcttctt ggttgttact atcttggctt tgactttgcc attcttgggt  60
gct                                                                63

SEQ ID NO: 139         moltype = DNA  length = 69
FEATURE                Location/Qualifiers
source                 1..69
                       mol_type = other DNA
                       organism = synthetic construct
SEQUENCE: 139
atgaggcaag tttggtttag ttggattgtt ggactgttcc tgtgcttttt caacgtgtca  60
tccgctgcc                                                          69

SEQ ID NO: 140         moltype = DNA  length = 69
FEATURE                Location/Qualifiers
source                 1..69
                       mol_type = other DNA
                       organism = synthetic construct
SEQUENCE: 140
atgcgacagg tatggttttc ttggattgtg gggttgtttc tatgtttctt taacgtttct  60
tctgctgca                                                          69

SEQ ID NO: 141         moltype = DNA  length = 48
FEATURE                Location/Qualifiers
source                 1..48
                       mol_type = other DNA
                       organism = synthetic construct
SEQUENCE: 141
atgaagttgg cttactcctt gttgttgcca ttggctggtg tttctgct               48

SEQ ID NO: 142         moltype = DNA  length = 57
FEATURE                Location/Qualifiers
source                 1..57
                       mol_type = other DNA
                       organism = synthetic construct
SEQUENCE: 142
atgttgttgc aggctttctt gttcttgttg gctggtttcg ctgctaagat ctctgct     57

SEQ ID NO: 143         moltype = DNA  length = 489
FEATURE                Location/Qualifiers
source                 1..489
                       mol_type = genomic DNA
                       organism = Bos taurus
SEQUENCE: 143
ttaatcgtca ctcagacaat gaaaggtttg gacatccaaa aagttgctgg aacttggtat  60
tcattggcaa tggctgcaag cgatatctcc ctgttagacg cccaatcagc tccactaaga  120
gtgtatgtgg aggagctgaa gcccactcca gaaggtgatc ttgaaattct gttgcaaaaa  180
tgggaaaatg gtgagtgtgc tcagaaaaag attatcgccg agaaaaccaa gattccggct  240
gtattcaaga tagatgctct gaacgagaat aaggtgttgg tcctcgatac agactacaaa  300
aagtaccttc tattctgtat ggaaaattcg gcagaacctg agcaatcctt ggcttgtcaa  360
tgcttggtta gaactccaga agttgacgac gaggctttgg aaaagtttga taaagccctg  420
aaagccttgc ctatgcatat tcgtttaagt tttaacccaa cacaattgga ggaacagtgt  480
cacatttaa                                                          489

SEQ ID NO: 144         moltype = DNA  length = 630
FEATURE                Location/Qualifiers
source                 1..630
                       mol_type = genomic DNA
                       organism = Bos taurus
SEQUENCE: 144
agagagttgg aagagttgaa cgttccaggt gagatcgttg agtctttgtc ctcttcagaa  60
gagtccatca ctagaatcaa caagaagatc gagaagttcc agtccgagga acaacaacaa  120
```

```
actgaggacg agttgcagga caagattcac ccattcgctc aaactcagtc cttggtttac  180
ccattcccag gtccaattcc aaactccttg ccacagaaca tcccaccatt gactcagact  240
ccagttgttg ttccaccatt cttgcagcca gaggttatgg gtgtttccaa ggttaaggaa  300
gctatggctc caaagcacaa agagatgcca ttcccaaagt acccagttga gccattcact  360
gagtcccagt ccttgacttt gactgacgtt gagaacttgc acttgccatt gcctttgttg  420
caatcctgga tgcaccaacc acatcaacca ttgccaccaa ctgttatgtt cccaccacaa  480
tccgttttgt ccttgtccca atccaaggtt ttgccagttc cacagaaggc tgttccatac  540
cctcaaagag acatgccaat ccaggctttc ttgttgtacc aagagccagt tttgggtcca  600
gttagaggtc cattccctat catcgtttga                                    630

SEQ ID NO: 145         moltype = DNA  length = 624
FEATURE                Location/Qualifiers
source                 1..624
                       mol_type = genomic DNA
                       organism = Bos taurus
SEQUENCE: 145
aagaacacta tggaacacgt ttcatcctcc gaagagtcca tcatctccca agagacttac  60
aagcaagaga agaacatgga catcaaccca tccaaagaaa acttgtgttc cactttctgt  120
aaagaggttg ttagaaacgc taacgaggaa gagtactcca tcggttcctc atctgaagaa  180
tctgctgagg ttgctactga agaggttaag atcactgttg acgacaagca ctaccagaag  240
gctttgaacg agatcaacca gttctacaga aaattcccac aatacttgca gtacttgtac  300
cagggtccaa tcgttttgaa cccatgggac caggttaaga gaaacgctgt tcctatcact  360
ccaactttga acagagagca gttgtccact tccgaagaga actccaagaa aactgttgac  420
atggaatcca ctgaggtttt cactaagaaa actaagttga ctgaggaaga aaagaacaga  480
ttgaacttct tgaagaagat ctcccagaga taccagaagt tcgctttgcc acagtacttg  540
aaaacagttt accagcacca aaaggctatg aagccatgga tccagccaaa gactaaggtt  600
atcccatacg ttagatactt gtga                                          624

SEQ ID NO: 146         moltype = DNA  length = 624
FEATURE                Location/Qualifiers
source                 1..624
                       mol_type = genomic DNA
                       organism = Bos taurus
SEQUENCE: 146
aagaacacta tggaacacgt ttcatcctcc gaagagtcca tcatctccca agagacttac  60
aagcaagaga agaacatgga catcaaccca tccaaagaaa acttgtgttc cactttctgt  120
aaagaggttg ttagaaacgc taacgaggaa gagtactcca tcggttcctc atctgaagaa  180
tctgctgagg ttgctactga agaggttaag atcactgttg acgacaagca ctaccagaag  240
gctttgaacg agatcaacca gttctacaga aaattcccac aatacttgca gtacttgtac  300
cagggtccaa tcgttttgaa cccatgggac caggttaagg aaaacgctgt tcctatcact  360
ccaactttga acagagagca gttgtccact tccgaagaga actccaagaa aactgttgac  420
atggaatcca ctgaggtttt cactaagaaa actaagttga ctgaggaaga aaagaacaga  480
ttgaacttct tgaagaagat ctcccagaga taccagaagt tcgctttgcc acagtacttg  540
aaaacagttt accagcacca aaaggctatg aagccatgga tccagccaaa gactaaggtt  600
atcccatacg ttagatactt gtga                                          624

SEQ ID NO: 147         moltype = DNA  length = 600
FEATURE                Location/Qualifiers
source                 1..600
                       mol_type = genomic DNA
                       organism = Bos taurus
SEQUENCE: 147
agacctaagc acccaatcaa gcaccaaggt ttgccacaag aggttttgaa cgagaacttg  60
ttgagattct tcgttgctcc attcccagag gttttcggta aagagaaggt taacgagttg  120
tccaaggaca tcggttctga atccactgag gaccaggcta tggaagatat caagcagatg  180
gaagctgagt ccatctcctc atccgaagag atcgttccaa actccgttga gcagaagcac  240
atccagaaag aggacgttcc atccgagaga tacttgggtt acttggagca gttgttgaga  300
ttgaagaagt acaaggttcc acagttggaa atcgttccta attccgctga agaaagattg  360
cactccatga aggaaggtat ccacgctcag cagaaagaac ctatgatcgg tgttaatcaa  420
gagttggctt acttctaccc agagttgttc agacagttct accagttgga cgcttaccca  480
tctggtgctt ggtactacgt tccattgggt actcagtaca ctgacgctcc atctttctcc  540
gacattccaa acccaattgg ttccgagaac tccggtaaga ctactatgcc attgtggtaa  600

SEQ ID NO: 148         moltype = DNA  length = 510
FEATURE                Location/Qualifiers
source                 1..510
                       mol_type = genomic DNA
                       organism = Bos taurus
SEQUENCE: 148
caagagcaaa atcaagagca gccaatcaga tgtgagaagg acgagagatt cttctcagac  60
aagatcgcta agtacatccc aatccagtac gttttgtcca gatacccatc ctacggtttg  120
aactactacc agcagaagcc agttgctttg atcaacaacc agttcttgcc atacccttac  180
tacgctaagc cagctgctgt tagatctcct gctcaaatct tgcagtggca ggttttgtct  240
aacactgttc cagctaagtc ctgtcaggct cagccaacta ctatggctag acatccacat  300
ccacacttgt ccttcatggc tatcccacca aagaagaacc aggacaagac tgagatccca  360
actatcaaca ctatcgcttc cggtgagcca acttccactc caactattga agctgttgag  420
tccactgttg ctactttgga agcttctcca gaggttattg aatccccacc agagatcaac  480
acagttcagg ttacttccac tgctgtttaa                                    510
```

```
SEQ ID NO: 149         moltype = DNA  length = 279
FEATURE                Location/Qualifiers
source                 1..279
                       mol_type = other DNA
                       organism = synthetic construct
SEQUENCE: 149
ggttaaaggg gcggccgctc aagaggatgt cagaatgcca tttgcctgag agatgcaggc  60
ttcatttttg atactttttt atttgtaacc tatatagtat aggatttttt ttgtcatttt  120
gtttcttctc gtacgagctt gctcctgatc agcctatctc gcagcagatg aatatcttgt  180
ggtaggggtt tgggaaaatc attcgagttt gatgtttttc ttggtatttc ccactcctct  240
tcagagtaca gaagattaag tgaaaccttc gtttgtgcg                         279

SEQ ID NO: 150         moltype = DNA  length = 271
FEATURE                Location/Qualifiers
source                 1..271
                       mol_type = other DNA
                       organism = synthetic construct
SEQUENCE: 150
atcatgtaat tagttatgtc acgcttacat tcacgccctc cccccacatc cgctctaacc  60
gaaaaggaag gagttagaca acctgaagtc taggtcccta tttatttttt tatagttatg  120
ttagtattaa gaacgttatt tatatttcaa atttttcttt tttttctgta cagacgcgtg  180
tacgcatgta acattatact gaaaaccttg cttgagaagg ttttgggacg ctcgaaggct  240
ttaatttgcg gcccctcacc tgcacgcaaa a                                 271

SEQ ID NO: 151         moltype = DNA  length = 375
FEATURE                Location/Qualifiers
source                 1..375
                       mol_type = other DNA
                       organism = synthetic construct
SEQUENCE: 151
atggctaaac tcacctctgc tgttccagtc ctgactgctc gtgatgttgc tggtgctgtt  60
gagttctgga ctgatagact cggtttctcc cgtgacttcg tagaggacga ctttgccggt  120
gttgtacgtg acgacgttac cctgttcatc tccgcagttc aggaccaggt tgtgccagac  180
aacactctgg catgggtatg ggttcgtggt ctggacgaac tgtacgctga gtggtctgag  240
gtcgtgtcta ccaacttccg tgatgcatct ggtccagcta tgaccgagat cggtgaacag  300
ccctggggtc gtgagtttgc actgcgtgat ccagctggta actgcgtgca tttcgtcgca  360
gaagaacagg actaa                                                   375

SEQ ID NO: 152         moltype = DNA  length = 816
FEATURE                Location/Qualifiers
source                 1..816
                       mol_type = other DNA
                       organism = synthetic construct
SEQUENCE: 152
atgagccata ttcaacggga aacgtcttgc tcgaggccgc gattaaattc caacatggat  60
gctgatttat atgggtataa atgggctcgc gataatgtcg ggcaatcagg tgcgacaatc  120
tatcgattgt atgggaagcc cgatgcgcca gagttgtttc tgaaacatgg caaaggtagc  180
gttgccaatg atgttacaga tgagatggtc agactaaact ggctgacgga atttatgcct  240
cttccgacca tcaagcattt tatccgtact cctgatgatg catggttact caccactgcg  300
atccccggga aaacagcatt ccaggtatta gaagaatatc ctgattcagg tgaaaatatt  360
gttgatgcgc tggcagtgtt cctgcgccgg ttgcattcga ttcctgtttg taattgtcct  420
tttaacagcg atcgcgtatt tcgtctcgct caggcgcaat cacgaatgaa taacggtttg  480
gttgatgcga gtgattttga tgacgagcgt aatggctggc ctgttgaaca agtctggaaa  540
gaaatgcata agcttttgcc attctcaccg gattcagtcg tcactcatgg tgatttctca  600
cttgataacc ttatttttga cgaggggaaa ttaataggtt gtattgatgt tggacgagtc  660
ggaatcgcag accgatacca ggatcttgcc atcctatgga actgcctcgg tgagttttct  720
ccttcattac agaaacggct tttcaaaaa tatggtattg ataatcctga tatgaataaa  780
ttgcagtttc atttgatgct cgatgagttt ttctaa                            816

SEQ ID NO: 153         moltype = DNA  length = 939
FEATURE                Location/Qualifiers
source                 1..939
                       mol_type = other DNA
                       organism = synthetic construct
SEQUENCE: 153
gatctaacat ccaaagacga aaggttgaat gaaacctttt tgccatccga catccacagg  60
tccattctca cacataagtg ccaaacgcaa caggaggga tacactagca gcagaccgtt  120
gcaaacgcag gacctccact cctcttctcc tcaacaccca cttttgccat cgaaaaacca  180
gcccagttat tgggcttgat tggagctcgc tcattccaat tccttctatt aggctactaa  240
caccatgact ttattagcct gtctatcctg gcccccctgg cgaggttcat gtttgtttat  300
ttccgaatgc aacaagctcc gcattacacc cgaacatcac tccagatgag ggctttctga  360
gtgtggggtc aaatagtttc atgttcccca aatggcccaa aactgacagt ttaaacgctg  420
tcttggaacc taatatgaca aaagcgtgat ctcatccaag atgaactaag tttggttcgt  480
tgaaatgcta acggccagtt ggtcaaaaag aaacttccaa aagtcggcat accgtttgtc  540
ttgtttggta ttgattgacg aatgctcaaa aataatctca ttaatgctta gcgcagtctc  600
tctatcgctt ctgaaccccg gtgcacctgt gccgaaacgc aaatggggaa acacccgctt  660
tttggatgat tatgcattgt ctccacattg tatgcttcca agattctggt gggaatactg  720
ctgatagcct aacgttcatg atcaaaattt aactgttcta acccctactt gacagcaata  780
tataaacaga aggaagctgc cctgtcttaa accttttttt ttatcatcat tattagctta  840
```

```
ctttcataat tgcgactggt tccaattgac aagcttttga ttttaacgac ttttaacgac  900
aacttgagaa gatcaaaaaa caactaatta ttcgaaacg                         939

SEQ ID NO: 154         moltype = DNA  length = 267
FEATURE                Location/Qualifiers
source                 1..267
                       mol_type = other DNA
                       organism = synthetic construct
SEQUENCE: 154
atgagatttc cttcaatttt tactgctgtt ttattcgcag catcctccgc attagctgct  60
ccagtcaaca ctacaacaga agatgaaacg gcacaaattc cggctgaagc tgtcatcggt  120
tactcagatt tagaagggga tttcgatgtt gctgttttgc cattttccaa cagcacaaat  180
aacgggttat tgtttataaa tactactatt gccagcattg ctgctaaaga agaaggggta  240
tctctcgaga aaagagaggc tgaagct                                     267

SEQ ID NO: 155         moltype = DNA  length = 66
FEATURE                Location/Qualifiers
source                 1..66
                       mol_type = other DNA
                       organism = synthetic construct
SEQUENCE: 155
atgagacaag tttggttctc atggattgtt ggtttattct tgtgtttctt caacgtttct  60
tccgct                                                            66

SEQ ID NO: 156         moltype = DNA  length = 57
FEATURE                Location/Qualifiers
source                 1..57
                       mol_type = other DNA
                       organism = synthetic construct
SEQUENCE: 156
atgatgtcat ttgtttcttt gttgttggtt ggtatcctgt tccacgccac tcaagct     57

SEQ ID NO: 157         moltype = DNA  length = 372
FEATURE                Location/Qualifiers
source                 1..372
                       mol_type = genomic DNA
                       organism = Bos taurus
SEQUENCE: 157
gagcaattga ccaagtgtga agttttcaga gagttgaagg atttgaaggg ttacggtggt  60
gtttctcttc cagaatgggt ttgtaccgct ttccacactt ccggatacga tacacaagct  120
atcgttcaaa acaacgactc caccgagtac ggtttgttcc aaatcaacaa caagatttgg  180
tgtaaagacg atcaaaaccc tcactcttcc aacatttgca acatctcttg tgataagttc  240
ttggatgatg atctcaccga tgatatcatg tgtgttaaga agattttgga caaagttgga  300
atcaactact ggttggctca caaggctctt tgttcagaga agttggacca atggctatgt  360
gagaagttgt aa                                                     372

SEQ ID NO: 158         moltype = DNA  length = 350
FEATURE                Location/Qualifiers
source                 1..350
                       mol_type = other DNA
                       organism = synthetic construct
SEQUENCE: 158
tcaagaggat gtcagaatgc catttgcctg agagatgcag gcttcatttt tgatactttt  60
ttatttgtaa cctatatagt ataggatttt ttttgtcatt ttgtttcttc tcgtacgagc  120
ttgctcctga tcagcctatc tcgcagctga tgaatatctt gtggtagggg tttgggaaaa  180
tcattcgagt ttgatgtttt tcttggtatt tcccactcct cttcagagta cagaagatta  240
agtgacacgt tcgtttgtgc aagcttcaac gatgccaaaa gggtataata agcgtcattt  300
gcagcattgt gaagaaaact atgtggcaag ccaagcctgc gaagaatgta            350

SEQ ID NO: 159         moltype = DNA  length = 810
FEATURE                Location/Qualifiers
source                 1..810
                       mol_type = other DNA
                       organism = synthetic construct
SEQUENCE: 159
atgggtaagg aaaagactca cgtttccaga ccaagattga actctaacat ggacgctgac  60
ttgtacggtt acaagtgggc tagagacaac gttggtcaat ctggtgctac tatttacaga  120
ttgtacggta agccagacgc tccagagttg ttcttgaagc acggtaaggg ttctgttgct  180
aacgacgtta ctgacgagat ggttagattg aactggttga ctgagttcat gccattgcca  240
actattaagc acttcattag aactccagac gacgcttggt tgttgactac tgctattcca  300
ggtaagactg ctttccaagt tttggaggag tacccagact ctggtgagaa cattgttgac  360
gctttggctg ttttcttgag aagattgcac tctattccag tttgtaactg tccattcaac  420
tctgacagag ttttcagatt ggctcaagct caatccagaa tgaacaacgg tttggttgac  480
gcttctgact tcgacgacga gagaaacggt tggccagttg agcaagtttg gaaggagatg  540
cacaagttgt tgccattctc tccagactct gttgttactc acggtgactt ctctttggac  600
```

-continued

```
aacttgattt tcgacgaggg taagttgatt ggttgtattg acgttggtag agttggtatt  660
gctgacagat accaagactt ggctattttg tggaactgtt tgggtgagtt ctctccatct  720
ttgcaaaaga gattgttcca aaagtacggt attgacaacc cagacatgaa caagttgcaa  780
ttccacttga tgttggacga gttcttctaa                                    810
```